(12) United States Patent
Vidal Juan et al.

(10) Patent No.: US 7,790,728 B2
(45) Date of Patent: Sep. 7, 2010

(54) PYRAZINE DERIVATIVES USEFUL AS ADENOSINE RECEPTOR ANTAGONISTS

(75) Inventors: Bernat Vidal Juan, Barcelona (ES); Christina Esteve Trias, Barcelona (ES); Lidia Soca Pueyo, Barcelona (ES); Paul Robert Eastwood, Barcelona (ES)

(73) Assignee: Laboratorios Almirall, S.A., Barcelona (ES)

( * ) Notice: Subject to any disclaimer, the term of this patent is extended or adjusted under 35 U.S.C. 154(b) by 0 days.

(21) Appl. No.: 11/997,048

(22) PCT Filed: Jul. 25, 2006

(86) PCT No.: PCT/EP2006/007318

§ 371 (c)(1),
(2), (4) Date: Mar. 6, 2008

(87) PCT Pub. No.: WO2007/017096

PCT Pub. Date: Feb. 15, 2007

(65) Prior Publication Data

US 2009/0042891 A1    Feb. 12, 2009

(30) Foreign Application Priority Data

Jul. 29, 2005   (ES) ............................. 200501876

(51) Int. Cl.
    *A61K 31/4965* (2006.01)
(52) U.S. Cl. .................. 514/255.05; 544/333; 544/405; 546/152; 546/268.1; 548/205; 548/235; 549/59; 549/471; 549/505
(58) Field of Classification Search ............ 514/255.05; 544/333, 405; 546/152, 268.1; 548/205, 548/235; 549/59, 471, 505
See application file for complete search history.

(56) References Cited

U.S. PATENT DOCUMENTS

| 5,763,448 A | 6/1998 | Carling et al. |
| 5,916,905 A | 6/1999 | Weier et al. |

(Continued)

FOREIGN PATENT DOCUMENTS

| CA | 2 463 284 | 5/2003 |
| EP | 1 221 444 | 7/2002 |
| EP | 1 283 056 | 2/2003 |
| EP | 1 308 441 | 5/2003 |
| EP | 1 439 175 | 7/2004 |
| WO | WO 97/33883 | 9/1997 |
| WO | WO 98/24782 | 6/1998 |
| WO | WO 99/32448 | 7/1999 |
| WO | WO 99/65897 | 12/1999 |
| WO | WO 00/73307 | 12/2000 |
| WO | WO 01/02400 | 1/2001 |
| WO | WO 01/16134 | 3/2001 |
| WO | WO 01/60350 | 8/2001 |
| WO | WO 01/62233 | 8/2001 |
| WO | WO 02/14282 | 2/2002 |
| WO | WO 02/20495 | 3/2002 |
| WO | WO 02/22608 | 3/2002 |
| WO | WO 02/24893 | 3/2002 |
| WO | WO 02/42298 | 5/2002 |
| WO | WO 03/002566 | 1/2003 |
| WO | WO 03/035639 | 5/2003 |
| WO | WO 03/042214 | 5/2003 |

(Continued)

OTHER PUBLICATIONS

Frank. D. King. Bioisosteres, Conformational Restriction, and Prodrugs—Case History: An Example of a Conformational Restriction Approach, Medicinal Chemistry: Principles and Practice, Chapter 14, 1994, 208.*

(Continued)

*Primary Examiner*—James O Wilson
*Assistant Examiner*—Douglas M Willis
(74) *Attorney, Agent, or Firm*—Finnegan, Henderson, Farabow, Garrett & Dunner, LLP

(57) ABSTRACT

The present disclosure relates to a compound of formula (I)

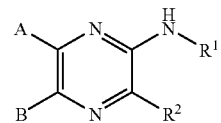

wherein:
A is an optionally substituted monocyclic or polycyclic aryl or heteroaryl group; B is an optionally substituted monocyclic nitrogen-containing heteroaryl group; and either a) $R^1$ and $R^2$ are chosen from a hydrogen atom and specified substituents, or b) $R^2$, $R^1$ and the —NH— group to which $R^1$ is attached, form a moiety chosen from the moiety of formulae (IIa) and (IIb):

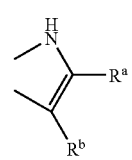

(IIa)

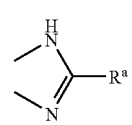

(IIb)

or a pharmaceutically acceptable salt thereof, or a N-oxide thereof. The present disclosure also relates to a method for treating a subject afflicted with a pathological condition or disease susceptible to amelioration by antagonism of the $A_{2B}$ adenosine receptor.

21 Claims, 6 Drawing Sheets

U.S. PATENT DOCUMENTS

| | | | |
|---|---|---|---|
| 6,750,232 | B2 | 6/2004 | Harada et al. |
| 6,841,549 | B1 | 1/2005 | Asano et al. |
| 7,396,836 | B2 | 7/2008 | Harada et al. |
| 2003/0229106 | A1 | 12/2003 | Kalla et al. |
| 2004/0006082 | A1 | 1/2004 | Harada et al. |
| 2004/0176399 | A1 | 9/2004 | Elzein et al. |
| 2005/0004149 | A1 | 1/2005 | Harada et al. |
| 2007/0265273 | A1 | 11/2007 | Vidal Juan et al. |
| 2008/0275038 | A1 | 11/2008 | Vidal Juan et al. |
| 2009/0023763 | A1 | 1/2009 | Vidal Juan et al. |
| 2009/0030023 | A1 | 1/2009 | Harada et al. |

FOREIGN PATENT DOCUMENTS

| | | |
|---|---|---|
| WO | WO 03/057689 | 7/2003 |
| WO | WO 03/063800 | 8/2003 |
| WO | WO 03/068773 | 8/2003 |
| WO | WO 03/082191 | 10/2003 |
| WO | WO 03/105666 | 12/2003 |
| WO | WO 2004/022540 | 3/2004 |
| WO | WO 2004/030635 | 4/2004 |
| WO | WO 2004/076450 | 9/2004 |
| WO | WO 2004/106337 | 12/2004 |
| WO | WO 2005/021548 | 3/2005 |
| WO | WO 2005/033085 | 4/2005 |
| WO | WO 2005/040151 | 5/2005 |
| WO | WO 2005/040155 | 5/2005 |
| WO | WO 2005/042534 | 5/2005 |
| WO | WO 2005/070926 | 8/2005 |
| WO | WO 2005/100353 | 10/2005 |
| WO | WO 2007/039297 | 4/2007 |
| WO | WO 2008/080461 A1 | 7/2008 |

OTHER PUBLICATIONS

Ried, et al. Chemiker-Zeitung, 1988, 112(12), 385.*

Bondavalli, F. et al., "3-5-diphenyl-1H-pyrazole derivatives IX. 2-substituted 4-phenyl-5-(3,5-diphenyl-1H-pyrazol-1-yl) pyrimidines with platelet antiaggregating and other activities," *II Farmaco*, 47(2):171-190 (1992).

Cacciari, B. et al., "A2B adenosine receptor antagonists: recent developments," *Mini-Reviews in Medicinal Chemistry*, 5:1053-1060 (2005).

Feoktistov, I. et al. "Adenosine A2B Receptors," *Pharmacological Reviews*, 49(4): 381-402 (1997).

Fischer, GW et al., "Tetrazole compounds. 8[1]. Synthesis of tetrazolylpyrimidines from tetrazolyl-substituted enamino ketones," *J. Heterocyclic Chem.*, 30:1517-1519 (1993).

Haskö, G. et al., "Adenosine: an endogenous regulator of innate immunity," *Trends in Immunology*, 25(1):33-51 (2004).

Haskö, G et al., "Adenosine receptors: therapeutic aspects for inflammatory and immune diseases," *Nature* Reviews, 7:759-770 (2008).

Holgate, ST, "The identification of the adenosine A2B receptor as a novel therapeutic target in asthma," *British Journal of Pharmacology*, 145:1009-1015 (2005).

International Search Report for Application No. PCT/EP2005/003818 dated Jul. 21, 2005.

International Search Report for PCT/EP2004/010664 dated Dec. 27, 2004.

International Search Report for PCT/EP2006/009620 dated Sep. 1, 2007.

Jacobson, KA et al, "Adenosine receptors as therapeutic targets," *Nature Reviews*, 5:247-264 (2006).

Office Action dated Mar. 30, 2009 for Co-pending U.S. Appl. No. 10/574,101.

Office Action dated Oct. 6, 2008 for Co-pending U.S. Appl. No. 10/574,101.

Palanki, MSS et al., "Structure-activity relationship studies of ethyl 2-[(3-methyl-2,5,dioxo(3-pyrrolinyl)amino]-4-(trifluoromethyl)pyrimidine-5-carboxylate: An inhibitor of AP-1 and KF-kB Mediated Gene Expression," *Bioorganic & Medicinal Chemistry Letters*, 12:2573-2577 (2002).

Polosa, R., "Adenosine-receptor subtypes: their relevance to adenosine-medicated responses in asthma and chronic obstructive pulmonary disease," *Eur Respir J.*, 20:488-496 (2002).

Schurreit, T. "4-Hydroxy-2H-[1]benzopyran-2on als Baustein zur Synthese von Bisbenzopyranopyridinen," *Archiv der Pharmazie* (1987) 320:500-506. (English Abstract).

Sitkovsky et al. "Adenosine A2A Receptor Antagonists: Blockade of Adenosinergic Effects and T Regulatory Cells," *British Journal of Pharmacology* (2008) 153:5457-5464.

Wilson, CN, "Adenosine receptors and asthma in humans," *British Journal of Pharmacology*, 155:475-486 (2008).

Gao et al., Expert Opin. Emerging Drugs (2008) 12(3) 479-492.

Peart, Jason N. et al., "Adenosinergic cardioprtection: multiple receptors, multiple pathways," Pharmacology & Therapeutics, 114:208-221 (2007).

Zablocki, J. et al., "A2B adenosine receptor antagonists and their potential indications," *Expert Opinion Ther. Patents*, 16(10): 1347-1357 (2006).

International Search Report mailed Nov. 22, 2006, for International Application No. PCT/EP2006/007318 (WO 2007/017096 Al).

Caplus English Abstract of journal article by Tarkhov, L.I. et al. Accession No. 2005:630607 (2005).

AL-Masoudi, N.A.L. et al. "Nucleosides LIII* Syntheses and Reactions of 6,7-Dipyridyllumazine and 2'- Deoxylumazine N-1 Nucleosides," *Pteridines*, 4(3): 119-125 (1993).

Rusinov, L.V. et al. "Synthesis and Antiviral Activity of 2-Amino-3-Ethoxycarbonylpyrazine Derivatives," *Pharmaceutical Chemistry Journal*, 39(12): 630-635 (2005).

Barnes, PJ, "Theophylline New Perspectives for an Old Drug," American Journal of Respiratory and Critical Care Medicine, 167: 813-818 (2003).

Caplus English Abstract of journal article by Tarkhov, L.I. et al. CAS Registry No. 875932-62-0 (2009).

Fozard, JR et al. "Adenosine receptor ligands as potential therapeutics in asthma," Current Opinion in Investigational Drugs, 3(1): 69-77 (2002).

International Search Report mailed Mar. 3, 2008, for International Application No. PCT/EP2007/010162 (WO 2008/080461 Al).

Lappas, CM et al. "Adenosine A2A agonists in development for the treatment of inflammation," Expert Opinion Investig. Drugs, 14(7): 797-806 (2005).

Notice of Allowance dated Aug. 28, 2009 for U.S. Appl. No. 10/574,101.

Tarkhov, LI et al. "Photoluminescence of some indolylpyrazines," Materialovedenie, (4): 16-22 (2005).

U.S. Appl. No. 12/521,133, filed Jun. 25, 2009, Aiguade Bosch et al.

* cited by examiner

PYRAZINE DERIVATIVES USEFUL AS ADENOSINE RECEPTOR ANTAGONISTS

This application is a national stage filing under 35 U.S.C. §371 of International Application No. PCT/EP2006/007318 filed on 25 Jul. 2006, the contents of which are incorporated herein by reference. This application claims priority of Spanish Patent Application No. P200501876, filed on 29 Jul. 2005.

The present invention relates to new antagonists of the $A_{2B}$ adenosine receptor. These compounds are useful in the treatment, prevention or suppression of diseases and disorders known to be susceptible to improvement by antagonism of the $A_{2B}$ adenosine receptor, such as asthma, chronic obstructive pulmonary disorder, pulmonary fibrosis, emphysema, allergic diseases, inflammation, reperfusion injury, myocardial ischemia, atherosclerosis, hypertension, retinopathy, diabetes mellitus, inflammatory gastrointestinal tract disorders, and/or autoimmune diseases.

Adenosine regulates several physiological functions through specific cell membrane receptors, which are members of the G-protein coupled receptor family. Four distinct adenosine receptors have been identified and classified: $A_1$, $A_{2A}$, $A_{2B}$ and $A_3$.

The $A_{2B}$ adenosine receptor subtype (see Feoktistov, I., Biaggioni, I. Pharmacol. Rev. 1997, 49, 381-402) has been identified in a variety of human and murine tissues and is involved in the regulation of vascular tone, smooth muscle growth, angiogenesis, hepatic glucose production, bowel movement, intestinal secretion, and mast cell degranulation.

In view of the physiological effects mediated by adenosine receptor activation, several $A_{2B}$ receptor antagonists have been recently disclosed for the treatment or prevention of, asthma, bronchoconstriction, allergic diseases, hypertension, atherosclerosis, reperfusion injury, myocardial ischemia, retinopathy, inflammation, gastrointestinal tract disorders, cell proliferation diseases and/or diabetes mellitus. See for example WO03/063800, WO03/042214, WO 03/035639, WO02/42298, EP 1283056, WO 01/16134, WO 01/02400, WO01/60350 or WO 00/73307.

It has now been found that certain pyrazine derivatives are novel potent antagonists of the $A_{2B}$ adenosine receptor and can therefore be used in the treatment or prevention of these diseases.

Further objectives of the present invention are to provide a method for preparing said compounds; pharmaceutical compositions comprising an effective amount of said compounds; the use of the compounds in the manufacture of a medicament for the treatment of pathological conditions or diseases susceptible to improvement by antagonism of the $A_{2B}$ adenosine receptor; and methods of treatment of pathological conditions or diseases susceptible to amelioration by antagonism of the $A_{2B}$ adenosine receptor comprising the administration of the compounds of the invention to a subject in need of treatment.

Thus, the present invention is directed to new pyrazine derivatives of formula (I)

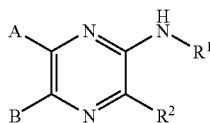

wherein:

A represents a monocyclic or polycyclic aryl or heteroaryl group optionally substituted by one or more substituents independently selected from the group comprising halogen atoms, $C_{1-4}$alkyl, $C_{3-8}$cycloalkyl, $C_{3-8}$cycloalkyl-$C_{1-4}$alkyl, $C_{1-4}$alkoxy, aryl-$C_{1-4}$alkoxy, $C_{1-4}$alkylthio, mono or di-$C_{1-4}$alkylamino, trifluoromethyl, hydroxy and cyano groups;

B represents a monocyclic nitrogen-containing heteroaryl group optionally substituted by one or more substituents independently selected from the group comprising halogen atoms, $C_{1-4}$alkyl, $C_{3-8}$cycloalkyl, $C_{3-8}$cycloalkyl-$C_{1-4}$alkyl, aryl, $C_{1-4}$alkylthio, mono or di-$C_{1-4}$alkylamino, trifluoromethyl and cyano groups;

and either a) $R^1$ represents a group of formula:

-L-(CR'R")$_n$-G 

wherein L represents a linking group selected from the group consisting of direct bond, —(CO)—, —(CO)O—, —(CO)NR'—, —SO$_2$— and —SO$_2$NR'—;

R' and R" are independently selected from the groups consisting of hydrogen atoms and $C_{1-4}$alkyl groups n is an integer from 0 to 6; and G is selected from the group consisting of hydrogen atom and $C_{1-4}$alkyl, aryl, heteroaryl, $C_{3-8}$cycloalkyl and saturated or unsaturated heterocyclic groups, wherein the alkyl, $C_{3-8}$cycloalkyl, aryl or heteroaryl groups are unsubstituted or substituted with one or more substituents selected from halogen atoms, $C_{1-4}$alkyl, $C_{1-4}$alkoxy, $C_{1-4}$alkylthio, mono or di-$C_{1-4}$alkylamino, trifluoromethyl, trifluoromethoxy, carbamoyl, carboxy and cyano groups;

and $R^2$ represents a group selected from hydrogen atoms, halogen atoms and $C_{1-4}$alkyl, $C_{2-5}$alkenyl, $C_{2-5}$alkynyl, $C_{1-4}$alkoxy, $C_{1-4}$alkylthio, mono or di-$C_{1-4}$alkylamino, $C_{1-4}$alkoxy-(CO)—, —NH$_2$, mono or di-$C_{1-4}$alkylamino-(CO)— and cyano groups wherein the alkyl, alkenyl and alkynyl groups may be unsubstituted or substituted by one aryl or heteroaryl group or b) $R^2$, $R^1$ and the —NH— group to which $R^1$ is attached, form a moiety selected from the moiety of formulae (IIa) and (IIb):

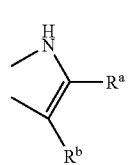

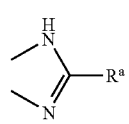

wherein:

$R^a$ is selected from hydrogen atom, halogen atoms, —OH, —NH$_2$ or groups selected from $C_{1-4}$alkyl, $C_{3-8}$cycloalkyl, $C_{3-8}$cycloalkylC$_{1-4}$alkyl, aryl, aryl-$C_{1-4}$alkyl, heteroaryl, heteroaryl-$C_{1-4}$alkyl, saturated heterocyclic rings, $C_{1-4}$alkoxy and $C_{1-4}$alkylthio; wherein the aryl or heteroaryl moieties are unsubstituted or substituted with one or more groups selected from halogen atoms, $C_{1-4}$alkyl, $C_{1-4}$alkylthio, $C_{1-4}$alkoxy, mono or di-$C_{1-4}$ alkylamino, cyano, trifluoromethyl, trifluoromethoxy, carbamoyl and carboxy;

$R^b$ is selected from hydrogen, halogen atoms and groups selected from $C_{1-4}$alkyl, $C_{1-4}$alkylamino, aryl$C_{1-4}$alkylamino and —$NH_2$;

and the pharmaceutically acceptable salts and N-oxides thereof; with the proviso that the compound is not selected from N-[6-(1-methyl-1H-indol-3-yl)-5-pyridin-2-ylpyrazin-2-yl]benzamide, N-[3-ethoxycarbonyl-6-(1-methyl-1H-indol-3-yl)-5-pyridin-2-yl-pyrazin-2-yl]-benzamide and N-[3-ethoxycarbonyl-6-(1-methyl-1H-indol-3-yl)-5-pyridin-2-yl-pyrazin-2-yl]-formamide.

As used herein the terms alkyl or lower alkyl embraces optionally substituted, linear or branched hydrocarbon radicals having 1 to 8, preferably 1 to 6 and more preferably 1 to 4 carbon atoms. Preferred substituents on the alkyl groups are halogen atoms and hydroxy groups.

Examples include methyl, ethyl, n-propyl, i-propyl, n-butyl, sec-butyl and tert-butyl, n-pentyl, 1-methylbutyl, 2-methylbutyl, isopentyl, 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 2-methylpentyl, 3-methylpentyl and iso-hexyl radicals.

As used herein the term alkynyl embraces optionally substituted, linear or branched radicals having 2 to 8, preferably 2 to 6 and more preferably 2 to 4 carbon atoms which contain 1 or 2, preferably 1 triple bond. The alkynyl groups are preferably unsubstituted or substituted by halogen atoms.

Examples include ethynyl, propyn-1-yl, propyn-2-yl, butyn-1-yl, butyn-2-yl, butyn-3-yl and 1-methyl-propyn-2-yl.

As used herein, the term cycloalkyl embraces saturated carbocyclic radicals and, unless otherwise specified, a cycloalkyl radical typically has from 3 to 7 carbon atoms.

Examples include cyclopropyl, cyclobutyl, cyclopentyl, cyclohexyl and cycloheptyl. When a cycloalkyl radical carries 2 or more substituents, the substituents may be the same or different. Preferred substituents on the cycloalkyl groups are halogen atoms and hydroxy groups.

As used herein, unless otherwise provided, the term aryl radical embraces typically a $C_5$-$C_{14}$ monocyclic or polycyclic aryl radical such as phenyl or naphthyl, anthranyl or phenanthryl. Optionally substituted phenyl is preferred. When an aryl radical carries 2 or more substituents, the substituents may be the same or different. Preferred substituents on the aryl radicals are halogen atoms and groups selected from —$OR^3$, —$SR^3$, —$R^3$, and —$NHR^3$. Halogen atoms are particularly preferred.

As used herein, unless otherwise provided, the term heteroaryl radical embraces typically a 5- to 14-membered ring system comprising at least one heteroaromatic ring and containing at least one heteroatom selected from O, S and N. A heteroaryl radical may be a single ring or two or more fused rings wherein at least one ring contains a heteroatom.

Examples of monocyclic heteroaryl radicals include pyridyl, pyrazinyl, pyrimidinyl, pyridazinyl, furyl, oxadiazolyl, oxazolyl, imidazolyl, thiazolyl, thiadiazolyl, thienyl, pyrrolyl, pyridinyl, triazolyl, imidazolidinyl and pyrazolyl radicals. Pyridyl, thienyl, furyl, pyridazinyl and pyrimidinyl radicals are preferred.

When a heteroaryl radical carries 2 or more substituents, the substituents may be the same or different. Preferred substituents on the heteroaryl radicals are halogen atoms and groups selected from —$OR^3$, —$SR^3$, —$R^3$, and —$NHR^3$.

As used herein, the term heterocyclic group embraces typically an heteroaromatic or non-aromatic, saturated or unsaturated $C_3$-$C_{10}$ carbocyclic ring, such as a 5, 6 or 7 membered radical, in which one or more, for example 1, 2, 3 or 4 of the carbon atoms, preferably 1 or 2, of the carbon atoms are replaced by a heteroatom selected from N, O and S. Non-saturated heterocyclyl radicals are preferred. A heterocyclic radical may be a single ring or two or more fused rings wherein at least one ring contains a heteroatom. When a heterocyclyl radical carries 2 or more substituents, the substituents may be the same or different.

Examples of monocyclic, nitrogen-containing heterocyclic radicals include pyridyl, pyrazinyl, pyrimidinyl, pyridazinyl, oxadiazolyl, oxazolyl, imidazolyl, thiazolyl, thiadiazolyl, pyrrolyl, pyridinyl, triazolyl, imidazolidinyl, pyrazolyl, piperidyl, pyrrolidyl, pyrrolinyl, piperazinyl, morpholinyl, thiomorpholinyl, pyrrolyl, pyrazolinyl, pirazolidinyl, quinuclidinyl, pyrazolyl, tetrazolyl, imidazolidinyl, imidazolyl, and 3-aza-tetrahydrofuranyl. Pyridyl, pyrimidinyl, pirazinyl and pyridazinyl are preferred radicals.

Where a heterocyclyl radical carries 2 or more substituents, the substituents may be the same or different. Preferred substituents on the aryl radicals are halogen atoms and group selected from —$OR^3$, —$SR^3$, —$R^3$, and —$NHR^3$. Halogen atoms are particularly preferred.

As used herein, some of the atoms, radicals, moieties, chains or cycles present in the general structures of the invention are "optionally substituted". This means that these atoms, radicals, moieties, chains or cycles can be either unsubstituted or substituted in any position by one or more, for example 1, 2, 3 or 4, substituents, whereby the hydrogen atoms bound to the unsubstituted atoms, radicals, moieties, chains or cycles are replaced by chemically acceptable atoms, radicals, moieties, chains or cycles. When two or more substituents are present, each substituent may be the same or different.

As used herein, the term halogen atom embraces chlorine, fluorine, bromine or iodine atoms typically a fluorine, chlorine or bromine atom, most preferably chlorine or fluorine. The term halo when used as a prefix has the same meaning.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic, cyclohexylsulfamic (cyclamic) or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the invention are quaternary ammonium compounds wherein an equivalent of an anion (X—) is associated with the positive charge of the N atom. X— may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X— is preferably an anion selected from chloride, bromide, iodide, sulphate, nitrate, acetate, maleate, oxalate, succinate or trifluoroacetate. More preferably X— is chloride, bromide, trifluoroacetate or methanesulphonate.

As used herein, an N-oxide is formed from the tertiary basic amines or imines present in the molecule, using a convenient oxidising agent.

In one embodiment the present invention is also directed to new pyrazine derivatives of formula (I):

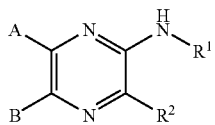

wherein:

A represents a monocyclic or polycyclic aryl or heteroaryl group optionally substituted by one or more substituents independently selected from the group comprising halogen atoms, $C_{1-4}$alkyl, $C_{3-8}$cycloalkyl, $C_{3-8}$cycloalkyl-$C_{1-4}$alkyl, $C_{1-4}$alkoxy, aryl-$C_{1-4}$alkoxy, $C_{1-4}$alkylthio, mono or di-$C_{1-4}$ alkylamino, trifluoromethyl, hydroxy, and cyano groups;

B represents a monocyclic nitrogen-containing heteroaryl group optionally substituted by one or more substituents independently selected from the group comprising halogen atoms, $C_{1-4}$alkyl, $C_{3-8}$cycloalkyl, $C_{3-8}$cycloalkyl-$C_{1-4}$alkyl, aryl, $C_{1-4}$alkylthio, mono or di-$C_{1-4}$alkylamino, trifluoromethyl and cyano groups;

and either a) $R^1$ represents a group of formula:

-L-(CR'R")$_n$-G wherein L represents a linking group selected from the group consisting of direct bond, —(CO)—, —(CO)O—, —(CO)NR'—, —SO$_2$— and —SO$_2$NR'—;

R' and R" are independently selected from the groups consisting of hydrogen atoms and $C_{1-4}$alkyl groups n is an integer from 0 to 6; and G is selected from the group consisting of hydrogen atom and $C_{1-4}$alkyl, aryl, heteroaryl, $C_{3-8}$cycloalkyl and saturated or unsaturated heterocyclic groups, wherein the aryl or heteroaryl groups are unsubstituted or substituted with one or more substituents selected from halogen atoms, $C_{1-4}$alkyl, $C_{1-4}$alkoxy, $C_{1-4}$alkylthio, mono or di-$C_{1-4}$alkylamino, trifluoromethyl and cyano groups;

and $R^2$ represents a group selected from hydrogen atoms, halogen atoms and $C_{1-4}$alkyl, $C_{1-5}$alkenyl, $C_{1-5}$alkynyl, $C_{1-4}$alkoxy, $C_{1-4}$alkylthio, mono or di-$C_{1-4}$alkylamino, $C_{1-4}$alkoxy-(CO)—, mono or di-$C_{1-4}$alkylamino-(CO)— and cyano groups wherein the alkyl, alkenyl and alkynyl groups may be unsubstituted or substituted by one aryl or heteroaryl group or b) $R^2$, $R^1$ and the —NH— group to which $R^1$ is attached form a moiety selected from the moiety of formulae (IIa) and (IIb):

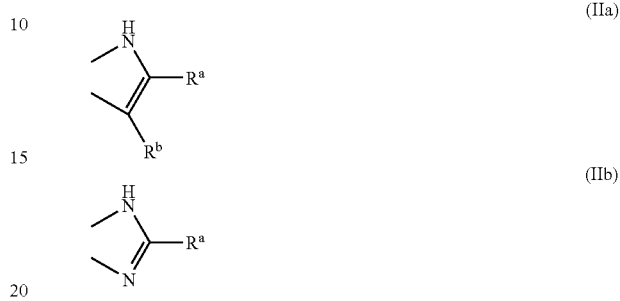

wherein:

$R^a$ is selected from hydrogen atom, halogen atoms, —OH, —NH$_2$ or groups selected from $C_{1-4}$alkyl, $C_{3-8}$cycloalkyl, $C_{3-8}$cycloalkylC$_{1-4}$alkyl, aryl, aryl-$C_{1-4}$alkyl, heteroaryl, heteroaryl-$C_{1-4}$alkyl, saturated heterocyclic rings, $C_{1-4}$alkoxy and $C_{1-4}$alkylthio; wherein the aryl or heteroaryl moieties are unsubstituted or substituted with one or more groups selected from halogen atoms, $C_{1-4}$alkyl, $C_{1-4}$alkylthio, $C_{1-4}$alkoxy, mono or di-$C_{1-4}$ alkylamino, cyano and trifluoromethyl;

$R^b$ is selected from hydrogen, halogen atoms and groups selected from $C_{1-4}$alkyl, $C_{1-4}$alkylamino, arylC$_{1-4}$alkylamino and —NH$_2$;

and the pharmaceutically acceptable salts and N-oxides thereof, with the proviso that the compound is not selected from N-[6-(1-methyl-1H-indol-3-yl)-5-pyridin-2-ylpyrazin-2-yl]benzamide, N-[3-ethoxycarbonyl-6-(1-methyl-1H-indol-3-yl)-5-pyridin-2-yl-pyrazin-2-yl]-benzamide and N-[3-ethoxycarbonyl-6-(1-methyl-1H-indol-3-yl)-5-pyridin-2-yl-pyrazin-2-yl]-formamide.

In one embodiment of the present invention the group G is selected from the group consisting of hydrogen atom and $C_{1-4}$alkyl, aryl, $C_{3-8}$cycloalkyl and saturated or unsaturated non-aromatic heterocyclic groups, wherein the aryl groups are unsubstituted or substituted with one or more substituents selected from halogen atoms, $C_{1-4}$alkyl, $C_{1-4}$alkoxy, $C_{1-4}$alkylthio, mono or di-$C_{1-4}$alkylamino, trifluoromethyl and cyano groups;

Preferred compounds of the invention are those wherein A represents an optionally substituted monocyclic five or six-membered heterocyclic ring or an optionally substituted phenyl ring. More preferably A represents an optionally substituted pyridine, oxazol, furan, pyrazol, pyrazine or phenyl group; still more preferably A represents an optionally substituted pyridine, oxazol, furan or pyrazol group. More preferably A represents a pyridine ring which is either unsubstituted or substituted with alkoxy group or halogen atom, still more preferably A represents a pyridine ring which is either unsubstituted or substituted with halogen atom. Yet still preferably A represents a pyridine ring unsubstituted or substituted with one or two halogen atoms; more preferably A represents a pyridine ring unsubstituted or substituted with one halogen atom.

In another embodiment of the present invention the group B represents an optionally substituted monocyclic, five or six-membered heterocyclic ring having one or two nitrogen atoms. More preferably B represents an optionally substituted pyridine or pyrimidine group. Still more preferably B represents a pyridine ring either unsubstituted or substituted with one or two halogen atoms; more preferably B represents a pyridine ring either unsubstituted or substituted with one halogen atom.

In an alternative embodiment of the present invention $R^1$ represents a group of formula:

-L-(CR'R")$_n$-G wherein L represents a direct bond or a group —(CO)—,
R' and R" are independently selected from the groups consisting of hydrogen atom and methyl groups
n is an integer from 0 to 6; and G is selected from the group consisting of hydrogen atom, $C_{1-4}$alkyl, $C_{3-8}$cycloalkyl, aryl or heteroaryl groups wherein the $C_{1-4}$alkyl, $C_{3-8}$cycloalkyl aryl or heteroaryl groups are unsubstituted or substituted with one or more substituents selected from halogen atoms.

In a further alternative embodiment of the present invention G is selected from the group consisting of hydrogen atom, $C_{1-4}$alkyl, $C_{3-8}$cycloalkyl, aryl or heteroaryl groups wherein the aryl or heteroaryl groups are unsubstituted or substituted with one or more substituents selected from halogen atoms.

More preferably $R^1$ represents a group of formula:

-L-(CR'R")$_n$-G wherein L represents a group —(CO)—,
R' and R" are independently selected from the groups consisting of hydrogen atom and methyl groups
n is an integer from 0 to 6; and
G is selected from the group consisting of hydrogen atom and $C_{3-8}$cycloalkyl groups.

Still more preferably $R^1$ represents a group of formula:

-L-(CR'R")$_n$-G wherein L represents a group —(CO)—,
R' and R" are independently selected from the groups consisting of hydrogen atom and methyl groups
n is an integer from 0 to 3; and
G represents a $C_{3-8}$cycloalkyl group substituted with one or more substituents selected from halogen atoms.

In still another embodiment of the present invention $R^2$ represents a hydrogen atom.

In still another embodiment of the present invention $R^2$, $R^1$ and the —NH— group to which $R^1$ is attached form a moiety of formula (IIa) or (IIb):

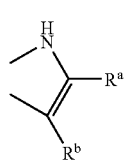

(IIa)

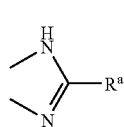

(IIb)

wherein:
$R^a$ is selected from $C_{3-8}$cycloalkyl, saturated heterocyclic ring, aryl and heteroaryl groups; wherein the aryl or heteroaryl moieties are unsubstituted or substituted with one or more halogen atoms; and
$R^b$ represents a hydrogen atom.

In still another embodiment of the present invention $R^2$, $R^1$ and the —NH— group to which $R^1$ is attached form a moeity of formula (IIb):

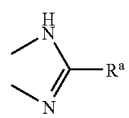

(IIb)

wherein:
$R^1$ is selected from $C_{3-8}$cycloalkyl, saturated heterocyclic ring, aryl and heteroaryl groups; wherein the aryl or heteroaryl moieties are unsubstituted or substituted with one or more halogen atoms.

Particular individual compounds of the invention for their use in the manufacture of a medicament for the treatment of a pathological condition or disease susceptible to improvement by antagonism of the $A_{2B}$ adenosine receptor include:

6-(3-Fluorophenyl)-5-pyridin-4-ylpyrazin-2-amine
5-(3-Chloropyridin-4-yl)-6-(3-fluorophenyl)pyrazin-2-amine
6-(3-Fluorophenyl)-5-(3-fluoropyridin-4-yl)pyrazin-2-amine
6-(3-Fluorophenyl)-5-(1,3-thiazol-5-yl)pyrazin-2-amine
6-(2-Furyl)-5-pyridin-4-ylpyrazin-2-amine
6-(2-Furyl)-5-[2-(methylthio)pyrimidin-4-yl]pyrazin-2-amine
5-Pyridin-4-yl-6-(2-thienyl)pyrazin-2-amine
6-(2-Furyl)-5-pyrimidin-4-ylpyrazin-2-amine
6-(2-Furyl)-5-(2-methylpyrimidin-4-yl)pyrazin-2-amine
5-(2-Cyclopropylpyrimidin-4-yl)-6-(2-furyl)pyrazin-2-amine
6-(2-Furyl)-5-(2-phenylpyrimidin-4-yl)pyrazin-2-amine
6-Pyridin-2-yl-5-pyridin-4-ylpyrazin-2-amine
6-Pyridin-3-yl-5-pyridin-4-ylpyrazin-2-amine
5,6-Dipyridin-4-ylpyrazin-2-amine
N-[6-(5-Methyl-2-furyl)-5-pyridin-4-ylpyrazin-2-yl]cyclopropanecarboxamide
6-(2-Fluorophenyl)-5-pyridin-4-ylpyrazin-2-amine
N-[6-(3-Fluoropyridin-4-yl)-5-pyridin-4-ylpyrazin-2-yl]cyclopropanecarboxamide
N-[6-(3-Chloropyridin-4-yl)-5-pyridin-4-ylpyrazin-2-yl]cyclopropanecarboxamide
N-[6-(1,3-Oxazol-5-yl)-5-pyridin-4-ylpyrazin-2-yl]cyclopropanecarboxamide
N-[6-(1,3-Oxazol-2-yl)-5-pyridin-4-ylpyrazin-2-yl]cyclopropanecarboxamide
N-[5-(3-Chloropyridin-4-yl)-6-pyridin-3-ylpyrazin-2-yl]cyclopropanecarboxamide
N-[5-(3-Chloropyridin-4-yl)-6-pyridin-2-ylpyrazin-2-yl]cyclopropanecarboxamide
N-[5-(3-Chloropyridin-4-yl)-6-pyridin-4-ylpyrazin-2-yl]cyclopropanecarboxamide
N-[5-(3-Chloropyridin-4-yl)-6-pyridin-3-ylpyrazin-2-yl]-2,2-dimethylpropanamide
N-[5-(3-Fluoropyridin-4-yl)-6-pyridin-3-ylpyrazin-2-yl]cyclopropanecarboxamide
N-[5-(3-Fluoropyridin-4-yl)-6-pyridin-4-ylpyrazin-2-yl]cyclopropanecarboxamide
6-(3-Fluorophenyl)-N-pyridin-3-yl-5-pyridin-4-ylpyrazin-2-amine N-[6-(3-Fluorophenyl)-5-pyridin-4-ylpyrazin-2-yl]pyrimidin-5-amine
N-[6-(3-Fluorophenyl)-5-pyridin-4-ylpyrazin-2-yl]acetamide
N-[6-(3-Fluorophenyl)-5-pyridin-4-ylpyrazin-2-yl]cyclopropanecarboxamide
6-(2-Furyl)-N-pyridin-3-yl-5-pyridin-4-ylpyrazin-2-amine
N-[6-(2-Furyl)-5-pyridin-4-ylpyrazin-2-yl]pyrimidin-5-amine
N-[6-(2-Furyl)-5-pyridin-4-ylpyrazin-2-yl]acetamide
N-[6-(2-Furyl)-5-pyridin-4-ylpyrazin-2-yl]propanamide
N-[6-(2-Furyl)-5-pyridin-4-ylpyrazin-2-yl]cyclopropanecarboxamide
N-[6-(2-Furyl)-5-pyridin-4-ylpyrazin-2-yl]cyclobutanecarboxamide
N-[6-(2-Furyl)-5-pyridin-4-ylpyrazin-2-yl]cyclopentanecarboxamide
N-[6-(2-Furyl)-5-pyridin-4-ylpyrazin-2-yl]-2-methylpropanamide
2-Cyclopentyl-N-[6-(2-furyl)-5-pyridin-4-ylpyrazin-2-yl]acetamide
4-Fluoro-N-[6-(2-furyl)-5-pyridin-4-ylpyrazin-2-yl]benzamide
N-Cyclopentyl-N'-[6-(2-furyl)-5-pyridin-4-ylpyrazin-2-yl]urea
N-{6-(2-Furyl)-5-[2-(methylthio)pyrimidin-4-yl]pyrazin-2-yl}acetamide
N-{6-(2-Furyl)-5-[2-(methylthio)pyrimidin-4-yl]pyrazin-2-yl}cyclopropanecarboxamide
N-[5-Pyridin-4-yl-6-(2-thienyl)pyrazin-2-yl]acetamide
N-[6-(2-Furyl)-5-pyrimidin-4-ylpyrazin-2-yl]acetamide
N-[6-(2-Furyl)-5-pyrimidin-4-ylpyrazin-2-yl]cyclopropanecarboxamide
N-[6-(2-Furyl)-5-(2-methylpyrimidin-4-yl)pyrazin-2-yl]cyclopropanecarboxamide
N-[5-(2-Cyclopropylpyrimidin-4-yl)-6-(2-furyl)pyrazin-2-yl]cyclopropanecarboxamide
N-[6-(2-Furyl)-5-(2-phenylpyrimidin-4-yl)pyrazin-2-yl]acetamide
N-[6-(2-Furyl)-5-(2-phenylpyrimidin-4-yl)pyrazin-2-yl]cyclopropanecarboxamide
N-(6-Pyridin-2-yl-5-pyridin-4-ylpyrazin-2-yl)acetamide
N-(6-Pyridin-2-yl-5-pyridin-4-ylpyrazin-2-yl)cyclopropanecarboxamide
N-Cyclopentyl-N'-(6-pyridin-2-yl-5-pyridin-4-ylpyrazin-2-yl)urea
N-(4-Fluorophenyl)-N'-(6-pyridin-2-yl-5-pyridin-4-ylpyrazin-2-yl)urea
N-(6-Pyridin-3-yl-5-pyridin-4-ylpyrazin-2-yl)cyclopropanecarboxamide
N-(6-Pyridin-3-yl-5-pyridin-4-ylpyrazin-2-yl)cyclobutanecarboxamide
N-Cyclopentyl-N'-(6-pyridin-3-yl-5-pyridin-4-ylpyrazin-2-yl)urea
N-(4-Fluorophenyl)-N'-(6-pyridin-3-yl-5-pyridin-4-ylpyrazin-2-yl)urea
6-Pyridin-3-yl-5-pyridin-4-yl-N-1,3-thiazol-2-ylpyrazin-2-amine
N-(5,6-Dipyridin-4-ylpyrazin-2-yl)cyclopropanecarboxamide
3-Bromo-6-(3-fluorophenyl)-5-pyridin-4-ylpyrazin-2-amine
3-Bromo-6-(2-furyl)-5-pyridin-4-ylpyrazin-2-amine
3-Bromo-6-pyridin-3-yl-5-pyridin-4-ylpyrazin-2-amine
3-Amino-5-(2-furyl)-6-pyridin-4-ylpyrazine-2-carbonitrile
3-Ethynyl-6-(2-furyl)-5-pyridin-4-ylpyrazin-2-amine
6-(2-Furyl)-3-(phenylethynyl)-5-pyridin-4-ylpyrazin-2-amine
6-(2-Furyl)-3-methoxy-5-pyridin-4-ylpyrazin-2-amine
3-Ethyl-6-(2-furyl)-5-pyridin-4-ylpyrazin-2-amine
N-[3-Cyano-6-(2-furyl)-5-pyridin-4-ylpyrazin-2-yl]acetamide
N-[6-(2-Furyl)-3-methoxy-5-pyridin-4-ylpyrazin-2-yl]cyclopropanecarboxamide
N-[3-Ethyl-6-(2-furyl)-5-pyridin-4-ylpyrazin-2-yl]acetamide
5-Phenyl-6-pyridin-4-ylpyrazine-2,3-diamine
5-(3-Fluorophenyl)-6-pyridin-4-ylpyrazine-2,3-diamine
3-Amino-5-(3-fluorophenyl)-6-pyridin-4-ylpyrazin-2-ol
6-(3-Fluorophenyl)-5-pyridin-4-yl-1H-imidazo[4,5-b]pyrazine
6-(3-Fluorophenyl)-2-methyl-5-pyridin-4-yl-1H-imidazo[4,5-b]pyrazine
5-(3-Fluorophenyl)-6-pyridin-4-yl-1,3-dihydro-2H-imidazo[4,5-b]pyrazin-2-one
6-(3-Fluorophenyl)-5-pyridin-4-yl-2-(trifluoromethyl)-1H-imidazo[4,5-b]pyrazine
5-(4-Fluorophenyl)-6-pyridin-4-ylpyrazine-2,3-diamine
5-(3-Methylphenyl)-6-pyridin-4-ylpyrazine-2,3-diamine
5-(2-Fluorophenyl)-6-[2-(methylthio)pyrimidin-4-yl]pyrazine-2,3-diamine
6-(2-Fluorophenyl)-5-[2-(methylthio)pyrimidin-4-yl]-1H-imidazo[4,5-b]pyrazine
5-(3-Chlorophenyl)-6-[2-(methylthio)pyrimidin-4-yl]pyrazine-2,3-diamine
6-(3-Chlorophenyl)-5-[2-(methylthio)pyrimidin-4-yl]-1H-imidazo[4,5-b]pyrazine
5-(3-Fluorophenyl)-6-[2-(methylthio)pyrimidin-4-yl]pyrazine-2,3-diamine
6-(3-Fluorophenyl)-5-[2-(methylthio)pyrimidin-4-yl]-1H-imidazo[4,5-b]pyrazine
5-(2-Furyl)-6-pyridin-4-ylpyrazine-2,3-diamine
3-Amino-5-(2-furyl)-6-pyridin-4-ylpyrazin-2-ol
6-(2-Furyl)-5-pyridin-4-yl-1H-imidazo[4,5-b]pyrazine
2-Cyclopentyl-6-(2-furyl)-5-pyridin-4-yl-1H-imidazo[4,5-b]pyrazine
2,6-Di-2-furyl-5-pyridin-4-yl-1H-imidazo[4,5-b]pyrazine
6-(2-Furyl)-2-pyridin-3-yl-5-pyridin-4-yl-1H-imidazo[4,5-b]pyrazine
6-(2-Furyl)-2,5-dipyridin-4-yl-1H-imidazo[4,5-b]pyrazine
6-(2-Furyl)-2-pyridin-2-yl-5-pyridin-4-yl-1H-imidazo[4,5-b]pyrazine
6-(2-Furyl)-2-pyrazin-2-yl-5-pyridin-4-yl-1H-imidazo[4,5-b]pyrazine
5-(5-Methyl-2-furyl)-6-pyridin-4-ylpyrazine-2,3-diamine
5-(1-Benzofuran-2-yl)-6-pyridin-4-ylpyrazine-2,3-diamine
5-Pyridin-3-yl-6-pyridin-4-ylpyrazine-2,3-diamine
5-Pyridin-3-yl-6-pyridin-4-yl-1,3-dihydro-2H-imidazo[4,5-b]pyrazin-2-one
2-(4-Fluorophenyl)-6-pyridin-3-yl-5-pyridin-4-yl-1H-imidazo[4,5-b]pyrazine
5-(2-Furyl)-6-pyrimidin-4-ylpyrazine-2,3-diamine
3-Amino-5-(2-furyl)-6-pyrimidin-4-ylpyrazin-2-ol
6-(2-Furyl)-5-pyrimidin-4-yl-1H-imidazo[4,5-b]pyrazine
5-(2-Furyl)-6-pyrimidin-4-yl-1,3-dihydro-2H-imidazo[4,5-b]pyrazin-2-one
6-(2-Furyl)-2-pyridin-3-yl-5-pyrimidin-4-yl-1H-imidazo[4,5-b]pyrazine
5-(2-Furyl)-6-[2-(methylthio)pyrimidin-4-yl]pyrazine-2,3-diamine
3-Amino-5-(2-furyl)-6-[2-(methylthio)pyrimidin-4-yl]pyrazin-2-ol
6-(2-Furyl)-5-[2-(methylthio)pyrimidin-4-yl]-1H-imidazo[4,5-b]pyrazine
5-(3-Methyl-2-furyl)-6-pyrimidin-4-ylpyrazine-2,3-diamine 5-[2-(Methylthio)pyrimidin-4-yl]-6-(2-thienyl)pyrazine-2,3-diamine
5-[2-(Methylthio)pyrimidin-4-yl]-6-(2-thienyl)-1H-imidazo[4,5-b]pyrazine
3-(2-Furyl)-2-pyridin-4-yl-5H-pyrrolo[2,3-b]pyrazine
3-(2-Furyl)-6-phenyl-2-pyridin-4-yl-5H-pyrrolo[2,3-b]pyrazine
6-Cyclohexyl-3-(2-furyl)-2-pyridin-4-yl-5H-pyrrolo[2,3-b]pyrazine
5-(3-Fluoropyridin-4-yl)-6-pyridin-3-ylpyrazin-2-amine
5-(3,5-Difluoropyridin-4-yl)-6-pyridin-3-ylpyrazin-2-amine
N-[6-(6-Hydroxypyridin-3-yl)-5-pyridin-4-ylpyrazin-2-yl]cyclopropanecarboxamide
1-Cyclopropyl-3-(6-(pyridin-2-yl)-5-(pyridin-4-yl)pyrazin-2-yl)urea
N-[5-(3-Fluoropyridin-4-yl)-6-(6-methoxypyridin-3-yl)pyrazin-2-yl]cyclopropane carboxamide
N-[5,6-bis(3-Fluoropyridin-4-yl)pyrazin-2-yl]cyclopropanecarboxamide
N-[5-(3-Fluoropyridin-4-yl)-6-quinolin-3-ylpyrazin-2-yl]cyclopropanecarboxamide
N-[5-(3-Fluoropyridin-4-yl)-6-(5-methoxypyridin-3-yl)pyrazin-2-yl]cyclopropanecarboxamide
N-[5-(3-Fluoropyridin-4-yl)-6-(6-hydroxypyridin-3-yl)pyrazin-2-yl]cyclopropane carboxamide
N-[5-(3-Fluoropyridin-4-yl)-6-(1-oxidopyridin-3-yl)pyrazin-2-yl]cyclopropane carboxamide
N-[5-(3-fluoropyridin-4-yl)-6-pyrimidin-5-ylpyrazin-2-yl]cyclopropanecarboxamide
N-[3-(3-fluoropyridin-4-yl)-2,2'-bipyrazin-6-yl]cyclopropanecarboxamide
N-[5-(3-Fluoro-1-oxidopyridin-4-yl)-6-pyridin-3-ylpyrazin-2-yl]cyclopropanecarboxamide
N-[5-(3-fluoropyridin-4-yl)-6-(5-fluoropyridin-2-yl)pyrazin-2-yl]cyclopropane-carboxamide
N-[6-(2-Fluorophenyl)-5-(3-fluoropyridin-4-yl)pyrazin-2-yl]cyclopropane-carboxamide
N-[6-(2,4-Difluorophenyl)-5-(3-fluoropyridin-4-yl)pyrazin-2-yl]cyclopropane-carboxamide
N-[5-(3-Fluoropyridin-4-yl)-6-(1,3-oxazol-2-yl)pyrazin-2-yl]cyclopropane-carboxamide
N-[5-(3-Fluoropyridin-4-yl)-6-pyridin-3-ylpyrazin-2-yl]propanamide
2-Cyclopentyl-N-[5-(3-fluoropyridin-4-yl)-6-pyridin-3-ylpyrazin-2-yl]acetamide
N-[5-(3-Fluoropyridin-4-yl)-6-pyridin-3-ylpyrazin-2-yl]cyclopentanecarboxamide
3,3,3-Trifluoro-N-[5-(3-fluoropyridin-4-yl)-6-pyridin-3-ylpyrazin-2-yl]propanamide
N-[5-(3-Fluoropyridin-4-yl)-6-pyridin-3-ylpyrazin-2-yl]cyclobutanecarboxamide
N-[5-(3-Fluoropyridin-4-yl)-6-pyridin-3-ylpyrazin-2-yl]acetamide
2-Cyclopropyl-N-[5-(3-fluoropyridin-4-yl)-6-pyridin-3-ylpyrazin-2-yl]acetamide
N-[5-(3-Fluoropyridin-4-yl)-6-pyridin-3-ylpyrazin-2-yl]-2-morpholin-4-ylacetamide
N-[5-(3-Fluoropyridin-4-yl)-6-pyridin-3-ylpyrazin-2-yl]-2-methylpropanamide
N-[5-(3-Fluoropyridin-4-yl)-6-pyridin-3-ylpyrazin-2-yl]methanesulfonamide
N-[5-(3,5-Difluoropyridin-4-yl)-6-pyridin-3-ylpyrazin-2-yl]cyclopropane carboxamide
N-[5-(3,5-Difluoropyridin-4-yl)-6-pyridin-4-ylpyrazin-2-yl]cyclopropane carboxamide
N-[5-(3,5-difluoropyridin-4-yl)-6-(1-oxidopyridin-3-yl)pyrazin-2-yl]cyclopropane-carboxamide
N-[5-(3,5-difluoro-1-oxidopyridin-4-yl)-6-pyridin-3-ylpyrazin-2-yl]cyclopropane-carboxamide
N-[6-(3,5-Difluoropyridin-2-yl)-5-(3-fluoropyridin-4-yl)pyrazin-2-yl]cyclopropanecarboxamide
6-(4-Fluorophenyl)-2-(3-fluoropyridin-4-yl)-3-pyridin-3-yl-5H-pyrrolo[2,3-b]pyrazine
2-(3-Fluoropyridin-4-yl)-6-pyridin-2-yl-3-pyridin-3-yl-5H-pyrrolo[2,3-b]pyrazine
2-(3-Fluoropyridin-4-yl)-3,6-dipyridin-3-yl-5H-pyrrolo[2,3-b]pyrazine
4-[2-(3-Fluoropyridin-4-yl)-3-pyridin-3-yl-5H-pyrrolo[2,3-b]pyrazin-6-yl]benzonitrile
4-[2-(3-Fluoropyridin-4-yl)-3-pyridin-3-yl-5H-pyrrolo[2,3-b]pyrazin-6-yl]benzamide
2-(3-Fluoropyridin-4-yl)-3-pyridin-3-yl-5H-pyrrolo[2,3-b]pyrazine
5-(3-Fluoropyridin-4-yl)-6-pyridin-3-ylpyrazine-2,3-diamine
2-(4-Fluorophenyl)-5-(3-fluoropyridin-4-yl)-6-pyridin-3-yl-1H-imidazo[4,5-b]pyrazine
5-(3-Fluoropyridin-4-yl)-6-pyridin-3-yl-2-[4-(trifluoromethoxy)phenyl]-1H-imidazo[4,5-b]pyrazine
2-[1-(4-Chlorophenyl)ethyl]-5-(3-fluoropyridin-4-yl)-6-pyridin-3-yl-1H-imidazo[4,5-b]pyrazine
5-(3-Fluoropyridin-4-yl)-2-(methylthio)-6-pyridin-3-yl-1H-imidazo[4,5-b]pyrazine
5-(3-Fluoropyridin-4-yl)-2-morpholin-4-yl-6-pyridin-3-yl-1H-imidazo[4,5-b]pyrazine
5-(3-Fluoropyridin-4-yl)-6-pyridin-3-yl-N-(2,2,2-trifluoro-1-methylethyl)pyrazin-2-amine
5-(3-Fluoropyridin-4-yl)-6-pyridin-3-yl-N-(2,2,2-trifluoroethyl)pyrazin-2-amine Of outstanding interest are:

6-(3-Fluorophenyl)-5-(3-fluoropyridin-4-yl)pyrazin-2-amine
N-[6-(1,3-Oxazol-5-yl)-5-pyridin-4-ylpyrazin-2-yl]cyclopropanecarboxamide
N-[5-(3-Chloropyridin-4-yl)-6-pyridin-2-ylpyrazin-2-yl]cyclopropanecarboxamide
N-[5-(3-Chloropyridin-4-yl)-6-pyridin-4-ylpyrazin-2-yl]cyclopropanecarboxamide
N-[5-(3-Fluoropyridin-4-yl)-6-pyridin-3-ylpyrazin-2-yl]cyclopropanecarboxamide
N-[5-(3-Fluoropyridin-4-yl)-6-pyridin-4-ylpyrazin-2-yl]cyclopropanecarboxamide
N-(6-Pyridin-2-yl-5-pyridin-4-ylpyrazin-2-yl)cyclopropanecarboxamide
N-(4-Fluorophenyl)-N'-(6-pyridin-2-yl-5-pyridin-4-ylpyrazin-2-yl)urea
N-(6-Pyridin-3-yl-5-pyridin-4-ylpyrazin-2-yl)cyclopropanecarboxamide
6-(2-Furyl)-3-methoxy-5-pyridin-4-ylpyrazin-2-amine
5-(3-Fluorophenyl)-6-pyridin-4-yl-1,3-dihydro-2H-imidazo[4,5-b]pyrazin-2-one
6-(2-Furyl)-5-pyridin-4-yl-1H-imidazo[4,5-b]pyrazine
N-[5-(3-Fluoropyridin-4-yl)-6-(6-methoxypyridin-3-yl)pyrazin-2-yl]cyclopropane carboxamide
N-[3-(3-fluoropyridin-4-yl)-2,2'-bipyrazin-6-yl]cyclopropanecarboxamide
N-[5-(3,5-Difluoropyridin-4-yl)-6-pyridin-3-ylpyrazin-2-yl]cyclopropanecarboxamide
6-(4-Fluorophenyl)-2-(3-fluoropyridin-4-yl)-3-pyridin-3-yl-5H-pyrrolo[2,3-b]pyrazine 2-(3-Fluoropyridin-4-yl)-3,6-dipyridin-3-yl-5H-pyrrolo[2,3-b]pyrazine

Figure 1:
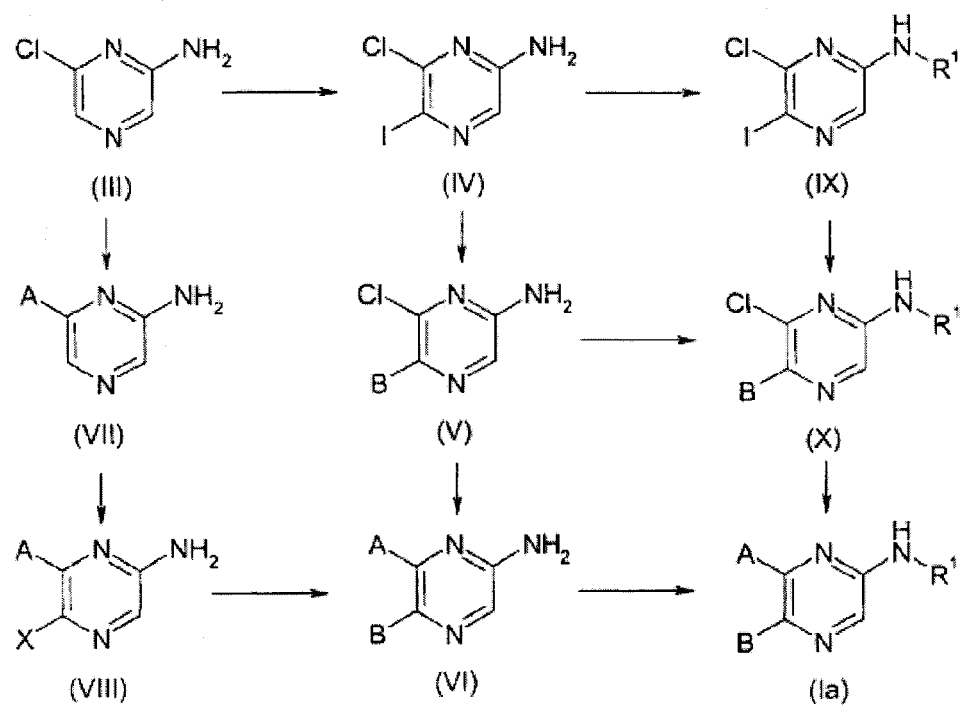
FIG. 1 exemplifies a synthetic scheme used for the preparation of compounds of general formula (I) wherein $R^2$ is hydrogen (general formula 1(a)).

Compounds of general formula (I) and in particular those wherein A, B and $R^1$ are as hereinabove defined and $R^2$ is hydrogen (general formula (Ia)) may be prepared following the synthetic scheme depicted in FIG. 1.

Treatment of 2-amino-6-chloropyrazine (III) with iodinating agents such as N-iodosuccinimide or iodine in polar solvents such as DMO, DMF or water at a temperature in a range of 0° C. to 80° C. provides compounds of general formula (IV). Regioselective Suzuki-type coupling of 2-amino-6-chloro-5-iodopyrazine (IV) using the boronic acid or boronate derivative of B using a palladium catalyst such as tetrakis(triphenylphosphine)palladium(0) or [1,1'-bis(diphenylphosphino)ferrocene]palladium(II)dichloride dichloromethane complex (1:1) in solvents such as toluene or dioxane in the presence of an aqueous solution of a base such as sodium or cesium carbonate and at a temperature between 25° C. to 200° C. provides compounds of general formula (V).

Similarly, Stille-type cross coupling of 2-amino-6-chloro-5-iodopyrazine (IV) using the organotin derivative of B in the presence of palladium catalysts such as tetrakis(triphenylphosphine)palladium (0) in solvents such as xylene or dimethylformamide at a temperature between 25° C. to 200° C. also provides compounds of general formula (V).

Similarly, Negishi-type cross coupling of 2-amino-6-chloro-5-iodopyrazine (IV) using the organozinc derivative of B in the presence of palladium catalysts such as tetrakis (triphenylphosphine)palladium (0) in solvents such as tetrahydrofuran at a temperature between 25° C. to 180° C. also provides compounds of general formula (V).

A further Suzuki, Stille or Negishi-type coupling of the compounds of formula (V) using the corresponding boronic acid, boronate, organotin or organozinc derivative of A under the standard procedures for Pd catalyzed reactions described above provides the 2-aminopyrazines (VI).

In another synthetic pathway, 2-aminopyrazines (VI) can be prepared starting from 2-amino-6-chloropyrazine (III) by Suzuki, Stille or Negishi-type coupling reactions using the corresponding boronic acid, boronate, organotin or organo- nozinc derivative of A under the standard procedures for Pd catalyzed reactions described above to yield the compounds of formula (VII).

Subsequent regioselective bromination or iodination of the compounds of formula (VII) using reagents such as $Br_2$, $I_2$ or N-halosuccinimide in polar aprotic solvents such as DMF and at temperatures ranging from 0° C. to 100° C., yield the compounds of formula (VII). A further Suzuki, Stille or Negishi-type coupling reaction of the compounds of formula (VIII) using the corresponding boronic acid, organotin or organozinc derivative of B under the standard procedures for Pd catalyzed reactions described above provides the compounds of formula (VI).

Compounds of general formula (Ia) wherein $R^1$ represents a group of formula -L-(CR'R")n-G and L represents a linking group selected from —(CO)—, —(CO)O—, —(CO)NR'—, —SO2— and —(SO2)NR'— are prepared by treatment of compounds of formula (VI) with acylating agents such as anhydrides, acid chlorides, acylcarbonates, isocianates, sulfonyl chlorides or sulfamoyl chlorides in apolar organic solvents such as THF or pyridine and in the presence of a convenient organic base (such as triethylamine) or inorganic base at a temperature between 25° C. to 100° C., and eventually acylating with carboxylic acids using coupling agents such as diethylcarbodiimide.

Similarly, compounds of general formula (IV) and (V) may be converted into the compounds of general formula (IX) and (X) respectively using the general coupling procedures described above.

Compound of formula (IX) may be converted into compounds of formula (X) using the procedures described above for converting compounds of formula (IV) into compounds of formula (V).

Similarly, compounds of formula (X) may be converted in compounds of formula (Ia) using the procedures described above for converting compounds of formula (V) into compounds of formula (VI).

Compounds of general formula (Ia) wherein $R^1$ represents a group of formula -L-(CR'R")n-G, L represents a direct bond and G represents an aryl or heteroaryl group may also be prepared by treatment of compounds of general formula (VI) with the corresponding aryl or heteroaryl halides (preferably bromides, iodides or chlorides) The reaction is carried out using the palladium and/or copper catalyzed general methods for the arylation of amines (for references see Yin, J. et al. Org. Lett. 2002, 4(20), 3481 and Buchwald S. L. et al. J. Am. Chem. Soc. 2002, 124, 7421).

Figure 2:
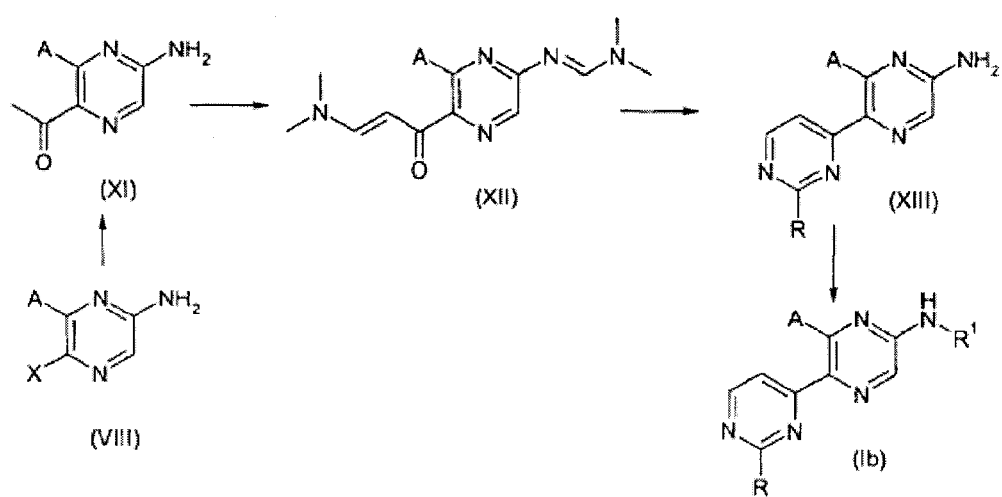
FIG. 2 exemplifies a synthetic scheme used for the preparation of compounds of general formula (I) wherein $R^2$ is hydrogen and B is an optionally substituted pyrimidine ring (general formula 1(b)).

Compounds of general formula (I) and in particular those wherein A and $R^1$ are as hereinabove defined, $R^2$ is hydrogen and B is an optionally substituted pyrimidine ring (general formula (Ib)) may be prepared following the synthetic scheme depicted in FIG. 2.

Treatment of halopyrazines of general formula (VIII) wherein X represents a bromine, chlorine or iodine atom under Heck-type coupling conditions using alkylvinyl ether derivatives such as butyl vinyl ether, palladium catalysts such as palladium (II) acetate, phosphine ligands such as 1,3-bis(diphenylphosphino)propane (DPPP), naphtalene, in solvents such as dimethylformamide in the presence of an aqueous solution of a base such as potassium carbonate and at a temperature between 25° C. to 180° C. provides compounds of general formula (XI). Further treatment with N,N-dimethylformamide diethyl acetal at a temperature between 250° C. to 110° C. provides compounds of general formula (XI).

These products are in turn cyclised to the corresponding pyrimidine derivatives (XIII) by reaction with the corresponding amidines (when $R=C_{1-4}$alkyl, $C_{3-8}$cycloalkyl, $C_{3-8}$cycloalkyl-$C_{1-4}$alkyl, trifluoromethyl, aryl or heteroaryl), imidothiocarbamates (when R is $C_{1-4}$alkylthio) or with guanidines (when R=mono or dialkylamino) in solvents such as ethanol, toluene or mixtures of them at a temperature between 50° C. to 180° C. In general, alkylthiopyrimidines can be converted into diversely substituted pyrimidines by nucleophilic displacement of the alkylthio group or the corresponding sulfone by a convenient nucleophile such as cyanide, mono or dialkylamine or halide. Compounds of general formula (Ib) are prepared using the general procedures described above for the synthesis of compounds (Ia) from compounds (VI).

Figure 3:
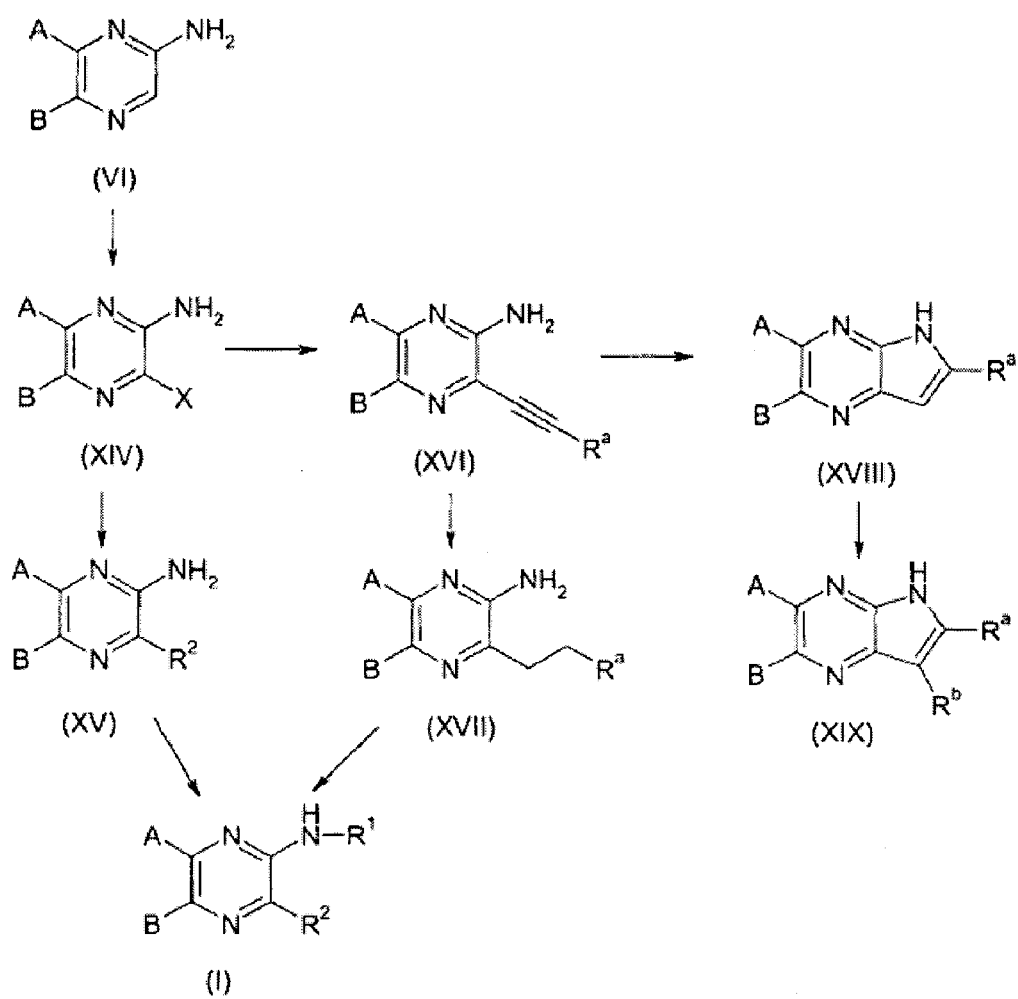
FIG. 3 exemplifies a synthetic scheme used for the preparation of compounds of general formula (I) wherein $R^2$ is not hydrogen.

Compounds of general formula (I) and in particular those wherein A, B and $R^1$ are as hereinabove defined and $R^2$ is not hydrogen may be prepared following the synthetic scheme depicted in FIG. 3.

Compounds of general formula (XIV) are prepared by halogenation of compounds of formula (VI) using reagents such as $Br_2$ or N-halosuccinimide in polar aprotic solvents such as DMF or in mixtures of DMSO-water and at temperatures ranging from 0° C. to 100° C. These compounds correspond to compounds of the invention wherein $R^2$ is a halogen atom.

Compounds of general formula (XV) and in particular those wherein A and B are as hereinabove defined and $R^2$ is $C_{1-4}$alkoxy, $C_{1-4}$alkylthio, mono or di-$C_{1-4}$alkylamino or cyano are prepared from compounds of formula (XIV) by nucleophilic displacement of the halogen by the appropriate alcoxide, thioalkoxide, amine or cyanide in solvents such as DMF, DMSO and at temperatures ranging from 0° C. to 180° C.

Compounds of formula (XV) wherein $R^2$ is a cyano group can be converted into compounds wherein $R^2$ is $C_{1-4}$alkoxy-(CO)— or mono or di-$C_{1-4}$alkylamino-(CO)— by hydrolysis followed by esterification or amidation reactions using the corresponding alcohol or amine respectively.

Compounds of general formula (XV) and in particular those wherein A and B are as hereinabove defined and $R^2$ is $C_{1-4}$alkyl or $C_{2-5}$alkenyl are prepared from compounds of formula (XIV) by carbon-carbon coupling reaction under Stille-type conditions using the general method described above.

Sonogashira-type coupling starting with compounds of formula (XIV) provides the alkynyl derivatives (XVI). Typically Sonogashira coupling takes place in the presence of the alkynyl derivative of Ra in a solvent that is inert to the reaction conditions such as THF, using an organic base, preferably triethylamine, copper (preferably copper (I) iodide) and palladium (such as dichlorobis(triphenylphosphine)palladium (II)) as catalysts. The temperature of the reaction could be from about 70° C. to 150° C.

Alternatively compounds of formula (XVII) wherein $R^2$ is alkyl may be prepared by catalytic hydrogenation of alkynyl derivatives (XVI) using catalysts such as palladium on carbon.

The compounds of formula (XV) and (XVII) are converted into the compounds of formula (I) by treatment with acylating agents such as anhydrides, acid chlorides, acylcarbonates, isocianates, sulfonyl chlorides or sulfamoyl chlorides in apolar organic solvents such as THF or pyridine and in the presence of a convenient organic base (such as triethylamine) or inorganic base at a temperature between 25° C. to 100° C., and eventually acylating with carboxylic acids using coupling agents such as diethylcarbodiimide Compounds of general formula (I) and in particular those of formula (XIX) wherein A and B are as hereinabove defined and $R^2$, $R^1$ and the —NH— group to which $R^1$ is attached form a moiety of formula (IIb), may be prepared by cyclisation of alkynyl derivatives of general formula (XVI) to compounds of formula (XVIII) mediated by the use of a suitable catalyst e.g. copper (preferably copper (I) iodide) or palladium in polar aprotic solvents such as dimethylformamide and at a temperature range of 70° C. to 150° C. to provide compounds of general formula (XVIII).

Another alternative method to promote the cyclisation of (XVI) to (XVIII) consists of the use of a suitable base, for example potassium tert-butoxide, in a polar aprotic solvent such as dimethylformamide or 1-methyl-2-pyrrolidinone at temperatures ranging from 60 to 100° C. Compounds of formula (XVIII) can be halogenated using an electrophilic source of halogen such as NBS, NIS. Further functional group transformations using methods known in the art lead to compounds of general formula (XIX) wherein $R_b$ is alkyl. Alternatively compounds of general formula (XVIII) can be nitrated using $HNO_3$—$H_2SO_4$ and the resulting products can be converted into compounds of formula (XIX) wherein $R_b$ is $C_{1-4}$alkylamino, aryl$C_{1-4}$alkylamino and —$NH_2$ using general methods known in the art.

Figure 4:
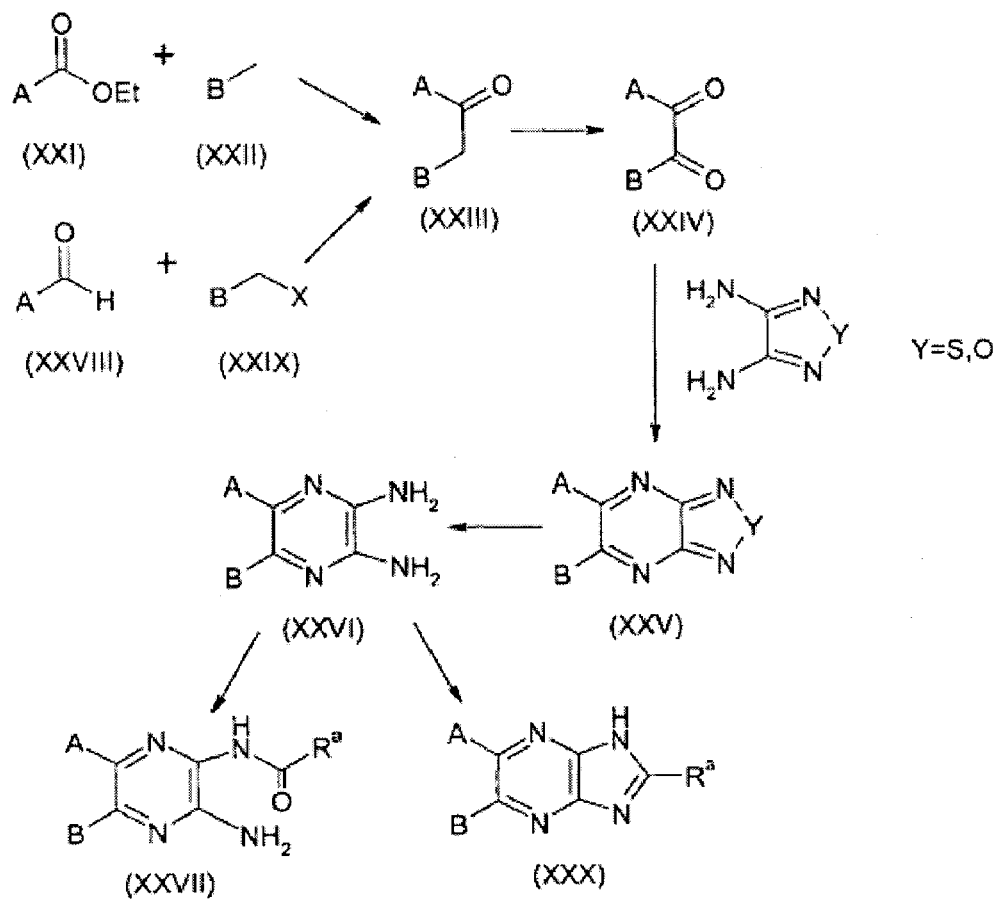
FIG. 4 exemplifies a synthetic scheme used for the preparation of compounds of general formula (I) wherein $R^2$, $R^1$, and the —NH— group to which $R^1$ is attached form a moiety of formula II(a).

Compounds of general formula (I) and in particular those of formula (XXX) wherein A and B are as hereinabove defined and $R^2$, $R^1$ and the —NH— group to which $R^1$ is attached form a moiety of formula (IIa) may be prepared following the synthetic scheme depicted in FIG. 4.

The aldehydes of formula (XXVIII) are reacted with the halomethyl derivatives of formula (XXIX) to yield the ketones of formula (XXIII) either via cyanohydrin intermediates or in a two step process involving addition of an organometallic derivative of (XIX), preferably magnesium or zinc derivative, followed by reoxidation of the resulting alcohol using oxidating agents such as manganese (IV) oxide.

Alternatively the ketones of formula (XXIII) may be obtained by condensation of the ethyl esters of formula (XXI) with the compounds of formula (XXII). This reaction is conveniently carried out in the presence of an organic base such as lithium bis(trimethylsilyl)amide in a range of temperature about –10° C. to about 50° C. and in organic aprotic solvents, preferably tetrahydrofuran or diethyl ether.

The ketones of formula (XXIII) are then oxidized to the diketone derivatives of general formula (XXIV) preferably by reaction with hydrobromic acid or N-bromosuccinimide in a polar aprotic solvent such as dimethylsulfoxide in a range of temperature about –10° C. to about 100° C.

Alternatively aldehydes of formula (XXVIII) are reacted with derivatives of formula (XIX) (wherein X represents a trialkylsilyloxy group) to yield the corresponding diol (figure not shown) via addition of an organometallic derivative of (XIX), preferably lithium derivative. Reoxidation of the resulting diol using oxidating agents such as oxalyl chloride, yields the diketone (XXIV).

Further condensation with 1,2,5-thiadiazole-3,4-diamine or 1,2,5-oxadiazole-3,4-diamine in a polar protic solvent such as acetic acid at temperatures ranging from 60 to 150° C. provides compounds of general formula (XXV)

Diaminopyrazines of general formula (XXVI) are obtained by ring opening of compounds of formula (XXV) by treatment with ammonia (when Y=S) or by catalytic hydrogenation (when Y=O).

Treatment of compounds of formula (XXVI) with acylating agents such as anhydrides, acid chlorides or acylcarbonates in apolar organic solvents such as THF and in the presence of a convenient organic base (such as triethylamine) or inorganic base, and eventually acylating with carboxylic acids using coupling agents such as diethylcarbodiimide, yields the compounds of formula (XXVII) which can be converted into the compounds of formula (XXX) by acid (for example acetic acid) or base (for example sodium hydroxide) catalyzed cyclization at temperatures between 70° C. and 200° C.

Alternatively, diamino derivatives (XXVI) can be cyclized to the imidazopyridines (XXX) by heating in neat trialkylorthoacid or in an acetic acid solution of the orthoacid derivatives and at temperatures between 70° C. and 200° C.

Following other synthetic pathways, treatment of (XXVI) with carbonylating agents such as carbonyldiimidazole in polar aprotic solvents such as DMF and heating at temperatures between 50° C. and 200° C. provides the imidazolone compounds (XXX) wherein $R^a$ is a hydroxy group.

Figure 5:
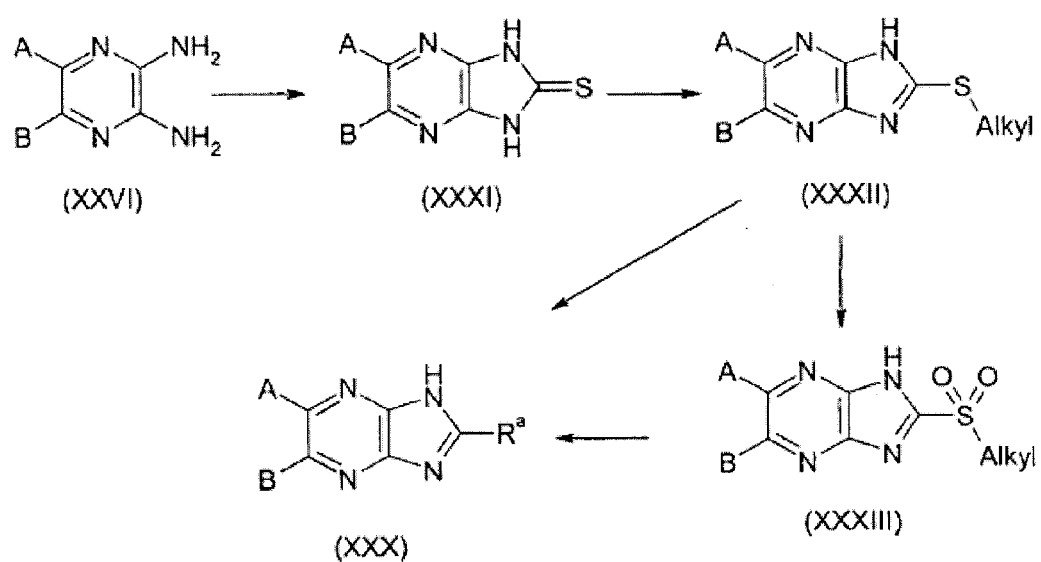
FIG. 5 exemplifies an alternative synthetic scheme used for the preparation of compounds of general formula (I) wherein $R^2$, $R^1$, and the —NH— group to which $R^1$ is attached form a moiety of formula II(a).

Alternatively, compounds of general formula (I) and in particular those of formula (XXX) wherein A, B are as hereinabove defined and $R^2$, $R^1$ and the —NH— group to which $R^1$ is attached form a moiety of formula (IIa) may be prepared following the synthetic scheme depicted in FIG. 5.

Treatment of diaminopyrazine derivatives of formula (XXVI) with thioacylating agents such as thiocarbonyldiimidazole in polar aprotic solvents such as THF and heating at temperatures between 50° C. and 200° C. provides the thioimidazolone compounds (XXXI) that can be transformed to compounds of general formula (XXXII) wherein $R^a$ is an alkylthio group by treatment with a base such as sodium hydride in polar aprotic solvents such as DMF and in the presence of the corresponding alkylating agent such as alkyl iodide or bromide. Compounds (XXXII) can be transformed to compounds of general formula (XXX) by direct treatment with neat mono or dialkylamines or in the presence of a convenient solvent at temperatures ranging from 25° C. to 200° C. Alternatively compounds (XXX) can be obtained by sequential oxidation to the corresponding sulfones (XXXIII) using oxidizing agents such as m-CPBA and further treatment with mono or dialkylamines under the same conditions as in the transformation from (XXXII) to (XXX)

Figure 6:
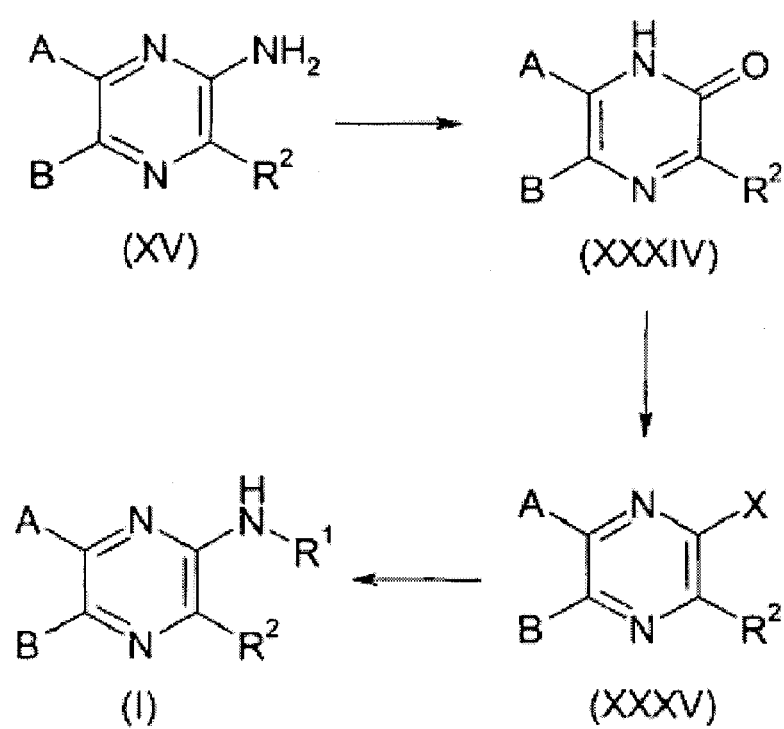
FIG. 6 exemplifies a synthetic scheme used for the preparation of compounds of general formula (I) wherein $R^1$ represents -L-(CR'R")n-G- wherein L represents a direct bond.

Compounds of general formula (I) and in particular those wherein A, B and $R^2$ are as hereinabove defined and $R^1$ represents a group of formula -L-(CR'R")n-G wherein L represents a direct bond may be prepared following the synthetic scheme depicted in FIG. 6.

Pyrazinones of general formula (XXXIV) can be prepared by diazoniation of aminopyrazines of general formula (XV) with organic or inorganic nitrites such as t-butyl or sodium nitrite and subsequent hydrolysis of the corresponding diazonium salt in the presence of an aqueous solution of an acid such as sulphuric acid. Treatment of pyrazinones (XXXIV) with reagents such as oxalyl chloride, phosphorus oxychloride, phosphorus pentachloride or a combination of them at a temperature ranging from 20° to 150° C. in a solvent like dichloromethane or acetonitrile provides the halo-derivatives (XXXV) that by treatment with a convenient primary or secondary amine, preferably in the presence of a palladium catalyst such as palladium(II) acetate, a phosphine ligand such as BINAP, a base such as caesium carbonate in a convenient solvent such as toluene at temperatures ranging from 25 to 200° C. can be converted into the pyrazines of general formula (I)

EXPERIMENTAL

Pharmacological Activity

Adenosine 2B Receptor Subtype Competition Radioligand Binding Assay

A2B membranes were prepared from HEK293 cells stably expressing the human A2B receptor that were purchased from Euroscreen (ES-013-C). Competition assays were carried out incubating in polypropylene 96 well-plates (n° 267245, NUNC) containing 2 µl of either 1% DMSO solution, test compound or 100 µM 5'NECA (SIGMA E-2387) for non-specific binding, 100 µg of A2B-membranes (prepared in Tris-HCl 50 mM pH 6.5, MgCl$_2$ 10 mM, EDTA 1 mM, benzamidine 0.1 mM; buffer A) and 35 nM [$^3$H]-DPCPX (TRK1064, 128 Ci/mmol, Amersham), in a total volume of 200 µl of buffer A+2 UI/ml adenosine deaminase, for 60 minutes at room temperature. At the end of the incubation, samples were transferred to a GF/C filter plates (Milipore MAFCN0B50) pretreated for 15 min. with 250 µl of Tris-HCl 50 mM pH 6.5 (Buffer B). Samples were then filtered 4 times with 250 µl of buffer B. Samples were counted using 30 µl of Hisafe II (Perkin Elmer) in a Trilux counter.

The compounds of formula (I) have been tested according to the assay described above and have shown to be potent inhibitors of the A2B adenosine receptor subtype. Preferred pyrazine derivatives of the invention possess a $K_i$ value for the antagonism of $A_{2B}$ (determined as defined above) of less than 100 nM, preferably less than 30 nM and more preferably less than 10 nM.

Table 1 shows the binding activities of some of the compounds of the present invention determined using the adenosine 2B receptor subtype competition radioligand binding assay described above.

TABLE 1

| Example | $K_I$ |
|---|---|
| 3 | 4 |
| 22 | 16 |
| 25 | 19 |
| 67 | 9 |
| 76 | 4 |
| 119 | 3 |
| 142 | 26 |
| 149 | 0.9 |

The pyrazine derivatives of the invention are useful in the treatment or prevention of diseases known to be susceptible to improvement by treatment with an antagonist of the $A_{2B}$ adenosine receptor. Such diseases include but are not limited to asthma, chronic obstructive pulmonary disorder, pulmonary fibrosis, emphysema, allergic diseases including allergic rhinitis (perennial, seasonal or occupational), inflammation, pain, reperfusion injury, myocardial ischemia, atherosclerosis, hypertension, retinopathy, diabetes mellitus, inflammatory gastrointestinal tract disorders, cell proliferation disorders such as cancer, wound healing and/or autoimmune diseases. Examples of autoimmune diseases which can be treated or prevented using the compounds of the invention are Addison's disease, autoimmune hemolytic anemia, Crohn's disease, Goodpasture's syndrome, Graves disease, Hashimoto's thyroiditis, idiopathic thrombocytopenic purpura, insulin-dependent diabetes mellitus, multiple sclerosis, myasthenia gravis, pemphigus vulgaris, pernicious anemia, poststreptococcal glomerulonephritis, psoriasis, rheumatoid arthritis, scleroderma, Sjogren's syndrome, spontaneous infertility, and systemic lupus erythematosus.

Accordingly, the pyrazine derivatives of the invention and pharmaceutical compositions comprising such compound and/or salts thereof may be used in a method of treatment of disorders of the human or animal body which comprises administering to a subject requiring such treatment an effective amount of pyrazine derivative of the invention or a pharmaceutically acceptable salt thereof.

The pyrazine derivatives of the invention may also be combined with other active compounds in the treatment of diseases known to be susceptible to improvement by treatment with an antagonist of the $A_{2B}$ adenosine receptor.

The combinations of the invention can optionally comprise one or more additional active substances which are known to be useful in the treatment of respiratory or inflammatory disorders, such as β2-agonists, antagonists of M3 muscarinic receptors, PDE4 inhibitors, corticosteroids or glucocorticoids, CysLT1 and/or CysLT2 antagonists (also known as leukotriene D4 antagonists), inhibitors of egfr-kinase, p38 kinase inhibitors, NK1-receptor antagonists, CRTh2 antagonists, syk kinase inhibitors, CCR3 antagonists, VLA-4 antagonists, H1 antagonists, H4 antagonists, 5-Lipoxygenase Inhibitors, A1 adenosine receptor antagonists, A3 adenosine receptor antagonists, A2a adenosine receptor agonists, CCR8 Receptor Antagonists.

When pyrazine derivatives of the invention are used for the treatment of respiratory diseases such as asthma, chronic obstructive pulmonary disorder, pulmonary fibrosis, emphysema it may be advantageous to use them in combination with other active compounds known to be useful in the treatment of respiratory diseases such as (1) antagonists of M3 muscarinic receptors, (2) β2-agonists, (3) PDE4 inhibitors, (4) cortiocosteroids, (5) CysLT1 and/or CysLT2 antagonists, (6) inhibitors of egfr-kinase, (7) p38 kinase inhibitors, (8) NK1 receptor agonists, (9) CRTh2 antagonists, (10) syk kinase inhibitors, (11) CCR3 antagonists, (12) VLA-4 antagonists, (13) H1 antagonists, (14) H4 antagonists, (15) 5-Lipoxygenase Inhibitors, (16) A1 adenosine receptor antagonists, (17) A3 adenosine receptor antagonists, (18) A2a adenosine receptor agonists and (19) CCR8 Receptor Antagonists.

When formulating combinations with the pyrazine derivatives of the present invention it is particularly preferred to combine the pyrazine derivatives with an active compound selected from the group consisting of antagonists of M3 muscarinic receptors, β2-agonists, H1 antagonists, H4 antagonists, cortiocosteroids and CysLT1 and/or CysLT2 antagonists (also known as leukotriene D4 antagonists).

Combinations of the pyrazine derivatives of the present invention with CysLT1 and/or CysLT2 antagonists, H1 antagonists and/or H4 antagonists are particularly good in the treatment of respiratory diseases by oral administration.

Combinations of the pyrazine derivatives of the present invention with corticosteroids, β2-agonists and/or M3 antagonists are particularly good in the treatment of respiratory diseases by inhalation.

Examples of suitable β2-agonists that can be combined with the antagonists of the $A_{2B}$ adenosine receptor of the present invention are: arformoterol, bambuterol, bitolterol, broxaterol, carbuterol, clenbuterol, dopexamine, fenoterol, formoterol, hexoprenaline, ibuterol, isoetharine, isoprenaline, levosalbutamol, mabuterol, meluadrine, metaproternerol, nolomirole, orciprenaline, pirbuterol, procaterol, reproterol, ritodrine, rimoterol, salbutamol, salmefamol, salmeterol, sibenadet, sotenerot, sulfonterol, terbutaline, tiaramide, tulobuterol, GSK-597901, GSK-159797, HOKU-81, (−)-2-[7(S)-[2(R)-Hydroxy-2-(4-hydroxyphenyl)ethylamino]-5,6,7,8-tetrahydro-2-naphthyloxy]-N,N-dimethylacetamide hydrochloride monohydrate, carmoterol, QAB-149 and 5-[2-(5,6-diethylindan-2-ylamino)-1-hydroxyethyl]-8-hydroxy-1H-quinolin-2-one, 4-hydroxy-7-[2-{[2-{[3-(2-phenylethoxy)propyl]sulfonyl}ethyl]amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert-butylamino)ethanol and 1-(4-ethoxycarbonylamino-3-cyano-5-fluorophenyl)-2-(tert-butylamino)ethanol optionally in the form of their racemates, their enantiomers, their diastereomers, and mixtures thereof, and optionally their pharmacologically-compatible acid addition salts and the compounds claimed in Spanish Patent application numbers P200501229 and P200601082. When the β2-agonists are in the form of a salt or derivative It is particularly preferred that it is in a form selected from the sodium salts, sulfobenzoates, phosphates, isonicotinates, acetates, propionates, dihydrogen phosphates, palmitates, pivalates, fumarates, furoates, xinafoates or mixtures thereof.

The following β2-agonists are of special interest for the combination with the compounds of formula (I): arformoterol, bambuterol, bitolterol, broxaterol, carbuterol, clenbuterol, dopexamine, fenoterol, formoterol, hexoprenaline, ibuterol, isoprenaline, levosalbutamol, mabuterol, meluadrine, nolomirole, orciprenaline, pirbuterol, procaterol, (R,R)-formoterol, reproterol, ritodrine, rimoterol, salbutamol, salmeterol, sibenadet, sulfonterol, terbutaline, tulobuterol, GSK-597901, GSK-159797, KUL-1248, TA-2005 and QAB-149 optionally in the form of their racemates, their enantiomers, their diastereomers, and mixtures thereof, and optionally their pharmacologically-compatible acid addition salts It is preferred that they compounds of the present invention are combined with long-acting β2-agonists (also known as LABAs). The combined drugs could thus be administered once a day.

It is also of interest that the β2-agonists are selected from the group consisting of fenoterol, formoterol, hexoprenaline, salmeterol, GSK-597901, GSK-159797, 3-(4-{6-[2-hydroxy-2-(4-hydroxy-3-hydroxymethylphenyl)ethylamino]hexyloxy}-butyl)benzene-sulfonamide, QAB-149, 5-[2-(5,6-diethylindan-2-ylamino)-1-hydroxyethyl]-8-hydroxy-1H-quinolin-2-one, 1-[3-(4-methoxybenzylamino)-4-hydroxyphenyl-]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, (−)-2-[7(S)-[2(R)-Hydroxy-2-(4-hydroxyphenyl)ethylamino]-5,6,7,8-tetrahydro-2-naphthyloxy]-N,N-dimethylacetamide hydrochloride monohydrate, carmoterol, or an enantiomer, racemate, pharmacologically acceptable acid addition salt, hydrate, or mixture thereof.

Still most preferred are the following β2-agonists: formoterol, salmeterol and GSK-597901, GSK-159797, QAB-149 optionally in the form of their racemates, their enantiomers, their diastereomers and mixtures thereof, and optionally their pharmacologically-compatible acid addition salts. Still more preferred are salmeterol and formoterol.

The following can be considered to represent examples of suitable acid for the formation of addition salts: hydrochloric acid, hydrobromic acid, sulphuric acid, phosphoric acid, methanosulphonic acid, acetic acid, fumaric acid, succinic acid, lactic acid, citric acid or maleic acid. Furthermore, mixtures of the aforementioned acids can be used.

A particularly preferred embodiment of the present invention is a combination of an antagonist of the $A2_B$ adenosine receptor of the present invention with a LABA selected from formoterol, salmeterol, GSK-597901, GSK-159797, (−)-2-[7(S)-[2(R)-Hydroxy-2-(4-hydroxyphenyl)ethylamino]-5,6,7,8-tetrahydro-2-naphthyloxy]-N,N-dimethylacetamide hydrochloride monohydrate, carmoterol, QAB-149 and 5-[2-(5,6-diethylindan-2-ylamino)-1-hydroxyethyl]-8-hydroxy-1H-quinolin-2-one.

Still most preferred is a combination of an antagonist of the $A2_B$ adenosine receptor of the present invention with a LABA selected from formoterol, salmeterol, GSK-597901, GSK-159797 and QAB-149. It is a further particularly preferred embodiment of the present invention the combination of an antagonist of the $A2_B$ adenosine receptor of the present invention with either formoterol or salmeterol.

Examples of suitable M3 antagonists (anticholinergics) that can be combined with the antagonists of the $A2_B$ adenosine receptor of the present invention are tiotropium salts, oxitropium salts, flutropium salts, ipratropium salts, glycopyrronium salts, trospium salts, revatropate, espatropate, 3-[2-Hydroxy-2,2-bis(2-thienyl)acetoxy]-1-(3-phenoxypropyl)-1-azoniabicyclo[2.2.2]octane salts, 1-(2-Phenylethyl)-3-(9H-xanthen-9-ylcarbonyloxy)-1-azoniabicyclo[2.2.2]octane salts, 2-oxo-1,2,3,4-tetrahydroquinazoline-3-carboxylic acid endo-8-methyl-8-azabicyclo[3.2.1]oct-3-yl ester salts (DAU-5884), 3-(4-Benzylpiperazin-1-yl)-1-cyclobutyl-1-hydroxy-1-phenylpropan-2-one (NPC-14695), N-[1-(6-Aminopyridin-2-ylmethyl)piperidin-4-yl]-2(R)-[3,3-difluoro-1(R)-cyclopentyl]-2-hydroxy-2-phenylacetamide (J-104135), 2(R)-Cyclopentyl-2-hydroxy-N-[1-[4(S)-methylhexyl]piperidin-4-yl]-2-phenylacetamide (J-106366), 2(R)-Cyclopentyl-2-hydroxy-N-[1-(4-methyl-3-pentenyl)-4-piperidinyl]-2-phenylacetamide (J-104129), 1-[4-(2-Aminoethyl)piperidin-1-yl]-2(R)-[3,3-difluorocyclopent-1(R)-yl]-2-hydroxy-2-phenylethan-1-one (Banyu-280634), N-[N-[2-[N-[1-(Cyclohexylmethyl)piperidin-3(R)-ylmethyl]carbamoyl]ethyl]carbamoylmethyl]-3,3,3-triphenylpropionamide (Banyu CPTP), 2(R)-Cyclopentyl-2-hydroxy-2-phenylacetic acid 4-(3-azabicyclo[3.1.0]hex-3-yl)-2-butynyl ester (Ranbaxy 364057), UCB-101333, Merck's OrM3, 7-endo-(2-hydroxy-2,2-diphenylacetoxy)-9,9-dimethyl-3-oxa-9-azoniatricyclo[3.3.1.0(2,4)]nonane salts, 7-(2,2-diphenylpropionyloxy)-7,9,9-trimethyl-3-oxa-9-azoniatricyclo[3.3.1.0*2,4*]nonane salts, 7-hydroxy-7,9,9-trimethyl-3-oxa-9-azoniatricyclo[3.3.1.0*2,4*]nonane 9-methyl-9H-fluorene-9-carboxylic acid ester salts, all of them optionally in the form of their racemates, their enantiomers, their diastereomers and mixtures thereof, and optionally in the form of their pharmacologically-compatible acid addition salts. Among the salts chlorides, bromides, iodides and methanesulphonates are preferred.

Examples of suitable PDE4 inhibitors that can be combined with the antagonists of the $A2_B$ adenosine receptor of the present invention are denbufylline, rolipram, cipamfylline, arofylline, filaminast, piclamilast, mesopram, drotaverine hydrochloride, lirimilast, cilomilast, 6-[2-(3,4-Diethoxyphenyl)thiazol-4-yl]pyridine-2-carboxylic acid, (R)-(+)-4-[2-(3-Cyclopentyloxy-4-methoxyphenyl)-2-phenylethyl] pyridine, N-(3,5-Dichloro-4-pyridinyl)-2-[1-(4-fluorobenzyl)-5-hydroxy-1H-indol-3-yl]-2-oxoacetamide, 9-(2-Fluorobenzyl)-N6-methyl-2-(trifluoromethyl)adenine, N-(3,5-Dichloro-4-pyridinyl)-8-methoxyquinoline-5-carboxamide, N-[9-Methyl-4-oxo-1-phenyl-3,4,6,7-tetrahydropyrrolo[3,2,1-jk][1,4]benzodiazepin-3(R)-yl]pyridine-4-carboxamide, 3-[3-(Cyclopentyloxy)-4-methoxybenzyl]-6-(ethylamino)-8-isopropyl-3H-purine hydrochloride, 4-[6,7-Diethoxy-2,3-bis(hydroxymethyl)naphthalen-1-yl]-1-(2-methoxyethyl)pyridin-2(1H)-one, 2-carbomethoxy-4-cyano-4-(3-cyclopropylmethoxy-4-difluromethoxyphenyl)cyclohexan1-one, cis[4-cyano-4-(3-cyclopropylmethoxy-4-difluoromethoxyphenyl) cyclohexan-1-ol, ONO-6126 (Eur Respir J 2003, 22(Suppl. 45): Abst 2557) and the compounds claimed in the PCT patent application numbers WO03/097613, WO2004/058729 A1 and WO 2005/049581 A1.

Examples of suitable corticosteroids and glucocorticoids that can be combined with the antagonists of the $A2_B$ adenosine receptor of the present invention are prednisolone, methylprednisolone, dexamethasone, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, deprodone propionate, fluticasone propionate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate and hydrocortisone probutate.

Examples of suitable CysLT1 and/or CysLT2 antagonists that can be combined with the antagonists of the $A2_B$ adenosine receptor of the present invention are tomelukast, Ibudilast, pobilukast, pranlukast hydrate, zafirlukast, ritolukast, verlukast, sulukast, tipelukast, cinalukast, iralukast sodium, masilukast, montelukast sodium, 5-[3-[3-(2-Quinolinylmethoxy)phenoxy]propyl]-1H-tetrazole, (E)-8-[2-[4-[4-(4-Fluorophenyl)butoxy]phenyl]vinyl]-2-(1H-tetrazol-5-yl)-4H-benzopyran-4-one sodium salt, 2-[N-[4-(4-Chlorophenylsulfonamido)butyl]-N-[3-(4-isopropylthiazol-2-ylmethoxy)benzyl]sulfamoyl]benzoic acid, (3R,4R)-3-[6-(5-Fluorobenzothiazol-2-ylmethoxy)-4-hydroxy-3,4-dihydro-2H-1-benzopyran-3-ylmethyl]benzoic acid, 2-[2-[2-(4-tert-Butylthiazol-2-yl)benzofuran-5-yloxymethyl] phenyl]acetic acid hydrochloride, 5-[2-[4-(Quinolin-2-ylmethoxy)phenoxymethyl]benzyl]-1H-tetrazole, (E)-2,2-Diethyl-3'-[2-[2-(4-isopropyl)thiazolyl]ethenyl]succinanilic acid; 4-[4-[3-(4-Acetyl-3-hydroxy-2-propylphenoxy)propylsulfonyl]phenyl]-4-oxobutyric acid, [[5-[[3-(4-Acetyl-3-hydroxy-2-propylphenoxy)propyl]thio]-1,3,4-thiadiazol-2-yl]thio]acetic acid, 9-[(4-Acetyl-3-hydroxy-2-n-propylphenoxy)methyl]-3-(1H-tetrazol-5-yl)-4H-pyrido[1,2-a]pyrimidin-4-one, 5-[3-[2-(7-Chloroquinolin-2-yl)vinyl] phenyl]-8-(N,N-dimethylcarbamoyl)-4,6-dithiaoctanoic acid sodium salt; 3-[1-[3-[2-(7-Chloroquinolin-2-yl)vinyl] phenyl]-1-[3-(dimethylamino)-3-oxopropylsulfanyl]methylsulfanyl]propionic acid sodium salt, 6-(2-Cyclohexylethyl)-[1,3,4]thiadiazolo[3,2-a]-1,2,3-triazolo[4,5-d]pyrimidin-9 (1H)-one, (R)-3-[2-Methoxy-4-[N-(2-methylphenylsulfonyl)carbamoyl]benzyl]-1-methyl-N-(4,4,4-trifluoro-2-methylbutyl)indole-5-carboxamide, MCC-847

(from AstraZeneca), (+)-4(S)-(4-Carboxyphenylthio)-7-[4-(4-phenoxybutoxy)phenyl]-5(Z)-heptenoic acid and the compounds claimed in PCT patent application WO2004/043966A1.

Examples of suitable inhibitors of egfr-kinase that can be combined with the antagonists of the $A2_B$ adenosine receptor of the present invention are palifermin, cetuximab, gefitinib, repifermin, erlotinib hydrochloride, canertinib dihydrochloride, lapatinib, and N-[4-(3-Chloro-4-fluorophenylamino)-3-cyano-7-ethoxyquinolin-6-yl]-4-(dimethylamino)-2(E)-butenamide.

Examples of suitable p38 kinase inhibitors that can be combined with the antagonists of the $A2_B$ adenosine receptor of the present invention are chlormethiazole edisylate, doramapimod, 5-(2,6-Dichlorophenyl)-2-(2,4-difluorophenylsulfanyl)-6H-pyrimido[3,4-b]pyridazin-6-one, 4-Acetamido-N-(tert-butyl)benzamide, SCIO-469 (described in Clin Pharmacol Ther 2004, 75(2): Abst PII-7 and VX-702 described in Circulation 2003, 108(17, Suppl. 4): Abst 882 and the compounds claimed in Spanish patent application number P200600396.

Examples of suitable NK1-receptor antagonists that can be combined with the antagonists of the $A2_B$ adenosine receptor of the present invention are nolpitantium besilate, dapitant, lanepitant, vofopitant hydrochloride, aprepitant, ezlopitant, N-[3-(2-Pentylphenyl)propionyl]-threonyl-N-methyl-2,3-dehydrotyrosyl-leucyl-D-phenylalanyl-allo-threonyl-asparaginyl-serine C-1.7-O-3.1 lactone, 1-Methylindol-3-ylcarbonyl-[4(R)-hydroxy]-L-prolyl-[3-(2-naphthyl)]-L-alanine N-benzyl-N-methylamide, (+)-(2S,3S)-3-[2-Methoxy-5-(trifluoromethoxy)benzylamino]-2-phenylpiperidine, (2R,4S)—N-[1-[3,5-Bis(trifluoromethyl)benzoyl]-2-(4-chlorobenzyl)piperidin-4-yl]quinoline-4-carboxamide, 3-[2(R)-[1(R)-[3,5-Bis(trifluoromethyl)phenyl]ethoxy]-3(S)-(4-fluorophenyl)morpholin-4-ylmethyl]-5-oxo-4,5-dihydro-1H-1,2,4-triazole-1-phosphinic acid bis(N-methyl-D-glucamine) salt; [3-[2(R)-[1(R)-[3,5-bis(trifluoromethyl)phenyl]ethoxy]-3(S)-(4-fluorophenyl)-4-morpholinylmethyl]-2,5-dihydro-5-oxo-1H-1,2,4-triazol-1-yl]phosphonic acid 1-deoxy-1-(methylamino)-D-glucitol (1:2) salt, 1'-[2-[2(R)-(3,4-Dichlorophenyl)-4-(3,4,5-trimethoxybenzoyl)morpholin-2-yl]ethyl]spiro[benzo[c]thiophen-1(3H)-4'-piperidine]2(S)-oxide hydrochloride and the compound CS-003 described in Eur Respir J 2003, 22(Suppl. 45): Abst P2664.

Examples of suitable CRTh2 antagonists that can be combined with the antagonists of the $A2_B$ adenosine receptor of the present invention are 2-[5-Fluoro-2-methyl-1-[4-(methylsulfonyl)phenylsulfonyl]-1H-indol-3-yl]acetic acid, Ramatroban, [(3R)-4-(4-chlorobenzyl)-7-fluoro-5-(methylsulfonyl)-1,2,3,4tetrahydrocyclopenta[b]indol-3-yl]acetic acid and (1R,2R,3S,5S)-7-[2-(5-Hydroxybenzothiophen-3-ylcarboxamido)-6,6-dimethylbicyclo[3.1.1]hept-3-yl]-5(Z)-heptenoic acid Examples of suitable Syk kinase inhibitors that can be combined with the antagonists of the $A2_B$ adenosine receptor of the present invention are piceatannol, 2-(2-Aminoethylamino)-4-[3-(trifluoromethyl)phenylamino]pyrimidine-5-carboxamide, R-091 (from Rigel), R-112 (from Rigel), R-343 (from Rigel), R-788 (from Rigel), 6-[5-Fluoro-2-(3,4,5-trimethoxyphenylamino)pyrimidin-4-ylamino]-2,2-dimethyl-3,4-dihydro-2H-pyrido[3,2-b][1,4]oxazin-3-one benzenesulfonate, 1-(2,4,6-Trihydroxyphenyl)-2-(4-methoxyphenyl)ethan-1-one, N-[4-[6-(Cyclobutylamino)-9H-purin-2-ylamino]phenyl]-N-methylacetamide, 2-[7-(3,4-Dimethoxyphenyl)imidazo[1,2-c]pyrimidin-5-ylamino]pyridine-3-carboxamide dihydrochloride and AVE-0950 (from Sanofi-Aventis).

Examples of CCR3 antagonists that can be combined with the antagonists of the $A2_B$ adenosine receptor of the present invention are 4-[3-[4-(3,4-Dichlorobenzyl)morpholin-2(S)-ylmethyl]ureidomethyl]benzamide, N-[1(R)-[4-(3,4-Dichlorobenzyl)piperidin-1-ylmethyl]-2-methylpropyl]-N'-(3,4,5-trimethoxyphenyl)urea, N-[1(S)-[4-(4-Chlorobenzyl)piperidin-1-ylmethyl]-2-hydroxypropyl]-N'-(3,4,5-trimethoxyphenyl)urea, 3-[3-(3-Acetylphenyl)ureido]-2-[4-(4-fluorobenzyl)piperidin-1-ylmethyl]-N-methylbenzamide, 4-(3,4-Dichlorobenzyl)-1-methyl-1-[3-methyl-2(R)-[3-(3,4,5-trimethoxyphenyl)ureido]butyl]piperidinium chloride, N-[2-[4(R)-(3,4-Dichlorobenzyl)pyrrolidin-2(S)-yl]ethyl]-2-[5-(3,4-dimethoxyphenyl)pyrimidin-2-ylsulfanyl]acetamide, CRIC-3 (from IPF Pharmaceuticals), 2(R)-[1-[1-(2,4-Dichlorobenzyl)-4(S)-(3-thienyl)pyrrolidin-3(S)-ylmethyl] piperidin-4-ylmethyl]pentanoic acid, 8-[1-(2,4-Dichlorobenzyl)-4(S)-(3-thienyl)pyrrolidin-3(S)-ylmethyl]-3,3-dipropyl-1-oxa-8-azaspiro[4.5]decane-2(S)-carboxylic acid, 11-[1-(2,4-Dichlorobenzyl)-4(S)-(3-thienyl)pyrrolidin-3(S)-ylmethyl]-3,14-dioxa-11-azadispiro[5.1.5.2]pentadecane-15(S)-carboxylic acid, W-56750 (from Mitsubishi Pharma), N-[1(S)-[3endo-(4-Chlorobenzyl)-8-azabicyclo [3.2.1]oct-8-ylmethyl]-2(S)-hydroxypropyl]-N'-(3,4,5-trimethoxyphenyl)urea, N-(3-Acetylphenyl)-N'-[(1R,2S)-2-[3(S)-(4-fluorobenzyl)piperidin-1-ylmethyl]cyclohexyl] urea benzenesulfonate, trans-1-(Cycloheptylmethyl)-4-(2,7-dichloro-9H-xanthen-9-ylcarboxamido)-1-methylpiperidinium iodide, GW-782415 (from GlaxoSmithKline), GW-824575 (from GlaxoSmithKline), N-[1'-(3,4-Dichlorobenzyl)-1,4'-bipiperidin-3-ylmethyl]quinoline-6-carboxamide, N-[1-(6-Fluoronaphthalen-2-ylmethyl)pyrrolidin-3 (R)-yl]-2-[1-(3-hydroxy-5-methylpyridin-2-ylcarbonyl) piperidin-4-ylidene]acetamide fumarate and DIN-106935 (from Bristol-Myers Squibb).

Examples of VLA4 antagonists that can be combined with the antagonists of the $A2_B$ adenosine receptor of the present invention are N-[4-[3-(2-Methylphenyl)ureido]phenylacetyl]-L-leucyl-L-aspartyl-L-valyl-L-proline, 3(S)-[2(S)-[4,4-Dimethyl-3-[4-[3-(2-methylphenyl)ureido]benzyl]-2,5-dioxoimidazolidin-1-yl]4-methylpentaoylamino]-3-phenylpropionic acid, 2(S)-(2,6-Dichlorobenzamido)-3-(2',6'-dimethoxybiphenyl-4-yl)propionic acid, RBx-4638 (from Ranbaxy), R-411 (from Roche), RBx-7796 (from Ranbaxy), SB-683699 (from GlaxoSmithKline), DW-908e (from Daiichi Pharmaceutical), RO-0270608 (from Roche), AJM-300 (from Ajinomoto), PS-460644 (from Pharmacopeia) and the compounds claimed in PCT patent application numbers WO 02/057242 A2 and WO 2004/099126 A1.

Examples of H1 antagonists that can be combined with the antagonists of the $A2_B$ adenosine receptor of the present invention are carebastine, azelastine hydrochloride, acrivastine, emedastine fumarate; emedastine difumarate, loratadine, picumast dihydrochloride, cyproheptadine hydrochloride, diphenhydramine hydrochloride, doxepin hydrochloride, promethazine hydrochloride, rocastine fumarate, fenclozine maleate, levocabastine hydrochloride, desloratadine, cinnarizine, setastine hydrochloride, tagorizine, mizolastine, ebastine, cetirizine hydrochloride, tazifylline hydrochloride, epinastine hydrochloride, olopatadine hydrochloride, 11-(1-Acetyl-4-piperidylidene)-8-chloro-5,6-dihydro-11H-benzo[5,6]cyclohepta[1,2-b]pyridine, noberastine, pibaxizine, flezelastine hydrochloride, alcaftadine, mapinastine maleate, bepotastine besilate; 3-[4-(8-Fluoro-5,11-dihydrobenz[b]oxepino[4,3-b]pyridin-11-ylidene)piperidin-1- yl]propionic acid dehydrate, rupatadine fumarate, triprolidine hydrochloride, LAS-X-113 (from Almirall Prodesfarma), terfenadine carboxylate hydrochloride; fexofenadine hydrochloride, 1-[3-(10,11-dihydro-5H-dibenzo [asd]cyclohepten-5-ylidene)propyl]piperidine-3(R)-carboxylic acid, bilastine, levocetirizine; ketotifen, azatadine maleate, clemastine fumarate, 5,6-Dihydrospiro[11H-imidazo[2,1-b][3]benzazepine-11,4'-piperidine]-3-carboxamide dihydrochloride, chlorpheniramine maleate; 5-[4-(N-Carbamoyl-N-hydroxyamino)-1-butynyl]-2-[2-[4-[1(R)-(4-chlorophenyl)-1-phenylmethyl]piperazin-1-yl]ethoxy] benzamide, K-123 (from Kowa) and the products claimed in PTC patent application numbers WO 00/75130 A1, WO 02/36589 A1, WO 03/099807 A1 and WO 03/082867 A1.

Examples of H4 antagonists that can be combined with the antagonists of the $A2_B$ adenosine receptor of the present invention are [3-(4-Chlorophenyl)propyl][3-(1H-imidazol-4-yl)propyl]ether, 1-(5-Chloro-1H-indol-2-yl)-1-(4-methylpiperazin-1-yl)methanone and 1-(5-Chloro-1H-benzimidazol-2-yl)-1-(4-methylpiperazin-1-yl)methanone.

Examples of 5-lipoxygensase inhibitors that can be combined with the antagonists of the $A2_B$ adenosine receptor of the present invention are 6-(3-Pyridylmethyl)-2,3,5-trimethyl-1,4-benzoquinone, tebufelone, zileuton, Hydroxy-4,5,7-trimethyl-2-(4-sulfamoylbenzylamino)benzothiazole hydrochloride, 3,5,6-Trimethyl-2-(3-pyridylmethyl)-1,4-benzoquinone hydrochloride, darbufelone mesilate, etalocib sodium, licofelone, 4-[3-Fluoro-5-[4-(2-methyl-1H-imidazol-1-yl)phenylsulfanyl]phenyl]tetrahydro-2H-pyran-4-carboxamide hydrochloride, 5-[4-(N-Carbamoyl-N-hydroxyamino)-1-butynyl]-2-[2-[4-[1(R)-(4-chlorophenyl)-1-phenylmethyl]piperazin-1-yl]ethoxy]benzamide, UP-0483/0530 (from Unigen Pharmaceuticals) and PEP-03 (from Pharmaengine).

Examples of A1 adenosine receptor antagonists that can be combined with the antagonists of the $A2_B$ adenosine receptor of the present invention are doxofylline, theophylline, (+)-2 (R)-(2-Hydroxyethyl)-1-[(E)-3-(2-phenylpyrazolo[1,5-a] pyridin-3-yl)acryloyl]piperidine; 8-(3-Oxocyclopentyl)-1,3-dipropylxanthine; 8-(3-Oxocyclopentyl)-1,3-dipropyl-3,7-dihydro-1H-purine-2,6-dione, 8-Cyclopentyl-1,3-dipropylxanthine; 8-Cyclopentyl-3,7-dihydro-1,3-dipropyl-1H-purine-2,6-dione, 3-[2-(3-Carboxypropyl)-3-oxo-2,3-dihydropyridazin-6-yl]-2-phenylpyrazolo[1,5-a]pyridine; 8-(Octahydro-2,5-methanopentalen-3a-yl)-1,3-dipropylxanthine; (±)-N6-(endo-2-Norbornyl)-9-methyladenine; (±)-N6-(Bicyclo[2.2.1]hept-2-yl)-9-methyladenine; 2-[1-[3-(2-Phenylpyrazolo[1,5-a]pyridin-3-yl)-2(E)-propenoyl] piperidin-2(R)-yl]acetic acid, apaxifylline, naxifylline, DTI-0017 (from Aderis), SLV-320 (from Solvay) and 3-[4-(2,6-Dioxo-1,3-dipropyl-2,3,6,9-tetrahydro-1H-purin-8-yl) bicyclo[2.2.2]oct-1-yl]propionic acid.

Examples of A3 adenosine receptor antagonists that can be combined with the antagonists of the $A2_B$ adenosine receptor of the present invention are N-[9-Chloro-2-(2-furyl)-1,2,4-triazolo[1,5-c]quinazolin-5-yl]-2-phenylacetamide, 5-Butyl-8-(4-chlorophenyl)-1H-[1,2,4]triazolo[5,1-i]purine, 5-Butyl-8-[4-(trifluoromethyl)phenyl]-1H-[1,2,4]triazolo[5,1-i] purine, N-[4-(3-Methylphenyl)-5-(4-pyridyl)thiazol-2-yl] acetamide, 4-(3,4-Dichlorophenyl)-5-(4-pyridinyl)thiazol-2-amine, 3-[5-(2-Methyl-1H-imidazol-1-yl)-2-(pyrazin-2-ylamino)thiazol-4-yl]benzonitrile and SSR-161421 (from Sanofi-Aventis).

Examples of A2a adenosine receptor agonists that can be combined with the antagonists of the $A2_B$ adenosine receptor of the present invention are 2-(1-Octynyl)adenosine, binodenoson, (1S,2R,3S,4R)-4-[7-[1(R)-(3-Chloro-2-thienylmethyl)propylamino]-3H-imidazo[4,5-b]pyridin-3-yl]-N-ethyl-2,3-dihydroxycyclopentane-1-carboxamide, GW-328267 (from GlaxoSmithKline), apadenoson, regadenoson, 2-[2-(4-Chlorophenyl)ethoxy]adenosine, UK-432097 (from Pfizer).

Examples of chemokine CCR8 receptor antagonists that can be combined with the antagonists of the $A2_B$ adenosine receptor of the present invention are 3-[1-(1H-Indol-2-ylmethyl)piperidin-4-yl]-5-(6-methoxyquinolin-4-yl)oxazolidin-2-one, 5-(6-Methoxyquinolin-4-yl)-3-[1-(1-methyl-1H-indol-2-ylmethyl)piperidin-4-yl]oxazolidin-2-one, 5-(6-Methoxyquinolin-4-yl)-3-[1-(3-phenylpropyl)piperidin-4-yl]oxazolidin-2-one, 3-[1-(1H-Indol-2-ylmethyl)piperidin-4-yl]-5-(6-methoxy-1,5-naphthyridin-4-yl)oxazolidin-2-one, 3-[1-(3,4-Dichlorobenzyl)piperidin-4-yl]-5-(6-methoxy-1,5-naphthyridin-4-yl)oxazolidin-2-one, 3-[1-(4-Bromobenzyl)piperidin-4-yl]-5-(6-methoxy-1,5-naphthyridin-4-yl)oxazolidin-2-one, 3-[1-(3-Chloro-4-methoxybenzyl)piperidin-4-yl]-5-(6-methoxyquinolin-4-yl) oxazolidin-2-one, 5-(6-Methoxyquinolin-4-yl)-3-[1-(4-methylbenzyl)piperidin-4-yl]oxazolidin-2-one, 3-[1-(3,5-Dimethylbenzyl)piperidin-4-yl]-5-(6-methoxyquinolin-4-yl)oxazolidin-2-one, N-[4-[N-(3-Methoxyphenyl) sulfamoyl]naphthalen-1-yl]benzamide, N-[4-[N-[1-(Morpholin-4-ylcarbonyl)piperidin-4-yl]sulfamoyl] naphthalen-1-yl]benzamide, 2-Methyl-N-[4-[N-(1-propionylpiperidin-4-yl)sulfamoyl]naphthalen-1-yl] benzamide, 2-Methyl-N-[4-[N-[1-[2-(1-pyrrolidinyl)acetyl] piperidin-4-yl]sulfamoyl]naphthalen-1-yl]benzamide, cis-3-Methyl-4-[4-(3-methylpyridin-2-ylcarboxamido) naphthalen-1-ylsulfonamido]piperidine-1-carboxylic acid ethyl ester, N-[4-(N-Cyclohexylsulfamoyl)-5,6,7,8-tetrahydronaphthalen-1-yl]cyclohexanecarboxamide, 2-Methyl-N-[4-[N-(tetrahydropyran-4-yl)sulfamoyl]-5,6,7,8-tetrahydronaphthalen-1-yl]benzamide, N-[5-(N-Cyclohexylsulfamoyl)naphthalen-1-yl]benzamide, 3-[7-(2-Methylbenzamido)-2,3-dihydro-1H-inden-4-ylsulfonamido]pyrrolidine-1-carboxylic acid tert-butyl ester, N-[4-(N-Benzylsulfamoyl)naphthalen-1-yl]benzamide, N-[4-[N-[1-(Cyclopentylcarbonyl)piperidin-4-yl]sulfamoyl]naphthalen-1-yl]benzamide, 4-[4-(2-Methylbenzamido)naphthalen-1-ylsulfonamido]-N-propylpiperidine-1-carboxamide, N-[4-[N-(1-Butyrylpiperidin-4-yl)sulfamoyl] naphthalen-1-yl]-2-methoxybenzamide, N-[4-[N-[1-[2(S)-Aminobutyryl]piperidin-4-yl]sulfamoyl]naphthalen-1-yl]-2-methylbenzamide, cis-N-[4-[N-(1-Butyryl-3-methylpiperidin-4-yl)sulfamoyl]naphthalen-1-yl]-3-methylpyridine-2-carboxamide, N-[4-[N-(4-Methoxyphenyl)sulfamoyl]-5,6,7,8-tetrahydronaphthalen-1-yl]benzamide, 4-[4-(2,3-Dimethylbenzamidomethyl) naphthalen-1-ylsulfonamido]piperidine-1-carboxylic acid ethyl ester, 4-[4-(Benzylaminomethyl)naphthalen-1-ylsulfonamido]piperidine-1-carboxylic acid ethyl ester, N-[3-(4-Butyl-1,4-diazepan-1-ylcarbonyl)phenyl]-3,4-dichlorobenzenesulfonamide, 3-Bromo-N-[3-(4-butyl-1,4-diazepan-1-ylcarbonyl)phenyl]benzenesulfonamide, N-[3-(4-Hexyl-1,4-diazepan-1-ylcarbonyl)phenyl]-3,4-dimethoxybenzenesulfonamide, 4-Chloro-2,5-dimethyl-N-[3-[4-(2-phenylethyl)-1,4-diazepan-1-ylcarbonyl]phenyl] benzenesulfonamide, N-[3-(4-Ethyl-1,4-diazepan-1-ylcarbonyl)phenyl]-3,4-dimethoxybenzenesulfonamide, N-[5-(4-Butyl-1,4-diazepan-1-ylcarbonyl)-2-methylphenyl]-3,4-dimethoxybenzenesulfonamide, N-[5-[4-(Cyclopropylmethyl)-1,4-diazepan-1-ylcarbonyl]-2-methylphenyl]-3,4-dimethoxybenzenesulfonamide, N-[4-Bromo-3-(4-butyl-1,4-diazepan-1-ylcarbonyl)phenyl]-3,4-dimethoxybenzenesulfonamide, N-[3-(4-Butyl-1,4- diazepan-1-ylcarbonyl)phenyl]-4-chloro-2,5-dimethylbenzenesulfonamide, N-[3-(4-Ethyl-1,4-diazepan-1-ylcarbonyl)phenyl]naphthalene-2-sulfonamide, N-[3-[4-(Cyclopropylmethyl)-1,4-diazepan-1-ylcarbonyl]phenyl]naphthalene-2-sulfonamide, N-[5-(4-Butyl-1,4-diazepan-1-ylcarbonyl)-2-methylphenyl]naphthalene-2-sulfonamide, N-[5-(4-Butyl-1,4-diazepan-1-ylcarbonyl)-2-chlorophenyl]naphthalene-2-sulfonamide, N-[5-[4-(Cyclopropylmethyl)-1,4-diazepan-1-ylcarbonyl]-2-methylphenyl]naphthalene-2-sulfonamide, N-[5-(4-Butyl-1,4-diazepan-1-ylcarbonyl)-2-methylphenyl]-1,3-benzodioxole-5-sulfonamide, N-[4-Bromo-3-(4-propyl-1,4-diazepan-1-ylcarbonyl)phenyl]naphthalene-2-sulfonamide, N-[4-Chloro-3-(4-pentyl-1,4-diazepan-1-ylcarbonyl)phenyl]naphthalene-2-sulfonamide and N-[5-(4-Ethyl-1,4-diazepan-1-ylcarbonyl)-2-methylphenyl]-2,3-dihydro-1,4-benzodioxine-6-sulfonamide.

The combinations of the invention may be used in the treatment of disorders which are susceptible to amelioration by antagonism of $A2_B$ receptors. Thus, the present application encompasses methods of treatment of these disorders, as well as the use of the combinations of the invention in the manufacture of a medicament for the treatment of these disorders.

Preferred examples of such disorders are those respiratory diseases, wherein the use of bronchodilating agents is expected to have a beneficial effect, for example asthma, acute or chronic bronchitis, emphysema, or Chronic Obstructive Pulmonary Disease (COPD).

The active compounds in the combinations of the invention may be administered by any suitable route, depending on the nature of the disorder to be treated, e.g. orally (as syrups, tablets, capsules, lozenges, controlled-release preparations, fast-dissolving preparations, lozenges, etc); topically (as creams, ointments, lotions, nasal sprays or aerosols, etc); by injection (subcutaneous, intradermic, intramuscular, intravenous, etc.) or by inhalation (as a dry powder, a solution, a dispersion, etc).

The active compounds in the combination, i.e. the $A2_B$ receptor antagonist of the invention, and the other optional active compounds may be administered together in the same pharmaceutical composition or in different compositions intended for separate, simultaneous, concomitant or sequential administration by the same or a different route.

One execution of the present invention consists of a kit of parts comprising an antagonist of $A2_B$ receptor antagonists of the present invention together with instructions for simultaneous, concurrent, separate or sequential use in combination with another active compound useful in the treatment of a respiratory disease which responds to $A2_B$ antagonism.

Another execution of the present invention consists of a package comprising an antagonist of $A2_B$ receptors of formula (I) and another active compound useful in the treatment of a respiratory disease for the simultaneous, concurrent, separate or sequential use in the treatment of a respiratory disease which responds to $A2_B$ antagonism.

In a preferred embodiment of the invention the active compounds in the combination are administered by inhalation through a common delivery device, wherein they can be formulated in the same or in different pharmaceutical compositions.

In the most preferred embodiment the $A2_B$ receptor antagonist of the invention and the other active compound as defined above are both present in the same pharmaceutical composition and are administered by inhalation through a common delivery device.

The pharmaceutical formulations may conveniently be presented in unit dosage form and may be prepared by any of the methods well known in the art of pharmacy. All methods include the step of bringing the active ingredient(s) into association with the carrier. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A syrup formulation will generally consist of a suspension or solution of the compound or salt in a liquid carrier for example, ethanol, peanut oil, olive oil, glycerine or water with flavouring or colouring agent.

Where the composition is in the form of a tablet, any pharmaceutical carrier routinely used for preparing solid formulations may be used. Examples of such carriers include magnesium stearate, talc, gelatine, acacia, stearic acid, starch, lactose and sucrose.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Where the composition is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 2 μg and 150 μg of each therapeutically active ingredient. Alternatively, the active ingredient(s) may be presented without excipients.

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

For inhalers of the first type, single doses have been weighed by the manufacturer into small containers, which are mostly hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients. Other drawbacks related to the use of hard gelatine capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported (e.g. Nielsen et al, 1997).

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e.g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets. Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (e.g. EP0069715) or disks (e.g. GB 2041763; EP 0424790; DE 4239402 and EP 0674533), rotatable cylinders (e.g. EP 0166294; GB 2165159 and WO 92/09322) and rotatable frustums (e.g. WO 92/00771), all having cavities which have to be filled with powder from the container. Other multi dose devices have measuring slides (e.g. U.S. Pat. No. 5,201,308 and WO 97/00703) or measuring plungers with a local or circumferential recess to displace a certain volume of powder from the container to a delivery chamber or an air conduit e.g. EP 0505321, WO 92/04068 and WO 92/04928.

Reproducible dose measuring is one of the major concerns for multi dose inhaler devices.

The powder formulation has to exhibit good and stable flow properties, because filling of the dose measuring cups or cavities is mostly under the influence of the force of gravity.

For reloaded single dose and multiple unit dose inhalers, the dose measuring accuracy and reproducibility can be guaranteed by the manufacturer. Multi dose inhalers on the other hand, can contain a much higher number of doses, whereas the number of handlings to prime a dose is generally lower.

Because the inspiratory air stream in multi-dose devices is often straight across the dose measuring cavity, and because the massive and rigid dose measuring systems of multi dose inhalers can not be agitated by this inspiratory air stream, the powder mass is simply entrained from the cavity and little de-agglomeration is obtained during discharge.

Consequently, separate disintegration means are necessary. However in practice, they are not always part of the inhaler design. Because of the high number of doses in multi-dose devices, powder adhesion onto the inner walls of the air conduits and the de-agglomeration means must be minimized and/or regular cleaning of these parts must be possible, without affecting the residual doses in the device. Some multi dose inhalers have disposable drug containers that can be replaced after the prescribed number of doses has been taken (e.g. WO 97/000703). For such semi-permanent multi dose inhalers with disposable drug containers, the requirements to prevent drug accumulation are even stricter.

Apart from applications through dry powder inhalers the compositions of the invention can be administered in aerosols which operate via propellant gases or by means of so-called atomisers, via which solutions of pharmacologically-active substances can be sprayed under high pressure so that a mist of inhalable particles results. The advantage of these atomisers is that the use of propellant gases can be completely dispensed with.

Such atomisers are described, for example, in PCT Patent Application No. W0 91/14468 and International Patent Application No. WO 97/12687, reference here being made to the contents thereof.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the active ingredient (s) and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants eg oleic acid or lecithin and cosolvens eg ethanol. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1-10µ, preferably 2-5µ. Particles having a size above 20µ are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline.

Achieving high dose reproducibility with micronised powders is difficult because of their poor flowability and extreme agglomeration tendency. To improve the efficiency of dry powder compositions, the particles should be large while in the inhaler, but small when discharged into the respiratory tract. Thus, an excipient such as lactose or glucose is generally employed. The particle size of the excipient will usually be much greater than the inhaled medicament within the present invention. When the excipient is lactose it will typically be present as milled lactose, preferably crystalline alpha lactose monohydrate.

Pressurized aerosol compositions will generally be filled into canisters fitted with a valve, especially a metering valve. Canisters may optionally be coated with a plastics material e.g. a fluorocarbon polymer as described in W0 96/32150. Canisters will be fitted into an actuator adapted for buccal delivery.

Typical compositions for nasal delivery include those mentioned above for inhalation and further include non-pressurized compositions in the form of a solution or suspension in an inert vehicle such as water optionally in combination with conventional excipients such as buffers, anti-microbials, tonicity modifying agents and viscosity modifying agents which may be administered by nasal pump.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

The amount of each active which is required to achieve a therapeutic effect will, of course, vary with the particular active, the route of administration, the subject under treatment, and the particular disorder or disease being treated.

Effective doses are normally in the range of 1-2000 mg of active ingredient per day. Daily dosage may be administered in one or more treatments, preferably from 1 to 4 treatments, per day. Preferably, the active ingredients are administered once or twice a day.

Each dosage unit may contain for example from 0.1 mg to 1000 mg and preferably from 1 mg to 100 mg of a pyrazine derivative of the invention or a pharmaceutical acceptable salt thereof.

When combinations of actives are used, it is contemplated that all active agents would be administered at the same time, or very close in time. Alternatively, one or two actives could be taken in the morning and the other (s) later in the day. Or in another scenario, one or two actives could be taken twice daily and the other (s) once daily, either at the same time as one of the twice-a-day dosing occurred, or separately. Preferably at least two, and more preferably all, of the actives would be taken together at the same time. Preferably, at least two, and more preferably all actives would be administered as an admixture.

The active substance compositions according to the invention are preferably administered in the form of compositions for inhalation delivered with the help of inhalers, especially dry powder inhalers; however, any other form or parenteral or oral application is possible. Here, the application of inhaled compositions embodies the preferred application form, especially in the therapy of obstructive lung diseases or for the treatment of asthma.

The syntheses of the compounds of the invention and of the intermediates for use therein are illustrated by the following Examples (1 to 160) including Preparation Examples (Intermediates 1 to 30) which do not limit the scope of the invention in any way.

¹H Nuclear Magnetic Resonance Spectra were recorded on a Varian Mercury spectrometer operating at 200 MHz. Melting points were recorded using a Büchi B-540 apparatus. The chromatographic separations were obtained using a Waters 2795 system equipped with a Symmetry $C_{18}$ (2.1×100 mm, 3.5 mm) column. As detectors a Micromass ZMD mass spectrometer using ES ionization and a Waters 996 Diode Array detector were used. The mobile phase was formic acid (0.46 ml), ammonia (0.115 ml) and water (1000 ml) (A) and formic acid (0.4 ml), ammonia (0.1 ml), methanol (500 ml) and acetonitrile (500 ml) (B): initially from 0% to 95% of B in 20 min, and then 4 min. with 95% of B. The reequilibration time between two injections was 5 min. The flow rate was 0.4 ml/min. The injection volume was 5 μl. Diode array chromatograms were processed at 210 nm.

Preparation Examples

Preparation 1

Step a

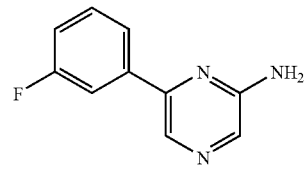

6-(3-Fluorophenyl)pyrazin-2-amine

To a stirred solution of 2-amino-6-chloropyrazine (2.0 g, 15.43 mmol) in a mixture of toluene (90 mL) and ethanol (8.5 mL) was added 3-fluorophenyl boronic acid (2.60 g, 18.51 mmol) and a 2M aqueous solution of sodium carbonate (16.2 mL, 32.40 mmol). The mixture was subjected to three cycles of evacuation-backfilling with argon, and tetrakis(triphenylphosphine)palladium (0.713 g, 0.617 mmol) was added. The mixture was subjected again to three cycles of evacuation-backfilling with argon the flask was capped and placed in a 110° C. oil bath. After 4 h, the mixture was cooled, partitioned between dichloromethane and water the organic layer was washed with brine, dried ($MgSO_4$) and evaporated. The residue was purified by silica gel flash chromatography (33% ethyl acetate in hexanes to 50% ethyl acetate in hexanes). Concentration in vaccuo of the product-rich fractions provided the titled compound (2.79 g, 95%) as a yellowish solid (2.79 g, 95%).

δ ¹H-NMR ($CDCl_3$): 8.38 (s, 1H), 7.95 (s, 1H), 7.60 (m, 2H), 7.40 (m, 1H), 4.65 (s, 2H).

Step b

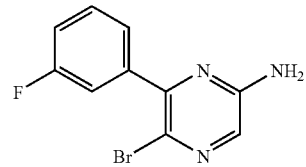

5-Bromo-6-(3-fluorophenyl)pyrazin-2-amine

To a 0° C. cooled stirred solution of 6-(3-fluorophenyl) pyrazin-2-ylamine (0.5 g, 2.64 mmol) in a mixture of DMSO (10 mL) and water (0.25 mL), was added N-bromosuccinimide (0.518 g, 2.90 mmol) in portions. After stirring for 5 h, the mixture was poured into water, the precipitate collected by filtration, washed with water and dried to give the title compound as a yellow solid (0.60 g, 85%).

δ ¹H-NMR (CDCl₃): 7.65 (s, 1H), 7.4 (m, 3H), 7.05 (m, 1H), 4.70 (s, 2H).
ESI/MS m/e: 268 ([M+H]⁺, C₁₀H₇BrFN₃).

Preparation 2

Step a

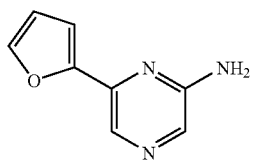

6-(2-Furyl)pyrazin-2-amine

Obtained as a yellowish solid (65%) from 6-chloropyrazin-2-ylamine and 2-furylboronic acid following the procedure of Preparation 1, step a.

δ ¹H-NMR (CDCl₃): 8.25 (s, 1H), 7.80 (s, 1H), 7.48 (d, 1H), 7.00 (d, 2H), 6.48 (m, 1H), 4.62 (bs, 2H).

Step b

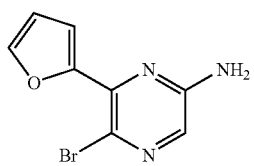

5-Bromo-6-(2-furyl)pyrazin-2-amine

Obtained as a brown solid (44%) from 6-furylpyrazin-2-ylamine and N-bromo succinimide following the procedure of Preparation 1, step b.

δ ¹H-NMR (CDCl₃): 7.62 (d, 2H), 7.58 (d, 1H), 7.58 (m, 1H), 4.75 (bs, 2H).

Preparation 3

Step a

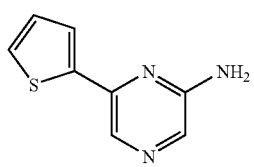

6-(2-Thienyl)pyrazin-2-amine

Obtained as a yellowish solid (39%) from 6-chloropyrazin-2-ylamine and thiophen-2-boronic acid following the procedure of Preparation 1, step a.

δ ¹H-NMR (CDCl₃): 8.02 (s, 1H), 7.61 (d, 1H), 7.42 (d, 1H), 7.05 (m, 1H), 5.05 (br, 2H).

Step b

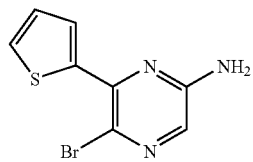

5-Bromo-6-(2-thienyl)pyrazin-2-amine

Obtained as a brown solid (14%) from 6-thiophen-2-ylpyrazin-2-ylamine and N-bromo succinimide following the procedure of Preparation 1, step b.

δ ¹H-NMR (CDCl₃): 8.35 (s, 1H), 7.80 (s, 1H), 7.60 (d, 1H), 7.43 (d, 1H), 7.15 (m, 1H), 4.60 (br, 2H).

Preparation 4

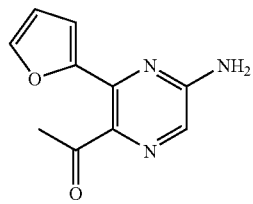

1-[5-Amino-3-(2-furyl)pyrazin-2-yl]ethanone

To a stirred solution of 5-bromo-6-(2-furyl)pyrazin-2-amine (Preparation 2, 1.5 g, 6.3 mmol) in a mixture of DMF (16 mL) and water (4 mL) was added butyl vinyl ether (4.10 mL, 31.5 mmol), potassium acetate (3.80 mL, 7.56 mmol), 1,3-bis-(diphenylphosphino)propane (0.172 g, 0.416 mmol) and palladium(II) acetate (42.0 mg, 0.189 mmol)[1]. The mixture was subjected to three cycles of evacuation-backfilling with argon and heated at 122° C. under microwave irradiation. After 4 h, the mixture was cooled to room temperature and hydrolyzed by adding of HCl 2N (30 mL) for 30 min. The mixture was then neutralized with a saturated solution of potassium carbonate and diluted with dichloromethane. The organic layer was separated, dried (Na₂SO₄) and evaporated. The residue was purified by silica gel flash chromatography (2% methanol in dichloromethane). Concentration in vacuo of the product-rich fractions provided the titled compound as a pale-yellow solid (0.77 g, 60%).

[1] K. S. A. Vallin, M. Larhed, A. Hallberg, *J. Org. Chem.*, 2001, 66, 4340.

δ ¹H-NMR (CDCl₃): 7.85 (s, 1H), 7.60 (d, 1H), 7.15 (d, 1H), 6.55 (dd, 1H), 5.05 (bs, 2H), 2.60 (s, 3H).
ESI/MS m/e: 204 ([M+H]⁺, C₁₀H₉N₃O₂)

Preparation 5

Step a

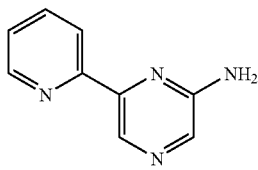

6-Pyridin-2-ylpyrazin-2-amine

An oven dried resealable Schlenk tube was charged with 2-amino-6-chloropyrazine (1.00 g, 7.72 mmol), 2-(tributyl-stannyl)pyridine (3.55 g, 7.72 mmol) and xylene (40 mL). The Schlenk tube was subjected to three cycles of evacuation-backfilling with argon, and tetrakis(triphenylphosphine)palladium (446 mg, 0.38 mmol) was added. After three new cycles of evacuation-backfilling with argon, the Schlenk tube was capped and placed in a 150° C. oil bath. After 20 h, the mixture was cooled, partitioned between water and ethyl acetate, the aqueous phase was extracted twice with ethyl acetate, the organic layers washed with brine, dried ($MgSO_4$) and evaporated. Silica gel flash chromatography (dichloromethane/methanol 98:2 to dichloromethane/methanol 90:10) provided the title compound as a light brown solid (950 mg, 71%).

δ $^1$H-NMR ($CDCl_3$): 8.90 (s, 1H), 8.70 (d, 1H), 8.20 (d, 1H), 8.00 (s, 1H), 7.80 (dd, 1H). 7.30 (m, 1H), 4.65 (s, 2H).

ESI/MS m/e: 173 ([M+H]$^+$, $C_9H_8N_4$)

Step b

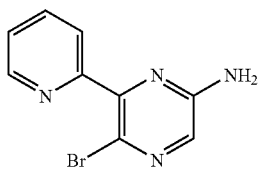

5-Bromo-6-pyridin-2-ylpyrazin-2-amine

Obtained as a brown solid (36%) from 6-pyridin-2-ylpyrazin-2-amine and N-bromosuccinimide following the procedure of Preparation 1, step b.

δ $^1$H-NMR ($CDCl_3$): 8.75 (d, 1H), 7.8 (m, 3H), 7.35 (m, 1H), 4.75 (s, 2H).

ESI/MS m/e: 252 ([M+H]$^+$, $C_9H_7BrN_4$)

Preparation 6

Step a

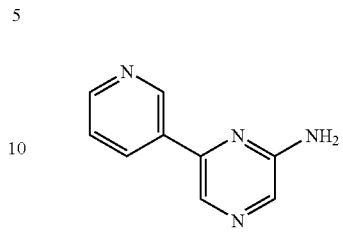

6-Pyridin-3-ylpyrazin-2-amine

An oven dried resealable Schlenk tube was charged with 6-chloropyrazin-2-amine (0.73 g, 5.71 mmol), 3-pyridineboronic acid (0.91 g, 7.42 mmol), dioxane (50 mL) and a 2M aqueous solution of cesium carbonate (8.5 mL, 17.13 mmol). The Schlenk tube was subjected to three cycles of evacuation-backfilling with argon, and 1,1'-bis(diphenylphosphino)ferrocene-palladium(II) dichloride dichloromethane complex (290 mg, 0.35 mmol) was added. After three new cycles of evacuation-backfilling with argon, the Schlenk tube was capped and placed in a 90° C. oil bath. After 16 h, the mixture was cooled, partitioned between water and ethyl acetate, the aqueous phase extracted twice with ethyl acetate, the organic layers washed with brine, dried ($MgSO_4$) and evaporated. The residue was purified by silica gel flash chromatography (95:5 dichloromethane/methanol) to give the title compound (845 mg, 86%) as a solid.

δ $^1$H-NMR ($CDCl_3$): 9.18 (s, 1H), 8.67 (d, 1H), 8.38 (s, 1H), 8.25 (m, 1H), 7.99 (s, 1H), 7.41 (m, 1H), 4.77 (s, 2H).

ESI/MS (m/e, %): 172 [(M+1)$^+$, $C_9H_8N_4$].

Step b

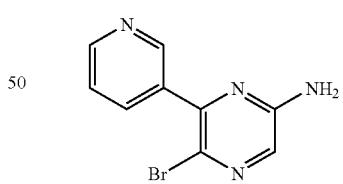

5-Bromo-6-pyridin-3-ylpyrazin-2-amine

Obtained as a brown solid (72%) from 6-pyridin-3-ylpyrazin-2-amine and N-bromosuccinimide following the procedure of Preparation 1, step b.

δ $^1$H-NMR ($CDCl_3$): 8.93 (s, 1H), 8.65 (d, 1H), 8.10 (m, 1H), 7.80 (s, 1H), 7.43 (dd, 1H).

ESI/MS (m/e, %): 251 [(M+1)$^+$, $C_9H_7BrN_4$]

Preparation 7

Step a

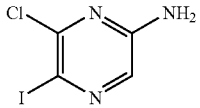

6-Chloro-5-iodo-4-ylpyrazin-2-amine

To a 0° C. cooled stirred solution of 2-amino-6-chloropyrazine (3 g, 23 mmol) in a mixture of DMSO (90 mL) and water (2.2 mL), was added N-iodosuccinimide (5.2 g, 23 mmol) in portions. After stirring for 72 h, the mixture was poured into water, extracted twice with ethyl acetate, the organic layers washed with brine, dried (MgSO$_4$) and evaporated. Flash chromatography (98:2 dichloromethane/methanol) furnished the title compound as a yellow solid (4.43 g, 76%).

δ $^1$H-NMR (CDCl$_3$): 7.73 (s, 1H), 4.72 (s, 2H).
ESI/MS (m/e, %): 255 [(M+1)$^+$, C$_4$H$_3$ClIN$_3$].

Step b

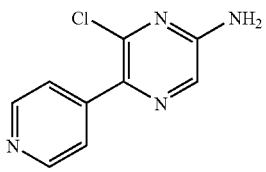

6-Chloro-5-pyridin-4-ylpyrazin-2-amine

An oven dried resealable Schlenk tube was charged with 6-chloro-5-iodo-4-ylpyrazin-2-amine (1.68 g, 6.57 mmol), 4-(4,4,5,5-tetramethyl-1,3,2-dioxaborolan-2-yl)pyridine (1.61 g, 7.89 mmol), dioxane (120 mL) and a 2M aqueous solution of cesium carbonate (10 mL, 20 mmol). The Schlenk tube was subjected to three cycles of evacuation-backfilling with argon, and 1,1'-bis(diphenylphosphino)ferrocene-palladium(II) dichloride dichloromethane complex [PdCl2dppf.DCM] (322 mg, 0.39 mmol) was added. After three new cycles of evacuation-backfilling with argon, the Schlenk tube was capped and placed in a 90° C. oil bath. After 20 h, the mixture was cooled, partitioned between water and ethyl acetate, the aqueous phase extracted twice with ethyl acetate, the organic layers washed with brine, dried (MgSO$_4$) and evaporated. The residue was triturated with diethyl ether and methanol and the precipitate was collected by filtration and dried to furnish the title compound as a light brown solid (0.85 g, 63%).

δ $^1$H-NMR (DMSO-d$_6$): 8.60 (d, 2H), 7.95 (s, 1H), 7.65 (d, 2H), 7.20 (s, 2H).
ESI/MS m/e: 206 ([M+H]$^+$, C$_9$H$_7$ClN$_4$)

Preparation 8

N-(6-Chloro-5-pyridin-4-ylpyrazin-2-yl)cyclopropanecarboxamide

To a stirred solution of 6-chloro-5-pyridin-4-ylpyrazin-2-amine (Preparation 7, 0.73 g, 3.56 mmol) in pyridine (15 mL) was added cyclopropanecarbonyl chloride (648 μL, 7.1 mmol). The solution was stirred at 70° C. for 1 h 30 min, evaporated, partitioned between dichloromethane and a 4% sodium bicarbonate aqueous solution, the aqueous phase extracted twice with dichloromethane, the organic layers washed with brine, dried (MgSO$_4$) and evaporated. The residue was triturated with diethyl ether and methanol and the precipitate was collected by filtration and dried to furnish the title compound as a light brown solid (0.69 g, 70%).

δ $^1$H-NMR (DMSO-d$_6$): 9.55 (s, 1H), 8.75 (d, 2H), 8.55 (s, 1H), 7.75 (d, 2H), 1.65 (m, 1H), 1.2 (m, 2H), 0.95 (m, 2H).
ESI/MS m/e: 274 ([M+H]$^+$, C$_{13}$H$_{11}$ClN$_4$O)

Preparation 9

6-Chloro-5-(3-chloropyridin-4-yl)pyrazin-2-amine

An oven dried resealable Schlenk tube was charged with 6-chloro-5-iodo-4-ylpyrazin-2-amine (Preparation 7 step a, 1.02 g, 3.98 mmol), 3-cloro-4-(tributylstannyl)pyridine[1] (1.76 g, 4.38 mmol) and dimethylformamide (15 mL). The Schlenk tube was subjected to three cycles of evacuation-backfilling with argon, and bis(triphenylphosphino)-palladium (II) chloride (129 mg, 0.185 mmol) and copper (I) iodide (77 mg, 0.040 mmol) were added. After three new cycles of evacuation-backfilling with argon, the Schlenk tube was capped and placed in a 160° C. oil bath. After 20 h, the mixture was cooled, partitioned between water and ethyl acetate, the aqueous phase extracted twice with ethyl acetate, the organic layers washed twice with water, brine, dried (MgSO$_4$) and evaporated. Silica gel flash chromatography (98:2 dichloromethane/methanol) provided the title compound as a solid (0.72 g, 74%).

[1] Prepared according to Yue et al. Org. Lett. 2002, 4(13), 2201-2203.

δ $^1$H-NMR (CDCl$_3$): 8.72 (s, 1H), 8.59 (d, 1H), 7.99 (s, 1H), 7.35 (d, 1H), 4.95 (s, 2H).
ESI/MS (m/e, %): 240 [(M+1)$^+$, C$_9$H$_6$Cl$_2$N$_4$].

Preparation 10

Step a

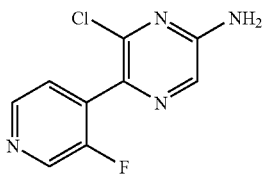

6-Chloro-5-(3-fluoropyridin-4-yl)pyrazin-2-amine

Obtained as a yellowish solid (57%) from 6-chloro-5-iodo-4-ylpyrazin-2-amine and 3-fluoro-4-(tributylstannyl)pyridine[(2)] following the procedure of Preparation 9.

[(2)]Prepared according to EP1104754 (Reference Example 197)

δ $^1$H-NMR (DMSO-d$_6$): 8.65 (s, 1H), 8.45 (d, 1H), 7.90 (s, 1H), 7.55 (t, 1H), 7.30 (s, 2H).

ESI/MS m/e: 224 ([M+H]$^+$, C$_9$H$_6$ClFN$_4$)

Step b

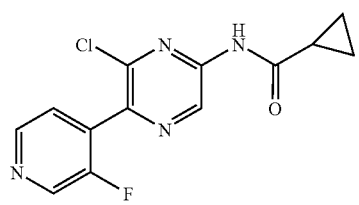

N-[6-Chloro-5-(3-fluoropyridin-4-yl)pyrazin-2-yl]cyclopropanecarboxamide

Obtained as a brown solid (78%) from 6-chloro-5-(3-fluoropyridin-4-yl)pyrazin-2-amine and cyclopropanecarbonyl chloride (607 μL, 6.67 mmol) following the same procedure as in Preparation 8.

δ $^1$H-NMR (CDCl$_3$): 9.58 (s, 1H), 8.62 (s, 1H), 8.58 (d, 1H), 8.22 (bs, 1H), 7.50 (dd, 1H), 1.65 (m, 1H), 1.2 (m, 2H), 0.95 (m, 2H).

ESI/MS m/e: 292 ([M+H]$^+$, C$_{13}$H$_{10}$ClFN$_4$O)

Preparation 11

Step a

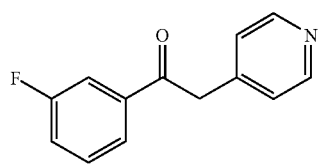

1-(3-Fluorophenyl)-2-pyridin-4-ylethanone

To a solution of ethyl 3-fluorobenzoate (2.0 g, 11.9 mmol) and 4-methylpyridine (1.1 mL, 1.0 g, 10.8 mmol) in THF (9 mL) at 0° C. under nitrogen atmosphere was added dropwise lithium bis(trimethylsilyl)amide (23.8 mL, 1.0M in hexane, 23.8 mmol) During the addition a precipitate was formed and the suspension was stirred at room temperature overnight. The reaction was diluted with hexane (40 mL) and filtered. The solid was partitioned between ethyl acetate and a saturated solution of ammonium chloride. The organic phase was dried (MgSO$_4$) and evaporated under reduced pressure to give the title compound as a yellow solid (2.09 g, 82%).

δ $^1$H-NMR (CDCl$_3$): 8.58 (d, 2H), 7.75 (m, 1H), 7.46 (m, 1H), 7.28 (m, 2H), 7.20 (d, 2H), 4.26 (s, 2H).

ESI/MS m/e: 216 ([M+H]$^+$, C$_{13}$H$_{10}$FNO)

Step b

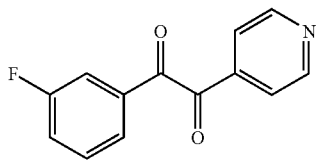

1-(3-Fluorophenyl)-2-pyridin-4-ylethane-1,2-dione

Hydrobromic acid (7.9 mL, 48% in H$_2$O, 69.7 mmol) was added with caution to a stirred solution of 1-(3-fluorophenyl)-2-pyridin-4-ylethanone (5.0 g, 23.2 mmol) in DMSO (40 mL) at 55° C. The reaction was stirred for 2 h and then allowed to cool to room temperature. Water was added and the aqueous phase was neutralized with solid sodium carbonate and extracted twice with ethyl acetate. The organic extracts were washed with brine, dried (MgSO$_4$) and evaporated under reduced pressure to provide the title compound as a yellow solid (2.85 g, 67%).

δ $^1$H-NMR (CDCl$_3$): 8.88 (d, 2H), 7.79 (d, 2H), 7.72 (m, 2H), 7.60-7.34 (m, 2).

GC/MS m/e: 229 (M$^+$, C$_{13}$H$_8$FNO$_2$)

Step c

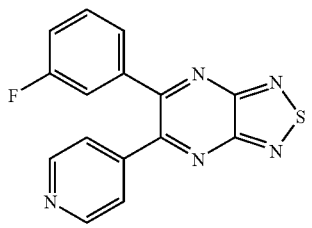

5-(3-Fluorophenyl)-6-pyridin-4-yl[1,2,5]thiadiazolo[3,4-b]pyrazine

A mixture of 1-(3-fluorophenyl)-2-pyridin-4-ylethane-1,2-dione (1.5 g, 6.5 mmol) and 1,2,5-thiadiazole-3,4-diamine (1.1 g, 9.8 mmol) in AcOH (30 mL) was stirred and heated at reflux for 1 h. The mixture was cooled to room temperature and the solvent was removed under reduced pressure. The residue was partitioned between ethyl acetate and a solution of NaHCO3 4%. The organic phase was dried (MgSO$_4$) and evaporated to dryness to give the title compound as a dark oil (1.7 g, 82%).

δ $^1$H-NMR (CDCl$_3$): 8.68 (d, 2H), 7.81 (m, 2H), 7.44 (d, 2H), 7.40-7.20 (m, 2H).
ESI/MS m/e: 216 ([M+H]$^+$, C$_{15}$H$_8$FN$_5$S)

Preparation 12

Step a

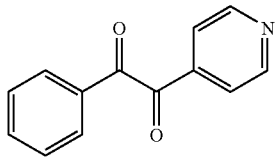

1-Phenyl-2-pyridin-4-ylethane-1,2-dione

Obtained (74%) from 1-phenyl-2-pyridin-4-ylethanone following the procedure described in Preparation 11, step b.
δ $^1$H-NMR (CDCl$_3$): 8.90 (d, 2H), 8.00 (d, 2H), 7.79 (d, 2H), 7.71 (d, 1H), 7.68 (t, 2H).

Step b

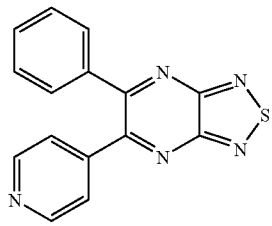

5-Phenyl-6-pyridin-4-yl[1,2,5]thiadiazolo[3,4-b]pyrazine

Obtained (97%) from 1-phenyl-2-pyridin-4-ylethane-1,2-dione and 1,2,5-thiadiazole-3,4-diamine following the procedure described in Preparation 11, step c.
ESI/MS m/e: 292 ([M+H]+, C$_{15}$H$_9$N$_5$S)

Preparation 13

Step a

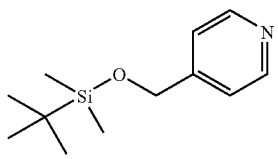

4-({[tert-Butyl(dimethyl)silyl]oxy}methyl)pyridine

A mixture of pyridin-4-ylmethanol (8.0 g, 73 mmol), tert-butyldimethylsilyl chloride (14.3 g, 95 mmol) and imidazole (12.9 g, 0.19 mol) in DMF (40 mL) was stirred overnight at room temperature. The reaction was poured onto water and extracted twice with ethyl acetate. The combined organic phases were dried (MgSO$_4$) and evaporated under reduced pressure to yield the title compound as yellow oil (7.5 g, 46%).
δ $^1$H-NMR (CDCl$_3$): 8.42 (d, 2H), 7.19 (d, 2H), 4.64 (s, 2H), 0.81 (brs, 12H), 0.00 (s, 6H).

Step b

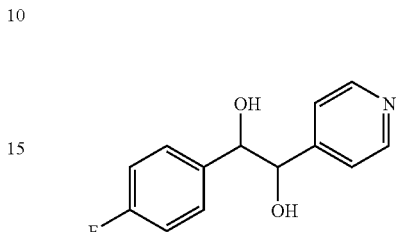

1-(4-Fluorophenyl)-2-pyridin-4-ylethane-1,2-diol

To a cooled solution (−78° C.) of diisopropylamine (6.3 mL, 4.5 g, 45 mmol), n-butyllithium (30 mL, 1.6 N in hexanes) was added dropwise under nitrogen atmosphere. After stirring for 30 min. at 0° C., the mixture was cooled to −20° C. and a solution of 4-({[tert-butyl(dimethyl)silyl]oxy}methyl)pyridine (7.5 g, 34 mmol) in THF (24 mL) was added dropwise. 30 min later a solution of 4-fluorobenzaldehyde (4.4 mL, 5.1 g, 41 mmol) in THF (10 mL) was finally added. The reaction was allowed to reach room temperature and quenched with water and a saturated solution of ammonium chloride. The crude product was recovered with diethyl ether.
The resulting yellow oil was redissolved in THF (210 mL) and treated with TBAF. 3H$_2$O (5.4 g, 17 mmol) stirring at room temperature for 1 hour. The solvent was evaporated under vacuum and the residue partitioned between water and ethyl acetate. The organic phase was dried (MgSO$_4$), concentrated and the solid obtained was washed with diethyl ether to provide the title compound as a yellow solid (4.0 g, 51%).
ESI/MS m/e: 234 ([M+H]$^+$, C$_{13}$H$_{12}$FO$_2$)

Step c

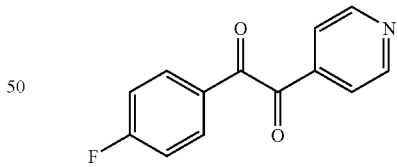

1-(4-Fluorophenyl)-2-pyridin-4-ylethane-1,2-dione

To a stirred cooled solution (−60° C.) of oxalyl chloride (3.55 mL, 40.8 mmol) in CH$_2$Cl$_2$ (16 mL) a solution of dimethyl sulfoxide (4.0 mL) in CH$_2$Cl$_2$ was added dropwise. Five minutes later a solution of 1-(4-fluorophenyl)-2-pyridin-4-ylethane-1,2-diol (4.0 g, 17 mmols) in DMSO/CH$_2$Cl$_2$ (32 mL/13 mL) was dropped. The mixture was allowed to stir for 30 min at −60° C. and then triethylamine (24 mL) was added. When the reaction reached room temperature was diluted with water and dichloromethane. The organic phases were washed with water and brine and dried (MgSO$_4$). After removal of the solvent under vacuum, the resulting solid was triturated with hexane to afford the title compound as an orange solid (3.68 g, 94%).

δ $^1$H-NMR (CDCl$_3$): 8.90 (d, 2H), 8.01 (m, 2H), 7.79 (d, 2H), 7.22 (dd, 2H).

Step d

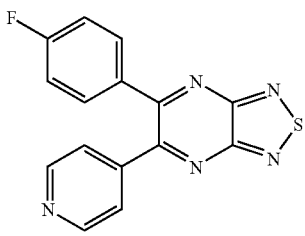

5-(4-Fluorophenyl)-6-pyridin-4-yl[1,2,5]thiadiazolo [3,4-b]pyrazine

Obtained as an orange solid (81%) from 1-(4-fluorophenyl)-2-pyridin-4-ylethane-1,2-dione and 1,2,5-thiadiazole-3,4-diamine following the procedure described in Preparation 11, step c.

ESI/MS m/e: 310 ([M+H]+, C$_{15}$H$_8$FN$_5$S)

Preparation 14

Step a

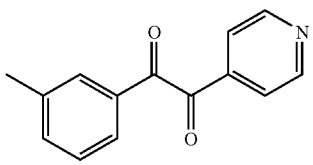

1-(3-Methylphenyl)-2-pyridin-4-ylethane-1,2-dione

Obtained (73%) from 1-(3-methylphenyl)-2-pyridin-4-ylethanone following the procedure described in Preparation 11, step b.

δ $^1$H-NMR (CDCl$_3$): 8.87 (d, 2H), 7.79 (d+s, 2H+2H), 7.48 (m, 2H), 2.41 (s, 3H).

Step b

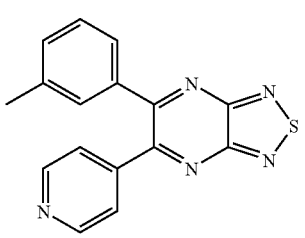

5-(3-Methylphenyl)-6-pyridin-4-yl[1,2,5]thiadiazolo [3,4-b]pyrazine

Obtained from 1-(3-methylphenyl)-2-pyridin-4-ylethane-1,2-dione and 1,2,5-thiadiazole-3,4-diamine following the procedure described in Preparation 11, step c.

δ $^1$H-NMR (CDCl$_3$): 8.64 (d, 2H), 7.43 (d+s, 2H+1H), 7.32-7.18 (m, 3H), 2.38 (s, 3H).

ESI/MS m/e: 306 ([M+H]+, C$_{16}$H$_{11}$N$_5$S)

Preparation 15

Step a

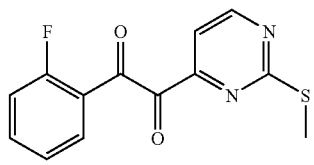

1-(2-Fluorophenyl)-2-[2-(methylthio)pyrimidin-4-yl] ethane-1,2-dione

Obtained (93%) from 1-(2-fluorophenyl)-2-[2-(methylthio)pyrimidin-4-yl]ethanone following the procedure described in Preparation 11, step b.

δ $^1$H-NMR (CDCl$_3$): 8.81 (d, 1H), 8.10 (t, 1H), 7.64 (m+d, 1H+1H), 7.39 (t, 1H), 7.26 (s, 1H), 7.15 (t, 1H), 2.22 (s, 3H).

ESI/MS m/e: 277 ([M+H]+, C$_{13}$H$_9$FN$_2$O$_2$S)

Step b

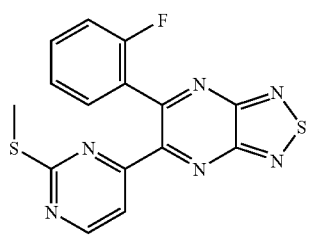

5-(2-Fluorophenyl)-6-[2-(methylthio)pyrimidin-4-yl] [1,2,5]thiadiazolo[3,4-b]pyrazine Obtained (97%) from 1-(2-fluorophenyl)-2-[2-(methylthio)pyrimidin-4-yl]ethane-1,2-dione and 1,2,5-thiadiazole-3,4-diamine following the procedure described in Preparation 11, step c.

δ $^1$H-NMR (CDCl$_3$): 8.79 (d, 1H), 7.96-7.84 (m, 2H), 7.49-7.38 (m, 2H), 6.98 (t, 3H), 1.91 (s, 3H).

Preparation 16

Step a

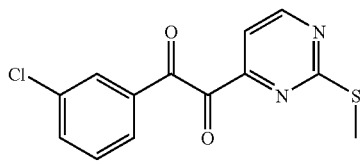

1-(3-Chlorophenyl)-2-[2-(methylthio)pyrimidin-4-yl]ethane-1,2-dione

Obtained (77%) from 1-(3-chlorophenyl)-2-[2-(methylthio)pyrimidin-4-yl]ethanone, following the procedure described in Preparation 11, step b.

δ $^1$H-NMR (CDCl$_3$): 8.85 (d, 1H), 7.91 (s, 1H), 7.77 (d, 1H), 7.66-7.63 (m, 2H), 7.50 (t, 1H), 2.36 (s, 3H).

Step b

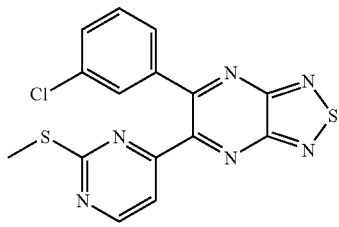

5-(3-Chlorophenyl)-6-[2-(methylthio)pyrimidin-4-yl][1,2,5]thiadiazolo[3,4-b]pyrazine Obtained (39%) from 1-(3-chlorophenyl)-2-[2-(methylthio)pyrimidin-4-yl]ethane-1,2-dione and 1,2,5-thiadiazole-3,4-diamine following the procedure described in Preparation 11, step c.

ESI/MS m/e: 373 ([M+H]+, C$_{15}$H$_9$ClN$_6$S$_2$)

Preparation 17

Step a

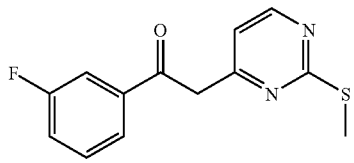

2-(3-Fluorophenyl)-1-[2-(methylthio)pyrimidin-4-yl]ethanone

Following the same procedure as in Preparation 11, step a, the title compound was obtained (88% yield) from ethyl 3-fluorobenzoate and 4-methyl-2-(methylthio) pyrimidine.

δ $^1$H-NMR (CDCl$_3$): exists as a 2:1 mixture of enol:keto tautomers: 8.44 (d, 1H, keto form), 8.34 (d, 1H, enol form), 7.88-7.03 (m, 4H, enol+keto form), 6.99 (d, 1H, keto form), 6.63 (d, 1H, enol form), 5.98 (s, 1H, enol from), 4.36 (s, 2H, keto form), 2.98 (s, 3H, enol+keto form).

ESI/MS m/e: 263 ([M+H]$^+$, C$_{13}$H$_{11}$FN$_2$OS)

Step b

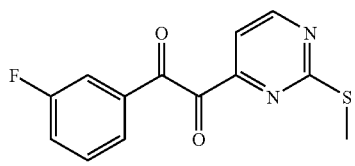

1-(3-Fluorophenyl)-2-[2-(methylthio)pyrimidin-4-yl]ethane-1,2-dione

Following the same procedure as in Preparation 11, step b, the title compound was obtained after purification of the crude by silica gel chromatography eluting with 5% MeOH/CH$_2$Cl$_2$ to afford the title compound as yellow oil (0.34 g, 10%).

δ $^1$H-NMR (CDCl$_3$): 8.83 (d, 1H), 7.62 (d, 1H), 7.62-7.36 (m, 4H), 2.36 (s, 3H).

GC/MS m/e: 276 ([M+H]$^+$, C$_{13}$H$_9$FN$_2$O$_2$S)

Step c

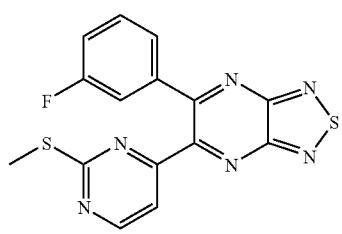

5-(3-Fluorophenyl)-6-[2-(methylthio)pyrimidin-4-yl][1,2,5]thiadiazolo[3,4-b]pyrazine Following the same procedure as in Preparation 11, step c, the title compound was obtained after purification of the crude by silica gel column chromatography with hexane/AcOEt 3:1 to afford the title compound as a yellow solid (0.21 g, 47%).

ESI/MS m/e: 357 ([M+H]$^+$, C$_{15}$H$_9$FN$_6$S$_2$)

Preparation 18

Step a

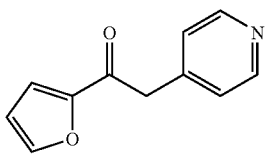

1-(2-Furyl)-2-pyridin-4-ylethanone

Obtained as an orange solid (75%) from ethyl 2-furoate and 4-methylpyridine following the procedure described in Preparation 11, step a.

δ $^1$H-NMR (DMSO-d$_6$): 8.50 (d, 2H), 8.04 (s, 1H), 7.66 (m, 1H), 7.32 (d, 2H), 6.78 (m, 1H).

ESI/MS m/e: 188 ([M+H]$^+$, C$_{11}$H$_9$NO$_2$)

Step b

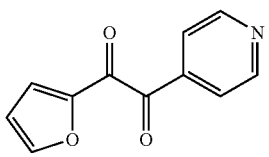

1-(2-Furyl)-2-pyridin-4-ylethane-1,2-dione

Obtained as a brown solid (78%) from 1-(2-furyl)-2-pyridin-4-ylethanone following the procedure described in Preparation 11, step b.

δ $^1$H-NMR (CDCl$_3$): 8.86 (d, 2H), 7.84 (d, 2H+s, 1H), 7.52 (d, 1H), 6.64 (d, 1H).

GC/MS m/e: 201 (M$^+$, C$_{11}$H$_7$NO$_3$)

Step c

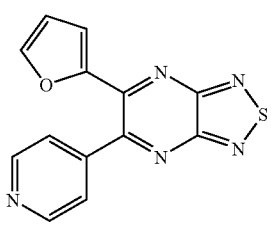

5-(2-Furyl)-6-pyridin-4-yl[1,2,5]thiadiazolo[3,4-b]pyrazine

Obtained as a brown solid (92%) from 1-(2-furyl)-2-pyridin-4-ylethane-1,2-dione and 1,2,5-thiadiazole-3,4-diamine following the procedure described in Preparation 11, step c.

δ $^1$H-NMR (DMSO-d$_6$): 8.78 (d, 2H), 7.81 (m, 2H), 7.96 (s, 1H), 7.62 (s, 1H), 6.70 (m, 2H).

ESI/MS m/e: 282 ([M+H]$^+$, C$_{13}$H$_7$N$_5$OS)

Preparation 19

Step a

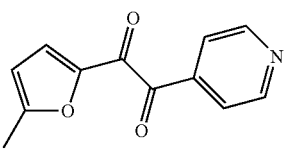

1-(5-Methyl-2-furyl)-2-pyridin-4-ylethane-1,2-dione

Obtained (28%) from 1-(5-methyl-2-furyl)-2-pyridin-4-ylethanone (crude product), following the procedure described in Preparation 11, step b.

GC/MS m/e: 215 (M$^+$, C$_{12}$H$_9$NO$_3$)

Step b

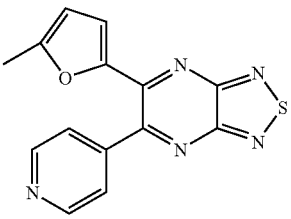

5-(5-Methyl-2-furyl)-6-pyridin-4-yl[1,2,5]thiadiazolo[3,4-b]pyrazine

Obtained (82%) from 1-(5-methyl-2-furyl)-2-pyridin-4-ylethane-1,2-dione and 1,2,5-thiadiazole-3,4-diamine, following the procedure described in Preparation 11, step c.

ESI/MS m/e: 296 ([M+H]$^+$, C$_{14}$H$_9$N$_5$OS)

Preparation 20

Step a

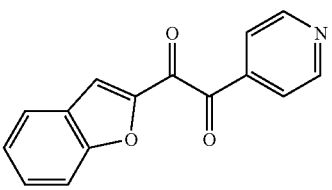

1-(1-Benzofuran-2-yl)-2-pyridin-4-ylethane-1,2-dione

Obtained (87%) from 1-(1-benzofuran-2-yl)-2-pyridin-4-ylethanone, following the procedure described in Preparation 11, step b.
GC/MS m/e: 251 ([M+H]+, $C_{15}H_9NO_3$)

Step b

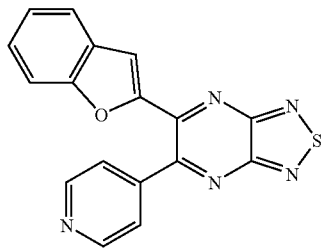

5-(1-Benzofuran-2-yl)-6-pyridin-4-yl[1,2,5]thiadiazolo[3,4-b]pyrazine

Obtained (74%) from 1-(1-benzofuran-2-yl)-2-pyridin-4-ylethane-1,2-dione and 1,2,5-thiadiazole-3,4-diamine, following the procedure described in Preparation 11, step c.
ESI/MS m/e: 332 ([M+H]+, $C_{17}H_9N_5OS$)

Preparation 21

Step a

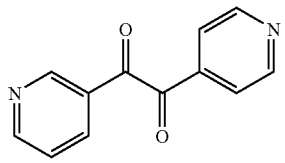

1-Pyridin-3-yl-2-pyridin-4-ylethane-1,2-dione

Obtained (30%) from 1-pyridin-3-yl-2-pyridin-4-ylethanone following the procedure described in Preparation 11, step b.
GC/MS m/e: 212 (M+, $C_{12}H_2N_2O_2$)

Step b

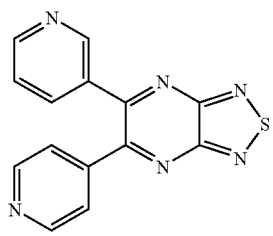

5-Pyridin-3-yl-6-pyridin-4-yl[1,2,5]thiadiazolo[3,4-b]pyrazine

Obtained (55%) from 1-pyridin-3-yl-2-pyridin-4-ylethane-1,2-dione and 1,2,5-thiadiazole-3,4-diamine, following the procedure described in Preparation 11, step c.
ESI/MS m/e: 293 ([M+H]+, $C_{14}H_8N_6S$)

Preparation 22

Step a

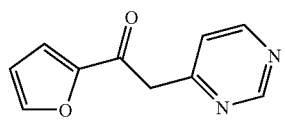

1-(2-Furyl)-2-pyrimidin-4-ylethanone

Obtained as a yellow solid (91%) from ethyl 2-furoate and 4-methylpyrimidine following the procedure described in Preparation 11, step a.
δ $^1$H-NMR (DMSO-$d_6$) exists as a 1.2:1 mixture of enol:keto tautomers: enol form: 14.6 (brs, 1H), 9.09 (s, 1H), 8.63 (brs, 1H), 8.78 (d, 1H), 8.03 (s, 1H), 7.62 (d, 1H), 7.04 (m, 1H), 6.63 (brs, 1H), 6.01 (s, 1H); keto form: 8.78 (d, 1H), 8.21 (d, 1H), 7.86 (s, 1H), 7.58 (d, 1H), 7.04 (m, 1H), 6.79 (m, 1H), 4.40 (s, 2H)
ESI/MS m/e: 189 ([M+H]+, $C_{10}H_8N_2O_2$)

Step b

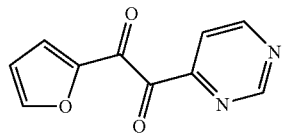

1-(2-Furyl)-2-pyrimidin-4-ylethane-1,2-dione

Obtained as a brown oil (82%) from 1-(2-furyl)-2-pyrimidin-4-ylethanone following the procedure described in Preparation 11, step b.
ESI/MS m/e: 203 ([M+H]+, $C_{10}H_6N_2O_3$)

Step c

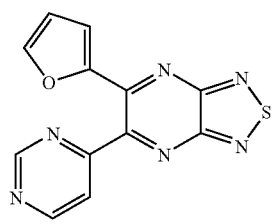

5-(2-Furyl)-6-pyrimidin-4-yl[1,2,5]thiadiazolo[3,4-b]pyrazine

Obtained as a brown solid (82%) from 1-(2-furyl)-2-pyrimidin-4-ylethane-1,2-dione and 1,2,5-thiadiazole-3,4-diamine following the procedure described in Preparation 11, step c.

δ $^1$H-NMR (DMSO-$d_6$): 9.05 (s, 1H), 8.90 (d, 1H), 7.79 (d, 1H), 7.59 (s, 1H), 6.78 (m, 1H), 6.45 (m, 1H).

ESI/MS m/e: 283 ([M+H]$^+$, $C_{12}H_6N_6OS$)

Preparation 23

Step a

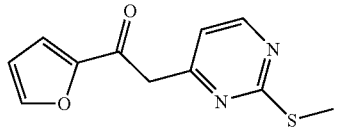

1-(2-Furyl)-2-[2-(methylthio)pyrimidin-4-yl]ethanone

Obtained as a yellow solid (73%) from ethyl 2-furoate and 4-methyl-2-(methylthio) pyrimidine following the procedure described in Preparation 11, step a.

δ $^1$H-NMR (CDCl$_3$):(most in enol form): 7.89 (d, 1H), 7.18 (brs, 1H), 6.59 (m, 1H), 6.24 (d, 1H), 6.20 (brs, 1H), 5.41 (s, 1H), 2.21 (s, 1H).

ESI/MS m/e: 235 ([M+H]$^+$, $C_{11}H_{10}N_2O_2S$)

Step b

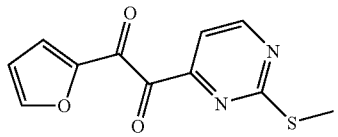

1-(2-Furyl)-2-[2-(methylthio)pyrimidin-4-yl]ethane-1,2-dione

Obtained as a brown oil (68%) from 1-(2-furyl)-2-[2-(methylthio)pyrimidin-4-yl]ethanone following the procedure described in Preparation 11, step b.

δ $^1$H-NMR (CDCl$_3$): 8.82 (d, 1H), 7.79 (d, 1H), 6.62 (d, 1H), 7.40 (d, 1H), 6.65 (d, 1H), 2.20 (s, 3H).
ESI/MS m/e: 249 ([M+H]$^+$, $C_{11}H_8N_2O_3S$)

Step c

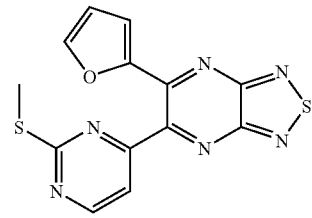

5-(2-Furyl)-6-[2-(methylthio)pyrimidin-4-yl][1,2,5]thiadiazolo[3,4-b]pyrazine

Obtained as a brown solid (82%) from 1-(2-furyl)-2-[2-(methylthio)pyrimidin-4-yl]ethane-1,2-dione and 1,2,5-thiadiazole-3,4-diamine following the procedure described in Preparation 11, step c.

δ $^1$H-NMR (CDCl$_3$): 8.80 (d, 1H), 7.59 (d, 1H), 7.47 (s, 1H), 7.21 (brs, 1H), 6.59 (brs, 1H), 2.34 (s, 3H).
ESI/MS m/e: 329 ([M+H]$^+$, $C_{13}H_8N_6OS_2$)

Preparation 24

Step a

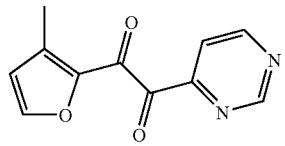

1-(3-Methyl-2-furyl)-2-pyrimidin-4-ylethane-1,2-dione

Obtained (91%) from 1-(3-methyl-2-furyl)-2-pyrimidin-4-ylethanone, following the procedure described in Preparation 11, step b.

δ $^1$H-NMR (CDCl$_3$): 9.39 (s, 1H), 9.10 (d, 1H), 8.03 (d, 1H), 7.50 (s, 1H), 6.52 (s, 1H), 2.46 (s, 3H).
GC/MS m/e: 216 ([M+H]+, $C_{11}H_8N_2O_3$)

Step b

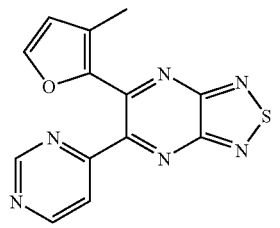

5-(3-Methyl-2-furyl)-6-pyrimidin-4-yl[1,2,5]thiadiazolo[3,4-b]pyrazine

Obtained (80%) from 1-(3-methyl-2-furyl)-2-pyrimidin-4-ylethane-1,2-dione, following the procedure described in Preparation 11, step c.
ESI/MS m/e: 297 ([M+H]+, $C_{13}H_8N_6OS$)

Preparation 25

Step a

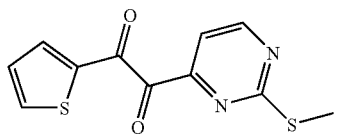

1-[2-(Methylthio)pyrimidin-4-yl]-2-(2-thienyl)ethane-1,2-dione

Obtained (99%) from 2-[2-(methylthio)pyrimidin-4-yl]-1-(2-thienyl)ethanone, following the procedure described in Preparation 11, step b.
δ $^1$H-NMR (CDCl$_3$): 8.82 (d, 1H), 7.89 (d, 1H), 7.68 (brs, 1H), 7.61 (d, 1H), 7.10 (brs, 1H), 2.21 (s, 3H).

Step b

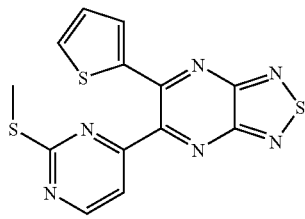

5-[2-(Methylthio)pyrimidin-4-yl]-6-(2-thienyl)[1,2,5]thiadiazolo[3,4-b]pyrazine

Obtained (70%) from 1-[2-(methylthio)pyrimidin-4-yl]-2-(2-thienyl)ethane-1,2-dione, following the procedure described in Preparation 11, step c.
δ $^1$H-NMR (DMSO-d$_6$): 8.99 (d, 1H), 7.91 (d, 1H), 7.72 (d, 1H), 7.13 (dd, 1H), 6.88 (brs, 1H), 2.39 (s, 3H).
ESI/MS m/e: 332 ([M+H]+, $C_{17}H_9N_5OS$)

Preparation 26

Step a

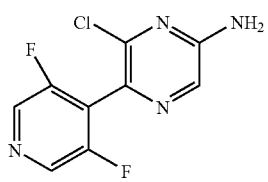

6-Chloro-5-(3,5-difluoropyridin-4-yl)pyrazin-2-amine

Obtained as an orange oil (42%) from 6-chloro-5-iodo-4-ylpyrazin-2-amine and 3,5-difluoro-4-(tributylstannyl)pyridine following the procedure of Preparation 9.
$^1$H-NMR (CDCl$_3$): 8.50 (s, 1H), 7.70 (m, 1H), 7.50 (m, 1H), 5.20 (s, 2H).
ESI/MS m/e: 242 ([M+H]$^+$, $C_9H_5ClF_2N_4$).

Step b

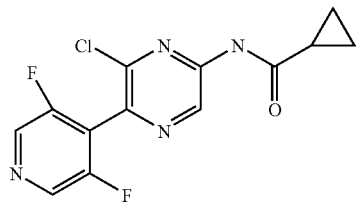

N-[6-Chloro-5-(3,5-difluoropyridin-4-yl)pyrazin-2-yl]cyclopropanecarboxamide

Obtained as a light yellow solid (40%) from 6-Chloro-5-(3,5-difluoropyridin-4-yl)pyrazin-2-amine and cyclopropanecarbonyl chloride following the same procedure of Preparation 8.

$^1$H-NMR (CDCl$_3$): 9.60 (s, 1H), 8.45 (s, 2H), 8.20 (s, 1H), 1.60 (m, 1H), 1.20 (m, 2H), 1.00 (m, 2H).

ESI/MS m/e: 311 [M+H]$^+$, $C_{13}H_9ClF_2N_4O$)

Preparation 27

Step a

N-(5-Bromo-6-pyridin-3-ylpyrazin-2-yl)cyclopropanecarboxamide

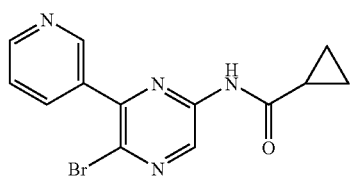

Obtained as a white solid (79%) from 5-bromo-6-pyridin-3-ylpyrazin-2-amine (Preparation 6) and cyclopropanecarbonyl chloride following the same procedure of Preparation 8.

Step b

N-[5-Bromo-6-(1-oxidopyridin-3-yl)pyrazin-2-yl]cyclopropanecarboxamide

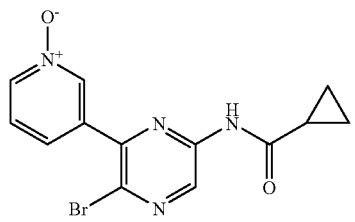

To a suspension of N-(5-bromo-6-pyridin-3-ylpyrazin-2-yl)cyclopropanecarboxamide (4.02 g, 12.6 mmol) in $CH_2Cl_2$ (45 mL), cooled at 0° C., was added mCPBA (3.11 g, 12.6 mmol) in small portions. Upon addition completion the ice bath was removed and the reaction continued at room temperature for 4 h. The mixture was diluted with $CH_2Cl_2$ (30 mL) and washed with saturated $NaHCO_3$ (1×25 mL) and saturated NaCl (1×25 mL). The organic layer was concentrated in vaccuo up to 25 mL volume, and the precipitated product was filtered and washed with $Et_2O$ (4×5 mL), giving the title compound as a white powder (3.03 g, 72% yield).

$^1$H-RMN (DMSO-$d_6$, 250 MHz, δ): 9.18 (s, 1H); 8.56 (s, 1H); 8.37 (d, 1H); 7.67 (d, 1H); 7.59 (dd, 1H); 2.03 (m, 1H); 11.47 (s, 1H); 0.91 (s, 2H); 0.88 (s, 2H).

EM (IE) m/e: 334-336 (M+, 35), 266-268 (62).

Preparation 28

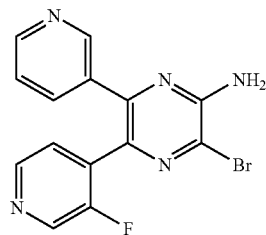

3-Bromo-5-(3-fluoropyridin-4-yl)-6-pyridin-3-ylpyrazin-2-amine

To a 0° C. stirred solution of 5-(3-fluoropyridin-4-yl)-6-pyridin-3-ylpyrazin-2-amine (Example 115) (1.10 g, 4.11 mmol) in a mixture of DMSO (13 mL) and water (0.34 mL), was added N-bromosuccinimide (0.77 g, 4.32 mmol) in portions. After stirring for 5 h at room temperature, the mixture was poured into water, the precipitate collected by filtration, washed with water and dried to give the title compound as a green solid (0.44 g, 31%).

$^1$H-NMR (CDCl$_3$): 8.65 (d, 2H), 8.50 (d, 1H), 8.30 (s, 1H), 7.70 (dd, 1H), 7.50 (dd, 1H), 7.20 (m, 1H), 5.45 (s, 2H).

ESI/MS m/e: 345 [M+H]$^+$, $C_{21}H_{13}FN_6$).

Preparation 29

Step a

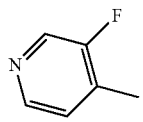

3-Fluoro-4-methylpyridine

To a cooled (−78° C.) solution of N,N-diisopropylamine (15.92 mL, 113.4 mmol) in THF (140 mL) a solution of BuLi 2.5M in hexane (45.4 ml, 113.4 mmol) was added dropwise over 30 minutes under an atmosphere of Argon. The mixture was stirred for 30 min. at −78° C. and a solution of 3-fluoropyridine (10 g, 103.1 mmol) in THF (5 ml) was added. After 1 h at −78° C., the mixture was treated with MeI (7 ml, 113.4 mmol) and then was allowed to reach 25° C. A solution of NaHCO$_3$ saturated (30 ml) was added and the aqueous phase was extracted with diethyl ether. The organic layer was dried (MgSO$_4$) and upon distillation the product was collected as a colourless liquid, bp 130° C., yield 5.3 g (47%)

δ 1H-NMR (CDCl$_3$): 8.25 (s, 1H), 8.18 (m, 1H), 7.02 (m, 1H).

ESI/MS m/e: 112 ([M+H]+, $C_6H_6FN$)

Step b

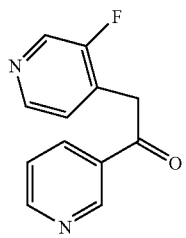

2-(3-fluoropyridin-4-yl)-1-pyridin-3-ylethanone

Obtained (46%) from 3-fluoro-4-methylpyridine and ethylnicotinate following the procedure described in Preparation 11, step a.

δ 1H-NMR (CDCl$_3$): 9.25 (s, 1H), 8.83 (m, 1H), 8.50 (s, 1H), 8.40 (m, 1H), 8.35 (m, 1H), 7.61 (m, 1H), 7.20 (m, 1H), 4.38 (s, 2H).

ESI/MS m/e: 217 ([M+H]+, $C_{12}H_9FN_2O$)

Step c

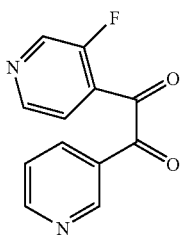

1-(3-Fluoropyridin-4-yl)-2-pyridin-3-ylethane-1,2-dione

Obtained (57%) from 2-(3-fluoropyridin-4-yl)-1-pyridin-3-ylethanone following the procedure described in Preparation 11, step b.

δ 1H-NMR (DMSO-d6): 9.21 (d, 1H), 8.90 (dd, 1H), 8.82 (s, 1H), 8.70 (dd, 1H), 8.44 (dd, 1H), 7.94 (dd, 1H), 7.67 (ddd, 1H).

ESI/MS m/e: 231 ([M+H]+, $C_{12}H_7FN_2O_2$)

Step d

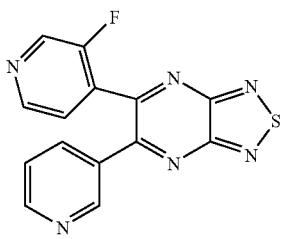

5-(3-fluoropyridin-4-yl)-6-pyridin-3-yl[1,2,5]thiadiazolo[3,4-b]pyrazine

Obtained as a solid (63%) from 1-(3-fluoropyridin-4-yl)-2-pyridin-3-ylethane-1,2-dione and 1,2,5-thiadiazole-3,4-diamine following the procedure of Preparation 11, step c.

δ 1H-NMR (DMSO-d6): 8.64 (m, 3H), 8.58 (dd, 1H), 7.91 (m, 1H), 7.78 (dd, 1H), 7.43 (ddd, 1H).

ESI/MS m/e: 311 ([M+H]+, $C_{14}H_7FN_6S$)

Preparation 30

Step a

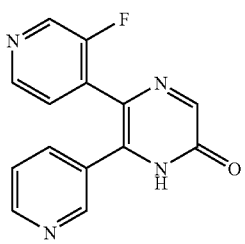

5-(3-Fluoropyridin-4-yl)-6-pyridin-3-ylpyrazin-2(1H)-one

A solution of sodium nitrite (0.248 g, 3.6 mmol) in water (2.5 mL) was added dropwise to a stirred, cooled (ice-bath) mixture of 5-(3-fluoropyridin-4-yl)-6-pyridin-3-ylpyrazin-2-amine (Example 115) (0.80 g, 3.0 mmol) and 5% aqueous sulphuric acid (18 mL). After 1 hour, the mixture was taken to pH 5-6 with aqueous sodium hydroxide solution with external cooling. The mixture was concentrated to low bulk then extracted with chloroform. The organic layer was dried (MgSO$_4$) and concentrated in vaccuo to give the title compound (0.793 g, 99%) as a white solid.

δ 1H-NMR (DMSO-d6): 8.55 (dd, 1H), 8.43 (m, 3H), 8.21 (s, 1H), 7.73 (dd, 1H), 7.53 (dd, 1H), 7.34 (ddd, 1H).

ESI/MS m/e: 269 ([M+H]+, $C_{14}H_9FN_4O$)

Step b

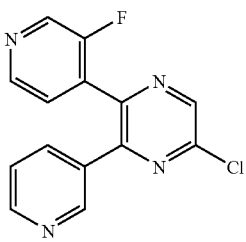

5-Chloro-2-(3-fluoropyridin-4-yl)-3-pyridin-3-ylpyrazine

A suspension of 5-(3-fluoropyridin-4-yl)-6-pyridin-3-ylpyrazin-2(1H)-one (0.79 g, 2.95 mmol) in phosphorus oxychloride (5 mL) was heated to reflux and stirred overnight. The mixture was evaporated and carefully neutralised with 4% aqueous sodium hydrogen carbonate solution with external cooling. The mixture was extracted with ethyl acetate and the organic layer was washed with brine, dried (MgSO$_4$) and evaporated. The residue was purified by silica gel chromatography (CH$_2$Cl$_2$ to CH$_2$Cl$_2$/MeOH 98:2) to give the title compound (0.279 g, 33%) as an off-white solid.

δ 1H-NMR (DMSO-d6): 9.02 (s, 1H), 8.48 (m, 4H), 7.82 (m, 1H), 7.65 (dd, 1H), 7.41 (ddd, 1H).

ESI/MS m/e: 287 ([M+H]+, $C_{14}H_8ClFN_4$)

Examples

TABLE 2

| Example | Structure |
| --- | --- |
| 1 | 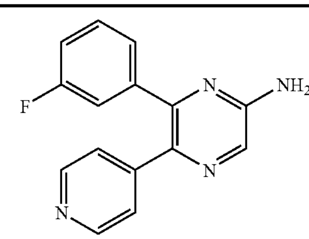 |

TABLE 2-continued
| Example | Structure |
|---|---|
| 2 | 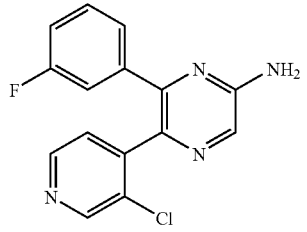 |
| 3 | 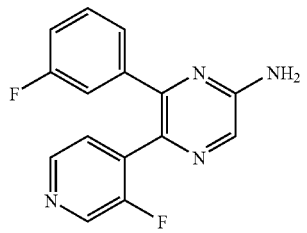 |
| 4 | 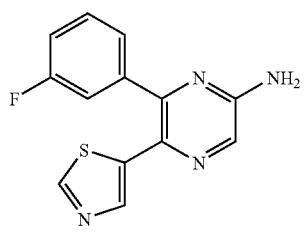 |
| 5 | 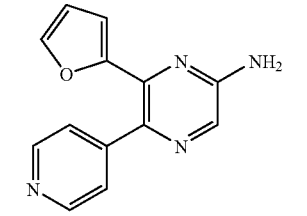 |
| 6 | 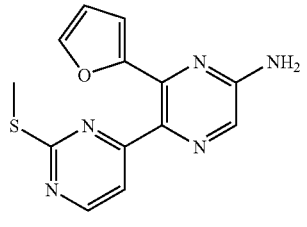 |
| 7 | 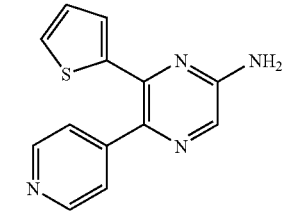 |
| 8 | 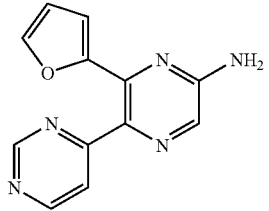 |
| 9 | 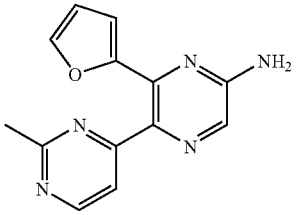 |
| 10 | 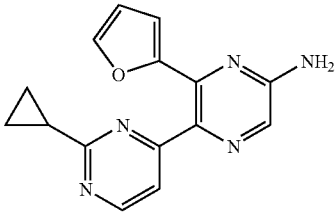 |
| 11 | 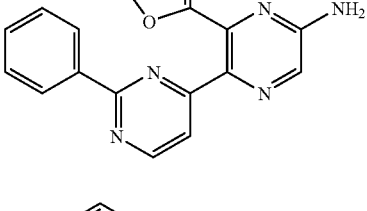 |
| 12 | 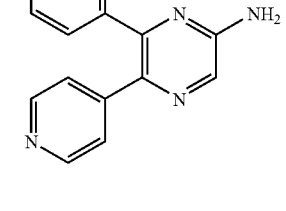 |
| 13 | 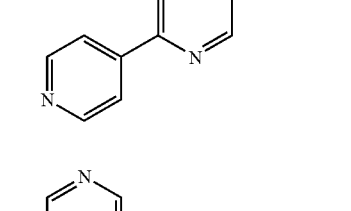 |

TABLE 2-continued

| Example | Structure |
|---|---|
| 14 | 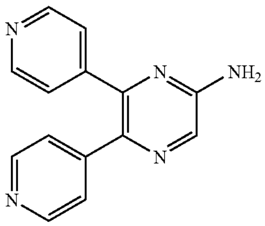 |
| 15 | 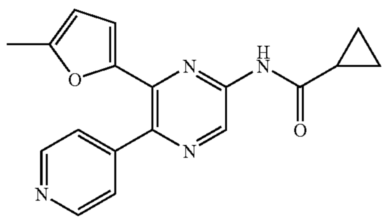 |
| 16 | 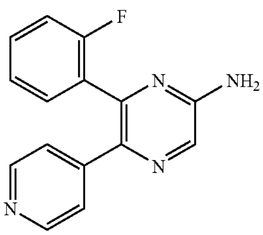 |
| 17 | 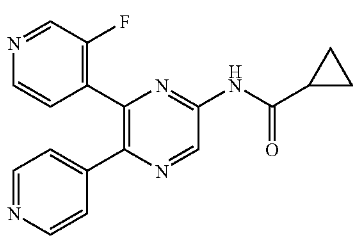 |
| 18 | 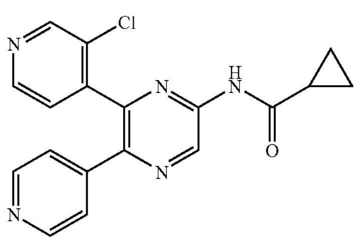 |
| 19 | 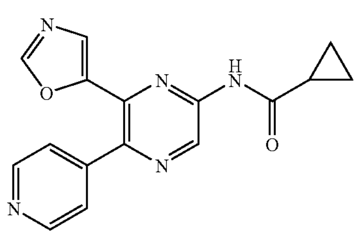 |
| 20 | |
| 21 | |
| 22 | |
| 23 | |
| 24 | |
| 25 | |

TABLE 2-continued

| Example | Structure |
|---|---|
| 26 | |
| 27 | |
| 28 | |
| 29 | |
| 30 | |
| 31 | |
| 32 | 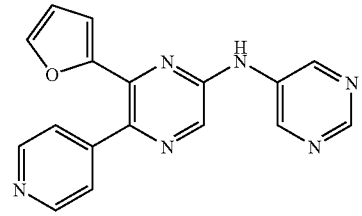 |
| 33 | 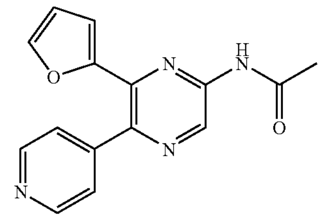 |
| 34 | 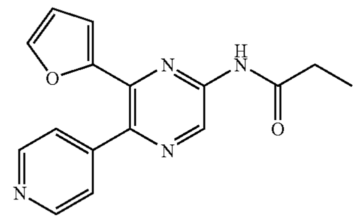 |
| 35 | 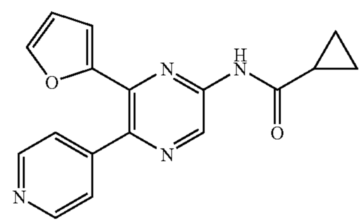 |
| 36 | 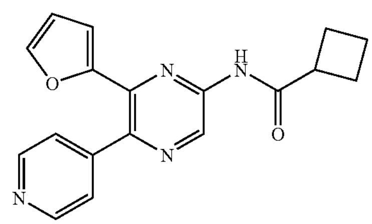 |
| 37 | 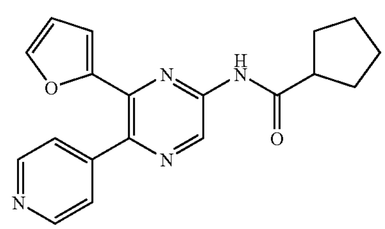 |
| 38 | 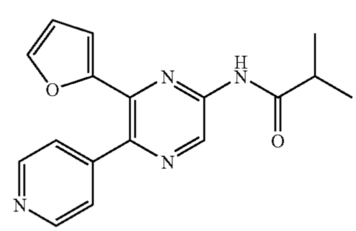 |

TABLE 2-continued
| Example | Structure |
|---------|-----------|
| 39 | 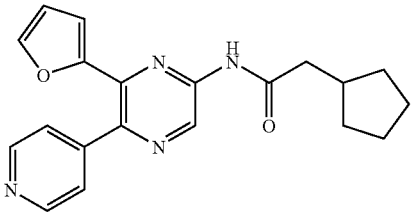 |
| 40 | 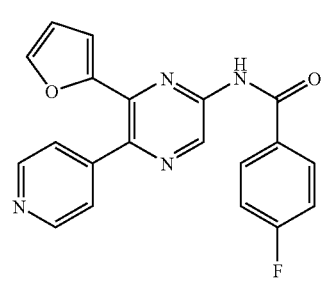 |
| 41 | 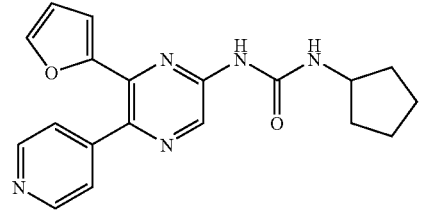 |
| 42 | 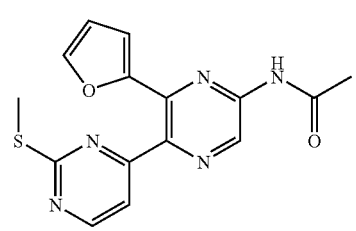 |
| 43 | 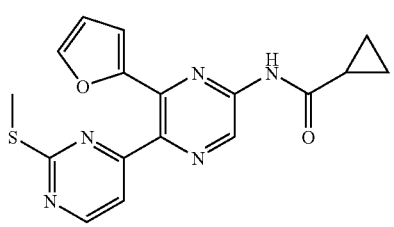 |
| 44 | 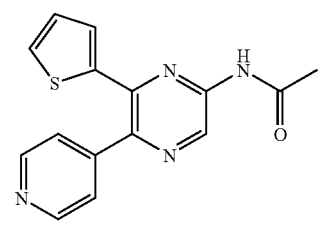 |
| 45 | 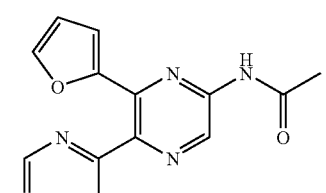 |
| 46 | 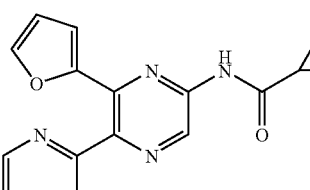 |
| 47 | 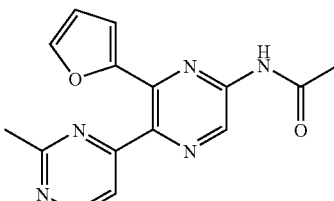 |
| 48 | 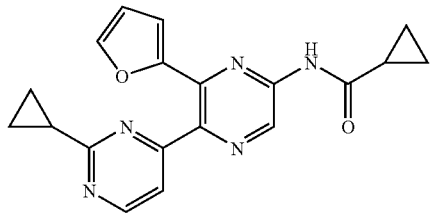 |
| 49 | 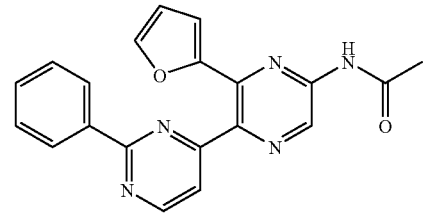 |
| 50 | 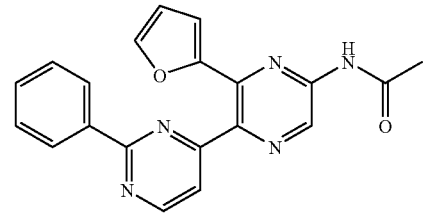 |

TABLE 2-continued

| Example | Structure |
|---|---|
| 51 | 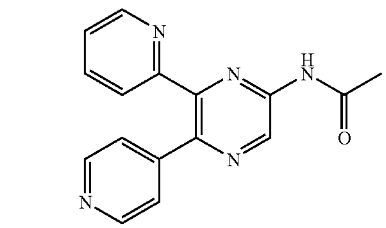 |
| 52 | 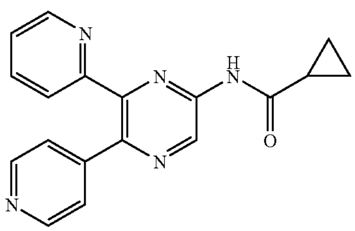 |
| 53 | 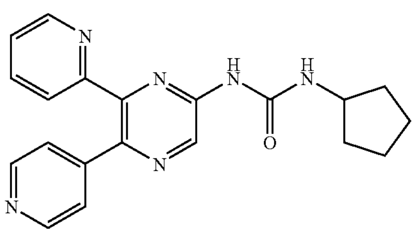 |
| 54 | 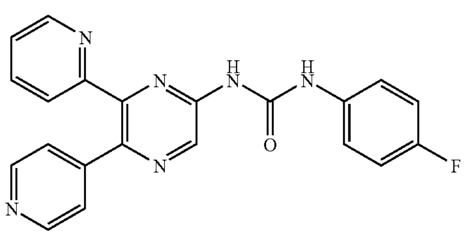 |
| 55 | 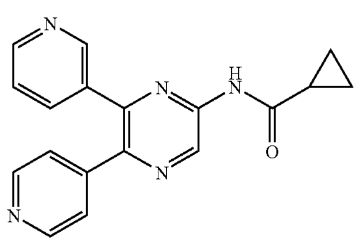 |
| 56 | 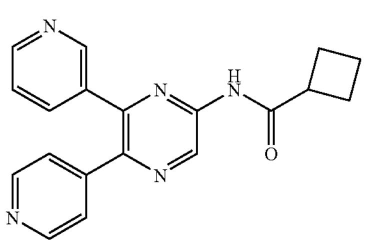 |
| 57 | |
| 58 | |
| 59 | |
| 60 | |
| 61 | |
| 62 | |

TABLE 2-continued
| Example | Structure |
|---------|-----------|
| 63 | 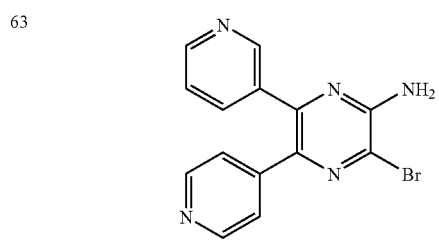 |
| 64 | 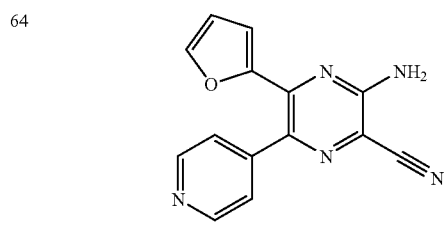 |
| 65 | 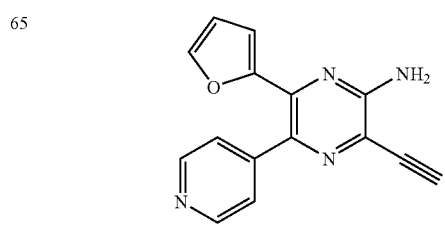 |
| 66 | 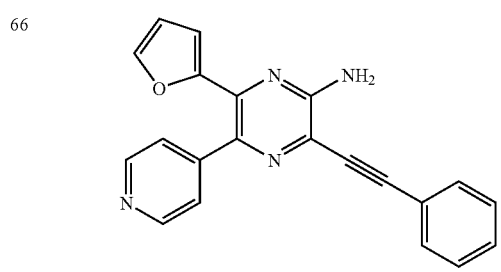 |
| 67 | 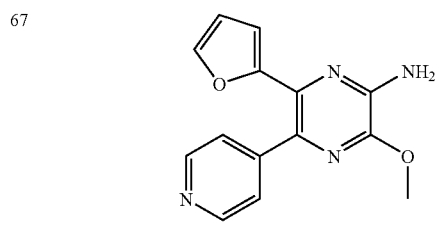 |
| 68 | 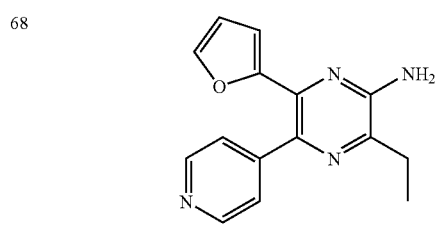 |
| 69 | 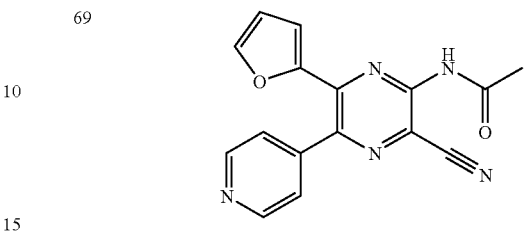 |
| 70 | 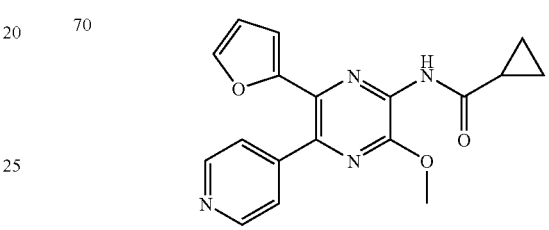 |
| 71 | 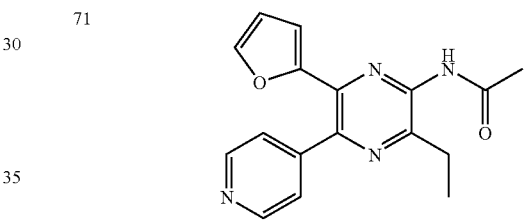 |
| 72 | 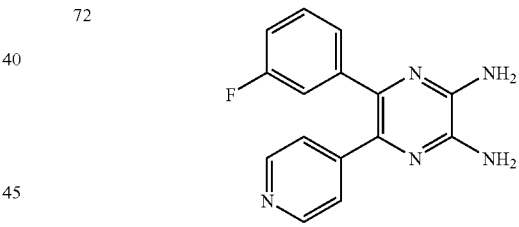 |
| 73 | 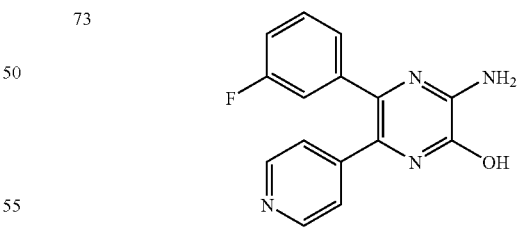 |
| 74 | 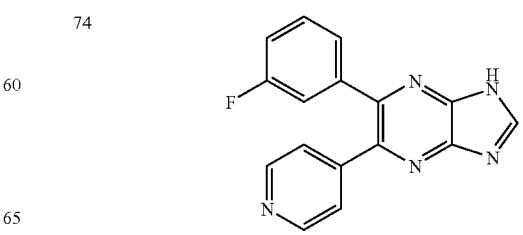 |

TABLE 2-continued
| Example | Structure |
|---|---|
| 75 | 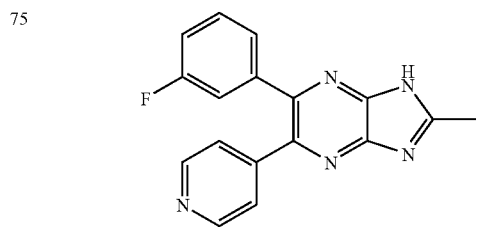 |
| 76 | 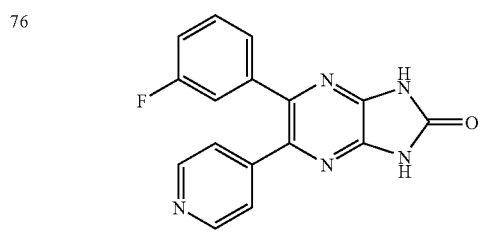 |
| 77 | 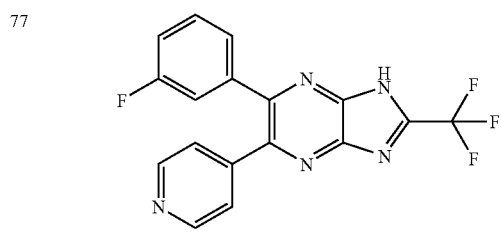 |
| 78 | 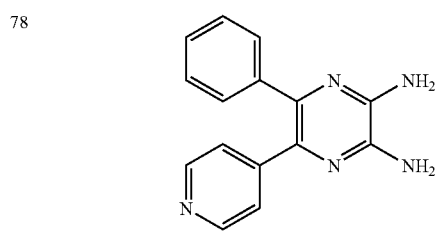 |
| 79 | 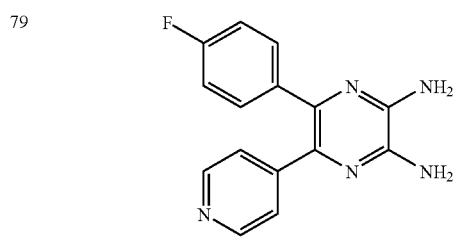 |
| 80 | 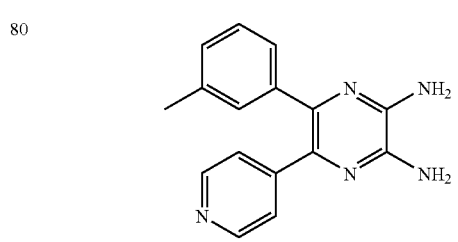 |
TABLE 2-continued
| Example | Structure |
|---|---|
| 81 | 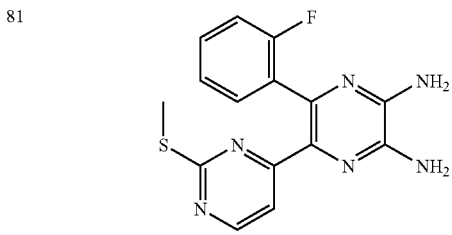 |
| 82 | 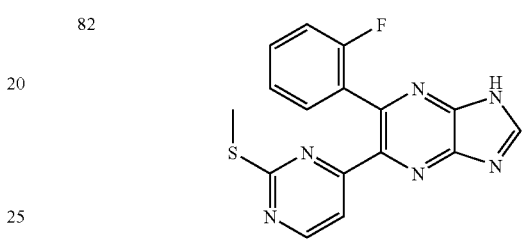 |
| 83 | 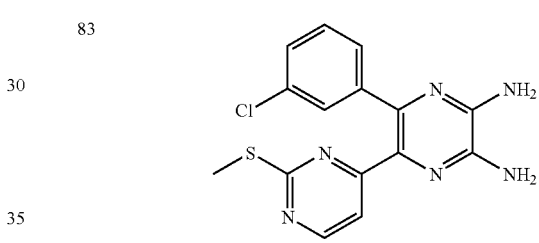 |
| 84 | 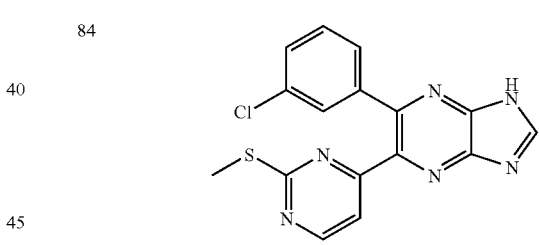 |
| 85 | 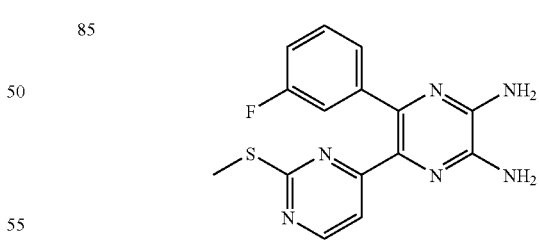 |
| 86 | 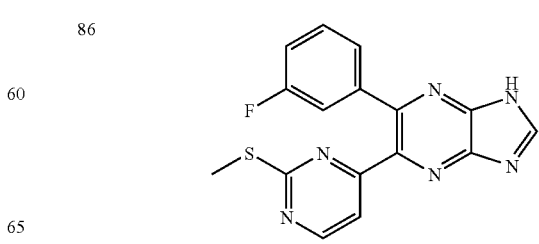 |

TABLE 2-continued
| Example | Structure |
|---|---|
| 87 | 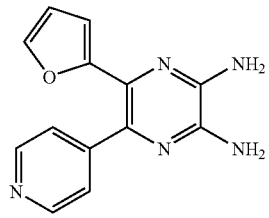 |
| 88 | 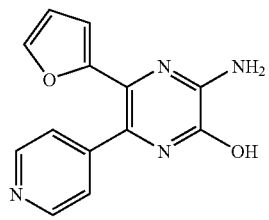 |
| 89 | 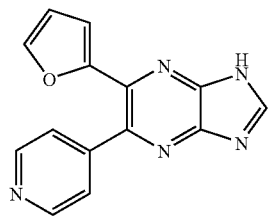 |
| 90 | 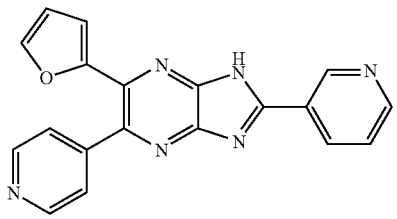 |
| 91 | 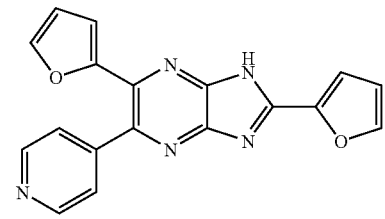 |
| 92 | 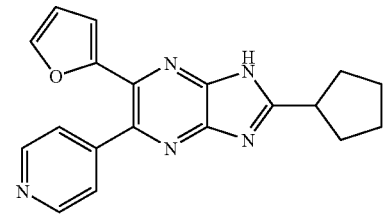 |
TABLE 2-continued
| Example | Structure |
|---|---|
| 93 | 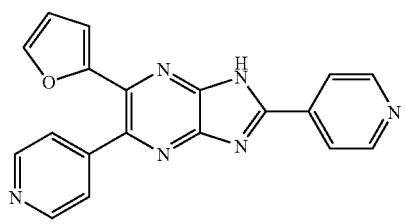 |
| 94 | 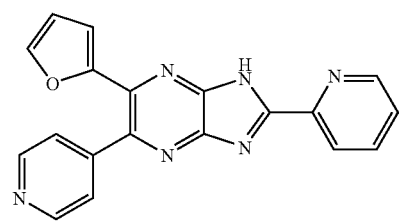 |
| 95 | 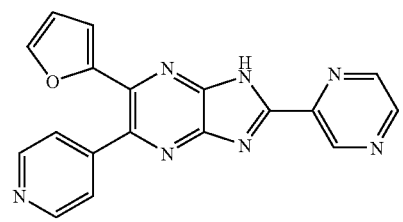 |
| 96 | 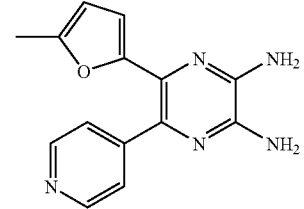 |
| 97 | 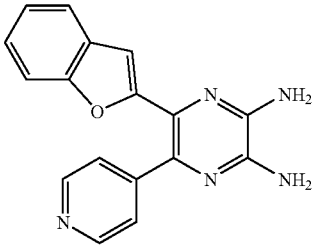 |
| 98 | 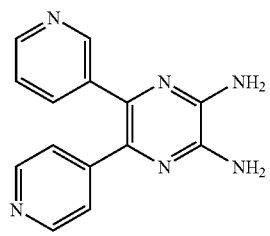 |

TABLE 2-continued
| Example | Structure |
|---|---|
| 99 | 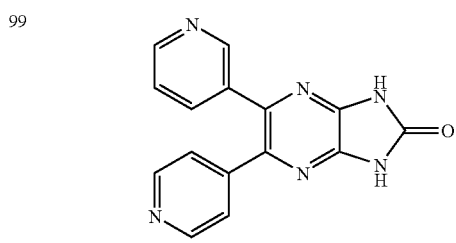 |
| 100 | 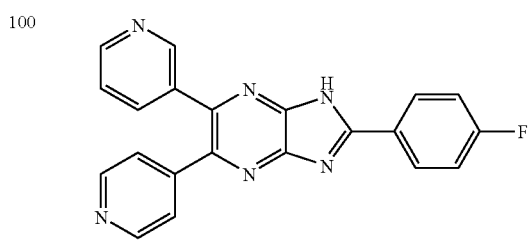 |
| 101 | 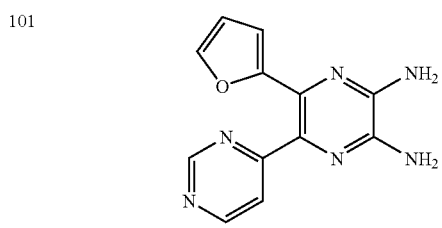 |
| 102 | 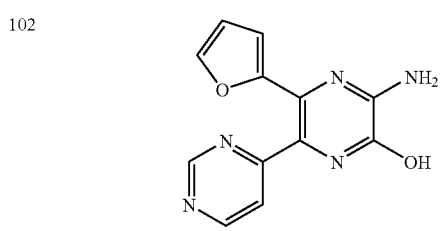 |
| 103 | 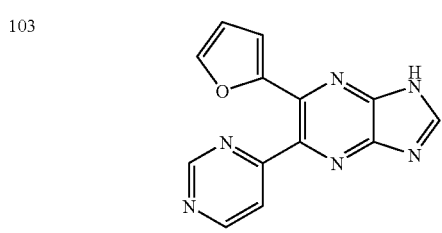 |
| 104 | 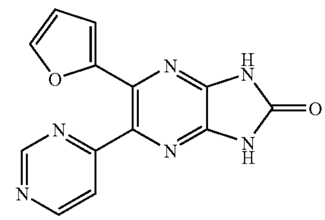 |
| 105 | 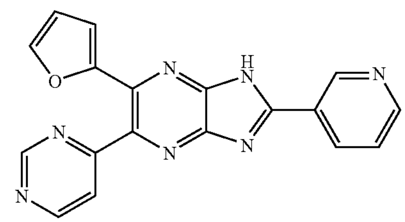 |
| 106 | 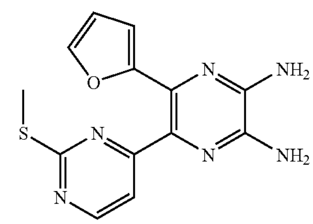 |
| 107 | 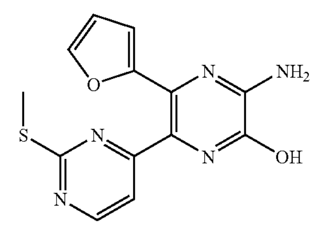 |
| 108 | 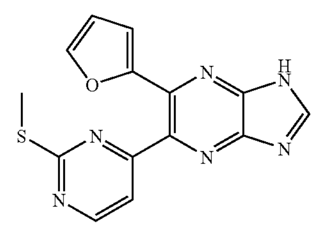 |
| 109 | 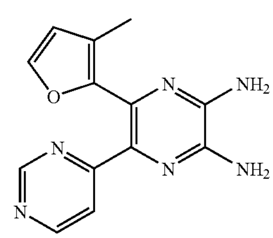 |
| 110 | 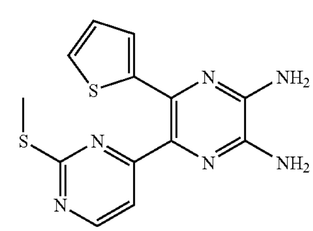 |
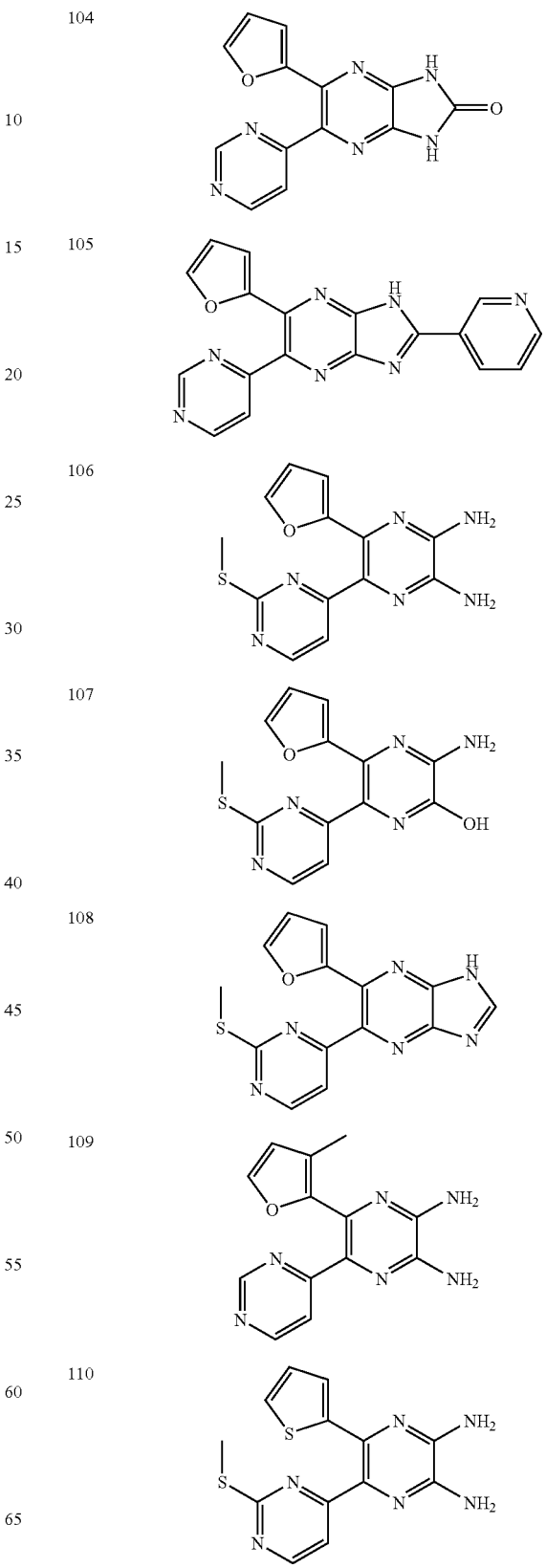

TABLE 2-continued

| Example | Structure |
|---|---|
| 111 | 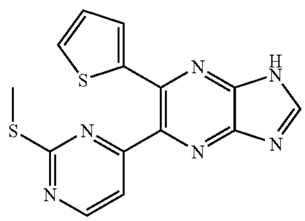 |
| 112 | 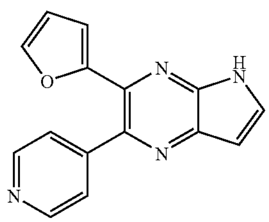 |
| 113 | 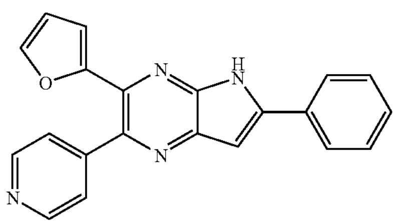 |
| 114 | 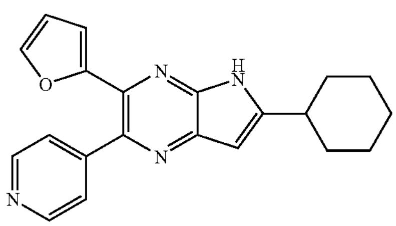 |
| 115 | 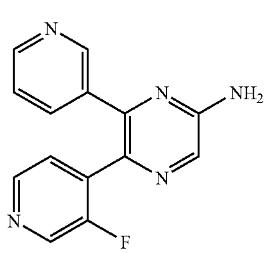 |
| 116 | 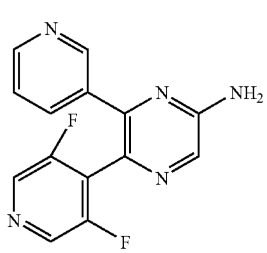 |

TABLE 2-continued

| Example | Structure |
|---|---|
| 117 | 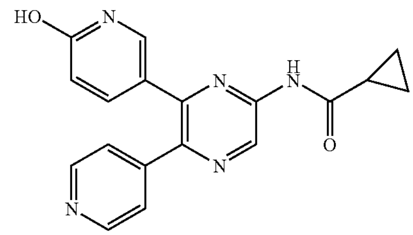 |
| 118 | 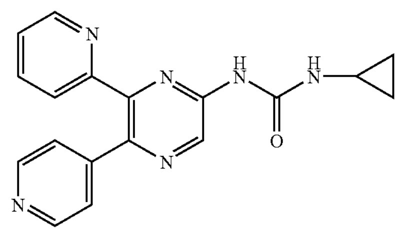 |
| 119 | 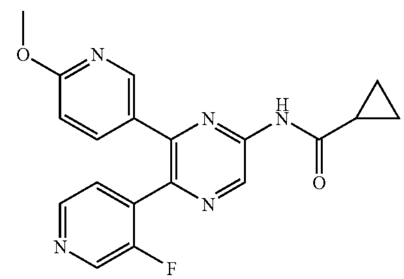 |
| 120 | 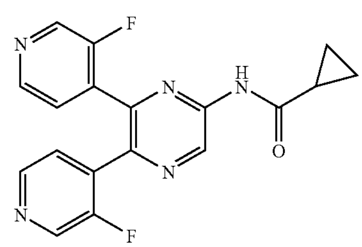 |
| 121 | 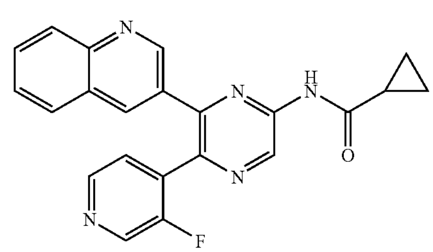 |
| 122 | 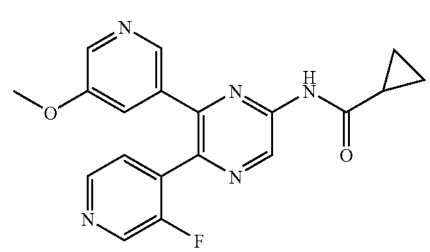 |

TABLE 2-continued
| Example | Structure |
|---|---|
| 123 | 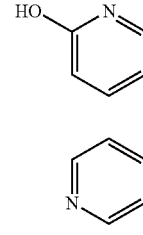 |
| 124 | 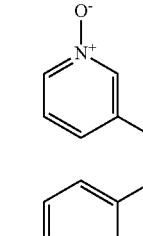 |
| 125 | 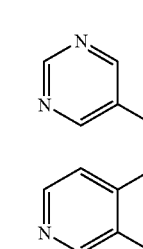 |
| 126 | 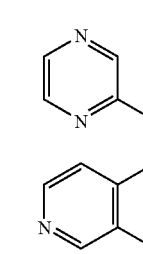 |
| 127 | 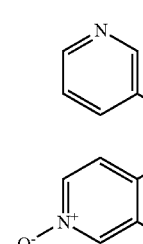 |
| 128 | 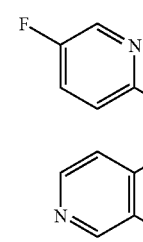 |
| 129 | 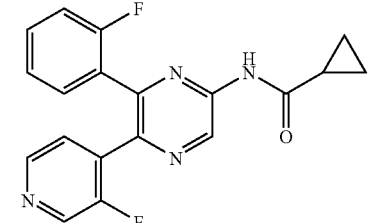 |
| 130 | 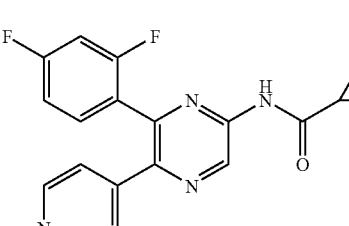 |
| 131 | 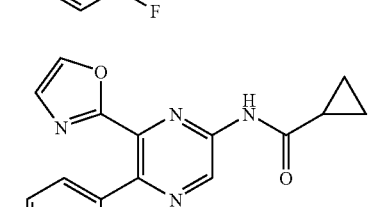 |
| 132 | 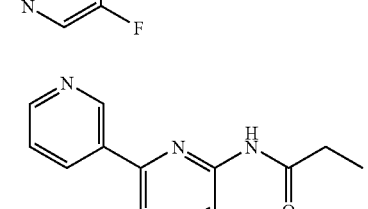 |
| 133 | 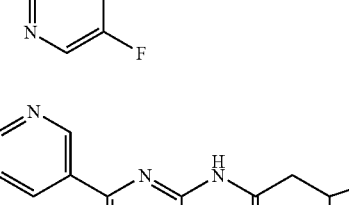 |
| 134 | 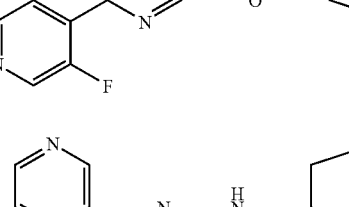 |

TABLE 2-continued

| Example | Structure |
|---|---|
| 135 | 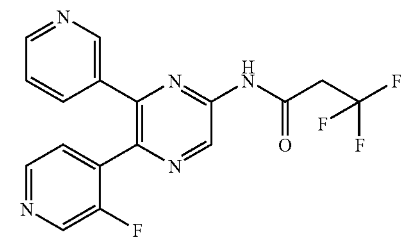 |
| 136 | 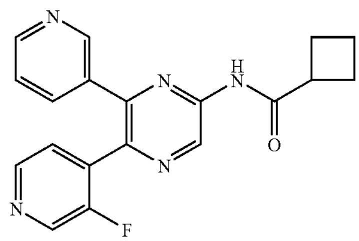 |
| 137 | 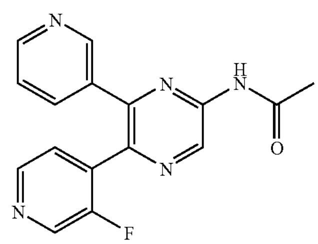 |
| 138 | 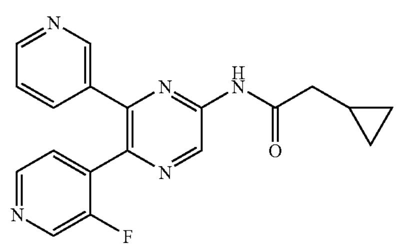 |
| 139 | 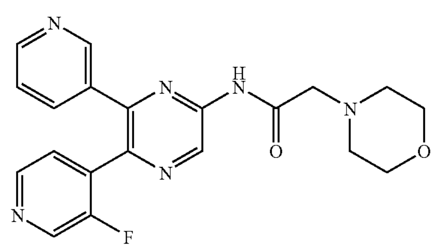 |
| 140 | 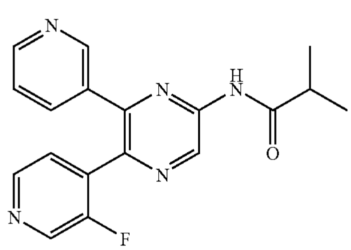 |

TABLE 2-continued

| Example | Structure |
|---|---|
| 141 | 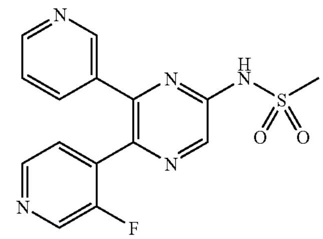 |
| 142 | 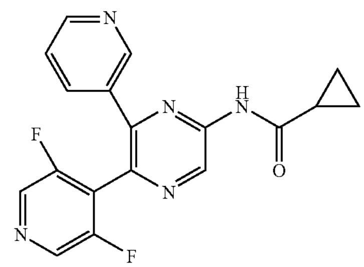 |
| 143 | 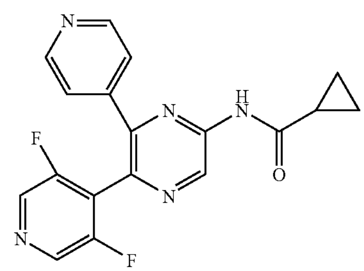 |
| 144 | 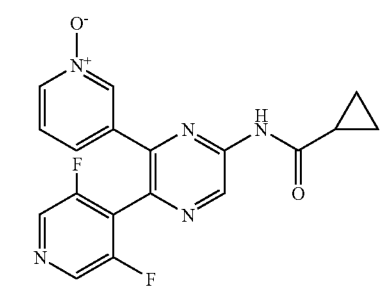 |
| 145 | 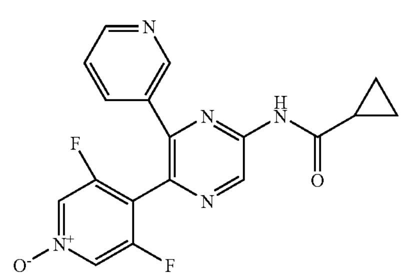 |

TABLE 2-continued
| Example | Structure |
|---|---|
| 146 | 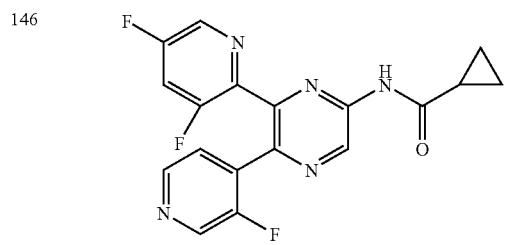 |
| 147 | 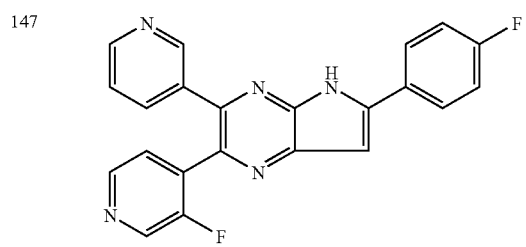 |
| 148 | 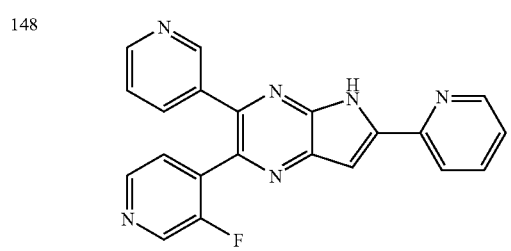 |
| 149 | 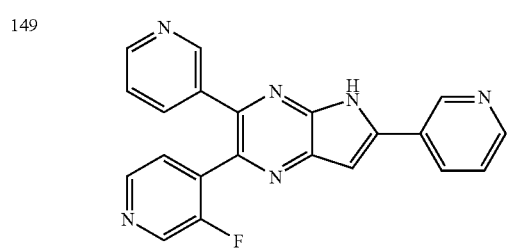 |
| 150 | 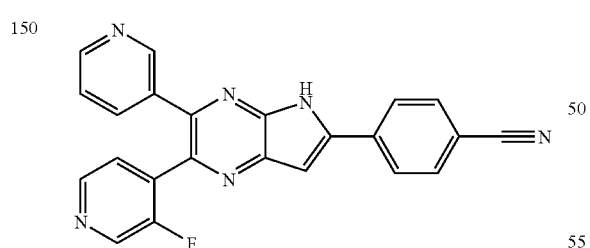 |
| 151 | 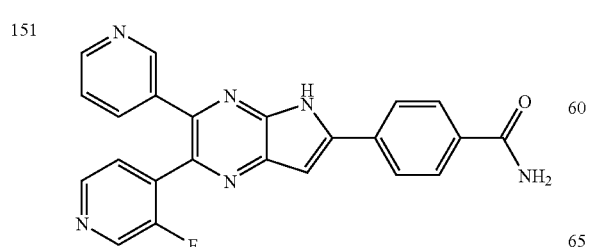 |
| 152 | 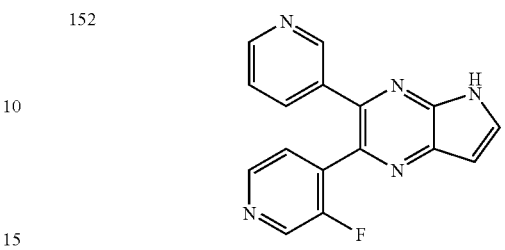 |
| 153 | 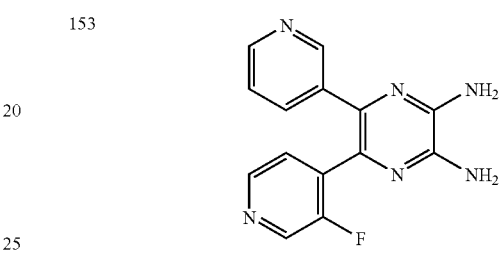 |
| 154 | 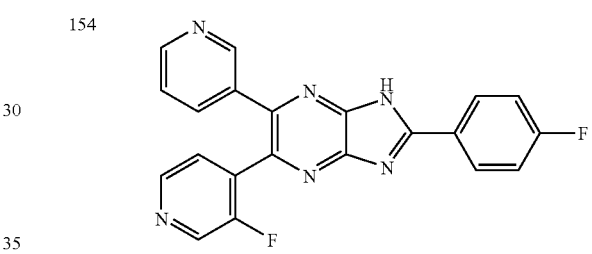 |
| 155 | 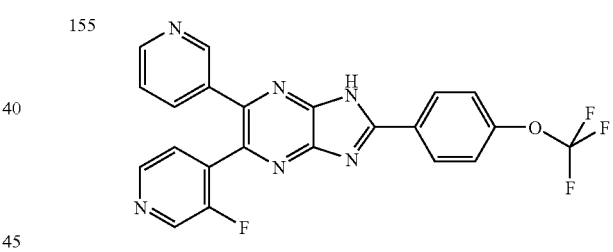 |
| 156 | 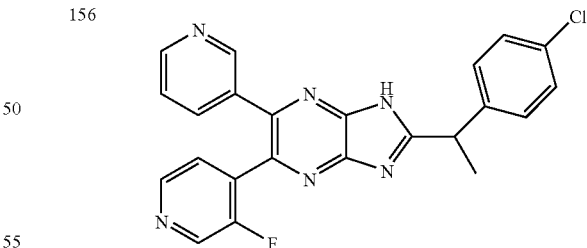 |
| 157 | 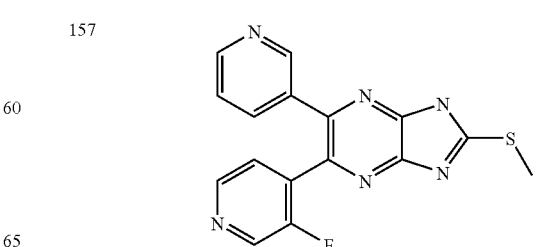 |

TABLE 2-continued

| Example | Structure |
|---|---|
| 158 | 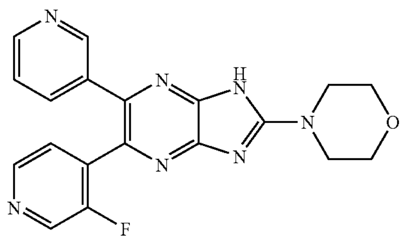 |
| 159 | 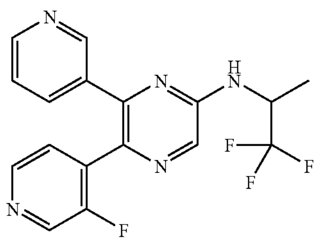 |
| 160 | 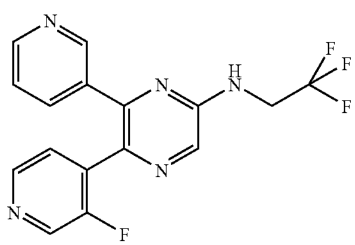 |

Examples

Example 1

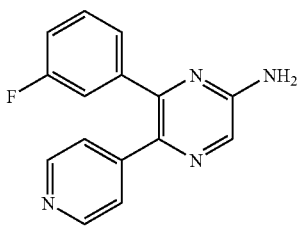

6-(3-Fluorophenyl)-5-pyridin-4-ylpyrazin-2-amine

An oven dried resealable Schlenk tube was charged with 5-bromo-6-(3-fluorophenyl)pyrazin-2-amine (Preparation 1, 0.3 g, 1.11 mmol), 4-(4,4,5,5-tetramethyl-[1,3,2]dioxaborolan-2-yl)pyridine (459 mg, 2.23 mmol), dioxane (35 mL) and a 2M aqueous solution of cesium carbonate (3.3 mL, 6.66 mmol) were added. The Schienk tube was subjected to three cycles of evacuation-backfilling with argon, and 1,1'-bis(diphenylphosphino)ferrocene-palladium(II) dichloride dichloromethane complex [PdCl$_2$dppf.DCM] (45 mg, 0.055 mmol) was added. After three new cycles of evacuation-backfilling with argon, the Schlenk tube was capped and placed in a 100° C. oil bath. After 20 h, the mixture was cooled, partitioned between water and ethyl acetate, the aqueous phase extracted twice with ethyl acetate the organic layers washed with brine, dried (MgSO$_4$) and evaporated. Flash chromatography (dichloromethane/methanol 98:2 to dichloromethane/methanol 95:5) provided the title compound as a yellowish solid (178 mg, 60%)

m.p.: 221-222° C.

δ $^1$H-NMR (CDCl$_3$): 8.45 (d, 2H), 8.05 (s, 1H), 7.24 (m, 4H), 7.05 (d, 2H), 4.86 (s, 2H).

ESI/MS m/e: 267 ([M+H]$^+$, C$_{15}$H$_{11}$FN$_4$).

Retention time (min.): 6

Example 2

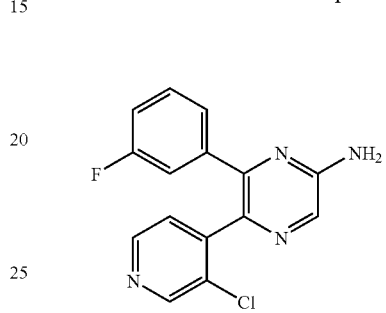

5-(3-Chloropyridin-4-yl)-6-(3-fluorophenyl)pyrazin-2-amine

A microwave oven reactor was charged with 5-bromo-6-(3-fluorophenyl)pyrazin-2-amine (Preparation 1, 0.3 g, 1.11 mmol), (3-chloropyridin-4-yl)boronic acid (212 mg, 1.03 mmol), [1,1'-bis(diphenylphosphino)ferrocene]palladium (II)dichloride dichloromethane complex (1:1) (39 mg, 0.047 mmol), dioxane (8 mL) and a 1.2M aqueous solution of cesium carbonate was added (1.9 mL, 2.39 mmol). The mixture was heated to 150° C. for 10 min in the microwave oven, then cooled, partitioned between water and ethyl acetate, the aqueous phase extracted twice with ethyl acetate, the organic layers washed with brine, dried (MgSO$_4$) and evaporated. Flash chromatography (dichloromethane to dichloromethane/methanol 90:10) furnished the title compound as a yellowish solid (78 mg, 39%).

δ $^1$H-NMR (CDCl$_3$): 8.55 (s, 1H), 8.45 (d, 1H), 8.05 (s, 1H), 7.30 (d, 1H), 7.15 (m, 2H), 7.00 (m, 2H), 4.85 (bs, 2H).

ESI/MS m/e: 301 ([M+H]$^+$, C$_{15}$H$_{10}$ClFN$_4$)

Retention time (min.): 12

Example 3

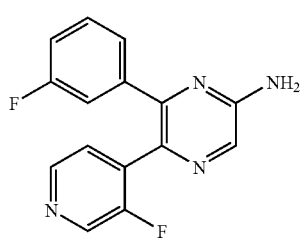

6-(3-Fluorophenyl)-5-(3-fluoropyridin-4-yl)pyrazin-2-amine

Obtained as a brown solid (24%) from 5-bromo-6-(3-fluorophenyl)pyrazin-2-amine (Preparation 1) and (3-fluoropyridin-4-yl)boronic acid following the procedure of Example 2.

ESI/MS m/e: 285 ([M+H]$^+$, $C_{15}H_{10}F_2N_4$).

Retention time (min.): 11

Example 4

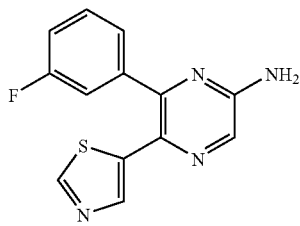

6-(3-Fluorophenyl)-5-(1,3-thiazol-5-yl)pyrazin-2-amine

A mixture of 5-bromo-6-(3-fluorophenyl)pyrazin-2-amine (Preparation 1, 100 mg, 0.37 mmol), thiazole (0.06 mL, 0.88 mmol) and potassium acetate (54 mg, 0.56 mmol) in N,N-dimethylacetamide (1 mL) was degassed with argon. The catalyst Pd(PPh$_3$)$_4$ (23 mg, 0.02 mmol, 5 mol %) was added and degassing was repeated. The mixture was heated to 150° C. in a sealed tube and stirred overnight. The mixture was cooled and ethyl acetate and aqueous NH$_4$Cl were added. The aqueous layer was extracted with ethyl acetate. The organic layer was dried and concentrated. The residue was purified by flash silica gel chromatography (hexanes/EtOAc 1:1) to give the title compound (15 mg, 15%) as a yellow solid.

ESI/MS (m/e, %): 273 [(M+1)$^+$, 100]

Retention time (min.): 11

Example 5

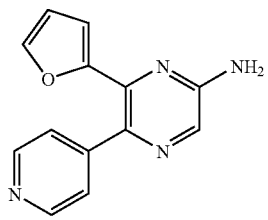

6-(2-Furyl)-5-pyridin-4-ylpyrazin-2-amine

Obtained as a yellowish solid (68%) from 5-bromo-6-furan-2-ylpyrazin-2-ylamine (Preparation 2) and 4-(4,4,5,5-tetramethyl-[1,3,2]dioxaborolan-2-yl)pyridine following the procedure of Example 1.

δ $^1$H-NMR (DMSO-d$_6$): 8.61 (d, 2H), 8.00 (s, 1H), 7.40 (d, 2H), 7.38 (d, 1H), 6.58 (d, 1H), 6.40 (m, 1H), 4.85 (s, 1H).

ESI/MS m/e: 239 ([M+H]$^+$, $C_{13}H_{10}N_4O$).

Retention time (min.): 5

Example 6

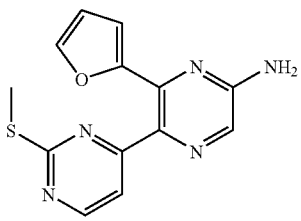

6-(2-Furyl)-5-[2-(methylthio)pyrimidin-4-yl]pyrazin-2-amine

A microwave oven reactor was charged with 5-bromo-6-furan-2-ylpyrazin-2-ylamine (Preparation 2, 220 mg, 0.91 mmol), 2-methylsulfanyl-4-trimethylstannanylpyrimidine* (500 mg, 1.74 mmol), bis-(triphenylphosphin)palladium (II) chloride (60 mg, 0.08 mmol) and dimethylformamide (2.5 mL). The mixture was heated at 150° C. for 10 min in the microwave oven, then cooled, partitioned between water and ethyl acetate, the aqueous phase extracted twice with ethyl acetate, the organic layers washed with brine, dried (MgSO$_4$) and evaporated. Flash chromatography (dichloromethane to dichloromethane/methanol 95:5) gave the title compound as a yellowish solid (123 mg, 47%).

*Prepared according to Sandosham J.; Undheim, K. Tetrahedron 1994, 50 (1), 275-284.

ESI/MS m/e: 286 ([M+H]$^+$, $C_{13}H_{11}N_5OS$).

Retention time (min.): 11

Example 7

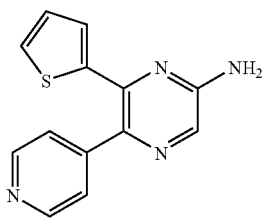

5-Pyridin-4-yl-6-(2-thienyl)pyrazin-2-amine

Obtained as a brown solid (91%) from 5-bromo-6-thiophen-2-ylpyrazin-2-ylamine (Preparation 3) and 4-(4,4,5,5-tetramethyl-1,3,2-dioxaborolan-2-yl)pyridine following the procedure of Example 1.

ESI/MS m/e: 255 ([M+H]$^+$, $C_{13}H_{10}N_4S$).

Retention time (min.): 6

Example 8

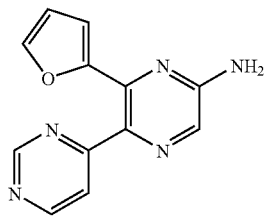

6-(2-Furyl)-5-pyrimidin-4-ylpyrazin-2-amine

A solution of 1-[5-amino-3-(2-furyl)pyrazin-2-yl]ethanone (Preparation 4, 388 mg, 1.91 mmol) in N,N-dimethylformamide dimethyl acetal (1.3 mL) was heated to 100° C. After 9 h, the mixture was concentrated under reduced pressure to yield brown oil. Formamidine acetate (795 mg, 7.64 mmol) was added to this oily residue previously dissolved in ethanol (6.4 mL) and toluene (0.96 mL). Molecular sieves (4 Å) were added to the solution and the whole reaction mixture was heated to 115° C. in a sealed tube and stirred for 20 h. The crude reaction was filtered and concentrated to dryness. The residue was partitioned between ethyl acetate and water, the organic layer was washed with brine, dried ($Na_2SO_4$) and evaporated. The residue was purified by silica gel flash chromatography (100% ethyl acetate). Concentration in vacuo of the product-rich fractions provided the titled compound as a pale-yellow solid (137 mg, 30%).

ESI/MS m/e: 240 ([M+H]$^+$, $C_{12}H_9N_5O$).

Retention time (min.): 7

Example 9

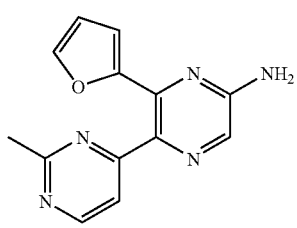

6-(2-Furyl)-5-(2-methylpyrimidin-4-yl)pyrazin-2-amine

Obtained as a pale-yellow solid (20%) using acetamidine hydrochloride following the procedure of Example 8.
ESI/MS m/e: 254 ([M+H]$^+$, $C_{13}H_{11}N_5O$).
Retention time (min.): 8

Example 10

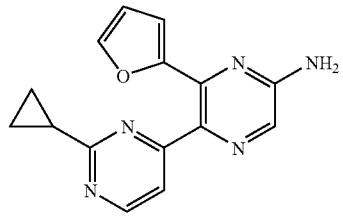

5-(2-Cyclopropylpyrimidin-4-yl)-6-(2-furyl)pyrazin-2-amine

Obtained as a pale-yellow solid (30%) using cyclopropanecarboximidamide hydrochloride following the procedure of Example 8.
ESI/MS m/e: 280 ([M+H]$^+$, $C_{15}H_{13}N_5O$).
Retention time (min.): 11

Example 11

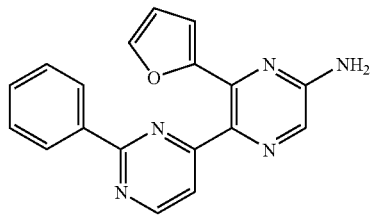

6-(2-Furyl)-5-(2-phenylpyrimidin-4-yl)pyrazin-2-amine

Obtained as a pale-yellow solid (79%) using benzamidine hydrochloride following the procedure of Example 8.
ESI/MS m/e: 316 ([M+H]$^+$, $C_{15}H_{13}N_5O$).
Retention time (min.): 14

Example 12

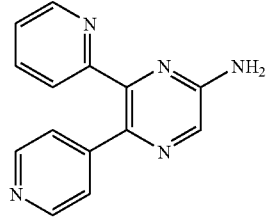

6-Pyridin-2-yl-5-pyridin-4-ylpyrazin-2-amine

Obtained as a brown solid (39%) from 5-bromo-6-pyridin-2-ylpyrazin-2-amine (Preparation 5) and 4-(4,4,5,5-tetramethyl-1,3,2-dioxaborolan-2-yl)pyridine following the procedure of Example 1.

δ $^1$H-NMR (CDCl$_3$): 8.65 (d, 1H), 8.50 (d, 2H), 8.15 (s, 1H), 7.65 (dd, 1H), 7.45 (d, 1H), 7.30 (m, 1H), 7.25 (d, 2H), 4.90 (bs, 2H).
ESI/MS m/e: 250 ([M+H]$^+$, C$_{14}$H$_{11}$N$_5$).
Retention time (min.): 4

Example 13

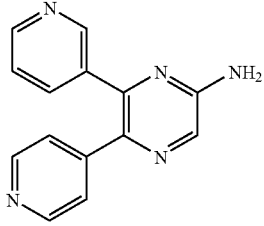

6-Pyridin-3-yl-5-pyridin-4-ylpyrazin-2-amine

A mixture of 5-bromo-6-pyridin-3-ylpyrazin-2-amine (Preparation 6, 0.4 g, 1.59 mmol), 4-(4,4,5,5-tetramethyl-1,3,2-dioxaborolan-2-yl)pyridine (0.424 g, 2.07 mmol), [1,1'-bis(diphenylphosphino)ferrocene]palladium(II)dichloride dichloromethane complex (1:1) (76 mg, 0.095 mmol) and cesium carbonate (1.55 g, 4.77 mmol) in dioxane (14 mL) and water (3.72 mL) was heated to 150° C. for 10 minutes in the microwave oven. The mixture was partitioned between ethyl acetate and water. The organic layer was dried (MgSO$_4$) and evaporated. Silica gel flash chromatography (95:5 dichloromethane/methanol) gave the title compound (0.37 g, 74%) as a solid.

δ $^1$H NMR (CDCl$_3$): 8.68 (dd, 1H), 8.61 (dd, 1H), 8.53 (d, 2H), 8.11 (s, 1H), 7.69 (dd, 1H), 7.26 (m, 3H), 4.93 (s, 2H).
ESI/MS (m/e, %): 249 [(M+1)$^+$, C$_{14}$H$_{11}$N$_5$]

Example 14

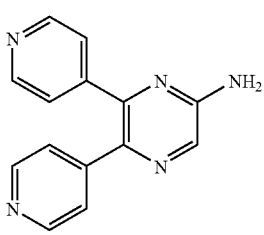

5,6-Dipyridin-4-ylpyrazin-2-amine

Obtained as a green solid (55%) from 6-chloro-5-pyridin-4-ylpyrazin-2-amine (Preparation 7) and 4-(4,4,5,5-tetramethyl-1,3,2-dioxaborolan-2-yl)pyridine following the procedure of Example 1.

δ $^1$H-NMR (CDCl$_3$): 8.50 (d, 2H), 8.40 (d, 2H), 8.05 (s, 1H), 7.30 (d, 2H), 7.20 (d, 2H), 7.00 (s, 2H).
ESI/MS m/e: 250 ([M+H]$^+$, C$_4$H$_{11}$N$_5$).
Retention time (min.): 4

Example 15

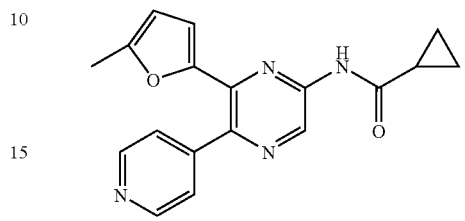

N-[6-(5-Methyl-2-furyl)-5-pyridin-4-ylpyrazin-2-yl] cyclopropanecarboxamide

Step a 6-(5-Methylfuran-2-yl)-5-phenylpyrazin-2-ylamine

An oven dried resealable Schlenk tube was charged with 6-chloro-5-pyridin-4-ylpyrazin-2-amine (Preparation 7, 300 mg, 1.45 mmol), 2-methylfuran (1.31 mL, 14.5 mmol), potassium acetate (213 mg, 2.17 mmol) and N,N-dimethylacetamide (6 mL). The Schlenk tube was subjected to three cycles of evacuation-backfilling with argon, and tetrakis(triphenylphosphine)palladium (117 mg, 0.10 mmol) was added. After three new cycles of evacuation-backfilling with argon, the Schlenk tube was capped and placed in a 150° C. oil bath. After 40 h, the mixture was cooled, partitioned between water and ethyl acetate, the aqueous phase extracted with ethyl acetate (×3), the organic layers washed with brine, dried (MgSO$_4$) and evaporated. Flash chromatography (dichloromethane/methanol 98:2 to dichloromethane/methanol 90:10) furnished the title compound as a brown solid (45 mg, 12%).

δ $^1$H-NMR (CDCl$_3$): 8.60 (d, 2H), 7.95 (s, 1H), 7.40 (d, 2H), 6.40 (d, 1H), 6.00 (d, 1H), 4.80 (bs, 2H), 2.25 (s, 3H).

Step b

N-[6-(5-methyl-2-furyl)-5-pyridin-4-ylpyrazin-2-yl] cyclopropanecarboxamide

To a stirred solution of 6-(5-methylfuran-2-yl)-5-phenylpyrazin-2-ylamine (42 mg, 0.166 mmol) in pyridine (1.8 mL) was added cyclopropanecarbonyl chloride (38 μL, 0.41 mmol). The solution was stirred at 70° C. for 6 h, evaporated, partitioned between dichloromethane and a 4% sodium bicarbonate aqueous solution, the aqueous phase extracted twice with dichloromethane, the organic layers washed with brine, dried (MgSO$_4$) and evaporated. The residue was triturated with diethyl ether and methanol and the precipitate was collected by filtration and dried to furnish the title compound as a brown solid (43 mg, 81%).

$^1$H-NMR (CDCl$_3$): 9.40 (s, 1H), 8.65 (d, 2H), 8.25 (s, 1H), 7.45 (d, 2H), 6.45 (d, 1H), 6.05 (d, 1H), 2.25 (s, 3H), 4.65 (m, 1H), 1.20 (m, 2H), 0.95 (m, 2H).
ESI/MS m/e: 321 ([M+H]$^+$, C$_{18}$H$_{16}$N$_4$O$_2$).
Retention time (min.): 11

Example 16

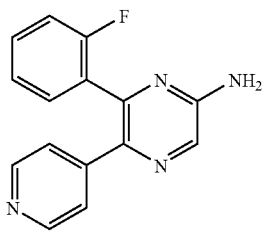

6-(2-Fluorophenyl)-5-pyridin-4-ylpyrazin-2-amine

Obtained as a white solid (56%) from 6-chloro-5-pyridin-4-ylpyrazin-2-amine (Preparation 7) and 2-fluorophenylboronic acid following the procedure of Example 1.

$^1$H-NMR (CDCl$_3$): 8.45 (d, 2H), 8.05 (s, 1H), 7.40 (m, 2H), 7.20 (m, 4H), 7.00 (dd, 1H), 4.90 (bs, 2H).

ESI/MS m/e: 267 ([M+H]$^+$, C$_{15}$H$_{11}$FN$_4$).

Retention time (min.): 6

Example 17

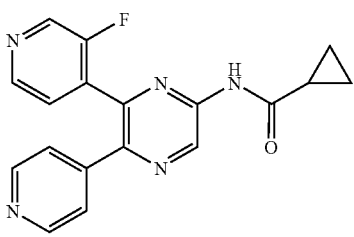

N-[6-(3-Fluoropyridin-4-yl)-5-pyridin-4-ylpyrazin-2-yl]cyclopropanecarboxamide

Obtained as a yellow solid (34%) from N-(6-chloro-5-pyridin-4-ylpyrazin-2-yl)cyclopropanecarboxamide (Preparation 8) and 3-fluoro-4-(4,4,5,5-tetramethyl-1,3,2-dioxaborolan-2-yl)pyridine* following the procedure of Example 1.

*Prepared according to Bouillon A. et al. Tetrahedron 2002, 58, 4369-4373.

$^1$H-NMR (CDCl$_3$): 9.65 (s, 1H), 8.55 (m, 3H), 8.45 (s, 1H), 8.30 (s, 1H), 7.45 (m, 1H), 7.30 (d, 2H), 3.45 (s, 1H), 1.60 (m, 1H), 1.20 (m, 2H), 1.0 (m, 2H).

ESI/MS m/e: 336 ([M+H]$^+$, C$_{18}$H$_{14}$FN$_5$O).

Retention time (min.): 10

Example 18

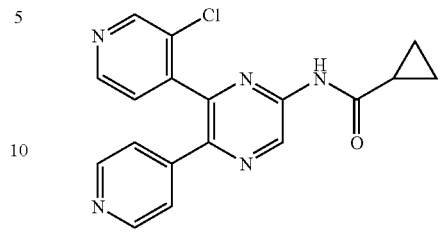

N-[6-(3-Chloropyridin-4-yl)-5-pyridin-4-ylpyrazin-2-yl]cyclopropanecarboxamide

Obtained as a light brown solid (28%) from N-(6-chloro-5-pyridin-4-ylpyrazin-2-yl)cyclopropanecarboxamide* (Preparation 8) and 3-chloro-4-(4,4,5,5-tetramethyl-1,3,2-dioxaborolan-2-yl)pyridine following the procedure of Example 1.

*Prepared according to Bouillon A. et al. Tetrahedron 2002, 58, 4369-4373.

$^1$H-NMR (CDCl$_3$): 9.65 (s, 1H), 8.70 (s, 1H), 8.60 (m, 3H), 8.20 (s, 1H), 7.30 (d, 2H), 1.65 (m, 1H), 1.20 (m, 2H), 1.00 (m, 2H).

ESI/MS m/e: 352 ([M+H]$^+$, C$_{18}$H$_{14}$ClN$_5$O)

Retention time (min.): 11

Example 19

N-[6-(1,3-Oxazol-5-yl)-5-pyridin-4-ylpyrazin-2-yl]cyclopropanecarboxamide

Step a 5-(Tributylstannyl)-2-(triisopropylsilyl)-1,3-oxazole tert-BuLi (1.7M, 8.4 mL, 14.3 mmol) was added dropwise over 30 min. to a stirred solution of 2-(triisopropylsilyl)-1,3-oxazole* (3 g, 13 mmol) in THF (75 mL) at −78° C. under argon. The solution was allowed to stir for 20 min. at −78° C. and Bu$_3$SnCl (5.2 mL, 19.5 mmol) was then added over 20 min. The reaction mixture was warmed up to room temperature and stirred for an additional 16 h. The reaction was diluted with ethyl acetate and washed with water. The organic layer was dried over MgSO$_4$ and concentrated under reduced pressure. The crude product was dissolved in n-pentane, filtered through Celite and the solvent evaporated to give the title compound in quantitative yield as a pale-yellow oily residue, which was used without further purification in the next step.

*Prepared according to Ross A, et al. *Tetrahedron Letters* 2002, 43, 935.

δ $^1$H NMR (CDCl$_3$): 1.12 (d, 18H), 1.38 (m, 3H), 1.42 (d, 9H), 1.52-1.95 (m, 18H) 7.22 (s, 1H).

Step b

A mixture of N-(6-chloro-5-pyridin-4-ylpyrazin-2-yl)cyclopropanecarboxamide (100 mg, 0.36 mmol) and 5-(tributylstannyl)-2-(triisopropylsilyl)-1,3-oxazole (397 mg, 0.73 mmol) in xylene (3 mL) was degassed with argon. The catalyst Pd(PPh$_3$)$_4$ (25 mg, 0.022 mmol, 6 mol %) was added and degassing was repeated. The mixture was heated to 90° C. in a sealed tube and stirred overnight. The mixture was cooled and ethyl acetate and HCl 2N were added. The aqueous layer was washed with ethyl acetate and then neutralized with 6N NaOH. The cloudy solution was extracted with CH$_2$Cl$_2$. The organic layer was dried and concentrated. The residue was purified by flash silica gel chromatography (dichloromethane/methanol 95:5) to give the title compound (36 mg, 35%) as a white solid.

δ $^1$H NMR (CDCl$_3$): 1.04 (m, 2H), 1.21 (m, 2H), 1.64 (m, 1H), 7.45 (d, 1H), 7.88 (s, 1H), 8.28 (s, 1H), 8.74 (d, 1H), 9.56 (s, 1H).

ESI/MS (m/e, %): 308 [(M+1)$^+$, 100]

Example 20

N-[6-(1,3-Oxazol-2-yl)-5-pyridin-4-ylpyrazin-2-yl]cyclopropanecarboxamide

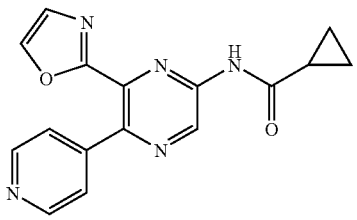

Step a (1,3-Oxazol-2-yl)zinc chloride n-Butyllithium (1.6M, 4.9 mL, 7.9 mmol) was added dropwise over 30 min. to a solution of oxazole (0.5 g, 7.2 mmol) in THF (7 mL) stirred at −78° C. under argon maintaining the mixture at a temperature below −55° C. Fused zinc chloride (1.96 g, 14.4 mmol) was added in two portions and the reaction mixture was warmed to room temperature and stirred for an additional 16 h. Two layers are formed and further THF (10 mL) was added to give a homogeneous solution of the zinc reagent. Approximate concentration. 0.33 M in THF.

Step b (1,3-Oxazol-2-yl)zinc chloride (0.33M in THF, 9.3 mL, 3.06 mmol) was added to a solution of N-(6-chloro-5-pyridin-4-ylpyrazin-2-yl)cyclopropanecarboxamide (Preparation 8, 280 mg, 1.02 mmol) in THF (2 mL) and the mixture was degassed Pd(PPh$_3$)$_4$ (118 mg, 0.102 mmol, 10 mol %) was added and degassing was repeated. The reaction mixture was heated to 90° C. in a sealed tube and stirred overnight. The mixture was cooled and more (1,3-oxazol-2-yl)zinc chloride (0.33M, 5.0 mL, 1.65 mmol) and Pd(PPh$_3$)$_4$ (90 mg, 8 mol %) were added and the mixture was degassed and heated to 90° C. overnight. The reaction mixture was cooled and concentrated. The residue was purified by flash silica gel chromatography (dichloromethane/methanol 98:2) to give the title compound (80 mg, 26%) as a pale yellow solid.

δ $^1$H NMR (DMSO): 0.95 (m, 4H), 1.18 (m, 1H), 1.64 (m, 1H), 7.40 (d, 3H), 7.88 (s, 1H), 8.29 (s, 1H), 8.60 (d, 2H), 9.53 (s, 1H).

ESI/MS (m/e, %): 308 [(M+1)$^+$, 100]

Example 21

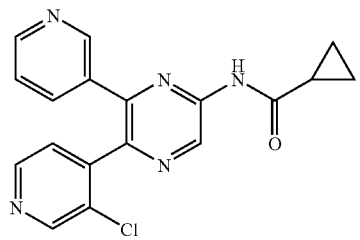

N-[5-(3-Chloropyridin-4-yl)-6-pyridin-3-ylpyrazin-2-yl]cyclopropanecarboxamide

Step a 5-(3-Chloropyridin-4-yl)-6-pyridin-3-ylpyrazin-2-amine

An oven dried resealable Schlenk tube was charged with 5-bromo-6-pyridin-3-ylpyrazin-2-amine (Preparation 6, 0.3 g, 1.17 mmol), 3-cloro-4-(4,4,5,5-tetramethyl-1,3,2-dioxaborolan-2-yl)pyridine (0.56 g, 2.35 mmol), cesium carbonate (1.15 g, 3.525 mmol) in dioxane (10 mL) and water (2.8 mL). The Schlenk tube was subjected to three cycles of evacuation-backfilling with argon, and 1,1'-bis(diphenylphosphino)ferrocene-palladium(II) dichloride dichloromethane complex (58 mg, 0.071 mmol) was added. After three new cycles of evacuation-backfilling with argon, the Schlenk tube was capped and placed in a 90° C. oil bath. After 16 h, the mixture was cooled, partitioned between water and ethyl acetate, the aqueous phase extracted twice with ethyl acetate, the organic layers washed with brine, dried (MgSO$_4$) and evaporated. Flash chromatography (95:5 dichloromethane/methanol) gave the title compound (0.16 g, 48%) as a solid.

δ $^1$H NMR (CDCl$_3$): 8.61-8.50 (m, 4H), 8.10 (s, 1H), 7.65 (dt, 1H), 7.34 (d, 1H), 7.21 (dd, 1H), 4.93 (s, 2H).

ESI/MS (m/e, %): 283 [(M+1)$^+$, C$_{14}$H$_{10}$ClN$_5$].

Step b

Title compound of Example 21 was obtained as a white solid (73%) from 5-(3-chloropyridin-4-yl)-6-pyridin-3-ylpyrazin-2-amine and cyclopropanecarbonyl following the procedure of Example 15, step b.

δ $^1$H NMR (CDCl$_3$): 9.66 (s, 1H), 9.20 (s, 1H), 8.80 (m, 1H), 8.58 (m, 2H), 7.56 (dd, 1H), 7.43 (d, 1H), 7.20 (dd, 1H), 1.75 (m, 1H), 1.22 (m, 2H), 1.01 (m, 2H).

ESI/MS (m/e, %): 351 [(M+1)$^+$, C$_{18}$H$_{14}$ClN$_5$O]

Example 22

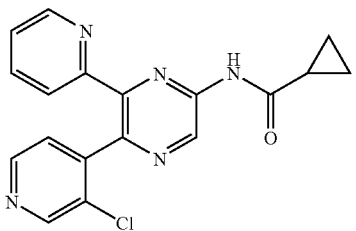

N-[5-(3-Chloropyridin-4-yl)-6-pyridin-2-ylpyrazin-2-yl]cyclopropanecarboxamide

Step a

N-[6-Chloro-5-(3-chloropyridin-4-yl)pyrazin-2-yl]cyclopropanecarboxamide

Obtained as a solid (200 mg, 26%) from 6-chloro-5-(3-chloropyridin-4-yl)pyrazin-2-amine (Preparation 9, 240 mg, 1 mmol) and cyclopropanecarbonyl chloride (136 μL, 1.5 mmol) following the procedure of Example 15, step b.

δ $^1$H NMR (CDCl$_3$): 9.55 (s, 1H), 8.73 (s, 1H), 8.62 (d, 1H), 7.38 (d, 1H), 1.70 (m, 1H), 1.17 (m, 1H), 1.00 (m, 1H).
ESI/MS (m/e, %): 308 [(M+1)$^+$, C$_{13}$H$_{10}$Cl$_2$N$_4$O]

Step b

An oven dried resealable Schlenk tube was charged with N-[6-chloro-5-(3-chloropyridin-4-yl)pyrazin-2-yl]cyclopropanecarboxamide (0.2 g, 0.65 mmol), 2-(tributylstannyl)pyridine (0.38 g, 1.04 mmol) and xylene (4 mL). The Schienk tube was subjected to three cycles of evacuation-backfilling with argon, and tetrakis(triphenylphosphine)palladium (75 mg, 0.065 mmol) was added. After three new cycles of evacuation-backfilling with argon, the Schlenk tube was capped and placed in a 150° C. oil bath. After 20 h, the mixture was cooled, partitioned between water and ethyl acetate, the aqueous phase was extracted twice with ethyl acetate, the organic layers washed with brine, dried (MgSO$_4$) and evaporated. Silica gel flash chromatography (98:2 dichloromethane/methanol) furnished the title compound of Example 22 as a light brown solid (110 mg, 48%).

δ $^1$H NMR (CDCl$_3$): 9.64 (s, 1H), 8.57 (d, 1H), 8.51 (s, 1H), 8.39 (d, 1H), 8.32 (s, 1H), 7.74 (m, 2H), 7.46 (d, 1H), 1.65 (m, 1H), 1.21 (m, 2H), 1.01 (m, 2H).
ESI/MS (m/e, %): 351 [(M+1)$^+$, C$_{18}$H$_{14}$ClN$_5$O]

Example 23

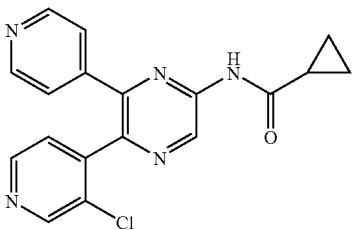

N-[5-(3-Chloropyridin-4-yl)-6-pyridin-4-ylpyrazin-2-yl]cyclopropanecarboxamide

Obtained as a solid (25%) from N-[6-chloro-5-(3-chloropyridin-4-yl)pyrazin-2-yl]cyclopropanecarboxamide (Example 22, step a, 0.37 g, 1.21 mmol) and 4-(4,4,5,5-tetramethyl-1,3,2-dioxaborolan-2-yl)pyridine following the procedure of Example 13.

δ $^1$H NMR (CDCl$_3$): 9.66 (s, 1H), 8.59 (m, 4H), 8.34 (s, 1H), 7.40 (d, 1H), 7.25 (s, 1H), 1.70 (m, 1H), 1.22 (m, 2H), 1.02 (m, 2H).
ESI/MS (m/e, %): 351 [(M+1)$^+$, C$_{18}$H$_{14}$CN$_5$O]

Example 24

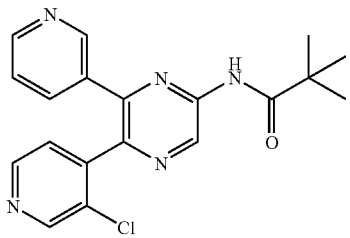

N-[5-(3-Chloropyridin-4-yl)-6-pyridin-3-ylpyrazin-2-yl]-2,2-dimethylpropanamide

Obtained as a solid (20 mg, 26%) from 5-(3-chloropyridin-4-yl)-6-pyridin-3-ylpyrazin-2-amine (Example 22, step a, 0.06 g, 0.21 mmol) and 2,2-dimethylpropanoyl chloride (39 μL, 0.32 mmol) following the procedure of Example 15, step b.

δ $^1$H NMR (CDCl$_3$): 8.66 (d, 1H), 8.62-8.56 (m, 2H), 8.17 (s, 1H), 7.66 (dt, 1H), 7.42 (d, 1H), 7.24 (m, 2H), 1.40 (s, 9H).
SI/MS (m/e, %): 367 [(M+1)$^+$, C$_{19}$H$_{18}$ClN$_5$O].

Example 25

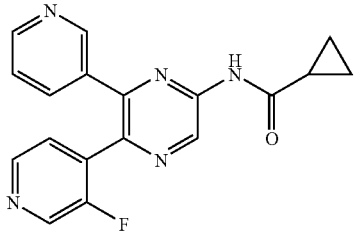

N-[5-(3-Fluoropyridin-4-yl)-6-pyridin-3-ylpyrazin-2-yl]cyclopropanecarboxamide

Obtained as an off-white solid (70%) from N-[6-chloro-5-(3-fluoropyridin-4-yl)pyrazin-2-yl]cyclopropanecarboxamide (Preparation 10) and pyridin-3-ylboronic acid following the procedure of Example 1.

δ $^1$H-NMR (CDCl$_3$): 9.65 (s, 1H), 9.20 (s, 1H), 8.80 (s, 1H), 8.65 (d, 1H), 8.55 (d, 1H), 8.35 (s, 1H), 7.60 (m, 2H), 7.20 (m, 1H), 1.80 (m, 1H), 1.20 (m, 2H), 1.00 (m, 2H).
ESI/MS m/e: 336 ([M+H]$^+$, C$_{18}$H$_{14}$FN$_5$O).
Retention time (min.): 11

Example 26

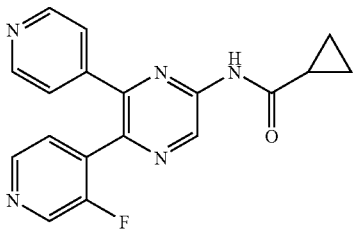

N-[5-(3-Fluoropyridin-4-yl)-6-pyridin-4-ylpyrazin-2-yl]cyclopropanecarboxamide

Obtained as a light green solid (74%) from N-[6-chloro-5-(3-fluoropyridin-4-yl)pyrazin-2-yl]cyclopropanecarboxamide (Preparation 10) and 4-(4,4,5,5-tetramethyl-1,3,2-dioxaborolan-2-yl)pyridine following the procedure of Example 1.

$^1$H-NMR (CDCl$_3$): 9.65 (s, 1H), 8.60 (d, 2H), 8.55 (m, 1H), 8.35 (s, 2H), 7.60 (m, 1H), 1.60 (m, 1H), 1.20 (m, 2H), 1.00 (m, 2H).

ESI/MS m/e: 336 ([M+H]$^+$, C$_{18}$H$_{14}$FN$_5$O).

Retention time (min.): 10

Example 27

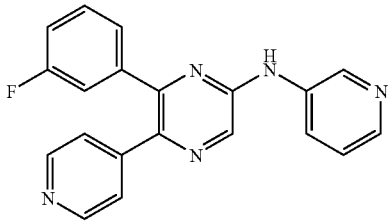

6-(3-Fluorophenyl)-N-pyridin-3-yl-5-pyridin-4-ylpyrazin-2-amine

An oven dried resealable Schlenk tube was charged with 6-(3-fluorophenyl)-5-pyridin-4-ylpyrazin-2-amine (Example 1, 100 mg, 0.37 mmol), 3-bromopyridine (43 μL, 0.45 mmol), 9,9-dimethyl-4,5-bis(diphenylphosphino)xanthene (17 mg, 0.03 mmol), cesium carbonate (171 mg, 0.52 mmol) and dioxane (2 mL). The Schlenk tube was subjected to three cycles of evacuation-backfilling with argon, and tris(dibenzilideneacetone) dipalladium (14 mg, 0.01 mmol) was added. After three new cycles of evacuation-backfilling with argon, the Schlenk tube was capped and placed in a 100° C. oil bath. After 20 h, the mixture was cooled and water was added. The solid was collected by filtration, washed with water, diethyl ether and dried, to give the title compound as a yellow solid (88 mg, 63%).

ESI/MS m/e: 344 ([M+H]$^+$, C$_{20}$H$_{14}$FN$_5$).

Retention time (min.): 8

Example 28

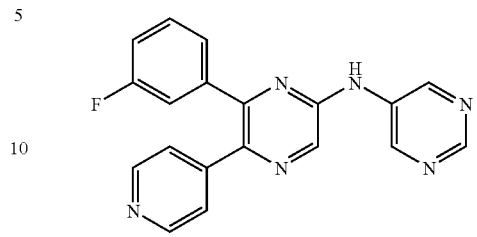

N-[6-(3-Fluorophenyl)-5-pyridin-4-ylpyrazin-2-yl]pyrimidin-5-amine

Obtained as a yellow solid (51%) from 6-(3-fluorophenyl)-5-pyridin-4-ylpyrazin-2-amine (Example 1) and 5-bromopyrimidine following the procedure of Example 27.

ESI/MS m/e: 345 ([M+H]$^+$, C$_{19}$H$_{13}$FN$_6$).

Retention time (min.): 10

Example 29

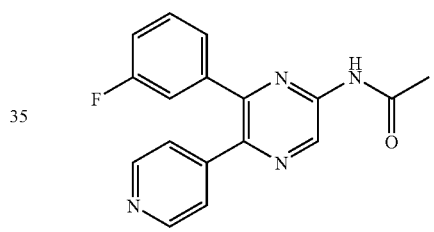

N-[6-(3-fluorophenyl)-5-pyridin-4-ylpyrazin-2-yl]acetamida

Obtained as a brown solid (99%) from 6-(3-fluorophenyl)-5-pyridin-4-ylpyrazin-2-amine (Example 1) and acetyl chloride following the procedure of Example 15 (step b).

ESI/MS m/e: 309 ([M+H]$^+$, C$_{17}$H$_{13}$FN$_4$O).

Retention time (min.): 10

Example 30

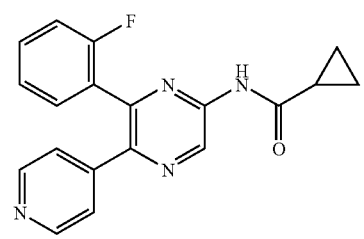

N-[6-(2-Fluorophenyl)-5-pyridin-4-ylpyrazin-2-yl]
cyclopropanecarboxamide

Obtained as a brown solid (40%) from 6-(2-fluorophenyl)-5-pyridin-4-ylpyrazin-2-amine (Example 16) and cyclopropanecarbonyl chloride following the procedure of Example 15 (step b).

ESI/MS m/e: 335 ([M+H]$^+$, $C_{19}H_{15}FN_4O$).

Retention time (min.): 12

Example 31

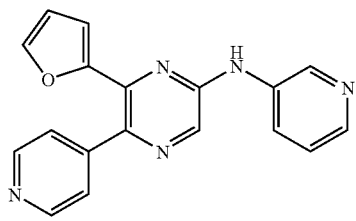

6-(2-Furyl)-N-pyridin-3-yl-5-pyridin-4-ylpyrazin-2-amine

Obtained as a yellow solid (29%) from 6-(2-furyl)-5-pyridin-4-ylpyrazin-2-amine (Example 5) and 3-bromopyridine following the procedure of Example 27.

ESI/MS m/e: 316 ([M+H]$^+$, $C_{18}H_{13}FN_5O$).

Retention time (min.): 6

Example 32

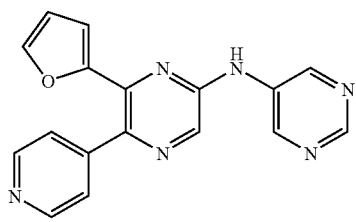

N-[6-(2-Furyl)-5-pyridin-4-ylpyrazin-2-yl]pyrimidin-5-amine

Obtained as a brown solid from 6-(2-furyl)-5-pyridin-4-ylpyrazin-2-amine (Example 5) and 5-bromopyrimidine following the procedure of Example 27.

ESI/MS m/e: 317 ([M+H]$^+$, $C_{17}H_{12}N_6O$).

Retention time (min.): 8.0

Example 33

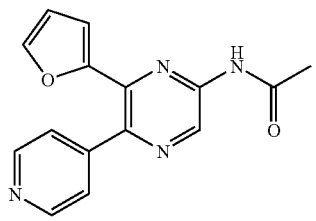

N-[6-(2-Furyl)-5-pyridin-4-ylpyrazin-2-yl]acetamide

Obtained as a light brown solid (90%) from 6-(2-furyl)-5-pyridin-4-ylpyrazin-2-amine (Example 5) and acetyl chloride following the procedure of Example 15 (step b).

ESI/MS m/e: 281 ([M+H]$^+$, $C_{15}H_{12}N_4O_2$).

Retention time (min.): 7

Example 34

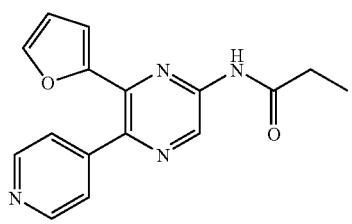

N-[6-(2-Furyl)-5-pyridin-4-ylpyrazin-2-yl]propanamide

Obtained as a light brown solid (74%) from 6-(2-furyl)-5-pyridin-4-ylpyrazin-2-amine (Example 5) and propionyl chloride following the procedure of Example 15 (step b).

ESI/MS m/e: 295 ([M+H]$^+$, $C_{16}H_{14}N_4O_2$).

Retention time (min.): 8

Example 35

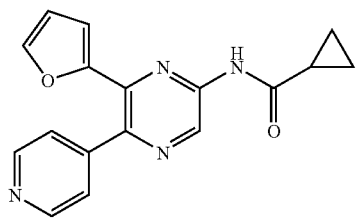

N-[6-(2-Furyl)-5-pyridin-4-ylpyrazin-2-yl]cyclopropanecarboxamide

Obtained as a white solid (100%) from 6-(2-furyl)-5-pyridin-4-ylpyrazin-2-amine (Example 5) and cyclopropanecarbonil chloride following the procedure of Example 15 (step b).

$^1$H-NMR (DMSO-$d_6$): 11.40 (s, 1H), 9.30 (s, 1H), 8.65 (d, 2H), 7.75 (s, 1H), 7.40 (d, 2H), 6.70 (d, 1H), 6.60 (m, 1H), 2.10 (m, 1H), 0.90 (d, 4H).

ESI/MS m/e: 307 ([M+H]$^+$, $C_{17}H_{14}N_4O_2$).

Retention time (min.): 13

Example 36

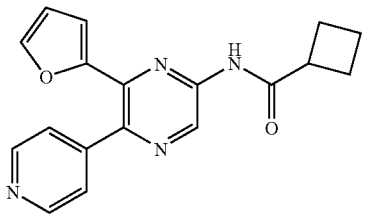

N-[6-(2-Furyl)-5-pyridin-4-ylpyrazin-2-yl]cyclobutanecarboxamide

Obtained as a light brown solid (74%) from 6-(2-furyl)-5-pyridin-4-ylpyrazin-2-amine (Example 5) and cyclobutanecarbonyl chloride following the procedure of Example 15 (step b).

$^1$H-NMR (DMSO-$d_6$): 10.90 (s, 1H), 9.35 (s, 1H), 8.65 (d, 2H), 7.70 (s, 1H), 7.40 (d, 2H), 6.70 (d, 1H), 6.60 (m, 1H), 3.50 (m, 1H), 2.25 (m, 2H), 2.10 (m, 2H), 2.00 (m, 2H).

ESI/MS m/e: 321 ([M+H]$^+$, $C_{18}H_{16}N_4O_2$).

Retention time (min.): 11

Example 37

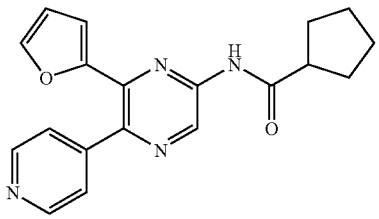

N-[6-(2-Furyl)-5-pyridin-4-ylpyrazin-2-yl]cyclopentanecarboxamide

Obtained as a light brown solid (61%) from 6-(2-furyl)-5-pyridin-4-ylpyrazin-2-amine (Example 5) and cyclopentanecarbonyl chloride following the procedure of Example 15 (step b).

$^1$H-NMR (DMSO-$d_6$): 11.0 (s, 1H), 9.35 (s, 1H), 8.65 (d, 2H), 7.75 (s, 1H), 7.40 (d, 2H), 6.70 (d, 1H), 6.60 (m, 1H), 3.00 (m, 1H), 1.90 (m, 2H), 1.70 (m, 4H), 1.50 (m, 2H).

ESI/MS m/e: 335 ([M+H]$^+$, $C_{19}H_{18}N_4O_2$).

Retention time (min.): 12

Example 38

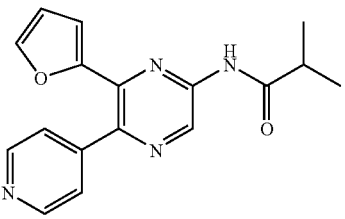

N-[6-(2-Furyl)-5-pyridin-4-ylpyrazin-2-yl]-2-methylpropanamide

Obtained as a light brown solid (98%) from 6-(2-furyl)-5-pyridin-4-ylpyrazin-2-amine (Example 5) and isobutyryl chloride following the procedure of Example 15 (step b).

ESI/MS m/e: 309 ([M+H]$^+$, $C_{17}H_{16}N_4O_2$).

Retention time (min.): 10

Example 39

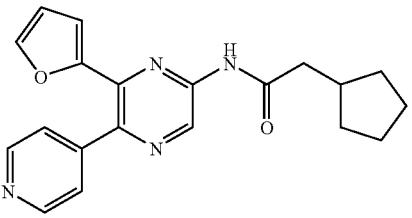

2-Cyclopentyl-N-[6-(2-furyl)-5-pyridin-4-ylpyrazin-2-yl]acetamide

Obtained as a light brown solid (48%) from 6-(2-furyl)-5-pyridin-4-ylpyrazin-2-amine (Example 5) and cyclopentylacetyl chloride following the procedure of Example 15 (step b).

ESI/MS m/e: 349 ([M+H]$^+$, $C_{20}H_{20}N_4O_2$).

Retention time (min.): 14

Example 40

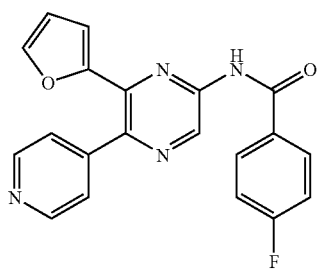

4-Fluoro-N-[6-(2-furyl)-5-pyridin-4-ylpyrazin-2-yl]benzamide

Obtained as a solid (50 mg, 45%) from 6-(2-furyl)-5-pyridin-4-ylpyrazin-2-amine (Example 5) and 4-fluorobenzoyl chloride following the procedure of Example 15 (step b).

δ $^1$H NMR (CDCl$_3$): 9.65 (s, 1H), 8.71 (m, 2H), 8.60 (s, 1H), 8.02 (m, 2H), 7.46 (m, 2H), 7.26 (m, 2H), 6.63 (d, 1H), 6.47 (m, 1H).

ESI/MS (m/e, %): 360 [(M+1)$^+$, C$_{20}$H$_{13}$FN$_4$O$_2$]

Example 41

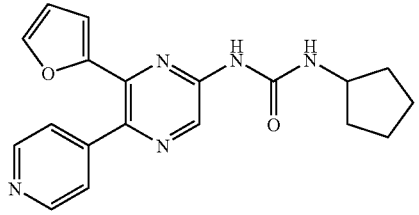

N-Cyclopentyl-N'-[6-(2-furyl)-5-pyridin-4-ylpyrazin-2-yl]urea

To a stirred solution of 6-(2-furyl)-5-pyridin-4-ylpyrazin-2-amine (Example 5, 90 mg, 0.378 mmol) in pyridine (1 mL) cyclopentylisocianate (42 μL, 0.378 mmol) was added and the solution was refluxed overnight. The residue was purified by silica gel flash column chromatography (98:2 dichloromethane/methanol) to give the title compound (58 mg, 44%) as a solid.

δ $^1$H NMR (CDCl$_3$): 9.26 (m, 2H), 8.69 (m, 2H), 8.26 (s, 1H), 7.45 (m, 3H), 4.29 (m, 1H), 2.13-1.62 (m, 8H).

ESI/MS (m/e, %): 349 [(M+1)$^+$, C$_{19}$H$_{19}$N$_5$O$_2$]

Example 42

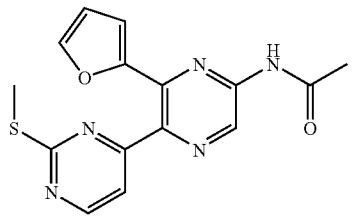

N-{6-(2-Furyl)-5-[2-(methylthio)pyrimidin-4-yl]pyrazin-2-yl}acetamide

Obtained as an off-white solid (53%) from 6-(2-furyl)-5-[2-(methylthio)pyrimidin-4-yl]pyrazin-2-amine (Example 6) and acetyl chloride following the same procedure of Example 15 (step b).

ESI/MS m/e: 328 ([M+H]$^+$, C$_{15}$H$_{13}$N$_5$O$_2$S).

Retention time (min.): 12

Example 43

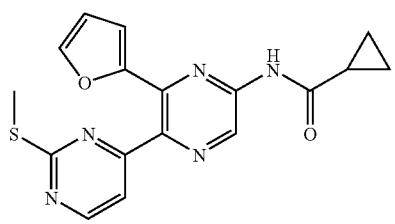

N-{6-(2-Furyl)-5-[2-(methylthio)pyrimidin-4-yl]pyrazin-2-yl}cyclopropane carboxamide Obtained as an off-white solid from 6-(2-furyl)-5-[2-(methylthio)pyrimidin-4-yl]pyrazin-2-amine (Example 6) and cyclopropanecarbonyl chloride following the same procedure of Example 15 (step b).

ESI/MS m/e: 354 ([M+H]$^+$, C$_{17}$H$_{15}$N$_5$O$_2$S).

Retention time (min.): 14

Example 44

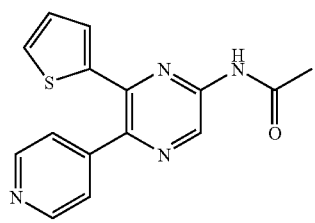

N-[5-Pyridin-4-yl-6-(2-thienyl)pyrazin-2-yl]acetamida

Obtained as an off-white solid (32%) from 5-pyridin-4-yl-6-(2-thienyl)pyrazin-2-amine (Example 7) and acetyl chloride following the same procedure of Example 15 (step b).

$^1$H-NMR (DMSO-$d_6$): 11.0 (s, 1H), 9.25 (s, 1H), 8.65 (d, 2H), 7.70 (d, 1H), 7.50 (d, 2H), 6.70 (dd, 1H), 6.80 (d, 1H), 2.20 (s, 3H).

ESI/MS m/e: 397 ([M+H]$^+$, $C_{15}H_{12}N_4OS$).
Retention time (min.): 9

Example 45

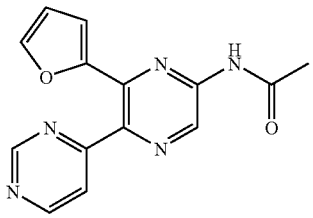

N-[6-(2-Furyl)-5-pyrimidin-4-ylpyrazin-2-yl]acetamide

Sodium hydride (42 mg, 1.05 mmol) was added to a stirred solution of 6-(2-furyl)-5-pyrimidin-4-ylpyrazin-2-amine (Example 8, 100 mg, 0.42 mmol) in DMF (4 mL) at 0° C. under nitrogen. The solution was allowed to stir for 30 min. at 0° C. Acetyl chloride (60.0 µL, 0.84 mmol) was then added and the reaction mixture was warmed up to room temperature and stirred for 3 days. The reaction was diluted with ethyl acetate and washed with water. The organic layer was washed with brine, dried (Na$_2$SO$_4$) and evaporated. The residue was purified by silica gel flash chromatography (50% ethyl acetate in hexanes to 75% ethyl acetate in hexanes). Concentration in vacuo of the product-rich fractions provided the titled compound as a pale-yellow solid (8 mg, 7%).

δ $^1$H NMR (CD$_3$OD): 9.40 (s, 1H), 9.15 (s, 1H), 8.90 (d, 1H), 7.90 (d, 1H), 7.20 (s, 1H), 7.05 (d, 1H), 6.55 (m, 1H), 3.30 (bs, 1H), 2.25 (s, 3H).

ESI/MS m/e: 282 ([M+H]$^+$, $C_{14}H_{11}N_5O_2$).

Retention time (min.): 9

Example 46

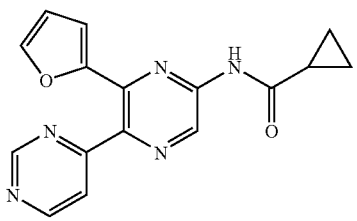

N-[6-(2-Furyl)-5-pyrimidin-4-ylpyrazin-2-yl]cyclopropanecarboxamide

Obtained as a pale-yellow solid (7%) using cyclopropanecarbonyl chloride following the procedure of Example 45.

δ $^1$H NMR (CDCl$_3$): 9.50 (s, 1H), 9.15 (s, 1H), 8.90 (d, 1H), 8.45 (bs, 1H), 7.70 (d, 1H), 7.35 (s, 1H), 6.80 (d, 1H), 6.50 (m, 1H), 1.65 (m, 1H), 1.20 (m, 2H), 0.95 (m, 2H).

ESI/MS m/e: 308 ([M+H]$^+$, $C_{16}H_{13}N_5O_2$).
Retention time (min.): 11

Example 47

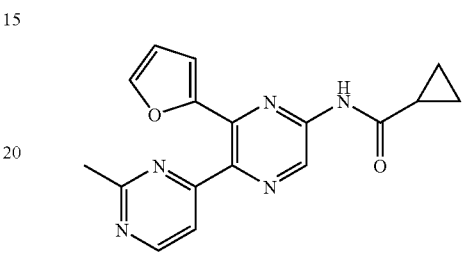

N-[6-(2-Furyl)-5-(2-methylpyrimidin-4-yl)pyrazin-2-yl]cyclopropanecarboxamide Cyclopropanecarbonyl chloride (0.028 mL, 0.30 mmol) was added to a stirred solution of 6-(2-furyl)-5-(2-methylpyrimidin-4-yl)pyrazin-2-amine (Example 9, 38 mg, 0.15 mmol) in pyridine (0.5 mL). The mixture was heated to 80° C. in a sealed tube and stirred for 3 h. The crude reaction was concentrated to dryness and the residue was diluted with ethyl acetate and washed with aqueous sodium bicarbonate 4%. The organic layer was dried (Na$_2$SO$_4$) and evaporated. The residue was purified with flash silica gel chromatography (30% ethyl acetate in hexanes). Concentration in vacuo of the product-rich fractions provided the titled compound as a pale-yellow solid (12 mg, 25%).

ESI/MS m/e: 322 ([M+H]$^+$, $C_{17}H_{15}N_5O_2$).
Retention time (min.): 11

Example 48

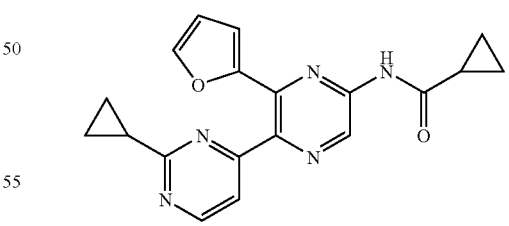

N-[5-(2-Cyclopropylpyrimidin-4-yl)-6-(2-furyl)pyrazin-2-yl]cyclopropane carboxamide Obtained as a pale-yellow solid (58%) from 5-(2-cyclopropylpyrimidin-4-yl)-6-(2-furyl)pyrazin-2-amine (Example 10) following the procedure of Example 47.

ESI/MS m/e: 348 ([M+H]$^+$, $C_{19}H_{17}N_5O_2$).
Retention time (min.): 13

Example 49

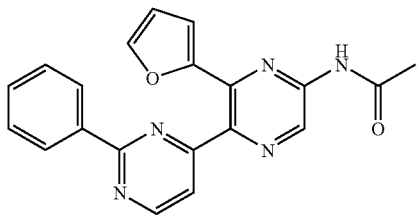

N-[6-(2-Furyl)-5-(2-phenylpyrimidin-4-yl)pyrazin-2-yl]acetamide

Obtained as a pale-yellow solid (17%) from 6-(2-furyl)-5-(2-phenylpyrimidin-4-yl)pyrazin-2-amine (Example 11) and acetyl chloride following the procedure of Example 47.

δ $^1$H NMR (CDCl$_3$): 9.50 (s, 1H), 8.95 (d, 1H), 8.25 (m, 2H), 8.10 (bs, 1H), 7.75 (d, 1H), 7.50 (m, 3H), 7.40 (bs, 1H), 6.90 (d, 1H), 6.50 (bs, 1H), 2.30 (s, 3H).

ESI/MS m/e: 358 ([M+H]$^+$, C$_{20}$H$_{15}$N$_5$O$_2$).

Retention time (min.): 15

Example 50

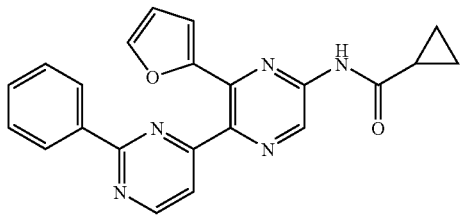

N-[6-(2-Furyl)-5-(2-phenylpyrimidin-4-yl)pyrazin-2-yl]cyclopropanecarboxamide

Obtained as a pale-yellow solid (22%) 6-(2-furyl)-5-(2-phenylpyrimidin-4-yl)pyrazin-2-amine (Example 11) following the procedure of Example 47.

δ $^1$H NMR (CDCl$_3$): 9.50 (s, 1H), 8.95 (d, 1H), 8.40 (bs, 1H), 8.25 (m, 2H), 7.70 (d, 1H), 7.50 (m, 3H), 7.40 (bs, 1H), 6.85 (d, 1H), 6.45 (bs, 1H), 1.70 (m, 1H), 1.20 (m, 2H), 0.95 (m, 2H).

ESI/MS m/e: 384 ([M+H]$^+$, C$_{22}$H$_{17}$N$_5$O$_2$).

Retention time (min.): 17

Example 51

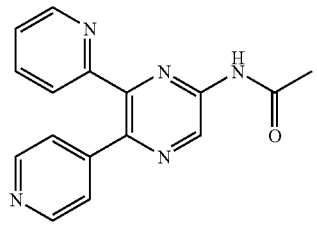

N-(6-Pyridin-2-yl-5-pyridin-4-ylpyrazin-2-yl)acetamide

Obtained as a brown solid (56%) from 6-pyridin-2-yl-5-pyridin-4-ylpyrazin-2-amine (Example 12) and acetyl chloride following the same procedure of Example 15 (step b).

ESI/MS m/e: 292 ([M+H]$^+$, C$_{16}$H$_{13}$N$_5$O).

Retention time (min.): 6

Example 52

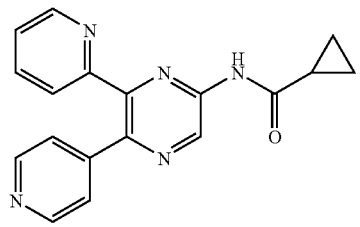

N-(6-Pyridin-2-yl-5-pyridin-4-ylpyrazin-2-yl)cyclopropanecarboxamide

Obtained as a brown solid (44%) from 6-pyridin-2-yl-5-pyridin-4-ylpyrazin-2-amine (Example 12) and cyclopropanecarbonyl chloride following the same procedure of Example 15 (step b).

$^1$H-NMR (DMSO-d$_6$): 11.40 (s, 1H), 9.45 (s, 1H), 8.40 (m, 3H), 7.95 (t, 1H), 7.50 (d, 2H), 7.80 (d, 1H), 7.25 (m, 1H), 2.05 (m, 1H), 0.95 (d, 4H).

ESI/MS m/e: 318 ([M+H]$^+$, C$_{18}$H$_{15}$N$_5$O).

Retention time (min.): 8

Example 53

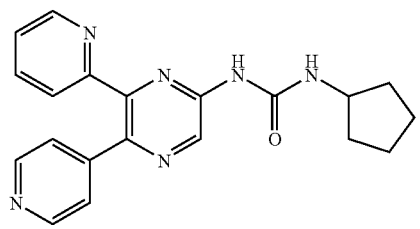

N-Cyclopentyl-N'-(6-pyridin-2-yl-5-pyridin-4-ylpyrazin-2-yl)urea

Sodium hydride (17 mg, 0.43 mmol) in anhydrous dimethylformamide (3.5 mL) was stirred at 0° C. under nitrogen atmosphere. 6-Pyridin-2-yl-5-pyridin-4-ylpyrazin-2-amine (Example 12, 90 mg, 0.36 mmol) in anhydrous dimethylformamide (2.5 mL) and cyclopentylisocianate (50 µL, 0.43 mmol) were sequentially added. The mixture was stirred at 70° C. under nitrogen atmosphere for 1 h 30 min. Dimethylformamide was removed in vacuo and the resulting solid was triturated with hexanes-dichloromethane, filtered, washed with hexanes and dried. Silica gel flash chromatography of the solid (dichloromethane to dichloromethane/methanol 95:5) afforded the title compound (53 mg, 41%) as a white solid.

ESI/MS m/e: 361 ([M+H]$^+$, $C_{20}H_{20}N_6O$).
Retention time (min.): 10

Example 54

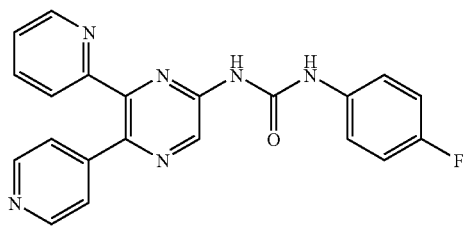

N-(4-Fluorophenyl)-N'-(6-pyridin-2-yl-5-pyridin-4-ylpyrazin-2-yl)urea

Obtained as a light yellow solid (37%) from 6-pyridin-2-yl-5-pyridin-4-ylpyrazin-2-amine (Example 12) and 4-fluorophenylisocianate following the same procedure of Example 53.

$^1$H-NMR (CDCl$_3$): 11.50 (s, 1H), 9.55 (s, 1H), 8.75 (d, 1H), 8.55 (d, 2H), 7.80 (t, 1H), 7.45 (m, 3H), 7.30 (m, 4H), 7.05 (t, 2H)

ESI/MS m/e: 387 ([M+H]$^+$, $C_{21}H_{15}FN_6O$).
Retention time (min.): 12

Example 55

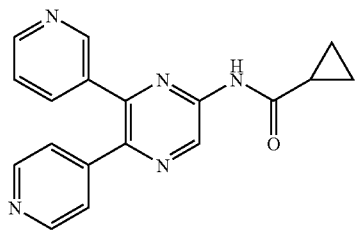

N-(6-Pyridin-3-yl-5-pyridin-4-ylpyrazin-2-yl)cyclopropanecarboxamide

Obtained as a solid (90%) from 6-pyridin-3-yl-5-pyridin-4-ylpyrazin-2-amine (Example 13) and cyclopropanecarbonyl chloride following the procedure of Example 15 (step b).

δ $^1$H NMR (CDCl$_3$): 9.62 (s, 1H), 8.77 (m, 1H), 8.64 (d, 1H), 8.58 (m, 2H), 8.65 (m, 1H), 7.33 (m, 2H), 7.26 (m, 1H), 1.72 (m, 1H), 1.22 (m, 2H), 1.01 (m, 1H).
ESI/MS (m/e, %): 317 [(M+1)$^+$, $C_{18}H_{15}N_5O$]

Example 56

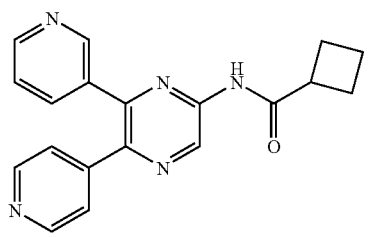

N-(6-Pyridin-3-yl-5-pyridin-4-ylpyrazin-2-yl)cyclobutanecarboxamide

Obtained as a white solid (57%) from 6-pyridin-3-yl-5-pyridin-4-ylpyrazin-2-amine (Example 13) and cyclobutanecarbonyl chloride following the same procedure of Example 15 (step b).

$^1$H-NMR (CDCl$_3$): 9.65 (s, 1H), 8.75 (s, 1H), 8.60 (d, 1H), 8.75 (d, 2H), 7.95 (s, 1H), 7.65 (d, 1H), 7.30 (d, 2H), 7.20 (s, 1H), 3.30 (m, 1H), 2.45 (m, 4H), 2.00 (m, 2H).

ESI/MS m/e: 332 ([M+H]$^+$, $C_{19}H_{17}N_5O$).
Retention time (min.): 9

Example 57

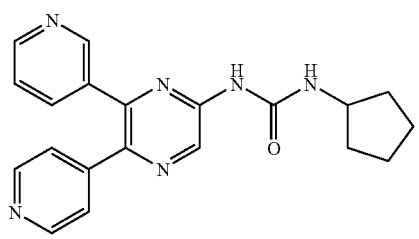

N-cyclopentyl-N'-(6-pyridin-3-yl-5-pyridin-4-ylpyrazin-2-yl)urea

Obtained as a white solid (90%) from 6-pyridin-3-yl-5-pyridin-4-ylpyrazin-2-amine (Example 13) and cyclopentylisocianate following the same procedure of Example 53.

δ $^1$H NMR (CDCl$_3$): 9.06 (s, 1H), 8.91 (d, 1H), 8.74 (m, 1H), 8.68 (m, 1H), 8.57 (d, 1H), 8.42 (s, 1H), 7.66 (m 1H), 7.32 (m, 2H), 4.27 (m, 1H), 2.08-1.47 (m, 8H).

ESI/MS (m/e, %): 360 [(M+1)$^+$, $C_{20}H_{20}N_6O$].

Example 58

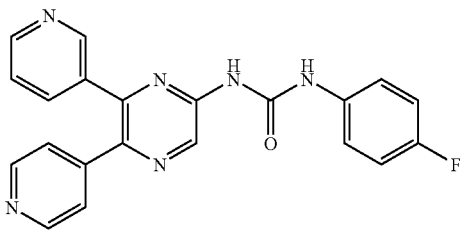

N-(4-fluorophenyl)-N'-(6-pyridin-3-yl-5-pyridin-4-ylpyrazin-2-yl)urea

Obtained as a solid (32%) from 6-pyridin-3-yl-5-pyridin-4-ylpyrazin-2-amine (Example 13) and 1-fluoro-4-isocyanatobenzene following the procedure of Example 53.

δ $^1$H NMR (CDCl$_3$): 8.80 (m, 1H), 8.69 (m, 2H), 8.56 (d, 2H), 7.70 (d, 1H), 7.45 (dd, 2H), 7.35 (m, 3H), 7.05 (t, 2H).

ESI/MS (m/e, %): 386 [(M+1)$^+$, C$_{21}$H$_{15}$FN$_6$O]

Example 59

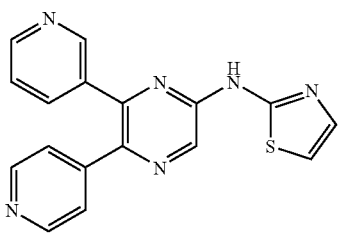

6-Pyridin-3-yl-5-pyridin-4-yl-N-1,3-thiazol-2-ylpyrazin-2-amine

An oven dried resealable Schlenk tube was charged with 6-pyridin-3-yl-5-pyridin-4-ylpyrazin-2-amine (Example 13, 60 mg, 0.241 mmol), 2-bromo-1,3-thiazole (22 μL, 0.241 mmol), cesium carbonate (110 mg, 0.337 mmol) and dioxane (2.5 mL). The Schlenk tube was subjected to three cycles of evacuation-backfilling with argon, and tris(dibenzylideneacetone)dipalladium(0) (9 mg, 0.01 mmol) and 9,9-dimethyl-4,5-bis(diphenylphosphino)xanthene (11 mg, 0.019 mmol) was added. After three new cycles of evacuation-backfilling with argon, the Schlenk tube was capped and placed in a 100° C. oil bath. After 16 h, the mixture was cooled, partitioned between water and ethyl acetate, the aqueous phase was extracted twice with ethyl acetate, the organic layers washed with brine, dried (MgSO$_4$) and evaporated. Flash chromatography (95:5 dichloromethane/methanol) furnished the title compound as a solid (35 mg, 44%).

δ $^1$H NMR (CDCl$_3$): 8.96 (m, 1H), 8.69 (d, 1H), 8.60 (d, 2H), 8.52 (s, 1H), 7.85 (d, 1H), 7.58 (d, 1H), 7.39 (m, 2H), 7.26 (s, 1H), 7.00 (d, 1H).

ESI/MS (m/e, %): 332 [(M+1)$^+$, C$_{17}$H$_{12}$N$_6$S]

Example 60

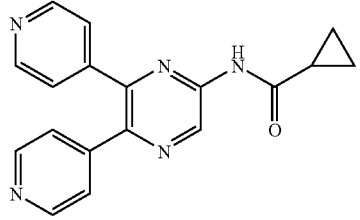

N-(5,6-Dipyridin-4-ylpyrazin-2-yl)cyclopropanecarboxamide

Obtained as an off-white solid (48%) from 5,6-dipyridin-4-ylpyrazin-2-amine (Example 14) and cyclopropanecarbonyl chloride following the same procedure of Example 15 (step b).

$^1$H-NMR (DMSO-d$_6$): 11.45 (s, 2H), 9.45 (s, 1H), 8.60 (d, 2H), 8.55 (d, 2H), 7.35 (d, 2H), 7.30 (d, 2H), 2.10 (m, 1H), 0.95 (d, 4H).

ESI/MS m/e: 318 ([M+H]$^+$, C$_{18}$H$_{15}$N$_5$O).

Retention time (min.): 7

Example 61

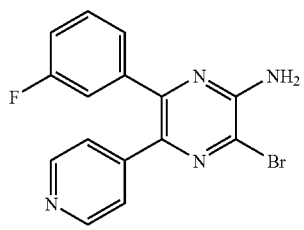

3-Bromo-6-(3-fluorophenyl)-5-pyridin-4-ylpyrazin-2-amine

To a solution of 6-(3-fluorophenyl)-5-pyridin-4-ylpyrazin-2-ylamine (Example 1, 70 mg, 0.26 mmol) in chloroform (4 mL) at 0° C. was added pyridine (22 μL, 0.27 mmol) and bromine (14 μL, 0.27 mmol). The reaction mixture was stirred at room temperature for 24 h, chloroform (20 mL) was added, the organic layer was washed with water and brine, dried (MgSO$_4$) and evaporated. The residue was purified by silica gel flash column chromatography (dichloromethane/methanol 95:5) to provide the title compound as a red solid (22 mg, 24%).

ESI/MS m/e: 345 ([M+H]$^+$, C$_{15}$H$_{10}$BrFN$_4$).

Retention time (min.): 9

Example 62

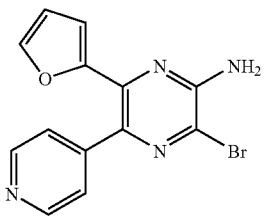

3-Bromo-6-(2-furyl)-5-pyridin-4-ylpyrazin-2-amine

To a 0° C. stirred solution of 6-(2-furyl)-5-pyridin-4-ylpyrazin-2-amine (Example 5, 195 mg, 0.82 mmol) in dimethylsulfoxide (1.5 mL) and water (40 µL), was added portionwise N-bromosuccinimide (146 mg, 0.82 mmol). The mixture was stirred at room temperature for 40 min, then poured into water, extracted with dichloromethane (×3), the organic layers washed with brine, dried (MgSO$_4$) and evaporated to furnish the title compound (198 mg, 75%) as a brown solid.

$^1$H-NMR (DMSO-d6): 8.55 (d, 2H), 7.65 (s, 1H), 7.25 (d, 2H), 7.10 (s, 2H), 6.65 (d, 2H), 6.55 (d, 2H).

ESI/MS m/e: 318 ([M+H]$^+$, C$_{13}$H$_9$BrN$_4$O).

Retention time (min.): 7

Example 63

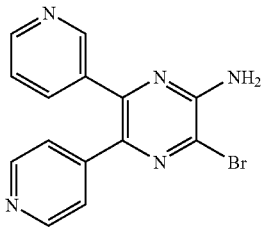

3-Bromo-6-pyridin-3-yl-5-pyridin-4-ylpyrazin-2-amine

Obtained as a brown solid (30%) from 6-pyridin-3-yl-5-pyridin-4-ylpyrazin-2-amine (Example 13) and N-bromosuccinimide following the same procedure of Example 62.

ESI/MS m/e: 329 ([M+H]$^+$, C$_{14}$H$_{10}$BrN$_5$).

Retention time (min.): 6

Example 64

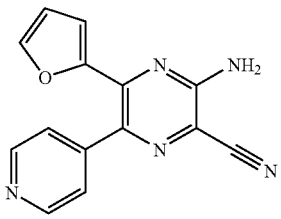

3-Amino-5-(2-furyl)-6-pyridin-4-ylpyrazine-2-carbonitrile

A mixture of sodium cyanide (21 mg, 0.42 mmol) and copper (I) cyanide (38 mg, 0.42 mmol) in anhydrous dimethylformamide (1.5 mL) was heated to 120° C. 3-Bromo-6-(2-furyl)-5-pyridin-4-ylpyrazin-2-amine (Example 62, 90 mg, 0.28 mmol) was added in portions. After stirring at 120° C. for two hours, the mixture was cooled and evaporated. A 0.75M aqueous solution of sodium cyanide (6 mL) was added, stirred for 10 min at room temperature and partitioned between water and ethyl acetate. The aqueous phase was extracted twice with ethyl acetate, the organic layers washed with brine, dried (MgSO$_4$), and evaporated. Silica gel flash column chromatography (dichloromethane/methanol 98:2) furnished the title compound as a dark yellow solid (52 mg, 70%).

$^1$H-NMR (DMSO-d$_3$): 8.60 (d, 2H), 7.75 (s, 1H), 7.65 (bs, 2H), 7.35 (m, 2H), 6.75 (s, 1H), 6.60 (m, 1H).

ESI/MS m/e: 264 ([M+H]$^+$, C$_{14}$H$_9$N$_5$O)

Retention time (min.): 7

Example 65

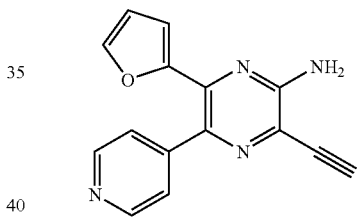

3-Ethynyl-6-(2-furyl)-5-pyridin-4-ylpyrazin-2-amine

Step a 6-(2-Furyl)-5-pyridin-3-trimethylsilyl-4-ylpyrazin-2-amine

An oven dried resealable Schlenk tube was charged with 3-bromo-6-(2-furyl)-5-pyridin-4-ylpyrazin-2-amine (Example 62, 90 mg, 0.28 mmol), trimethylsilylacetilene (80 µL, 0.56 mmol) and tetrahydrofuran (1 mL). The Schlenk tube was subjected to three cycles of evacuation-backfilling with argon, and tetrakis(triphenylphosphine)palladium (8 mg, 0.01 mmol) and copper (I) iodide (2.2 mg, 0.01 mmol) were added. After three new cycles of evacuation-backfilling with argon, the Schlenk tube was capped and placed in a 90° C. oil bath. After 3 h, the mixture was cooled, partitioned between water and ethyl acetate, the aqueous phase extracted twice with ethyl acetate, the organic layers washed with brine, dried (MgSO$_4$) and evaporated. Silica gel flash chromatography (dichloromethane/methanol 90:10) furnished the title compound as a orange oil (48 mg, 51%).

Step b

3-Ethynyl-6-(2-furyl)-5-pyridin-4-ylpyrazin-2-amine

A mixture of 6-(2-furyl)-5-pyridin-3-trimethylsilyl-4-ylpyrazin-2-amine (45 mg, 0.13 mmol) and potassium carbonate (28 mg, 0.20 mmol) in methanol (2 mL) was stirred at room temperature for 3 h. The mixture was partitioned between water and ethyl acetate, the aqueous phase extracted twice with ethyl acetate, the organic layers washed with brine, dried (MgSO$_4$) and evaporated to give the title compound (28 mg, 80%) as a brown solid.

$^1$H-NMR (CDCl$_3$): 8.60 (d, 2H), 7.45 (s, 1H), 7.40 (d, 2H), 6.55 (d, 1H), 6.45 (d, 1H), 5.5 (bs, 2H), 3.60 (s, 1H).

ESI/MS m/e: 263 ([M+H]$^+$, C$_{15}$H$_{10}$N$_4$O).
Retention time (min.): 6

Example 66

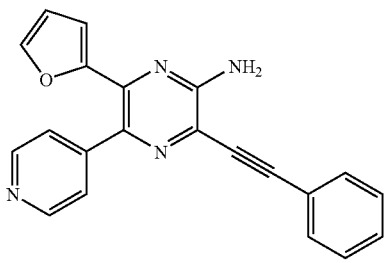

6-(2-Furyl)-3-(phenylethynyl)-5-pyridin-4-ylpyrazin-2-amine

Obtained as a brown solid (54%) 3-bromo-6-(2-furyl)-5-pyridin-4-ylpyrazin-2-amine (Example 62) and phenylacetylene following the same procedure of Example 65 (Step a).

ESI/MS m/e: 339 ([M+H]$^+$, C$_{21}$H$_{14}$N$_4$O)
Retention time (min.): 12

Example 67

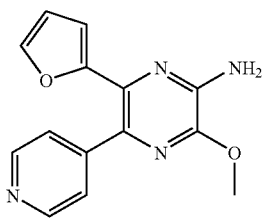

6-(2-Furyl)-3-methoxy-5-pyridin-4-ylpyrazin-2-amine

3-Bromo-6-(2-furyl)-5-pyridin-4-ylpyrazin-2-amine (Example 62, 160 mg, 0.5 mmol) was suspended in methanol (5 mL), sodium methoxide was added (0.12 mL, solution 30% in methanol, 0.5 mmol) and the solution was heated to 70° C. for 2 hours. The mixture was cooled, the solvent was evaporated in vacuo and the residue was partitioned between dichloromethane and brine. The aqueous layer was extracted with dichloromethane. The organic layer was dried and concentrated. The residue was triturated with diethyl ether to provide the target compound as a brownish solid (62 mg, 46%)

δ $^1$H NMR (CDCl$_3$): 4.08 (s, 3H), 5.03 (bs, 2H), 6.42 (s, 1H), 7.23 (s, 1H), 7.38 (m, 3H), 8.59 (d, 2H)

ESI/MS (m/e, %): 269 [(M+1)$^+$, 100]

Retention time (min.): 6

Example 68

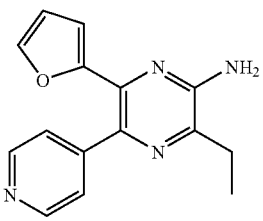

3-Ethyl-6-(2-furyl)-5-pyridin-4-ylpyrazin-2-amine

To a solution of 3-ethynyl-6-(2-furyl)-5-pyridin-4-ylpyrazin-2-amine (Example 65, 50 mg, 0.19 mmol) in ethanol (4 mL) was added platinum dioxide (5 mg). The mixture was hydrogenated at 1 atmosphere and at room temperature for 18 h, filtered, washed with methanol and dichloromethane and evaporated to give the title compound as a white solid (44 mg, 88%).

ESI/MS m/e: 267 ([M+H]$^+$, C$_{15}$H$_{14}$N$_4$O).
Retention time (min.): 12

Example 69

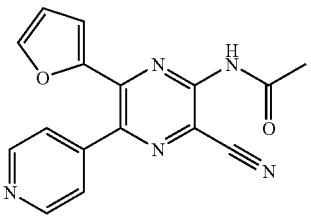

N-[3-Cyano-6-(2-furyl)-5-pyridin-4-ylpyrazin-2-yl]acetamide

Obtained as a yellow solid (45%) from 3-amino-5-(2-furyl)-6-pyridin-4-ylpyrazine-2-carbonitrile (Example 64) and acetyl chloride following the same procedure of Example 15 (step b).

ESI/MS m/e: 306 ([M+H]$^+$, C$_{16}$H$_{11}$N$_5$O$_2$).
Retention time (min.): 8

Example 70

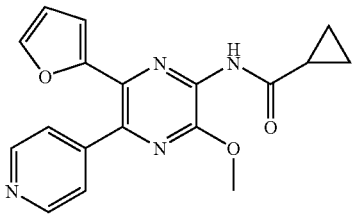

N-[6-(2-Furyl)-3-methoxy-5-pyridin-4-ylpyrazin-2-yl]cyclopropanecarboxamide

Obtained as a yellow solid (70%) from 6-(2-furyl)-3-methoxy-5-pyridin-4-ylpyrazin-2-amine (Example 67) and cyclopropanecarbonyl chloride following the same procedure of Example 15 (step b).

$^1$H-NMR (CDCl$_3$): 1.25 (m, 5H), 4.08 (s, 3H), 6.42 (m, 1H), 7.31 (s, 1H), 7.40 (m, 3H), 8.20 (bs, 1H), 8.70 (d, 2H)

ESI/MS m/e: 337 ([M+H]$^+$, C$_{18}$H$_{16}$N$_4$O$_3$)

Retention time (min.): 8

Example 71

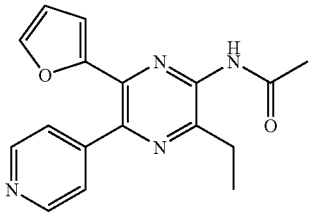

N-[3-ethyl-6-(2-furyl)-5-pyridin-4-ylpyrazin-2-yl]acetamide

Obtained as a yellow solid (45%) from 3-ethyl-6-(2-furyl)-5-pyridin-4-ylpyrazin-2-amine (Example 68) and acetyl chloride following the same procedure of Example 15 (step b).

ESI/MS m/e: 308 ([M+H]$^+$, C$_{18}$H$_{16}$N$_4$O$_2$).

Retention time (min.): 8

Example 72

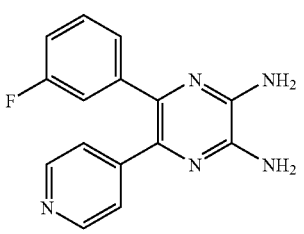

5-(3-Fluorophenyl)-6-pyridin-4-ylpyrazine-2,3-diamine

A mixture of 5-(3-fluorophenyl)-6-pyridin-4-yl[1,2,5]thiadiazolo[3,4-b]pyrazine (Preparation 11) (1.6 g, 5.2 mmol) in ammonia solution (32%, 30 mL) was stirred and heated under reflux for 1 h. The reaction was allowed to cool to room temperature, diluted with water and the suspension obtained was filtered to provide the title compound as a brown solid (0.7 g, 48%).

δ $^1$H-NMR (DMSO-d$_6$): 8.39 (d, J=6.0 Hz, 2H), 7.26 (m, 1H), 7.19 (d, J=6.0 Hz, 2H), 7.11-6.99 (m, 3H), 6.42 (s, 2H), 6.35 (s, 2H).

ESI/MS m/e: 282 ([M+H]+, C$_{15}$H$_{12}$FN$_5$)

Retention time (min.): 7

Example 73

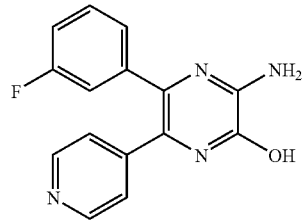

3-Amino-5-(3-fluorophenyl)-6-pyridin-4-ylpyrazin-2-ol

To a cooled solution (0° C.) of 5-(3-fluorophenyl)-6-pyridin-4-ylpyrazine-2,3-diamine (Example 72, 100 mg, 0.36 mmol) in HCl 1N (1 mL) was added dropwise a solution of sodium nitrite (35 mg, 0.50 mmol) in water (0.6 mL). The reaction was stirred for 1 h at room temperature and after this period was driven to pH7 by addition of a NaHCO$_3$ 4% solution. The suspension was filtered to leave a solid which was purified by silica gel chromatography eluting with CH$_2$Cl$_2$/MeOH/NH$_3$ (50:8:1) to afford the title compound (37 mg, 36%).

δ $^1$H-NMR (DMSO-d$_6$): 12.05 (s, 1H), 8.48 (d, J=5.4 Hz, 2H), 7.24 (m, 1H), 7.18 (d, 2H), 7.07-6.90 (m, 4H).

ESI/MS m/e: 283 ([M+H]+, C$_{15}$H$_{11}$FN$_4$O)

Retention time (min.): 8

Example 74

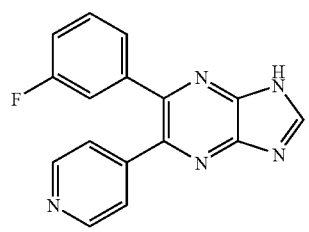

6-(3-Fluorophenyl)-5-pyridin-4-yl-1H-imidazo[4,5-b]pyrazine

A mixture of 5-(3-fluorophenyl)-6-pyridin-4-ylpyrazine-2,3-diamine (Example 72, 300 mg, 1.07 mmol) in 1,1',1''-[methanetriyltris(oxy)]triethane (3 mL) was stirred and heated at 140° C. overnight. The solvent was removed under vacuum and the residue was triturated with diethyl ether. The resulting solid was purified by silica gel column chromatography ($CH_2Cl_2$/MeOH 9:1) to afford the title compound as a yellow solid (136 mg, 44%)

δ $^1$H-NMR (DMSO-$d_6$): 13.78 (s, 1H), 8.94 (s, 1H), 8.55 (d, J=6.0 Hz, 2H), 7.42-7.36 (m+d, 3H), 7.23-7.16 (m, 3H).

ESI/MS m/e: 292 ([M+H]+, $C_{16}H_{10}FN_5$)

Retention time (min.): 8

Example 75

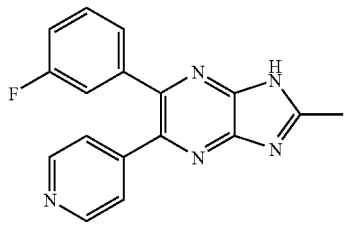

6-(3-Fluorophenyl)-2-methyl-5-pyridin-4-yl-1H-imidazo[4,5-b]pyrazine

A mixture of 5-(3-fluorophenyl)-6-pyridin-4-ylpyrazine-2,3-diamine (Example 72, 300 mg, 1.07 mmol) in acetic anhydride (3 mL) was stirred and heated at 140° C. for 4 h. Then polyphosphoric acid was added (0.32 g) and allowed to react at the same temperature for 2 h. Upon cooling, water was added and the product extracted with ethyl acetate. The crude obtained was purified by silica column chromatography eluting with a gradient from $CH_2Cl_2$ to $CH_2Cl_2$/MeOH 95:5 to afford the title compound as a yellow solid (36 mg, 52%).

δ $^1$H-NMR (DMSO-$d_6$): 13.34 (s, 1H), 8.39 (d, J=3.9 Hz, 2H), 7.25-7.20 (m+d, 3H), 7.10-7.00 (m, 3H).

ESI/MS m/e: 306 ([M+H]+, $C_{17}H_{12}FN_5$)

Retention time (min.): 8

Example 76

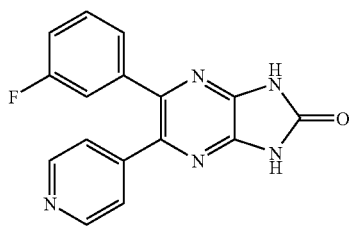

5-(3-Fluorophenyl)-6-pyridin-4-yl-1,3-dihydro-2H-imidazo[4,5-b]pyrazin-2-one A mixture of 5-(3-fluorophenyl)-6-pyridin-4-ylpyrazine-2,3-diamine (Example 72, 200 mg, 0.71 mmol), 1,1'-carbonylbis-1H-imidazole (138 mg, 0.85 mmol) in THF (3 mL) was stirred and heated at reflux overnight. Solvent was removed under reduced pressure and the residue was partitioned between water and ethyl acetate. The separated organic phase was dried ($MgSO_4$) and evaporated to dryness. The residue was recrystallized from ethanol to give the title compound as a white solid (96 mg, 44%).

δ $^1$H-NMR (DMSO-$d_6$): 12.03 (s, 2H), 8.50 (d, J=6.0 Hz, 2H), 7.35 (m, 1H), 7.27 (d, J=6.0 Hz, 2H), 7.18-7.07 (m, 3H).

ESI/MS m/e: 308 ([M+H]+, $C_{16}H_{10}FN_5O$)

Retention time (min.): 8

Example 77

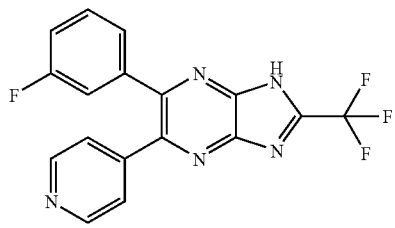

6-(3-Fluorophenyl)-5-pyridin-4-yl-2-(trifluoromethyl)-1H-imidazo[4,5-b]pyrazine A mixture of 5-(3-fluorophenyl)-6-pyridin-4-ylpyrazine-2,3-diamine (Example 72, 100 mg, 0.36 mmol) in trifluoroacetic anhydride (3 mL) was stirred and heated at 120° C. for 3 h. Then polyphosphoric acid was added (100 mg) and allowed to react at the same temperature for 2 h. Upon cooling, an aqueous solution of $NaHCO_3$ 4% was added and the crude product extracted with ethyl acetate. The organic phase was dried ($MgSO_4$), concentrated and the residue was purified by silica column chromatography ($CH_2Cl_2$/MeOH 95:5) to provide the title compound as a brown solid (58 mg, 45%).

δ $^1$H-NMR (DMSO-$d_6$): 8.62 (d, 2H), 7.63 (d, 2H), 7.42-7.20 (m, 4H). (200)

ESI/MS m/e: 360 ([M+H]$^+$, $C_{17}H_9F_4N_5$)

Retention time (min.): 12

Example 78

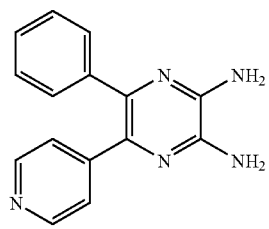

5-Phenyl-6-pyridin-4-ylpyrazine-2,3-diamine

Obtained (51%) from 5-phenyl-6-pyridin-4-yl[1,2,5]thiadiazolo[3,4-b]pyrazine (Preparation 12) following the procedure described in Example 72.

δ $^1$H-NMR (DMSO-d$_6$): 8.37 (d, 2H), 7.28 (brs, 5H), 7.19 (d, 2H), 6.37 (s, 2H), 6.21 (s, 2H).

ESI/MS m/e: 264 ([M+H]+, $C_{15}H_{13}N_5$)
Retention time (min.): 5

Example 79

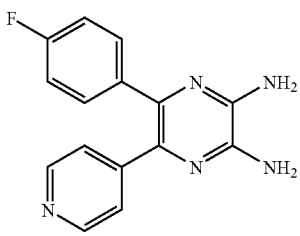

5-(4-Fluorophenyl)-6-pyridin-4-ylpyrazine-2,3-diamine

Obtained (69%) from 5-(4-fluorophenyl)-6-pyridin-4-yl[1,2,5]thiadiazolo[3,4-b]pyrazine (Preparation 13) following the procedure described in Example 72.

δ $^1$H-NMR (DMSO-d$_6$): 8.38 (d, 2H), 7.28-7.23 (m, 2H), 7.17 (d, 2H), 7.10 (t, 2H), 6.40 (s, 2H), 6.28 (s, 2H).

ESI/MS m/e: 282 ([M+H]+, $C_{15}H_{12}FN_5$)
Retention time (min.): 6

Example 80

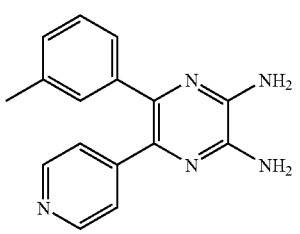

5-(3-Methylphenyl)-6-pyridin-4-ylpyrazine-2,3-diamine

Obtained (81%) from 5-(3-methylphenyl)-6-pyridin-4-yl[1,2,5]thiadiazolo[3,4-b]pyrazine (Preparation 14) following the procedure described in Example 72.

δ $^1$H-NMR (DMSO-d$_6$): 8.37 (d, 2H), 7.18 (d, 2H), 7.17-7.04 (m, 3H), 6.94 (brd, 1H), 2.23 (s, 3H).

ESI/MS m/e: 278 ([M+H]+, $C_{16}H_{15}N_5$)
Retention time (min.): 7

Example 81

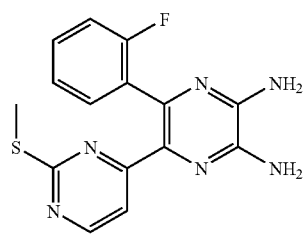

5-(2-Fluorophenyl)-6-[2-(methylthio)pyrimidin-4-yl]pyrazine-2,3-diamine

Obtained (52%) from 5-(2-fluorophenyl)-6-[2-(methylthio)pyrimidin-4-yl][1,2,5]thiadiazolo[3,4-b]pyrazine (Preparation 15) following the procedure described in Example 72.

δ $^1$H-NMR (DMSO-d$_6$): 8.51 (d, 1H), 7.44 (d, 1H), 7.40 (t, 1H), 7.30 (m, 1H), 7.20 (t, 1H), 7.04 (t, 1H), 1.71 (s, 3H).

ESI/MS m/e: 345 ([M+H]+, $C_{15}H_{13}FN_6S$)
Retention time (min.): 12

Example 82

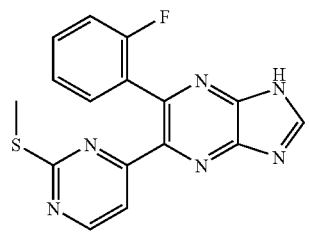

6-(2-Fluorophenyl)-5-[2-(methylthio)pyrimidin-4-yl]-1H-imidazo[4,5-b]pyrazine Obtained (64%) from 5-(2-fluorophenyl)-6-[2-(methylthio)pyrimidin-4-yl]pyrazine-2,3-diamine (Example 81) following the procedure described in Example 74.

ESI/MS m/e: 339 ([M+H]+, $C_{16}H_{11}FN_6S$)
Retention time (min.): 12

Example 83

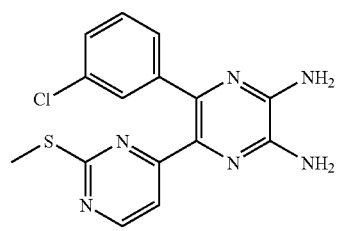

5-(3-Chlorophenyl)-6-[2-(methylthio)pyrimidin-4-yl]pyrazine-2,3-diamine

Obtained (52%) from 5-(3-chlorophenyl)-6-[2-(methylthio)pyrimidin-4-yl][1,2,5]thiadiazolo[3,4-b]pyrazine (Preparation 16) following the procedure described in Example 72.

ESI/MS m/e: 345 ([M+H]+, $C_{15}H_{13}ClN_6S$)
Retention time (min.): 14

Example 84

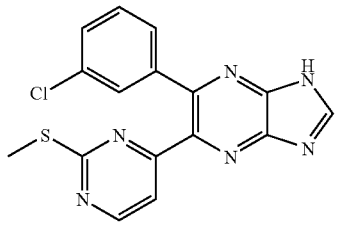

6-(3-Chlorophenyl)-5-[2-(methylthio)pyrimidin-4-yl]-1H-imidazo[4,5-b]pyrazine

Obtained (66%) from 5-(3-chlorophenyl)-6-[2-(methylthio)pyrimidin-4-yl]pyrazine-2,3-diamine (Example 83) following the procedure described in Example 74.

ESI/MS m/e: 355 ([M+H]+, $C_{16}H_{11}ClN_6S$)
Retention time (min.): 14

Example 85

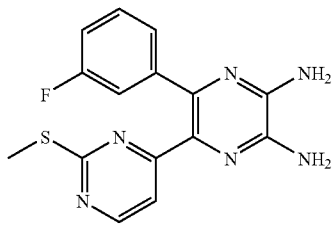

5-(3-Fluorophenyl)-6-[2-(methylthio)pyrimidin-4-yl]pyrazine-2,3-diamine

Obtained (73%) from 5-(3-fluorophenyl)-6-[2-(methylthio)pyrimidin-4-yl][1,2,5]thiadiazolo[3,4-b]pyrazine (Preparation 17) following the procedure described in Example 72.

δ $^1$H-NMR (DMSO-$d_6$): 8.53 (d, 1H), 7.44 (d, 1H), 7.25 (m, 1H), 7.03 (m, 3H), 6.65 (s, 2H), 6.38 (s, 2H).
ESI/MS m/e: 329 ([M+H]$^+$, $C_{15}H_{13}FN_6S$)
Retention time (min.): 13

Example 86

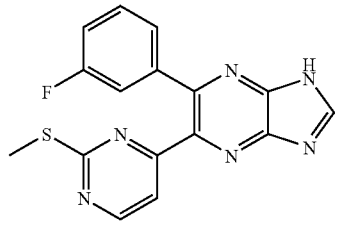

6-(3-Fluorophenyl)-5-[2-(methylthio)pyrimidin-4-yl]-1H-imidazo[4,5-b]pyrazine

Obtained (53%) from 5-(3-fluorophenyl)-6-[2-(methylthio)pyrimidin-4-yl]pyrazine-2,3-diamine (Example 85) following the procedure described in Example 74.

δ $^1$H-NMR (DMSO-$d_6$): 8.80 (s, 1H), 8.58 (d, 1H), 7.39-7.05 (m, 5H)
ESI/MS m/e: 339 ([M+H]+, $C_{16}H_{11}FN_6S$)
Retention time (min.): 13

Example 87

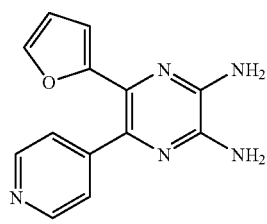

5-(2-Furyl)-6-pyridin-4-ylpyrazine-2,3-diamine

Obtained (92%) from 5-(2-furyl)-6-pyridin-4-yl[1,2,5]thiadiazolo[3,4-b]pyrazine (Preparation 18) following the procedure described in Example 72.

δ $^1$H-NMR (DMSO-$d_6$): 8.46 (d, 2H), 7.49 (s, 1H), 7.18 (d, 2H), 6.49-6.36 (m, 6H).
ESI/MS m/e: 254 ([M+H]+, $C_{13}H_{11}N_5O$)
Retention time (min.): 5

Example 88

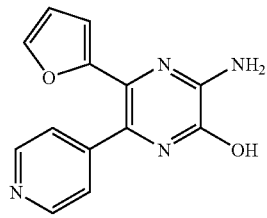

3-Amino-5-(2-furyl)-6-pyridin-4-ylpyrazin-2-ol

Obtained (25%) from 5-(2-furyl)-6-pyridin-4-ylpyrazine-2,3-diamine (Example 87) following the procedure described in Example 73.
ESI/MS m/e: 255 ([M+H]+, $C_{13}H_{10}N_4O_2$)
Retention time (min.): 5

Example 89

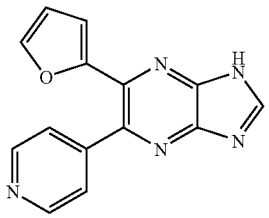

6-(2-Furyl)-5-pyridin-4-yl-1H-imidazo[4,5-b]pyrazine

Obtained (30%) from 5-(2-furyl)-6-pyridin-4-ylpyrazine-2,3-diamine (Example 87) following the procedure described in Example 74.
δ $^1$H-NMR (DMSO-$d_6$): 13.73 (brs, 1H), 8.92 (s, 1H), 8.65 (d, J=6.3 Hz, 2H), 7.67 (s, 1H), 7.42 (d, J=6.3 Hz, 2H), 6.65 (s, 1H), 6.59 (s, 1H).
ESI/MS m/e: 264 ([M+H]+, $C_{14}H_9N_5O$)
Retention time (min.): 6

Example 90

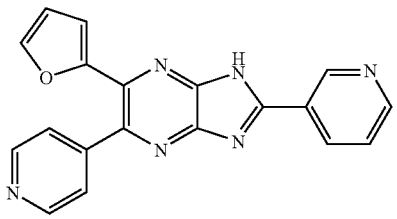

6-(2-Furyl)-2-pyridin-3-yl-5-pyridin-4-yl-1H-imidazo[4,5-b]pyrazine

A mixture of 5-(2-furyl)-6-pyridin-4-ylpyrazine-2,3-diamine (Example 87, 146 mg, 0.58 mmol) and nicotinoyl chloride hydrochloride (516 mg, 2.9 mmol) in pyridine (5 mL) was stirred and heated at reflux for 24 h. Then polyphosphoric acid was added and the stirring was continued at the same temperature for 24 h. The reaction was allowed to cool to room temperature and was poured into water and extracted with ethyl acetate. The organic phase was dried (MgSO$_4$), evaporated and the residue was purified by silica gel chromatography (CH$_2$Cl$_2$/MeOH/NH$_3$ 50:8:1). The appropriate fractions were concentrated to leave a solid which upon washing with diethyl ether give the title compound as a light brown solid (82 mg, 61%).

δ $^1$H-NMR (DMSO-$d_6$): 9.47 (s, 1H), 8.79 (d, J=3.9 Hz, 1H), 8.67-8.62 (m, 3H), 7.70-7.66 (m, 2H), 7.44 (d, J=5.7 Hz, 1H), 6.71 (d, J=3.3 Hz, 1H), 6.62 (d, J=3.3 Hz, 1H).
ESI/MS m/e: 341 ([M+H]+, $C_{19}H_{12}N_6O$)
Retention time (min.): 9

Example 91

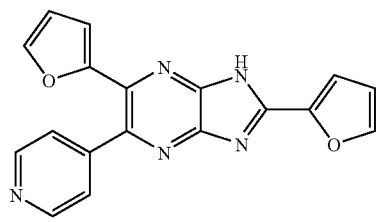

2,6-Di-2-furyl-5-pyridin-4-yl-1H-imidazo[4,5-b]pyrazine

Obtained (11%) from 5-(2-furyl)-6-pyridin-4-ylpyrazine-2,3-diamine (Example 87) and 2-furoyl chloride following the procedure described in Example 90.
ESI/MS m/e: 330 ([M+H]+, $C_{18}H_{11}N_5O_2$)
Retention time (min.): 9

Example 92

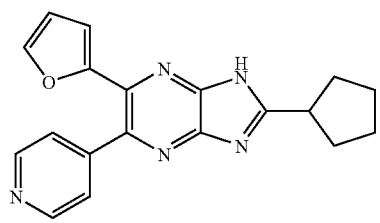

2-Cyclopentyl-6-(2-furyl)-5-pyridin-4-yl-1H-imidazo[4,5-b]pyrazine

Obtained (22%) from 5-(2-furyl)-6-pyridin-4-ylpyrazine-2,3-diamine (Example 87) and cyclopentanecarbonyl chloride following the procedure described in Example 90.
ESI/MS m/e: 332 ([M+H]+, $C_{19}H_{17}N_5O$)
Retention time (min.): 10

Example 93

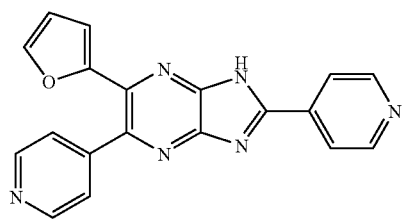

6-(2-Furyl)-2,5-dipyridin-4-yl-1H-imidazo[4,5-b]pyrazine

Obtained (19%) from 5-(2-furyl)-6-pyridin-4-ylpyrazine-2,3-diamine (Example 87) and 2-isonicotinyl chloride following the procedure described in Example 90.

δ $^1$H-NMR (CD$_3$OD): 8.81 (d, 2H), 8.60 (d, 2H), 8.21 (d, 2H), 7.57 (d, 2H), 7.48 (s, 1H), 6.82 (d, 1H), 6.58 (d, 1H).

ESI/MS m/e: 341 ([M+H]+, C$_{19}$H$_{12}$N$_6$O)

Retention time (min.): 8

Example 94

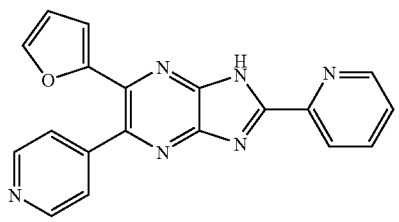

6-(2-Furyl)-2-pyridin-2-yl-5-pyridin-4-yl-1H-imidazo[4,5-b]pyrazine

Obtained (10%) from 5-(2-furyl)-6-pyridin-4-ylpyrazine-2,3-diamine (Example 87) and pyridine-2-carbonyl chloride following the procedure described in Example 90.

ESI/MS m/e: 341 ([M+H]+, C$_{19}$H$_{12}$N$_6$O)

Retention time (min.): 9

Example 95

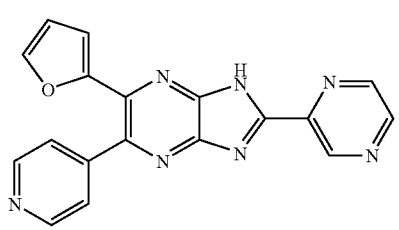

6-(2-Furyl)-2-pyrazin-2-yl-5-pyridin-4-yl-1H-imidazo[4,5-b]pyrazine

Obtained (10%) from 5-(2-furyl)-6-pyridin-4-ylpyrazine-2,3-diamine (Example 87) and pyrazine-2-carbonyl chloride following the procedure described in Example 90.

δ $^1$H-NMR (CD$_3$OD): 9.61 (s, 1H), 8.72 (d, 2H), 8.69 (brs, 2H), 7.73 (d, 2H), 7.46 (s, 1H), 6.91 (d, 1H), 6.59 (d, 1H).

ESI/MS m/e: 342 ([M+H]+, C$_{18}$H$_{11}$N$_7$O)

Retention time (min.): 8

Example 96

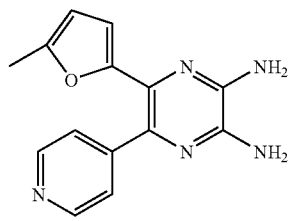

5-(5-Methyl-2-furyl)-6-pyridin-4-ylpyrazine-2,3-diamine

Obtained (49%) from 5-(5-methyl-2-furyl)-6-pyridin-4-yl[1,2,5]thiadiazolo[3,4-b]pyrazine (Preparation 19) following the procedure described in Example 72.

δ $^1$H-NMR (DMSO-d$_6$): 8.46 (d, 2H), 7.01 (d, 2H), 6.39 (s, 2H), 6.32 (s, 2H), 6.12 (d, 1H), 6.04 (d, 1H), 2.11 (s, 3H).

ESI/MS m/e: 268 ([M+H]+, C$_{14}$H$_{13}$N$_5$O)

Retention time (min.): 6

Example 97

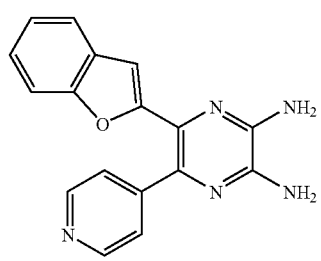

5-(1-Benzofuran-2-yl)-6-pyridin-4-ylpyrazine-2,3-diamine

Obtained (30%) from 5-(5-methyl-2-furyl)-6-pyridin-4-yl[1,2,5]thiadiazolo[3,4-b]pyrazine (Preparation 20) following the procedure described in Example 72.

ESI/MS m/e: 304 ([M+H]+, C$_{17}$H$_{13}$N$_5$O)

Retention time (min.): 8

Example 98

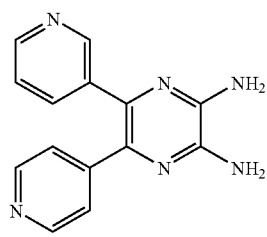

5-Pyridin-3-yl-6-pyridin-4-ylpyrazine-2,3-diamine

Obtained as a yellow solid (75%) from 5-(3-pyridyl)-6-pyridin-4-yl[1,2,5]thiadiazolo[3,4-b]pyrazine (Preparation 21) following the same procedure described in Example 72.

ESI/MS m/e: 265 ([M+H]+, $C_{14}H_{12}N_6$)

Retention time (min.): 3

Example 99

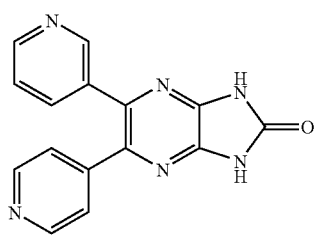

5-Pyridin-3-yl-6-pyridin-4-yl-1,3-dihydro-2H-imidazo[4,5-b]pyrazin-2-one

Obtained as yellow solid (88%) from 5-pyridin-3-yl-6-pyridin-4-ylpyrazine-2,3-diamine (Example 98) following the same procedure described in Example 76.

δ $^1$H-NMR (DMSO-$d_6$): 12.03 (bs, 2H), 8.45 (d, 2H), 8.40 (d, 2H), 7.70 (d, 1H), 7.30 (m, 1H), 7.20 (d, 2H).
ESI/MS m/e: 291 ([M+H]+, $C_{15}H_{10}N_6O$)
Retention time (min.): 5

Example 100

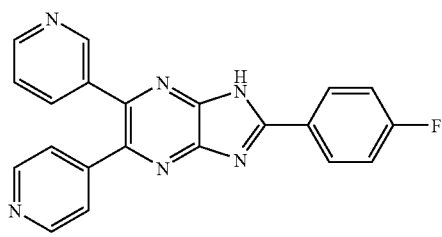

2-(4-Fluorophenyl)-6-pyridin-3-yl-5-pyridin-4-yl-1H-imidazo[4,5-b]pyrazine

Obtained as a yellow solid (23%) from 5-pyridin-3-yl-6-pyridin-4-ylpyrazine-2,3-diamine (Example 98) and 4-fluorobenzoyl chloride following the same procedure described in Example 90.
ESI/MS m/e: 369 ([M+H]+, $C_{21}H13FN_6$)
Retention time (min.): 10

Example 101

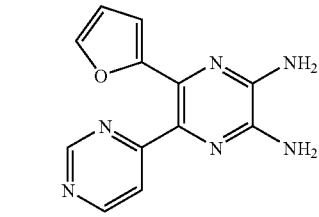

5-(2-Furyl)-6-pyrimidin-4-ylpyrazine-2,3-diamine

Obtained (27%) from 5-(2-furyl)-6-pyrimidin-4-yl[1,2,5]thiadiazolo[3,4-b]pyrazine (Preparation 22) following the procedure described in Example 72.
m.p.: 233.1-234.7° C.
δ $^1$H-NMR (DMSO-$d_6$): 9.00 (S, 1H), 8.75 (d, J=3.0 Hz, 1H), 7.56 (d, J=3.0 Hz, 1H), 7.42 (s, 1H), 6.55 (s, 2H), 6.43-6.39 (m, 4H).
ESI/MS m/e: 255 ([M+H]+, $C_{12}H_{10}N_6O$)
Retention time (min.): 7

Example 102

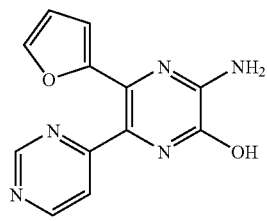

3-Amino-5-(2-furyl)-6-pyrimidin-4-ylpyrazin-2-ol

Obtained (13%) from 5-(2-furyl)-6-pyrimidin-4-ylpyrazine-2,3-diamine (Example 101) following the procedure described in Example 73.
ESI/MS m/e: 256 ([M+H]+, $C_{12}H_9N_5O_2$)
Retention time (min.): 7

Example 103

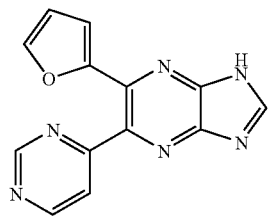

6-(2-Furyl)-5-pyrimidin-4-yl-1H-imidazo[4,5-b]pyrazine

Obtained (12%) from 5-(2-furyl)-6-pyrimidin-4-ylpyrazine-2,3-diamine (Example 101) following the procedure described in Example 74.
ESI/MS m/e: 265 ([M+H]+, $C_{13}H_8N_6O$)
Retention time (min.): 8

Example 104

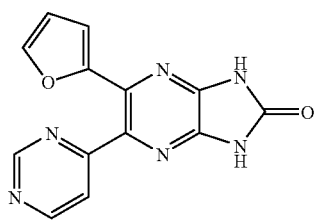

5-(2-Furyl)-6-pyrimidin-4-yl-1,3-dihydro-2H-imidazo[4,5-b]pyrazin-2-one

Obtained from 5-(2-furyl)-6-pyrimidin-4-ylpyrazine-2,3-diamine (Example 101) following the procedure described in Example 76. Purification by silica gel chromatography ($CH_2Cl_2$/MeOH/$NH_3$ 50:8:1) provided the title compound (23 mg, 21%).
δ $^1$H-NMR (DMSO-$d_6$): 12.05 (brs, 2H), 9.13 (s, 1H), 8.89 (d, 1H), 7.69 (d, 1H), 7.52 (s, 1H), 6.65 (s, 1H), 6.53 (s, 1H).
ESI/MS m/e: 281 ([M+H]+, $C_{13}H_8N_6O_2$)
Retention time (min.): 8

Example 105

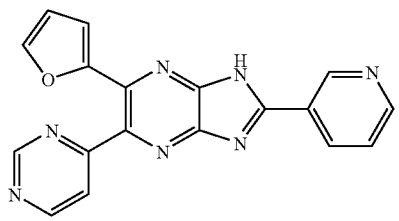

6-(2-Furyl)-2-pyridin-3-yl-5-pyrimidin-4-yl-1H-imidazo[4,5-b]pyrazine

Obtained (45%) from 5-(2-furyl)-6-pyrimidin-4-ylpyrazine-2,3-diamine (Example 101) and nicotinoyl chloride hydrochloride following the procedure described in Example 90.
δ $^1$H-NMR (DMSO-$d_6$): 9.44 (d, 1H), 9.19 (s, 1H), 8.98 (d, 1H), 8.70 (dd, 1H), 8.61 (m, 1H), 7.86 (d, 1H), 7.66 (dd, 1H), 7.59 (brs, 1H), 6.80 (d, 1H), 6.59 (m, 1H).
ESI/MS m/e: 342 ([M+H]+, $C_{18}H_{11}N_7O$)
Retention time (min.): 13

Example 106

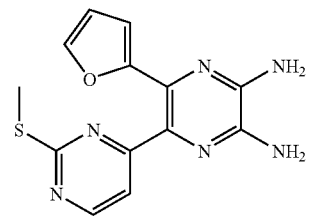

5-(2-Furyl)-6-[2-(methylthio)pyrimidin-4-yl]pyrazine-2,3-diamine

Obtained (92%) from 5-(2-furyl)-6-[2-(methylthio)pyrimidin-4-yl][1,2,5]thiadiazolo[3,4b]pyrazine (Preparation 23) following the procedure described in Example 72.
δ $^1$H-NMR (DMSO-$d_6$): 8.55 (d, J=5.1 Hz, 1H), 7.48 (s, 1H), 7.32 (d, J=5.1 Hz, 1H), 6.62 (s, 2H), 6.48-6.43 (m, 4H), 2.18 (s, 3H).
ESI/MS m/e: 301 ([M+H]+, $C_{13}H_{12}N_6OS$)
Retention time (min.): 11

Example 107

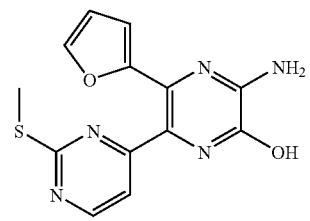

3-Amino-5-(2-furyl)-6-[2-(methylthio)pyrimidin-4-yl]pyrazin-2-ol

Obtained (39%) from 5-(2-furyl)-6-[2-(methylthio)pyrimidin-4-yl]pyrazine-2,3-diamine (Example 106) following the procedure described in Example 73.
ESI/MS m/e: 302 ([M+H]+, $C_{13}H_{11}N_5O_2S$)
Retention time (min.): 11

Example 108

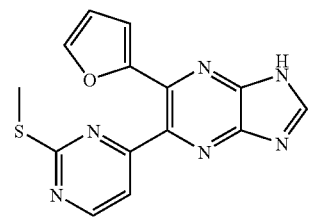

6-(2-Furyl)-5-[2-(methylthio)pyrimidin-4-yl]-1H-imidazo[4,5-b]pyrazine

Obtained (35%) from 5-(2-furyl)-6-[2-(methylthio)pyrimidin-4-yl]pyrazine-2,3-diamine (Example 106) following the procedure described in Example 74.

δ $^1$H-NMR (DMSO-$d_6$): 8.96 (s, 1H), 8.79 (d, 1H), 7.66 (s, 1H), 7.59 (d, 1H), 6.84 (s, 1H), 6.62 (s, 1H), 2.26 (s, 3H).

ESI/MS m/e: 311 ([M+H]+, $C_{14}H_{10}N_6OS$)

Retention time (min.): 11

Example 109

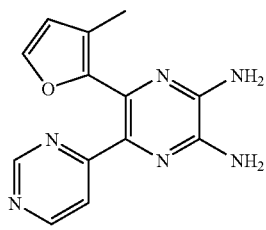

5-(3-Methyl-2-furyl)-6-pyrimidin-4-ylpyrazine-2,3-diamine

Obtained (27%) from 5-(3-methyl-2-furyl)-6-pyrimidin-4-yl[1,2,5]thiadiazolo[3,4-b]pyrazine (Preparation 24) following the procedure described in Example 72.

m.p.: 198.0-199.5° C.

δ $^1$H-NMR (DMSO-$d_6$): 8.91 (s, 1H), 8.69 (d, 1H), 7.51 (d, 1H), 7.37 (s, 1H), 6.56 (s, 2H), 6.41 (s, 2H), 6.29 (s, 1H), 1.79 (s, 3H).

ESI/MS m/e: 269 ([M+H]+, $C_{13}H_{12}N_6O$)

Retention time (min.): 8

Example 110

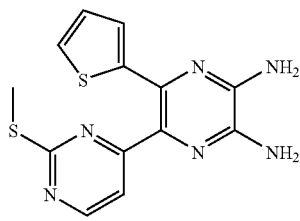

5-[2-(Methylthio)pyrimidin-4-yl]-6-(2-thienyl)pyrazine-2,3-diamine

Obtained (60%) from 5-[2-(methylthio)pyrimidin-4-yl]-6-(2-thienyl)[1,2,5]thiadiazolo[3,4-b]pyrazine (Preparation 25) following the procedure described in Example 72.

δ $^1$H-NMR (DMSO-$d_6$): 8.58 (d, 1H), 7.42 (d, 1H), 7.31 (d, 1H), 6.89 (dd, 1H), 6.64 (d, 1H), 6.58 (s, 2H), 6.41 (s, 2H), 2.20 (s, 3H).

ESI/MS m/e: 317 ([M+H]+, $C_{13}H_{12}N_6S_2$)

Retention time (min.): 11

Example 111

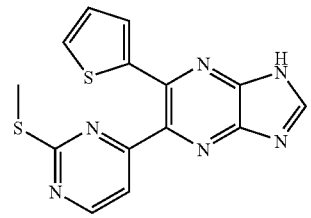

5-[2-(Methylthio)pyrimidin-4-yl]-6-(2-thienyl)-1H-imidazo[4,5-b]pyrazine

Obtained (33%) from 5-[2-(methylthio)pyrimidin-4-yl]-6-(2-thienyl)pyrazine-2,3-diamine (Example 110) following the procedure described in Example 74.

ESI/MS m/e: 327 ([M+H]+, $C_{14}H_{10}N_6S_2$)

Retention time (min.): 12

Example 112

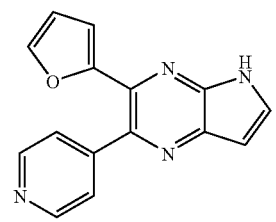

3-(2-Furyl)-2-pyridin-4-yl-5H-pyrrolo[2,3-b]pyrazine

A mixture of potassium t-butoxide (45 mg, 0.40 mmol) in N-methylpyrrolidone (1 mL) was stirred under nitrogen and a solution of 3-ethynyl-6-(2-furyl)-5-pyridin-4-ylpyrazin-2-amine (Example 65, 50 mg, 0.19 mmol) in N-methylpyrrolidone (1 mL) was added. The mixture was stirred at room temperature overnight, partitioned between water and ethyl acetate, the aqueous phase was extracted twice with ethyl acetate, the organic extracts washed with water and brine, dried (MgSO$_4$) and concentrated under vacuum. Silica gel flash column chromatography (dichloromethane/methanol 95:5) gave the title compound as a yellow solid (20 mg, 40%).

δ $^1$H-NMR (DMSO-$d_6$): 12.30 (bs, 1H), 8.60 (d, 1H), 8.05 (d, 1H), 7.65 (s, 1H), 7.45 (d, 2H), 6.70 (d, 1H), 6.55 (s, 2H).

ESI/MS m/e: 263 ([M+H]+, $C_{15}H_{10}N_4O$)

Retention time (min.): 7

Example 113

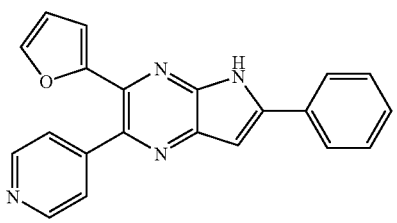

3-(2-Furyl)-6-phenyl-2-pyridin-4-yl-5H-pyrrolo[2,3-b]pyrazine

Obtained as a brown solid (54%) from 6-(2-furyl)-3-(phenylethynyl)-5-pyridin-4-ylpyrazin-2-amine (Example 66) following the same procedure described in Example 112.

δ $^1$H-NMR (CDCl$_3$): 9.75 (bs, 1H), 8.70 (d, 2H), 7.50 (m, 5H), 7.35 (s, 1H), 7.05 (s, 1H), 6.30 (m, 2H).

ESI/MS m/e: 339 ([M+H]+, C$_{21}$H$_{14}$N$_4$O)

Retention time (min.): 12

Example 114

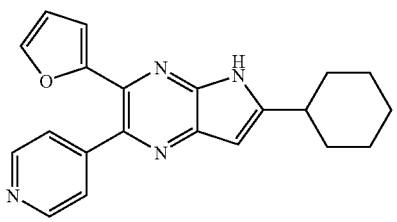

6-Cyclohexyl-3-(2-furyl)-2-pyridin-4-yl-5H-pyrrolo[2,3-b]pyrazine

Step a

3-Cyclohexylethynyl-6-(2-furyl)-5-pyridin-4-ylpyrazin-2-amine

Obtained as a brown solid (39%) from 3-bromo-6-(2-furyl)-5-pyridin-4-ylpyrazin-2-amine (Example 62) and cyclohexylacetylene following the same procedure of Example 65 (Step a).

Step b

The title compound of Example 114 was obtained as a brown solid (18%) from 3-cyclohexylethynyl-6-(2-furyl)-5-pyridin-4-ylpyrazin-2-amine following the same procedure described in Example 112.

ESI/MS m/e: 339 ([M+H]+, C$_{21}$H$_{20}$N$_4$O)

Retention time (min.): 14

Example 115

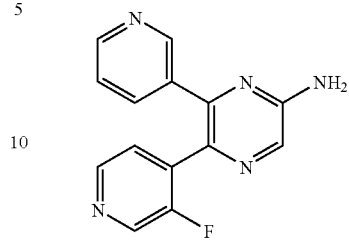

5-(3-Fluoropyridin-4-yl)-6-pyridin-3-ylpyrazin-2-amine

Obtained as a white solid (89%) from 6-chloro-5-(3-fluoropyridin-4-yl)pyrazin-2-amine (Preparation 10, step a) and pyridin-3-ylboronic acid following the procedure of Example 1.

$^1$H-NMR (CDCl$_3$): 8.65 (bs, 2H), 8.50 (d, 1H), 8.35 (s, 1H), 8.10 (s, 1H), 7.65 (d, 1H), 7.55 (m, 1H), 7.25 (m, 1H), 4.90 (bs, 2H).

ESI/MS m/e: 267 ([M+H]$^+$, C$_{14}$H$_{10}$FN$_5$).

Retention time (min.): 8

Example 116

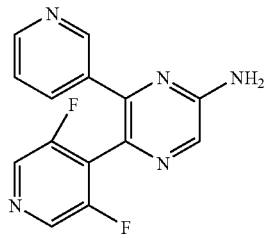

5-(3,5-Difluoropyridin-4-yl)-6-pyridin-3-ylpyrazin-2-amine

Obtained as a brownish solid (31%) from 5-bromo-6-pyridin-3-ylpyrazin-2-amine (Preparation 6,) and 3,5-difluoro-4-tributylstannylpyridine following the procedure of Preparation 9.

δ $^1$H-NMR (DMSO-d6): 8.49 (broad s, 4H), 8.04 (s, 1H), 7.68 (dt, 1H), 7.34 (dd, 1H), 7.15 (broad s, 2H).

ESI/MS m/e: 286 ([M+H]+, C$_{14}$H$_9$F$_2$N$_5$)

Example 117

N-[6-(6-Hydroxypyridin-3-yl)-5-pyridin-4-ylpyrazin-2-yl]cyclopropanecarboxamide

Step a

N-[6-(6-Benzyloxypyridin-3-yl)-5-pyridin-4-ylpyrazin-2-yl]cyclopropane carboxamide Obtained as a grey solid (78%) from N-(6-chloro-5-pyridin-4-ylpyrazin-2-yl)cyclopropanecarboxamide (Preparation 8) and 2-benzyloxy-5-(4,4,5,5-tetramethyl-[1,3,2]dioxaborolan-2-yl)pyridine* following the same procedure of Example 1.

*Prepared according to Bouillon A. et al. Tetrahedron 2002, 58, 4369-4373.

$^1$H-NMR (CDCl$_3$): 9.55 (s, 1H), 8.55 (d, 2H), 8.30 (d, 2H), 7.60 (d, 1H), 7.50 (m, 2H), 7.30 (m, 5H), 6.75 (d, 1H), 5.40 (s, 2H), 1.60 (m, 1H), 1.20 (m, 2H), 0.95 (m, 2H).

ESI/MS m/e: 424 ([M+H]$^+$, C$_{25}$H$_{21}$N$_5$O$_2$).

Retention time (min.): 16

Step b

To a stirred solution of N-[6-(6-benzyloxypyridin-3-yl)-5-pyridin-4-ylpyrazin-2-yl]cyclopropanecarboxamide (0.22 g, 0.51 mmol) in ethanol (11 mL) was added palladium on activated carbon (10%) (0.033 g) and the mixture was hydrogenated under atmospheric pressure. After 18 h, the mixture was filtered, washed with ethanol and evaporated under vacuum to provide the titled compound as a brown solid (0.046 g, 27%).

$^1$H-NMR (DMSO-d$_6$): 11.25 (s, 1H), 9.30 (s, 1H), 8.60 (d, 2H), 7.50 (m, 3H), 7.35 (m, 2H), 6.30 (d, 1H), 2.05 (m, 1H), 0.95 (m, 4H).

ESI/MS m/e: 334 ([M+H]$^+$, C$_{18}$H$_{15}$N$_5$O$_2$).

Retention time (min.): 8

Example 118

1-Cyclopropyl-3-(6-(pyridin-2-yl)-5-(pyridin-4-yl)pyrazin-2-yl)urea

Step a

Isocyanatocyclopropane

To a solution of cyclopropanecarboxylic acid (0.230 ml, 2.91 mmol) in toluene (2 ml) at 0° C. under nitrogen atmosphere, triethylamine (0.400 ml, 2.90 mmol) and diphenylphosphoryl azide (0.625 ml, 2.90 mmol) were sequentially added. The crude mixture was stirred at room temperature for 3 hours and at 80° C. for 3.5 hours and it was used in the next step without further elaboration.

Step b

To a suspension of 60% sodium hydride in mineral oil (0.014 g, 0.353 mmol) in DMF (0.5 ml) under nitrogen atmosphere, a solution of 6-pyridin-2-yl-5-pyridin-4-ylpyrazin-2-amine (Example 12) (0.080 g, 0.321 mmol) was added dropwise. After stirring for 20 minutes at room temperature, the crude mixture obtained in step a was added. The mixture was stirred at room temperature for 16 hours and it was partitioned between water and ethyl acetate. The organic layer was dried (Na$_2$SO$_4$) and evaporated. The residue was purified with flash silica gel chromatography (95:5 dichloromethane/methanol). Concentration in vaccuo of the product-rich fractions provided the titled compound (15 mg, 19%).

$^1$H-NMR (CDCl$_3$): 8.63-8.62 (m, 2H), 8.55-8.52 (m, 2H), 7.80-7.71 (m, 1H), 7.48-7.44 (m, 1H), 7.39-7.33 (m, 1H), 7.28-7.25 (m, 2H), 2.83-2.81 (m, 1H), 0.87-0.83 (m, 2H), 0.65-0.62 (m, 2H)

ESI/MS m/e: 333 ([M+H]$^+$, C$_{18}$H16N$_6$O)

Example 119

N-[5-(3-Fluoropyridin-4-yl)-6-(6-methoxypyridin-3-yl)pyrazin-2-yl]cyclopropane carboxamide Obtained as a white solid (11%) from N-[6-chloro-5-(3-fluoropyridin-4-yl)pyrazin-2-yl]cyclopropanecarboxamide (Preparation 10) and 2-methoxy-5-(4,4,5,5-tetramethyl-[1,3,2]dioxaborolan-2-yl)pyridine following the same procedure of Example 1.

$^1$H-NMR (CDCl$_3$): 9.60 (s, 1H), 8.55 (d, 1H), 8.40 (s, 1H), 8.20 (m, 2H), 7.65 (m, 2H), 6.75 (d, 1H), 3.95 (s, 3H), 1.60 (m, 1H), 1.20 (m, 2H), 0.95 (m, 2H).

ESI/MS m/e: 366 ([M+H]$^+$, C$_{19}$H$_{16}$FN$_5$O$_2$).

Retention time (min.): 13

Example 120

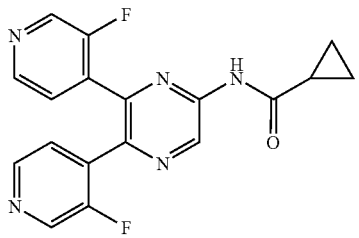

N-[5,6-bis(3-Fluoropyridin-4-yl)pyrazin-2-yl]cyclopropanecarboxamide

Obtained as a light yellow solid (12%) from N-[6-chloro-5-(3-fluoropyridin-4-yl)pyrazin-2-yl]cyclopropanecarboxamide (Preparation 10) and 3-fluoro-4-(4,4,5,5-tetramethyl-1,3,2-dioxaborolan-2-yl)pyridine* following the procedure of Example 1.

*Prepared according to Bouillon A. et al. Tetrahedron 2002, 58, 4369-4373.

$^1$H-NMR (CDCl$_3$): 9.75 (s, 1H), 8.55 (m, 2H), 8.40 (s, 1H), 8.35 (s, 1H), 8.25 (s, 1H), 7.55 (dd, 1H), 7.40 (dd, 1H), 7.30 (s, 1H), 1.60 (m, 1H), 1.20 (m, 2H), 1.00 (m, 2H).

ESI/MS m/e: 354 ([M+H]$^+$, C$_{18}$H$_{13}$F$_2$N$_5$O).

Retention time (min.): 12

Example 121

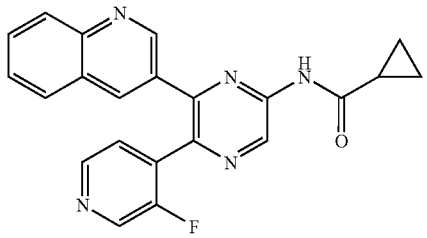

N-[5-(3-Fluoropyridin-4-yl)-6-quinolin-3-ylpyrazin-2-yl]cyclopropanecarboxamide

Obtained as a white solid (22%) from N-[6-chloro-5-(3-fluoropyridin-4-yl)pyrazin-2-yl]cyclopropanecarboxamide (Preparation 10) and isoquinoline-4-boronic acid following the same procedure of Example 1.

$^1$H-NMR (CDCl$_3$): 9.70 (s, 1H), 9.00 (s, 1H), 8.55 (d, 1H), 8.45 (s, 1H), 8.30 (s, 1H), 8.10 (m, 2H), 7.65 (m, 4H), 1.70 (m, 1H), 1.15 (m, 2H), 1.00 (m, 2H).

ESI/MS m/e: 386 ([M+H]$^+$, C$_{22}$H$_{16}$FN$_5$O).

Retention time (min.): 13

Example 122

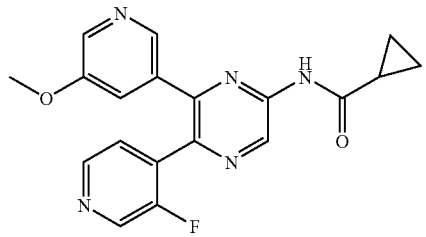

N-[5-(3-Fluoropyridin-4-yl)-6-(5-methoxypyridin-3-yl)pyrazin-2-yl]cyclopropane carboxamide Obtained as a white solid (50%) from N-[6-chloro-5-(3-fluoropyridin-4-yl)pyrazin-2-yl]cyclopropanecarboxamide (Preparation 10) and 3-methoxy-5-(4,4,5,5-tetramethyl-[1,3,2]dioxaborolan-2-yl)-pyridine following the same procedure of Example 1.

$^1$H-NMR (CDCl$_3$): 9.60 (s, 1H), 8.50 (m, 2H), 8.35 (m, 2H), 7.60 (m, 1H), 7.20 (m, 2H), 3.75 (s, 3H), 1.65 (m, 1H), 1.20 (m, 2H), 0.95 (m, 2H).

ESI/MS m/e: 366 [M+H]$^+$, C$_{19}$H$_{16}$FN$_5$O$_2$).

Retention time (min.): 12

Example 123

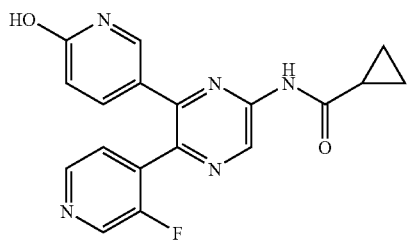

N-[5-(3-Fluoropyridin-4-yl)-6-(6-hydroxypyridin-3-yl)pyrazin-2-yl]cyclopropane carboxamide Step a N-[6-(6-Benzyloxypyridin-3-yl)-5-(3-fluoropyridin)-4-ylpyrazin-2-yl]cyclopropane carboxamide Obtained as a brown solid (43%) from N-[6-Chloro-5-(3-fluoropyridin-4-yl)pyrazin-2-yl]cyclopropanecarboxamide (Preparation 10) and 2-benzyloxy-5-(4,4,5,5-tetramethyl-[1,3,2]dioxaborolan-2-yl)pyridine* following the same procedure of Example 1.

*Prepared according to Bouillon A. et al. Tetrahedron 2002, 58, 4369-4373.

ESI/MS m/e: 442 ([M+H]$^+$, C$_{25}$H$_{20}$FN$_5$O$_2$).

Step b

To a stirred solution of N-[6-(6-benzyloxypyridin-3-yl)-5-(3-fluoropyridin)-4-ylpyrazin-2-yl]cyclopropanecarboxamide (0.13 g, 0.29 mmol) in ethanol (10 mL) was added palladium on activated carbon (10%) (0.033 g) and the mixture was hydrogenated under atmospheric pressure. After 18 h, the mixture was filtered, washed with ethanol and evaporated under vacuum to provide the titled compound as a brown solid (0.04 g, 40%).

$^1$H-NMR (DMSO-$d_6$): 11.65 (bs, 1H), 11.35 (s, 1H), 9.35 (s, 1H), 8.55 (m, 2H), 7.65 (m, 1H), 7.40 (m, 2H), 6.30 (dd, 1H), 2.00 (m, 1H), 0.95 (d, 4H).

ESI/MS m/e: 352 ([M+H]$^+$, $C_{18}H_{14}FN_5O_2$).

Retention time (min.): 10

Example 124

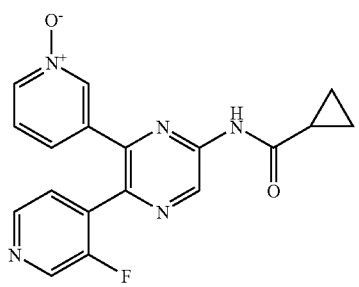

N-[5-(3-Fluoropyridin-4-yl)-6-(1-oxidopyridin-3-yl)pyrazin-2-yl]cyclopropane carboxamide In a sealed tube three cycles of vacuum and argon were applied to a mixture of Preparation 27 (0.15 g, 0.45 mmol), 3-fluoro-4-stannylpyridine (0.19 g, 0.49 mmol) and CuI (0.01 g, 0.04 mmol). DMF (5 mL) was added and argon was bubbled for 5 min, after which, Pd(Ph$_3$P)$_2$Cl$_2$ (0.02 g, 0.02 mmol) was added and argon was again bubbled for 5 min. The reaction mixture was heated at 120° C. for 2 h. Upon the reaction was completed the mixture was diluted with EtOAc (20 mL) and H$_2$O (20 mL) and filtered over celite. The organic layer was separated and the aqueous layer was extracted with EtOAc (3×15 mL). The combined organic layers were dried over Na$_2$SO$_4$, filtered and concentrated in vaccuo. The crude product was purified by column chromatography on silica gel, eluting with a MeOH/CH$_2$Cl$_2$ gradient (0→20%), yielding the desired product that was precipitated with Et$_2$O (3 mL) as a pale yellow solid (0.08 g, 51%).

$^1$H-RMN (DMSO-$d_6$, 250 MHz, δ): 9.49 (s, 1H); 8.58 (s, 1H); 8.29 (s, 1H); 8.25 (d, 1H); 7.69 (dd, 1H); 7.4 (dd, 1H); 7.25 (d, 1H); 2.08 (m, 1H); 11.53 (s, 1H); 0.93 (s, 2H); 0.91 (s, 2H).

MS (IE) m/e: 351 (M+, 49), 283 (100).

Example 125

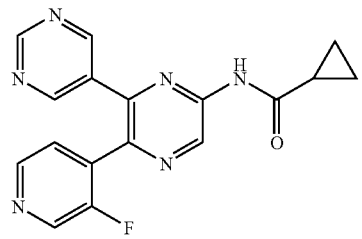

N-[5-(3-fluoropyridin-4-yl)-6-pyrimidin-5-ylpyrazin-2-yl]cyclopropanecarboxamide Obtained as a white solid (32%) from N-[6-chloro-5-(3-fluoropyridin-4-yl)pyrazin-2-yl]cyclopropanecarboxamide (Preparation 10) and 5-trimethylstannylpyrimidine following the procedure of Preparation 9.

δ 1H-NMR (DMSO-d6): 11.57 (s, 1H), 9.52 (s, 1H), 9.23 (s, 1H), 8.84 (s, 2H), 8.58 (m, 1H), 8.55 (m, 1H), 7.70 (m, 1H), 2.10 (m, 1H), 0.92 (d, 4H).

ESI/MS m/e: 337 ([M+H]+, $C_{17}H_{13}FN_6O$)

Example 126

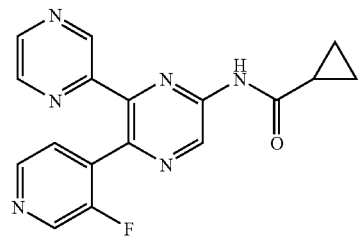

N-[3-(3-fluoropyridin-4-yl)-2,2'-bipyrazin-6-yl]cyclopropanecarboxamide

Obtained as a white solid (23%) from N-[6-chloro-5-(3-fluoropyridin-4-yl)pyrazin-2-yl]cyclopropanecarboxamide (Preparation 10) and 2-trimethylstannylpyrazine following the procedure of Preparation 9.

δ 1H-NMR (DMSO-d6): 11.58 (s, 1H), 9.47 (s, 1H), 9.21 (d, 1H), 8.66 (d, 1H), 8.43 (m, 3H), 7.62 (dd, 1H), 2.11 (m, 1H), 0.91 (d, 4H).

ESI/MS m/e: 337 ([M+H]+, $C_{17}H_{13}FN_6O$)

Example 127

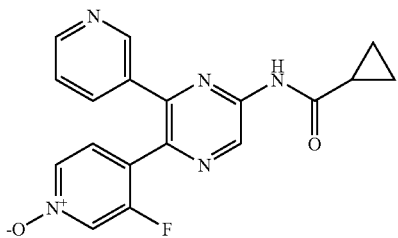

N-[5-(3-Fluoro-1-oxidopyridin-4-yl)-6-pyridin-3-ylpyrazin-2-yl]cyclopropane carboxamide

Step a

N-[6-Chloro-5-(3-fluoro-1-oxidopyridin-4-yl)pyrazin-2-yl]cyclopropanecarboxamide To a suspension of the title compound of Preparation 10 (2.54 g, 8.66 mmol) in CH$_2$Cl$_2$ (40 mL), cooled at 0° C., was added m-CPBA (2.78 g, 11.26 mmol) in small portions. Upon addition completion the ice bath was removed and the reaction continued at room temperature for 20 h. The precipitated product was filtered and washed with CH$_2$Cl$_2$ (3×10 mL), sat. NaHCO$_3$ (3×10 mL), H$_2$O (3×10 mL) and Et$_2$O (4×10 mL), giving the product as white powder (2.23 g, 84% yield).

$^1$H-RMN (DMSO-d$_6$, 250 MHz, δ): 9.39 (s, 1H); 8.73 (d, 1H); 8.29 (d, 1H); 7.9 (bs, 1H); 7.68 (m, 2H); 2.03 (m, 1H); 0.92 (m, 4H)

Step b

In a sealed tube three cycles of vacuum and argon were applied to a mixture of the N-[6-chloro-5-(3-fluoro-1-oxidopyridin-4-yl)pyrazin-2-yl]cyclopropanecarboxamide (2.23 g, 7.22 mmol), pyridin-3-ylboronic acid (1.15 g, 9.39 mmol) and Cs$_2$CO$_3$ (7.06 g, 21.66 mmol). A solution of 1,4-dioxane:H$_2$O (64 mL, 9:1) was added and argon was bubbled for 5 min, after which, PdCl$_2$dppfCH$_2$Cl$_2$ (0.59 g, 0.72 mmol) was added and argon was again bubbled other 5 min. The reaction mixture was heated at 90° C. for 1 h. Upon the reaction completion the 1,4-dioxane was concentrated in vaccuo, and the obtained residue was adsorbed onto silica gel with 10% MeOH/THF (150 mL) and purified by column chromatography on silica gel eluting with a MeOH/EtOAc gradient (0→20%). The green solid obtained was precipitated with 1% MeOH/CH$_2$Cl$_2$ (5 mL), and washed with 1% MeOH/CH$_2$Cl$_2$ (3×3 mL), CH$_2$Cl$_2$ (3×5 mL), 1% MeOH/Et$_2$O (3×5 mL) and Et$_2$O (4×5 mL) to yield the title compound as a white powder (1.41 g, 56%).

$^1$H-RMN (DMSO-d$_6$, 300 MHz, δ): 9.44 (s, 1H); 8.69 (s, 1H); 8.62 (d, 1H); 8.46 (d, 1H); 8.23 (d, 1H); 7.88 (d, 1H); 7.66 (dd, 1H); 7.45 (dd, 1H); 2.1 (m, 1H); 0.92 (s, 2H); 0.9 (s, 2H).

EM (IE) m/e: 351 (M+, 99.9), 283 (100).

Example 128

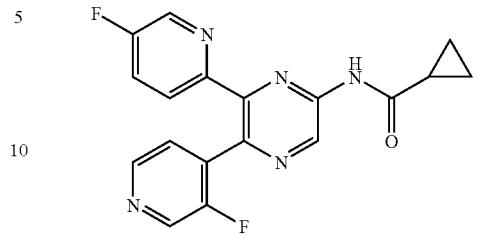

N-[5-(3-fluoropyridin-4-yl)-6-(5-fluoropyridin-2-yl)pyrazin-2-yl]cyclopropane carboxamide An oven dried resealable Schlenk tube was charged with 2-bromo-5-fluoropyridine (0.52 g, 2.9 mmol), hexamethylditin (0.97 g, 2.9 mmol) and toluene (15 mL). The Schlenk tube was subjected to three cycles of evacuation-backfilling with argon, and tetrakis(triphenylphosphine)palladium (0.162 g, 0.14 mmol) was added. After three new cycles of evacuation-backfilling with argon, the Schlenk tube was capped and placed in an oil bath at 80° C. After 5 hours, the mixture was cooled and N-[6-chloro-5-(3-fluoropyridin-4-yl)pyrazin-2-yl]cyclopropanecarboxamide (Preparation 10, 0.424 g, 1.45 mmol) and further tetrakis(triphenylphosphine)palladium (0.162 g, 0.14 mmol) were added. The mixture was heated to 110° C. and stirred overnight. The mixture was concentrated, ethyl acetate was added and the organic solution was washed with 4% aqueous sodium bicarbonate solution, brine, dried (MgSO$_4$) and evaporated. The residue was purified by silica gel chromatography (CH$_2$Cl$_2$/MeOH 98:2). The appropriate fractions were concentrated to leave a solid which, upon washing with a mixture of hexane and ethyl acetate, gave the title compound (0.077 g, 15%) as an off-white solid.

δ 1H-NMR (DMSO-d6): 11.47 (s, 1H), 9.46 (s, 1H), 8.47 (m, 1H), 8.44 (m, 1H), 8.32 (m, 1H), 8.06 (m, 1H), 7.92 (m, 1H), 7.59 (m, 1H), 2.08 (m, 1H), 0.90 (d, 4H)

ESI/MS m/e: 354 ([M+H]+, C$_{18}$H$_{13}$F$_2$N$_5$O)

Example 129

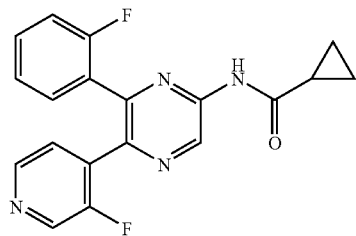

N-[6-(2-Fluorophenyl)-5-(3-fluoropyridin-4-yl)pyrazin-2-yl]cyclopropane-carboxamide Obtained as a white solid (28%) from N-[6-chloro-5-(3-fluoropyridin-4-yl)pyrazin-2-yl]cyclopropanecarboxamide (Preparation 10) and 2-fluorophenylboronic acid following the procedure of Example 1.

δ 1H-NMR (DMSO-d6): 8.69 (m, 1H), 8.54 (m, 1H), 7.90 (m, 1H), 7.64 (s, 1H), 7.45 (m, 1H), 6.80 (m, 1H), 6.52 (m, 1H), 6.40 (m, 1H), 2.07 (m, 1H), 0.99 (d, 4H).
ESI/MS m/e: 353 ([M+H]+, $C_{19}H_{14}F_2N_4O$)

Example 130

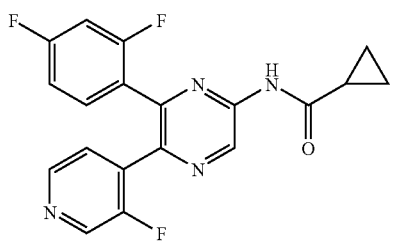

N-[6-(2,4-Difluorophenyl)-5-(3-fluoropyridin-4-yl)pyrazin-2-yl]cyclopropane-carboxamide Obtained as a white solid (19%) from N-[6-chloro-5-(3-fluoropyridin-4-yl)pyrazin-2-yl]cyclopropanecarboxamide (Preparation 10) and 2,4-difluorophenylboronic acid following the procedure of Example 1.

δ $^1$H-NMR (CDCl$_3$): 9.65 (s, 1H), 8.47 (m, 1H), 8.36 (m, 1H), 8.25 (s, 1H), 7.44 (m, 2H), 6.94 (m, 1H), 6.74 (m, 1H), 1.60 (m, 1H), 1.20 (m, 2H), 1.00 (d, 2H).
ESI/MS m/e: 371 ([M+H]+, $C_{19}H_{13}F_3N_4O$)

Example 131

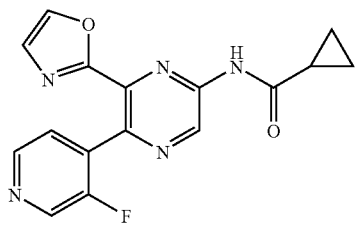

N-[5-(3-Fluoropyridin-4-yl)-6-(1,3-oxazol-2-yl)pyrazin-2-yl]cyclopropane-carboxamide Obtained as a white solid (65%) from N-[6-chloro-5-(3-fluoropyridin-4-yl)pyrazin-2-yl]cyclopropanecarboxamide (Preparation 10) and (1,3-oxazol-2-yl)zinc chloride following the procedure of Example 20, step b.

δ $^1$H-NMR (DMSO-d6): 11.66 (s, 1H), 9.52 (s, 1H), 8.56 (m, 2H), 8.30 (s, 1H), 7.65 (m, 1H), 7.34 (s, 1H), 2.10 (m, 1H), 0.90 (d, 4H).
ESI/MS m/e: 326 ([M+H]+, $C_{16}H_{12}FN_5O_2$)

Example 132

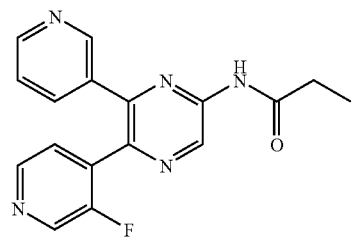

N-[5-(3-Fluoropyridin-4-yl)-6-pyridin-3-ylpyrazin-2-yl]propanamide

To a solution of 5-(3-fluoropyridin-4-yl)-6-pyridin-3-ylpyrazin-2-amine (Example 115) (150 mg, 0.56 mmol) in CH$_2$Cl$_2$ (5 mL) was added pyridine (1 mL), cooled at 0° C., propionyl chloride (57 mg, 0.62 mmol) was added dropwise. Upon complete addition, the ice bath was removed and the reaction continued at room temperature overnight. Then CH$_2$Cl$_2$ (10 mL) and aqueous NaOH 10% (10 mL) were added, the organic layer was separated, and washed with H$_2$O and saturated NaCl. The combined organic layers were dried over Na$_2$SO$_4$, filtered and concentrated in vaccuo. The crude product was purified by column chromatography on silica gel, eluting with an EtOAc/hexane gradient (80-100%), yielding the target product (100 mg, 55%)

$^1$H-RMN (CDCl$_3$, 250 MHz, δ): 9.71 (s, 1H); 9.17 (s, 1H); 8.83 (d, 1H); 8.6 (dd, 1H); 8.54 (d, 1H); 8.34 (d, 1H); 7.61 (m, 2H); 7.22 (dd, 1H); 2.57 (q, 2H); 1.31 (t, 3H)

Example 133

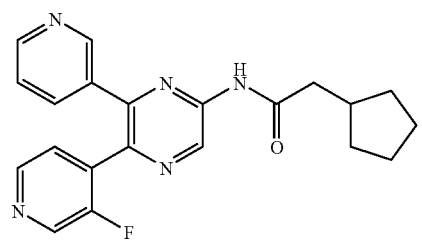

2-Cyclopentyl-N-[5-(3-fluoropyridin-4-yl)-6-pyridin-3-ylpyrazin-2-yl]acetamide

The title compound was obtained as a white solid (41%) from 5-(3-fluoropyridin-4-yl)-6-pyridin-3-ylpyrazin-2-amine (Example 115) and cyclopentylacetyl chloride following the same procedure of Example 132.

¹H-RMN (DMSO-d₆, 250 MHz, δ): 9.5 (s, 1H); 8.61-8.51 (m, 3H); 8.5 (d, 1H); 7.79 (dt, 1H); 7.68 (dd, 1H); 7.4 (ddd, 1H); 2.27 (m, 1H); 11.15 (s, 1H); 1.77 (m, 2H); 1.57 (m, 6H); 1.2 (m, 2H).

Example 134

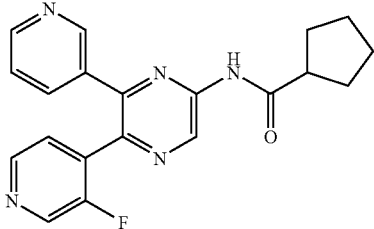

N-[5-(3-Fluoropyridin-4-yl)-6-pyridin-3-ylpyrazin-2-yl]cyclopentanecarboxamide

The title compound was obtained as a white solid (58%) from 5-(3-fluoropyridin-4-yl)-6-pyridin-3-ylpyrazin-2-amine (Example 115) and cyclopentanecarbonyl chloride following the same procedure of Example 132.

¹H-RMN (CDCl₃, 250 MHz, δ): 9.69 (s, 1H); 8.71 (bs, 1H); 8.61 (d, 1H); 8.54 (d, 1H); 8.43 (s, 1H); 8.33 (d, 1H); 7.65 (dt, 1H); 7.59 (d, 1H); 7.25 (dd, 1H); 2.87 (m, 1H); 2.08-1.56 (m, 8H)

Example 135

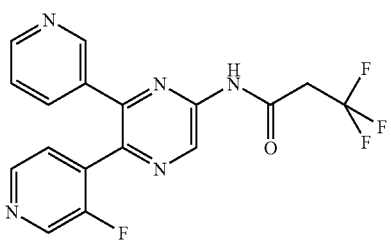

3,3,3-Trifluoro-N-[5-(3-fluoropyridin-4-yl)-6-pyridin-3-ylpyrazin-2-yl]propanamide The title compound was obtained as a white solid (13%) from 5-(3-fluoropyridin-4-yl)-6-pyridin-3-ylpyrazin-2-amine (Example 115) and 3,3,3-trifluoropropionyl chloride following the same procedure of Example 132.

¹H-RMN (CDCl₃, 250 MHz, δ): 9.89 (bs, 1H); 9.7 (s, 1H); 8.92 (s, 1H); 8.61 (dd, 1H); 8.57 (dd, 1H); 8.36 (s, 1H); 7.65-7.55 (m, 2H); 7.24 (m, 1H); 3.43 (q, 2H)

Example 136

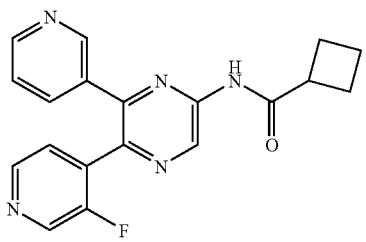

N-[5-(3-Fluoropyridin-4-yl)-6-pyridin-3-ylpyrazin-2-yl]cyclobutanecarboxamide

The title compound was obtained as a yellowish solid (91%) from 5-(3-fluoropyridin-4-yl)-6-pyridin-3-ylpyrazin-2-amine (Example 115) and cyclobutanecarbonyl chloride following the same procedure of Example 132.

¹H-RMN (DMSO-d₆, 250 MHz, δ): 9.58 (s, 1H); 8.88 (s, 1H); 8.85 (s, 1H); 8.59 (m, 2H); 8.28 (d, 1H); 7.85 (dd, 1H); 7.73 (dd, 1H); 3.46 (m, 1H); 2.36-2.05 (m, 4H); 2.05-1.75 (m, 2H)

Example 137

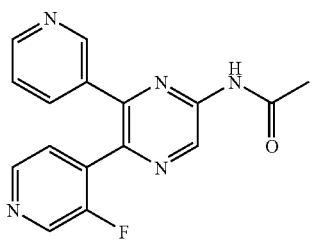

N-[5-(3-Fluoropyridin-4-yl)-6-pyridin-3-ylpyrazin-2-yl]acetamide

The title compound was obtained as a white solid (41%) from 5-(3-fluoropyridin-4-yl)-6-pyridin-3-ylpyrazin-2-amine (Example 115) and acetyl chloride following the same procedure of Example 132.

¹H-RMN (DMSO-d₆, 250 MHz, δ): 9.5 (s, 1H); 8.73 (s, 2H); 8.55 (m, 2H); 8.04 (d, 1H); 7.73-7.61 (m, 2H); 2.2 (s, 3H)

Example 138

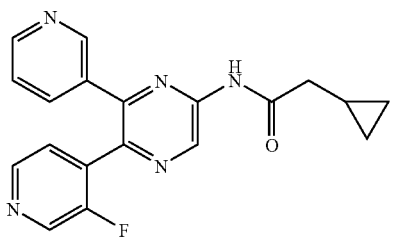

2-Cyclopropyl-N-[5-(3-fluoropyridin-4-yl)-6-pyridin-3-ylpyrazin-2-yl]acetamide

The title compound was obtained as a white solid (20%) from 5-(3-fluoropyridin-4-yl)-6-pyridin-3-ylpyrazin-2-amine (Example 115) and cyclopropylacetyl chloride following the same procedure of Example 132.

$^1$H-RMN (DMSO-$d_6$, 250 MHz, δ): 9.51 (s, 1H); 8.54 (m, 4H); 7.79 (dt, 1H); 7.67 (dd, 1H); 7.4 (dd, 1H); 2.38 (d, 2H); 11.11 (s, 1H); 1.16 (m, 1H); 0.53-0.46 (m, 2H); 0.24-0.18 (m, 2H)

Example 139

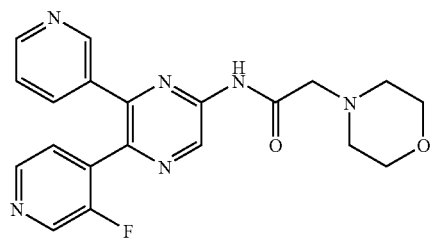

N-[5-(3-Fluoropyridin-4-yl)-6-pyridin-3-ylpyrazin-2-yl]-2-morpholin-4-ylacetamide Step a 2-Chloro-N-[5-(3-fluoropyridin-4-yl)-6-pyridin-3-ylpyrazin-2-yl]acetamide The title compound was obtained as a white solid (91%) from 5-(3-fluoropyridin-4-yl)-6-pyridin-3-ylpyrazin-2-amine (Example 115) and chloroacetyl chloride following the same procedure of Example 132.

Step b

To a solution of the previously obtained chloroacetamide (0.235 g, 0.68 mmol) and morpholine (0.07 mL, 0.75 mmol) in DMF (7 mL) was added $K_2CO_3$ (0.19 g, 1.36 mmol) and the reaction mixture was heated at 60° C. for 1 h. Upon reaction completion, the solvent was concentrated in vaccuo. The residue was diluted with $CH_2Cl_2$ (5 mL) and washed with sat. NaCl (1×5 mL) and $H_2O$ (1×5 mL). The organic layer was dried over $Na_2SO_4$, filtered and concentrated in vaccuo. The crude product was purified by column chromatography on silica gel, eluting with an EtOAc/hexane gradient (80→100%), yielding the desired product as a white powder (0.179 g, 67% yield).

$^1$H-RMN (DMSO-$d_6$, 250 MHz, δ): 9.5 (s, 1H); 8.59 (m, 3H); 8.53 (d, 1H); 7.82 (dt, 1H); 7.7 (t, 1H); 7.43 (dd, 1H); 3.64 (m, 6H); 2.58 (m, 4H)

Example 140

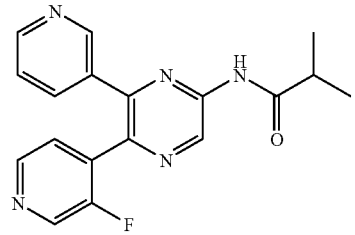

N-[5-(3-Fluoropyridin-4-yl)-6-pyridin-3-ylpyrazin-2-yl]-2-methylpropanamide

The title compound was obtained as a white solid (53%) from 5-(3-fluoropyridin-4-yl)-6-pyridin-3-ylpyrazin-2-amine (Example 115) and isobutyryl chloride following the same procedure of Example 132.

$^1$H-RMN (CDCl$_3$, 250 MHz, δ): 9.71 (s, 1H); 8.96 (s, 1H); 8.8 (d, 1H); 8.61 (dd, 1H); 8.53 (d, 1H); 8.33 (s, 1H); 7.6 (m, 2H); 7.23 (dd, 1H); 2.72 (m, 1H); 1.33 (s, 3H); 1.31 (s, 3H)

Example 141

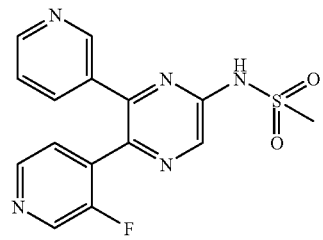

N-[5-(3-Fluoropyridin-4-yl)-6-pyridin-3-ylpyrazin-2-yl]methanesulfonamide

The title compound was obtained as an off-white solid (49%) from 5-(3-fluoropyridin-4-yl)-6-pyridin-3-ylpyrazin-2-amine (Example 115) and methanesulfonyl chloride following the same procedure of Example 132.

$^1$H-RMN (DMSO-$d_6$, 250 MHz, δ): 8.6-8.45 (m, 3H); 8.41 (s, 1H); 8.34 (s, 1H); 7.79 (d, 1H); 7.66 (dd, 1H); 7.4 (m, 1H); 3.33 (s, 3H)

Example 142

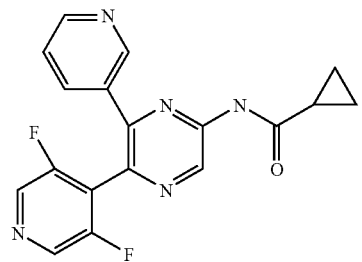

N-[5-(3,5-Difluoropyridin-4-yl)-6-pyridin-3-ylpyrazin-2-yl]cyclopropane carboxamide Obtained as a white solid (40%) from N-[6-chloro-5-(3,5-difluoropyridin-4-yl)pyrazin-2-yl]cyclopropanecarboxamide (Preparation 26) and pyridin-3-ylboronic acid following the same procedure of Example 1.

$^1$H-NMR (CDCl$_3$): 9.65 (s, 1H), 8.70 (m, 2H), 8.50 (s, 1H), 8.35 (s, 2H), 7.65 (d, 1H), 7.25 (m, 1H), 1.60 (m, 1H), 1.25 (m, 2H), 1.00 (m, 2H).

ESI/MS m/e: 354 ([M+H]$^+$, C$_{18}$H$_{13}$F$_2$N$_5$O).

Retention time (min.): 11

Example 143

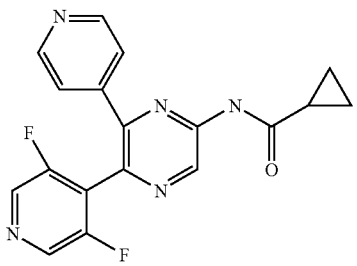

N-[5-(3,5-Difluoropyridin-4-yl)-6-pyridin-4-ylpyrazin-2-yl]cyclopropane carboxamide Obtained as a white solid (39%) from N-[6-chloro-5-(3,5-difluoropyridin-4-yl)pyrazin-2-yl]cyclopropanecarboxamide (Preparation 26) and 4-(4,4,5,5-tetramethyl-1,3,2-dioxaborolan-2-yl)pyridine following the same procedure of Example 1.

$^1$H-NMR (CDCl$_3$): 9.75 (s, 1H), 8.65 (bs, 2H), 8.35 (s, 2H), 8.25 (s, 1H), 7.25 (m, 2H), 1.65 (m, 1H), 1.25 (m, 2H), 1.00 (m, 2H).

ESI/MS m/e: 354 ([M+H]$^+$, C$_{18}$H$_{13}$F$_2$N$_5$O).

Retention time (min.): 11

Example 144

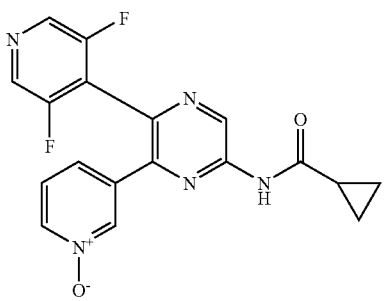

N-[5-(3,5-difluoropyridin-4-yl)-6-(1-oxidopyridin-3-yl)pyrazin-2-yl]cyclopropane carboxamide Obtained as a white solid (19%) from N-[5-bromo-6-(1-oxidopyridin-3-yl)pyrazin-2-yl]cyclopropanecarboxamide (Preparation 27) and 3,5-difluoro-4-(tributylstannyl) pyridine following the procedure of Example 124.

δ 1H-NMR (DMSO-d6): 11.59 (s, 1H), 9.50 (s, 1H), 8.63 (s, 2H), 8.31 (s, 1H), 8.24 (m, 1H), 7.37 (m, 1H), 7.22 (m, 1H), 2.07 (m, 1H), 0.90 (d, 4H).

ESI/MS m/e: 370 ([M+H]+, C$_{18}$H$_{13}$F$_2$N$_5$O$_2$)

Example 145

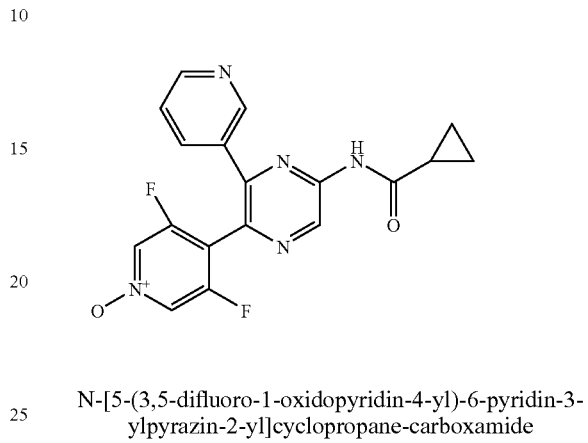

N-[5-(3,5-difluoro-1-oxidopyridin-4-yl)-6-pyridin-3-ylpyrazin-2-yl]cyclopropane-carboxamide Step a N-[6-chloro-5-(3,5-difluoro-1-oxidopyridin-4-yl)pyrazin-2-yl]cyclopropane-carboxamide The title compound was obtained as a white solid (72%) from N-[6-chloro-5-(3,5-difluoropyridin-4-yl)pyrazin-2-yl]cyclopropanecarboxamide (Preparation 26) following the same procedure of Example 127, step a.

δ 1H-NMR (DMSO-d6): 11.71 (s, 1H), 9.41 (s, 1H), 8.74 (m, 2H), 2.10 (m, 1H), 0.90 (d, 4H).

ESI/MS m/e: 327 ([M+H]+, C$_{13}$H$_9$ClF$_2$N$_4$O$_2$)

Step b

The title compound was obtained as a white solid (12%) from N-[6-chloro-5-(3,5-difluoro-1-oxidopyridin-4-yl)pyrazin-2-yl]cyclopropanecarboxamide and pyridin-3-ylboronic acid following the procedure of Example 127, step b.

δ 1H-NMR (DMSO-d6): 11.57 (s, 1H), 9.43 (s, 1H), 8.71 (s, 1H), 8.60 (m, 3H), 7.87 (m, 1H), 7.42 (m, 1H), 2.03 (m, 1H), 0.90 (d, 4H).

ESI/MS m/e: 370 ([M+H]+, C$_{18}$H$_{13}$F$_2$N$_5$O$_2$)

Example 146

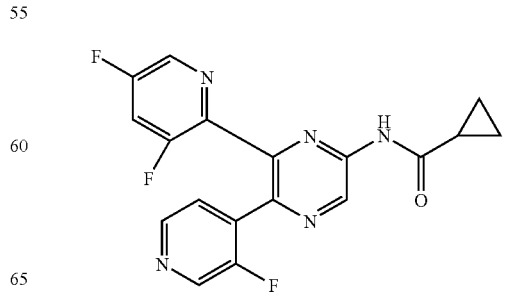

N-[6-(3,5-Difluoropyridin-2-yl)-5-(3-fluoropyridin-4-yl)pyrazin-2-yl]cyclopropane carboxamide In a Schienk tube were charged N-[6-chloro-5-(3-fluoropyridin-4-yl)pyrazin-2-yl]cyclopropanecarboxamide (Preparation 10, 70 mg, 0.24 mmol), 3,5-difluoro-2-tributylstannanyl-4-trimethylsilylpyridine (prepared according to the procedure described in *J. Med. Chem.* 2006, 49(1), 35-38) (177.6 mg, 0.48 mmol), copper(I) iodide (2.28 mg, 12 μmol), lithium chloride (previously dried) (10.14 mg, 0.24 mmol) and dioxane (1.5 mL). The mixture was submitted to three vacuum-argon cycles, then tetrakis(triphenylphosphine)palladium(0) (27.64 mg, 24 μmol) was added and the mixture purged in the same way and the mixture was heated at 100° C. for 18 h. The reaction was concentrated, ethyl acetate (1 ml) and HCl 2N (5 ml) were added and the reaction was stirred at room temperature for 1 h. Ethyl acetate was added, the organic layer was separated, and the aqueous phase was extracted with ethyl acetate. The combined extracts were washed with water and the organic layer was dried over magnesium sulphate and concentrated under reduced pressure. The residue was purified by column chromatography on silica flash, using dichloromethane/methanol (100:1) to yield the title compound (23 mg, 26%) as a yellowish solid.

δ $^1$H-NMR (DMSO-d6): 11.55 (s, 1H), 9.56 (s, 1H), 8.47 (m, 3H), 8.13 (m, 1H), 7.57 (m, 1H), 2.08 (m, 1H), 0.92 (d, 4H).

ESI/MS m/e: 372 ([M+H]+.

Example 147

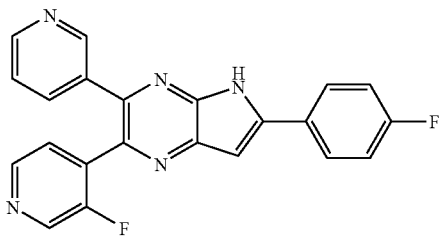

6-(4-Fluorophenyl)-2-(3-fluoropyridin-4-yl)-3-pyridin-3-yl-5H-pyrrolo[2,3-b]pyrazine

Step a

3-[(4-Fluorophenyl)ethynyl]-5-(3-fluoropyridin-4-yl)-6-pyridin-3-ylpyrazin-2-amine Obtained as a brown solid (100%) from 3-bromo-5-(3-fluoropyridin-4-yl)-6-pyridin-3-ylpyrazin-2-amine (Preparation 28) and 1-ethynyl-4-fluorobenzene following the same procedure described in Example 65 (Step a).

ESI/MS m/e: 386 ([M+H]+, $C_{22}H_{13}F_2N_5$).

Step b

The title compound was obtained as a brown solid (46%) from 3-[(4-fluorophenyl)ethynyl]-5-(3-fluoropyridin-4-yl)-6-pyridin-3-ylpyrazin-2-amine following the same procedure described in Example 112.

$^1$H-NMR (DMSO-d6): 12.95 (bs, 1H), 8.50 (m, 4H), 8.10 (dd, 2H), 7.70 (m, 2H), 7.35 (m, 3H), 7.25 (s, 1H).

ESI/MS m/e: 386([M+H]+, $C_{22}H_{13}F_2N_5$).

Retention time (min.): 13

Example 148

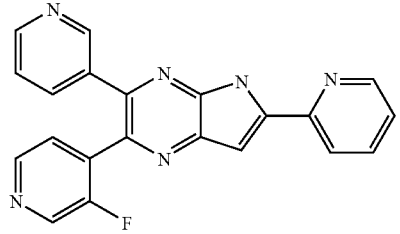

2-(3-Fluoropyridin-4-yl)-6-pyridin-2-yl-3-pyridin-3-yl-5H-pyrrolo[2,3-b]pyrazine

Step a 5-(3-Fluoropyridin-4-yl)-6-pyridin-3-yl-3-(pyridin-2-ylethynyl)pyrazin-2-amine Obtained as a brown solid (100%) from 3-bromo-5-(3-fluoropyridin-4-yl)-6-pyridin-3-ylpyrazin-2-amine (Preparation 28) and 2-ethynylpyridine following the same procedure described in Example 65 (Step a).

$^1$H-NMR (CDCl3): 8.70 (m, 3H), 8.55 (d, 1H), 8.35 (s, 1H), 7.80 (m, 4H), 7.605 (dd, 1H), 7.35 (m, 1H), 5.70 (s, 2H).

ESI/MS m/e: 369 [M+H]+, $C_{21}H_{13}FN_6$).

Step b

The title compound was obtained as a brown solid (38%) from 5-(3-fluoropyridin-4-yl)-6-pyridin-3-yl-3-(pyridin-2-ylethynyl)pyrazin-2-amine following the same procedure described in Example 112.

ESI/MS m/e: 369 [M+H]+, $C_{21}H_{13}FN_6$).

Retention time (min.): 11

Example 149

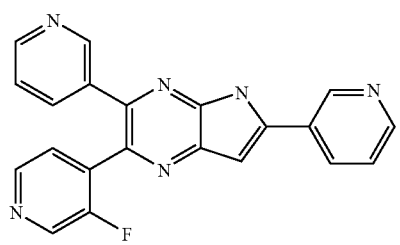

2-(3-Fluoropyridin-4-yl)-3,6-dipyridin-3-yl-5H-pyrrolo[2,3-b]pyrazine

Step a 5-(3-Fluoropyridin-4-yl)-6-pyridin-3-yl-3-(pyridin-3-ylethynyl)pyrazin-2-amine Obtained as a yellow solid (100%) from 3-bromo-5-(3-fluoropyridin-4-yl)-6-pyridin-3-ylpyrazin-2-amine (Preparation 28) and 3-ethynylpyridine following the same procedure described in Example 65 (Step a).

ESI/MS m/e: 369 [M+H]$^+$, $C_{21}H_{13}FN_6$).

Step b

The title compound was obtained as a brown solid (36%) from 5-(3-fluoropyridin-4-yl)-6-pyridin-3-yl-3-(pyridin-3-ylethynyl)pyrazin-2-amine following the same procedure described in Example 112.

$^1$H-NMR (DMSO-d$_6$): 13.10 (bs, 1H), 9.25 (s, 1H), 8.60 (d, 1H), 8.50 (m, 5H), 7.70 (m, 2H), 7.55 (dd, 1H), 7.40 (s, 1H), 7.35 (m, 1H).

ESI/MS m/e: 369 ([M+H]$^+$, $C_{21}H_{13}FN_6$).

Retention time (min.): 10

Example 150

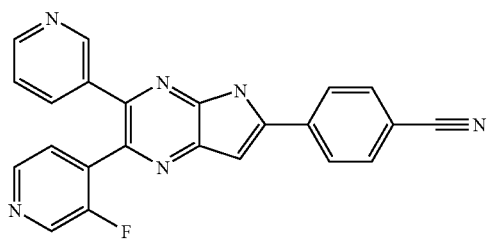

4-[2-(3-Fluoropyridin-4-yl)-3-pyridin-3-yl-5H-pyrrolo[2,3-b]pyrazin-6-yl]benzonitrile Step a 4-{[3-Amino-6-(3-fluoropyridin-4-yl)-5-pyridin-3-ylpyrazin-2-yl]ethynyl}benzonitrile Obtained as a brown solid (100%) from 3-bromo-5-(3-fluoropyridin-4-yl)-6-pyridin-3-ylpyrazin-2-amine (Preparation 28) and 4-ethynylbenzonitrile following the same procedure described in Example 65 (Step a).

ESI/MS m/e: 393 [M+H]$^+$, $C_{23}H_{13}FN_6$).

Step b

The title compound was obtained as a brown solid (53%) from 4-{[3-amino-6-(3-fluoropyridin-4-yl)-5-pyridin-3-ylpyrazin-2-yl]ethynyl}benzonitrile following the same procedure described in Example 112.

ESI/MS m/e: 393 ([M+H]$^+$, $C_{21}H_{13}FN_6$).

Retention time (min.): 13

Example 151

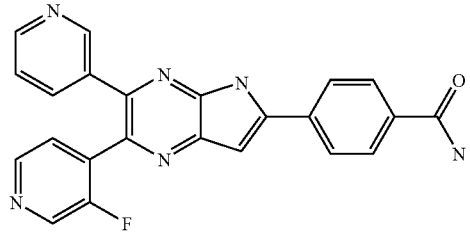

4-[2-(3-Fluoropyridin-4-yl)-3-pyridin-3-yl-5H-pyrrolo[2,3-b]pyrazin-6-yl]benzamide To a stirred solution of 4-[2-(3-fluoropyridin-4-yl)-3-pyridin-3-yl-5H-pyrrolo[2,3-b]pyrazin-6-yl]benzonitrile (Example 150) (0.050 g, 0.12 mmol) in ethanol (1.5 mL) was added a 2N aqueous solution of sodium hydroxide (0.127 mL, 0.25 mmol) and the mixture was stirred at 80° C. After 18 h, ethanol was evaporated and the aqueous phase was acidified until pH=6 with a 2N aqueous solution of hydrochloric acid. The resulting solid was filtered, washed with water and dried to furnish the titled compound (0.018 g, 36%) as a brown solid.

ESI/MS m/e: 411 ([M+H]$^+$, $C_{23}H_{15}FN_6O$).

Retention time (min.): 10

Example 152

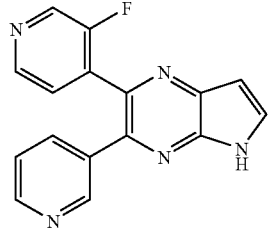

2-(3-Fluoropyridin-4-yl)-3-pyridin-3-yl-5H-pyrrolo[2,3-b]pyrazine

Step a

3-Ethynyl-5-(3-fluoropyridin-4-yl)-6-pyridin-3-ylpyrazin-2-amine

Obtained as a yellow solid (72%) from 3-bromo-5-(3-fluoropyridin-4-yl)-6-pyridin-3-ylpyrazin-2-amine (Preparation 28) and trimethylsilylacetylene following the same procedure described in Example 65 (steps a and b).

δ 1H-NMR (CDCl$_3$): 8.73-8.45 (m, 3H), 7.86-7.32 (m, 4H), 5.73 (s, 2H), 5.74 (s, 1H).

ESI/MS m/e: 292 ([M+H]+, $C_{16}H_{10}FN_5$)

Step b

The title compound was obtained as a yellow solid (28%) from 3-ethynyl-5-(3-fluoropyridin-4-yl)-6-pyridin-3-ylpyrazin-2-amine following the same procedure described in Example 112.

δ $^1$H-NMR (DMSO-d6): 8.53-8.50 (m, 2H), 8.47 (m, 1H), 8.10 (d, 1H), 7.79-7.65 (m, 3H), 7.37 (m, 1H), 6.77 (d, 1H).

ESI/MS m/e: 292 ([M+H]+, $C_{16}H_{10}FN_5$)

Example 153

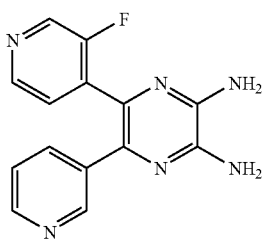

5-(3-Fluoropyridin-4-yl)-6-pyridin-3-ylpyrazine-2,3-diamine

Obtained as a white solid (70%) from 5-(3-fluoropyridin-4-yl)-6-pyridin-3-yl[1,2,5]thiadiazolo-[3,4-b]pyrazine (Preparation 29) following the procedure described in Example 72.

δ $^1$H-NMR (DMSO-d6): 7.52 (m, 4H), 6.72 (m, 1H), 6.6 (dd, 1H), 6.39 (ddd, 1H), 5.68 (s, 2H), 5.55 (s, 2H).

ESI/MS m/e: 283 ([M+H]+, $C_{14}H_{11}FN_6$)

Example 154

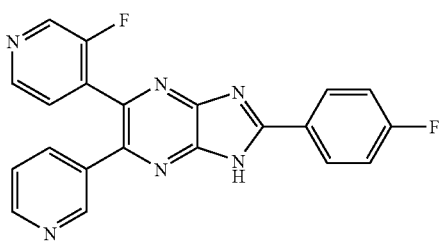

2-(4-Fluorophenyl)-5-(3-fluoropyridin-4-yl)-6-pyridin-3-yl-1H-imidazo[4,5-b]pyrazine A mixture of 5-(3-fluoropyridin-4-yl)-6-pyridin-3-ylpyrazine-2,3-diamine (Example 153, 0.100 g, 0.35 mmol) and 4-fluorobenzoyl chloride (0.074 g, 0.46 mmol) in pyridine (1 mL) was stirred and heated to 120° C. in a sealed tube for 24 hours. Water was added and the filtered solid was purified by silica gel chromatography eluting with CH$_2$Cl$_2$/MeOH (98:1 to 95:5) to give the title compound (0.045 g, 33%) as an off-white solid.

δ $^1$H-NMR (DMSO-d6): 8.54 (m, 3H), 8.5 (s, 1H), 8.39 (m, 2H), 7.79 (m, 1H), 7.69 (dd, 1H), 7.50 (m, 2H), 7.38 (ddd, 1H).

ESI/MS m/e: 387 ([M+H]+, $C_{21}H_{12}F_2N_6$)

Example 155

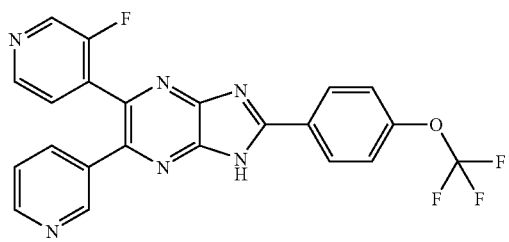

5-(3-Fluoropyridin-4-yl)-6-pyridin-3-yl-2-[4-(trifluoromethoxy)phenyl]-1H-imidazo[4,5-b]pyrazine Obtained as a solid (47%) from 5-(3-fluoropyridin-4-yl)-6-pyridin-3-ylpyrazine-2,3-diamine (Example 158) and 4-(trifluoromethoxy)benzoyl chloride following the procedure described in Example 154.

δ $^1$H-NMR (DMSO-d6): 8.54 (m, 3H), 8.50 (s, 1H), 8.45 (m, 2H), 7.79 (dd, 1H), 7.69 (dd, 1H), 7.65 (m, 2H), 7.38 (ddd, 1H).

ESI/MS m/e: 453 ([M+H]+, $C_{22}H_{12}F_4N_6O$)

Example 156

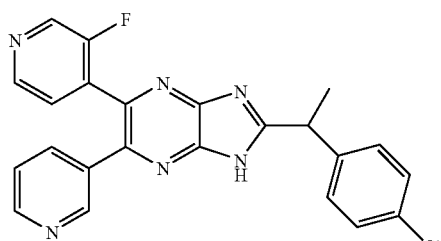

2-[1-(4-Chlorophenyl)ethyl]-5-(3-fluoropyridin-4-yl)-6-pyridin-3-yl-1H-imidazo[4,5-b]pyrazine Obtained as a solid (28%) from 5-(3-fluoropyridin-4-yl)-6-pyridin-3-ylpyrazine-2,3-diamine (Example 153) and 2-(4-chlorophenyl)propanoyl chloride following the procedure described in Example 154.

δ $^1$H-NMR (DMSO-d6): 8.52 (m, 3H), 8.48 (s, 1H), 7.76 (m, 1H), 7.63 (dd, 1H), 7.40 (m, 4H), 7.38 (ddd, 1H), 4.55 (q, 1H), 1.74 (d, 3H).

ESI/MS m/e: 431 ([M+H]+, $C_{23}H_{16}ClFN_6$)

Example 157

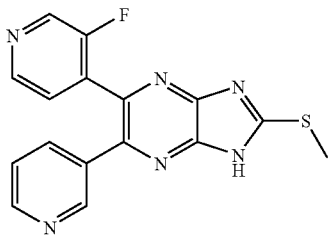

5-(3-Fluoropyridin-4-yl)-2-(methylthio)-6-pyridin-3-yl-1H-imidazo[4,5-b]pyrazine

Step a

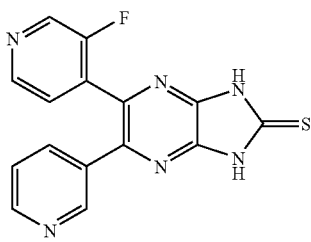

5-(3-Fluoropyridin-4-yl)-2-(methylthio)-6-pyridin-3-yl-1H-imidazo[4,5-b]pyrazine A stirred mixture of 5-(3-fluoropyridin-4-yl)-6-pyridin-3-ylpyrazine-2,3-diamine (Example 153, 1.00 g, 3.54 mmol), thiocarbonyldiimidazole (1.28 g, 7.1 mmol) and triethylamine (0.72 g, 7.1 mmol) in tetrahydrofuran (12 mL) was heated to 80° C. in sealed tube. After 24 hours, the mixture was cooled and evaporated in vacuo. The residue was purified by silica gel chromatography eluting with dichloromethane/methanol (95:5) to give the title compound (0.60 g, 53%) as a beige solid.

δ $^1$H-NMR (DMSO-d6): 13.77 (s, 2H), 8.49 (m, 3H), 8.44 (dd, 1H), 7.71 (m, 1H), 7.59 (dd, 1H), 7.35 (ddd, 1H).

ESI/MS m/e: 325 ([M+H]+, $C_{15}H_9FN_6S$)

Step b

To a suspension of sodium hydride (60% in mineral oil, 0.062 g, 1.54 mmol) in N,N-dimethylformamide (5 mL) at 0° C. was added dropwise a solution of 5-(3-fluoropyridin-4-yl)-2-(methylthio)-6-pyridin-3-yl-1H-imidazo[4,5-b]pyrazine (0.250 g, 0.77 mmol) in N,N-dimethylformamide (5 mL). After 30 minutes, methyl iodide (0.048 μL, 0.77 mmol) was added dropwise and stirring was continued at 0° C. After 3 hours, the solvent was evaporated and the mixture was partitioned between saturated aqueous ammonium chloride solution and ethyl acetate. The organic layer was dried (MgSO$_4$) and evaporated to give the title compound (235 mg, 90%) as an off-white solid.

δ $^1$H-NMR (DMSO-d6): 8.49 (m, 4H), 7.73 (m, 1H), 7.64 (dd, 1H), 7.36 (ddd, 1H), 7.04 (s, 1H), 2.75 (s, 3H).

ESI/MS m/e: 339 ([M+H]+, $C_{16}H_{11}FN_6S$)

Example 158

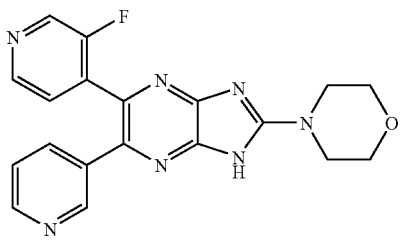

5-(3-Fluoropyridin-4-yl)-2-morpholin-4-yl-6-pyridin-3-yl-1H-imidazo[4,5-b]pyrazine

Step a

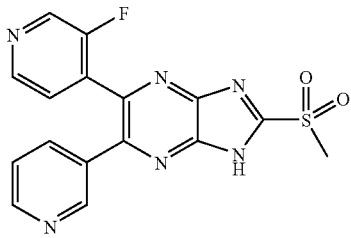

5-(3-Fluoropyridin-4-yl)-2-(methylsulfonyl)-6-pyridin-3-yl-1H-imidazo[4,5-b]pyrazine To a cooled (0° C.) solution of 5-(3-fluoropyridin-4-yl)-2-(methylthio)-6-pyridin-3-yl-1H-imidazo[4,5-b]pyrazine (Example 157, 0.235 g, 0.69 mmol) in dichloromethane (12 mL) and methanol (1 mL) was added m-chloroperbenzoic acid (77%, 310 mg, 1.39 mmol) in portions. The mixture was then warmed to room temperature and stirred for 3 days. The solid precipitate was filtered and dried to give the pure title compound (0.06 g, 23%) as a white solid.

HPLC-ESI/MS m/e: 4.58 min ((95% pure), 371 ([M+H]+, $C_{16}H_{11}FN_6O_2S$))

Step b

A mixture of 5-(3-fluoropyridin-4-yl)-2-(methylsulfonyl)-6-pyridin-3-yl-1H-imidazo[4,5-b]pyrazine (0.060 g, 0.16 mmol) and morpholine (1.5 mL) were heated to 120° C. in a sealed tube. After 3 hours, the mixture was evaporated and the residue was purified by silica gel chromatography eluting with dichloromethane/methanol (95:5) to give the title compound (0.029 g, 48%) as a white solid.

δ $^1$H-NMR (DMSO-d6): 8.47 (m, 4H), 7.67 (m, 1H), 7.58 (dd, 1H), 7.32 (ddd, 1H), 3.7 (m, 4H), 3.44 (m, 4H).

ESI/MS m/e: 378 ([M+H]+, $C_{19}H_{16}FN_7O$)

Example 159

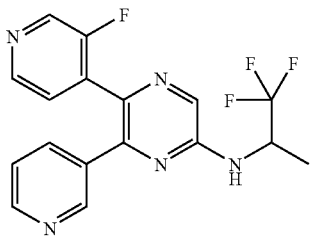

5-(3-Fluoropyridin-4-yl)-6-pyridin-3-yl-N-(2,2,2-trifluoro-1-methylethyl)pyrazin-2-amine An oven dried resealable Schlenk tube was charged with 5-chloro-2-(3-fluoropyridin-4-yl)-3-pyridin-3-ylpyrazine (Preparation 30, 0.100 g, 0.35 mmol), 1,1,1-trifluoropropan-2-amine hydrochloride (0.063 g, 0.42 mmol), caesium carbonate (0.273 g, 0.84 mmol), BINAP (0.0065 g, 0.01 mmol) and toluene (2 mL). The Schlenk tube was subjected to several cycles of evacuation-backfilling with argon, and palladium(II) acetate (0.0015 g, 0.007 mmol) was added. After three new cycles of evacuation-backfilling with argon, the Schlenk tube was capped and placed in an oil bath at 100° C. After stirring overnight, the mixture was cooled and partitioned between ethyl acetate and water. The organic layer was dried (MgSO$_4$) and evaporated and the residue was purified by silica gel chromatography (CH$_2$Cl$_2$/MeOH 95:5) to give the title compound (0.021 g, 17%) as an off-white solid.

δ $^1$H-NMR (DMSO-d6): 8.46 (m, 3H), 8.18 (s, 1H), 8.11 (m, 1H), 7.72 (m, 1H), 7.57 (dd, 1H), 7.34 (ddd, 1H), 5.13 (dd, 1H), 1.36 (d, 3H).

ESI/MS m/e: 364 ([M+H]+, C$_{17}$H$_{13}$F$_4$N$_5$)

Example 160

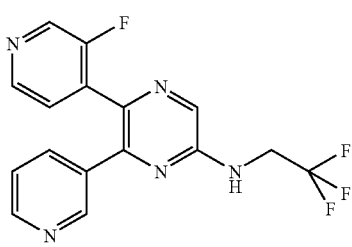

5-(3-Fluoropyridin-4-yl)-6-pyridin-3-yl-N-(2,2,2-trifluoroethyl)pyrazin-2-amine

Obtained (10%) from the title compound of Preparation 30 and 2,2,2-trifluoroethanamine following the procedure described in Example 159.

δ $^1$H-NMR (CD$_3$OD): 8.51 (m, 2H), 8.42 (dd, 1H), 8.3 (d, 1H), 8.17 (s, 1H), 7.84 (m, 1H), 7.68 (dd, 1H), 7.40 (ddd, 1H), 4.27 (q, 2H)

ESI/MS m/e: 350 ([M+H]+, C$_{16}$H$_{11}$F$_4$N$_5$)

Composition Example 1

50,000 capsules, each containing 100 mg N-[3-(3-fluoropyridin-4-yl)-2,2'-bipyrazin-6-yl]cyclopropanecarboxamide (active ingredient), were prepared according to the following formulation:

| Active ingredient | 5 Kg |
|---|---|
| Lactose monohydrate | 10 Kg |
| Colloidal silicon dioxide | 0.1 Kg |
| Corn starch | 1 Kg |
| Magnesium stearate | 0.2 Kg |

Procedure

The above ingredients were sieved through a 60 mesh sieve, and were loaded into a suitable mixer and filled into 50,000 gelatine capsules.

Composition Example 2

50,000 tablets, each containing 50 mg of N-[3-(3-fluoropyridin-4-yl)-2,2'-bipyrazin-6-yl]cyclopropanecarboxamide (active ingredient), were prepared from the following formulation:

| Active ingredient | 2.5 Kg |
|---|---|
| Microcrystalline cellulose | 1.95 Kg |
| Spray dried lactose | 9.95 Kg |
| Carboxymethyl starch | 0.4 Kg |
| Sodium stearyl fumarate | 0.1 Kg |
| Colloidal silicon dioxide | 0.1 Kg |

Procedure

All the powders were passed through a screen with an aperture of 0.6 mm, then mixed in a suitable mixer for 20 minutes and compressed into 300 mg tablets using 9 mm disc and flat bevelled punches. The disintegration time of the tablets was about 3 minutes.

The invention claimed is:

1. A compound of formula (I)

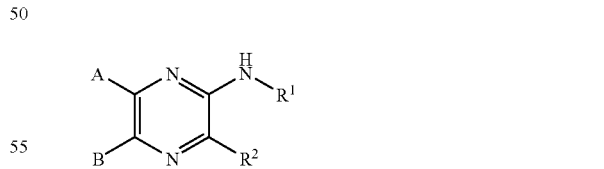

wherein:
A is a monocyclic, polycyclic aryl or heteroaryl group optionally substituted by one or more substituents each independently chosen from halogen atoms, C$_{1-4}$alkyl, C$_{3-8}$cycloalkyl, C$_{3-8}$cycloalkyl-C$_{1-4}$alkyl, C$_{1-4}$alkoxy, aryl-C$_{1-4}$alkoxy, C$_{1-4}$alkylthio, mono or di-C$_{1-4}$alkylamino, trifluoromethyl, hydroxy and cyano groups;
B is a monocyclic nitrogen-containing heteroaryl group optionally substituted by one or more substituents each independently chosen from halogen atoms, C$_{1-4}$alkyl, $C_{3-8}$cycloalkyl, $C_{3-8}$cycloalkyl-$C_{1-4}$alkyl, aryl, mono or di-$C_{1-4}$alkylamino, trifluoromethyl and cyano groups; and $R^1$ is a group of formula:

-L-(CR'R'')$_n$-G wherein L is a direct bond or a linking group chosen from —(CO)—, —(CO)O—, —(CO)NR'—, SO$_2$— and —SO$_2$NR'—;

R' and R'' are each independently chosen from a hydrogen atom and $C_{1-4}$alkyl groups;

n is an integer from 0 to 6; and

G is chosen from a hydrogen atom and $C_{1-4}$alkyl, aryl, heteroaryl, $C_{3-8}$cycloalkyl and saturated or unsaturated heterocyclic groups, wherein the $C_{1-4}$alkyl, $C_{3-8}$cycloalkyl, aryl or heteroaryl groups are each independently unsubstituted or substituted with one or more substituents chosen from halogen atoms, $C_{1-4}$alkyl, $C_{1-4}$alkoxy, $C_{1-4}$alkylthio, mono or di-$C_{1-4}$alkylamino, trifluoromethyl, trifluoromethoxy, carbamoyl, carboxy and cyano groups;

and $R^2$ is chosen from a hydrogen atom, halogen atoms and $C_{1-4}$alkyl, $C_{2-5}$alkenyl, $C_{2-5}$alkynyl, $C_{1-4}$alkoxy, $C_{1-4}$alkylthio, mono or di-$C_{1-4}$alkylamino, NH$_2$, mono or di-$C_{1-4}$alkylamino-(CO)— and cyano groups, wherein the $C_{1-4}$alkyl, $C_{2-5}$alkenyl and $C_{2-5}$alkynyl groups may be each independently unsubstituted or substituted by one aryl or heteroaryl group;

or a pharmaceutically acceptable salt thereof, or a N-oxide thereof; with the proviso that the compound is not chosen from N-[6-(1-methyl-1H-indol-3-yl)-5-pyridin-2-ylpyrazin-2-yl]benzamide, N-[3-ethoxycarbonyl-6-(1-methyl-1H-indol-3-yl)-5-pyridin-2-yl-pyrazin-2-yl]-benzamide and N-[3-ethoxycarbonyl-6-(1-methyl-1H-indol-3-yl)-5-pyridin-2-yl-pyrazin-2-yl]-formamide.

2. A compound of formula (I)

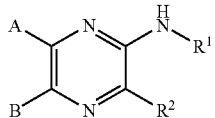

wherein:

A is a monocyclic, polycyclic aryl or heteroaryl group optionally substituted by one or more substituents each independently chosen from halogen atoms, $C_{1-4}$alkyl, $C_{3-8}$cycloalkyl, $C_{3-8}$cycloalkyl-$C_{1-4}$alkyl, aryl-$C_{1-4}$ alkoxy, $C_{1-4}$alkylthio, mono or di-$C_{1-4}$alkylamino, trifluoromethyl, hydroxy and cyano groups;

B is a monocyclic nitrogen-containing heteroaryl group optionally substituted by one or more substituents each independently chosen from halogen atoms, $C_{1-4}$alkyl, $C_{3-8}$cycloalkyl, $C_{3-8}$cycloalkyl-$C_{1-4}$alkyl, aryl, thio, mono or di-$C_{1-4}$alkylamino, trifluoromethyl and cyano groups;

and $R^1$ is a group of formula:

-L-(CR'R'')$_n$-G wherein L is a direct bond or a linking group chosen from —(CO)—, —(CO)O—, —(CO)NR'—, SO$_2$— and —SO$_2$NR'—;

R' and R'' are each independently chosen from a hydrogen atom and $C_{1-4}$alkyl groups;

n is an integer from 0 to 6; and

G is chosen from a hydrogen atom and $C_{1-4}$alkyl, aryl, heteroaryl, $C_{3-8}$cycloalkyl and saturated or unsaturated heterocyclic groups, wherein the $C_{1-4}$alkyl, $C_{3-8}$cycloalkyl, aryl or heteroaryl groups are each independently unsubstituted or substituted with one or more substituents chosen from halogen atoms, $C_{1-4}$alkyl, $C_{1-4}$alkoxy, $C_{1-4}$alkylthio, mono or di-$C_{1-4}$alkylamino, trifluoromethyl, trifluoromethoxy, carbamoyl, carboxy and cyano groups;

and $R^2$ is chosen from a hydrogen atom, halogen atoms and $C_{1-4}$alkyl, $C_{2-5}$alkenyl, $C_{2-5}$alkynyl, $C_{1-4}$alkoxy, $C_{1-4}$alkylthio, mono or di-$C_{1-4}$alkylamino, —NH$_2$, mono or di-$C_{1-4}$alkylamino-(CO)—, and cyano groups, wherein the $C_{1-4}$alkyl, $C_{2-5}$alkenyl and $C_{2-5}$alkynyl groups may be each independently unsubstituted or substituted by one aryl or heteroaryl group;

or a pharmaceutically acceptable salt thereof, or a N-oxide thereof; with the proviso that the compound is not chosen from N-[6-(1-methyl-1H-indol-3-yl)-5-pyridin-2-ylpyrazin-2-yl]benzamide, N-[3-ethoxycarbonyl-6-(1-methyl-1H-indol-3-yl)-5-pyridin-2-yl-pyrazin-2-yl]-benzamide and N-[3-ethoxycarbonyl-6-(1-methyl-1H-indol-3-yl)-5-pyridin-2-yl-pyrazin-2-yl]-formamide.

3. A compound of formula (I)

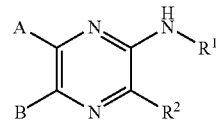

wherein:

A is a monocyclic, polycyclic aryl or heteroaryl group optionally substituted by one or more substituents each independently chosen from halogen atoms, $C_{1-4}$alkyl, $C_{3-8}$cycloalkyl, $C_{3-8}$cycloalkyl-$C_{1-4}$alkyl, $C_{1-4}$alkoxy, aryl-$C_{1-4}$alkoxy, $C_{1-4}$alkylthio, mono or di-$C_1$ alkylamino, trifluoromethyl, hydroxy and cyano groups;

B is a monocyclic nitrogen-containing heteroaryl group optionally substituted by one or more substituents each independently chosen from halogen atoms, $C_{1-4}$alkyl, $C_{3-8}$cycloalkyl, $C_{3-8}$cycloalkyl-$C_{1-4}$alkyl, aryl, mono or di-$C_{1-4}$alkylamino, trifluoromethyl and cyano groups;

and $R^1$ is a group of formula:

-L-(CR'R'')$_n$-G wherein L is a direct bond or a linking group chosen from —(CO)—, —(CO)O—, —(CO)NR'—, SO$_2$— and —SO$_2$NR'—;

R' and R'' are each independently chosen from a hydrogen atom and $C_{1-4}$alkyl groups;

n is an integer from 0 to 6; and

G is chosen from a hydrogen atom and $C_{1-4}$alkyl, aryl, heteroaryl, $C_{3-8}$cycloalkyl and saturated or unsaturated heterocyclic groups, wherein the $C_{1-4}$alkyl, $C_{3-8}$cycloalkyl, aryl or heteroaryl groups are each independently unsubstituted or substituted with one or more substituents chosen from halogen atoms, $C_{1-4}$alkyl, $C_{1-4}$alkoxy, $C_{1-4}$alkylthio, mono or di-$C_{1-4}$alkylamino, trifluoromethyl, trifluoromethoxy, carbamoyl, carboxy and cyano groups;

and $R^2$ is chosen from a hydrogen atom, halogen atoms and $C_{1-4}$alkyl, $C_{2-5}$alkenyl, $C_{2-5}$alkynyl, C₁₋₄alkoxy, C₁₋₄alkylthio, and cyano groups, wherein the C₂₋₅alkenyl and C₂₋₅alkynyl groups may be each independently unsubstituted or substituted by one aryl or heteroaryl group;

or a pharmaceutically acceptable salt thereof, or a N-oxide thereof; with the proviso that the compound is not chosen from N-[6-(1-methyl-1H-indol-3-yl)-5-pyridin-2-ylpyrazin-2-yl]benzamide, N-[3-ethoxycarbonyl-6-(1-methyl-1H-indol-3-yl)-5-pyridin-2-yl-pyrazin-2-yl]-benzamide and N-[3-ethoxycarbonyl-6-(1-methyl-1H-indol-3-yl)-5-pyridin-2-yl-pyrazin-2-yl]-formamide.

4. The compound according to claim 1, wherein A is an optionally substituted monocyclic five or six-membered heteroaryl ring or an optionally substituted phenyl ring.

5. The compound according to claim 1, wherein A is an optionally substituted pyridine, oxazole, furan, pyrazole, pyrazine or phenyl group.

6. The compound according to claim 1, wherein A is an optionally substituted pyridine, oxazole, furan or pyrazole group.

7. The compound according to claim 6, wherein A is a pyridine ring unsubstituted or substituted with alkoxy groups or halogen atoms.

8. The compound according to claim 1, wherein A is a pyridine ring either unsubstituted or substituted with one or two halogen atoms.

9. The compound according to claim 8, wherein A is a pyridine ring either unsubstituted or substituted with one halogen atom.

10. The compound according to claim 1, wherein B is an optionally substituted monocyclic, five or six-membered heteroaryl ring having one or two nitrogen atoms.

11. The compound according to claim 10, wherein B is an optionally substituted pyridine or pyrimidine group.

12. The compound according to claim 1, wherein B is a pyridine ring either unsubstituted or substituted with one or two halogen atoms.

13. The compound according to claim 12, wherein B is a pyridine ring either unsubstituted or substituted with one halogen atom.

14. The compound according to claim 1, wherein R¹ is a group of formula:

wherein L is a direct bond or a group —(CO)—;
R' and R" are each independently chosen from a hydrogen atom and methyl groups;
n is an integer from 0 to 6; and
G is chosen from a hydrogen atom, C₁₋₄alkyl, C₃₋₈cycloalkyl, aryl and heteroaryl groups, wherein the C₁₋₄alkyl, C₃₋₈cycloalkyl, aryl and heteroaryl groups are each independently unsubstituted or substituted with one or more halogen atoms.

15. The compound according to claim 14, wherein G is chosen from a hydrogen atom, C₁₋₄alkyl, C₃₋₈cycloalkyl, aryl and heteroaryl groups, wherein the aryl and heteroaryl group are each independently unsubstituted or substituted with at least one halogen atom.

16. The compound according to claim 14, wherein R¹ is a group of formula:

wherein L is —(O)—;
R' and R" are each independently chosen from a hydrogen atom and methyl groups;
n is an integer from 0 to 6; and G is chosen from a hydrogen atom and C₃₋₈cycloalkyl groups optionally substituted with one or more halogen atoms.

17. The compound according to claim 16, wherein G is chosen from a hydrogen atom and a C₃₋₈cycloalkyl group.

18. The compound according to claim 16, wherein:
G is a C₃₋₅cycloalkyl group optionally substituted with one or more halogen atoms, and
n is an integer from 0-3.

19. The compound according to claim 1, wherein R² is a hydrogen atom.

20. The compound according to claim 1, wherein the compound of formula (I) is chosen from:
6-(3-Fluorophenyl)-5-pyridin-4-ylpyrazin-2-amine;
5-(3-Chloropyridin-4-yl)-6-(3-fluorophenyl)pyrazin-2-amine;
6-(3-Fluorophenyl)-5-(3-fluoropyridin-4-yl)pyrazin-2-amine;
6-(3-Fluorophenyl)-5-(1,3-thiazol-5-yl)pyrazin-2-amine;
6-(2-Furyl)-5-pyridin-4-ylpyrazin-2-amine;
5-Pyridin-4-yl-6-(2-thienyl)pyrazin-2-amine;
6-(2-Furyl)-5-pyrimidin-4-ylpyrazin-2-amine;
6-(2-Furyl)-5-(2-methylpyrimidin-4-yl)pyrazin-2-amine;
5-(2-Cyclopropylpyrimidin-4-yl)-6-(2-furyl)pyrazin-2-amine;
6-(2-Furyl)-5-(2-phenylpyrimidin-4-yl)pyrazin-2-amine;
6-Pyridin-2-yl-5-pyridin-4-ylpyrazin-2-amine;
6-Pyridin-3-yl-5-pyridin-4-ylpyrazin-2-amine;
5,6-Dipyridin-4-ylpyrazin-2-amine;
N-[6-(5-Methyl-2-furyl)-5-pyridin-4-ylpyrazin-2-yl]cyclopropanecarboxamide;
6-(2-Fluorophenyl)-5-pyridin-4-ylpyrazin-2-amine;
N-[6-(3-Fluoropyridin-4-yl)-5-pyridin-4-ylpyrazin-2-yl]cyclopropanecarboxamide;
N-[6-(3-Chloropyridin-4-yl)-5-pyridin-4-ylpyrazin-2-yl]cyclopropanecarboxamide;
N-[6-(1,3-Oxazol-5-yl)-5-pyridin-4-ylpyrazin-2-yl]cyclopropanecarboxamide;
N-[6-(1,3-Oxazol-2-yl)-5-pyridin-4-ylpyrazin-2-yl]cyclopropanecarboxamide;
N-[5-(3-Chloropyridin-4-yl)-6-pyridin-3-ylpyrazin-2-yl]cyclopropanecarboxamide;
N-[5-(3-Chloropyridin-4-yl)-6-pyridin-2-ylpyrazin-2-yl]cyclopropanecarboxamide;
N-[5-(3-Chloropyridin-4-yl)-6-pyridin-4-ylpyrazin-2-yl]cyclopropanecarboxamide;
N-[5-(3-Chloropyridin-4-yl)-6-pyridin-3-ylpyrazin-2-yl]-2,2-dimethylpropanamide;
N-[5-(3-Fluoropyridin-4-yl)-6-pyridin-3-ylpyrazin-2-yl]cyclopropanecarboxamide;
N-[5-(3-Fluoropyridin-4-yl)-6-pyridin-4-ylpyrazin-2-yl]cyclopropanecarboxamide;
6-(3-Fluorophenyl)-N-pyridin-3-yl-5-pyridin-4-ylpyrazin-2-amine;
N-[6-(3-Fluorophenyl)-5-pyridin-4-ylpyrazin-2-yl]pyrimidin-5-amine;
N-[6-(3-Fluorophenyl)-5-pyridin-4-ylpyrazin-2-yl]acetamide;
N-[6-(2-Fluorophenyl)-5-pyridin-4-ylpyrazin-2-yl]cyclopropanecarboxamide;
6-(2-Furyl)-N-pyridin-3-yl-5-pyridin-4-ylpyrazin-2-amine;
N-[6-(2-Furyl)-5-pyridin-4-ylpyrazin-2-yl]pyrimidin-5-amine;
N-[6-(2-Furyl)-5-pyridin-4-ylpyrazin-2-yl]acetamide;
N-[6-(2-Furyl)-5-pyridin-4-ylpyrazin-2-yl]propanamide;
N-[6-(2-Furyl)-5-pyridin-4-ylpyrazin-2-yl]cyclopropanecarboxamide;

N-[6-(2-Furyl)-5-pyridin-4-ylpyrazin-2-yl]cyclobutanecarboxamide;
N-[6-(2-Furyl)-5-pyridin-4-ylpyrazin-2-yl]cyclopentanecarboxamide;
N-[6-(2-Furyl)-5-pyridin-4-ylpyrazin-2-yl]-2-methylpropanamide;
2-Cyclopentyl-N-[6-(2-furyl)-5-pyridin-4-ylpyrazin-2-yl]acetamide;
4-Fluoro-N-[6-(2-furyl)-5-pyridin-4-ylpyrazin-2-yl]benzamide;
N-Cyclopentyl-N-[6-(2-furyl)-5-pyridin-4-ylpyrazin-2-yl]urea;
N-[5-Pyridin-4-yl-6-(2-thienyl)pyrazin-2-yl]acetamide;
N-[6-(2-Furyl)-5-pyrimidin-4-ylpyrazin-2-yl]acetamide;
N-[6-(2-Furyl)-5-pyrimidin-4-ylpyrazin-2-yl]cyclopropanecarboxamide;
N-[6-(2-Furyl)-5-(2-methylpyrimidin-4-yl)pyrazin-2-yl]cyclopropanecarboxamide;
N-[5-(2-Cyclopropylpyrimidin-4-yl)-6-(2-furyl)pyrazin-2-yl]cyclopropanecarboxamide;
N-[6-(2-Furyl)-5-(2-phenylpyrimidin-4-yl)pyrazin-2-yl]acetamide;
N-[6-(2-Furyl)-5-(2-phenylpyrimidin-4-yl)pyrazin-2-yl]cyclopropanecarboxamide;
N-(6-Pyridin-2-yl-5-pyridin-4-ylpyrazin-2-yl)acetamide;
N-(6-Pyridin-2-yl-5-pyridin-4-ylpyrazin-2-yl)cyclopropanecarboxamide;
N-Cyclopentyl-N'-(6-pyridin-2-yl-5-pyridin-4-ylpyrazin-2-yl)urea;
N-(4-Fluorophenyl)-N'-(6-pyridin-2-yl-5-pyridin-4-ylpyrazin-2-yl)urea;
N-(6-Pyridin-3-yl-5-pyridin-4-ylpyrazin-2-yl)cyclopropanecarboxamide;
N-(6-Pyridin-3-yl-5-pyridin-4-ylpyrazin-2-yl)cyclobutanecarboxamide;
N-Cyclopentyl-N'-(6-pyridin-3-yl-5-pyridin-4-ylpyrazin-2-yl)urea;
N-(4-Fluorophenyl)-N'-(6-pyridin-3-O-5-pyridin-4-ylpyrazin-2-yl)urea;
6-Pyridin-3-yl-5-pyridin-4-yl-N-1,3-thiazol-2-ylpyrazin-2-amine;
N-(5,6-Dipyridin-4-ylpyrazin-2-yl)cyclopropanecarboxamide;
3-Bromo-6-(3-fluorophenyl)-5-pyridin-4-ylpyrazin-2-amine;
3-Bromo-6-(2-furyl)-5-pyridin-4-ylpyrazin-2-amine;
3-Bromo-6-pyridin-3-yl-5-pyridin-4-ylpyrazin-2-amine;
3-Amino-5-(2-furyl)-6-pyridin-4-ylpyrazine-2-carbonitrile;
3-Ethynyl-6-(2-furyl)-5-pyridin-4-ylpyrazin-2-amine;
6-(2-Furyl)-3-(phenylethynyl)-5-pyridin-4-ylpyrazin-2-amine;
6-(2-Furyl)-3-methoxy-5-pyridin-4-ylpyrazin-2-amine;
3-Ethyl-6-(2-furyl)-5-pyridin-4-ylpyrazin-2-amine;
N-[3-Cyano-6-(2-furyl)-5-pyridin-4-ylpyrazin-2-yl]acetamide;
N-[6-(2-Furyl)-3-methoxy-5-pyridin-4-ylpyrazin-2-yl]cyclopropanecarboxamide,
N-[3-Ethyl-6-(2-furyl)-5-pyridin-4-ylpyrazin-2-yl]acetamide;
5-Phenyl-6-pyridin-4-ylpyrazine-2,3-diamine;
5-(3-Fluorophenyl)-6-pyridin-4-ylpyrazine-2,3-diamine;
3-Amino-5-(3-fluorophenyl)-6-pyridin-4-ylpyrazin-2-ol;
5-(4-Fluorophenyl)-6-pyridin-4-ylpyrazine-2,3-diamine;
5-(3-Methylphenyl)-6-pyridin-4-ylpyrazine-2,3-diamine;
5-(2-Furyl)-6-pyridin-4-ylpyrazine-2,3-diamine;
3-Amino-5-(2-furyl)-6-pyridin-4-ylpyrazin-2-ol;
5-(5-Methyl-2-furyl)-6-pyridin-4-ylpyrazine-2,3-diamine;
5-(1-Benzofuran-2-yl)-6-pyridin-4-ylpyrazine-2,3-diamine;
5-Pyridin-3-yl-6-pyridin-4-ylpyrazine-2,3-diamine;
5-(2-Furyl)-6-pyrimidin-4-ylpyrazine-2,3-diamine;
3-Amino-5-(2-furyl)-6-pyrimidin-4-ylpyrazin-2-ol;
5-(3-Methyl-2-furyl)-6-pyrimidin-4-ylpyrazine-2,3-diamine;
5-(3-Fluoropyridin-4-yl)-6-pyridin-3-ylpyrazin-2-amine;
5-(3,5-Difluoropyridin-4-yl)-6-pyridin-3-ylpyrazin-2-amine;
N-[6-(6-Hydroxypyridin-3-yl)-5-pyridin-4-ylpyrazin-2-yl]cyclopropanecarboxamide;
1-Cyclopropyl-3-(6-(pyridin-2-yl)-5-(pyridin-4-yl)pyrazin-2-yl)urea;
N-[5-(3-Fluoropyridin-4-yl)-6-(6-methoxypyridin-3-yl)pyrazin-2-yl]cyclopropane carboxamide;
N-[5,6-bis(3-Fluoropyridin-4-yl)pyrazin-2-yl]cyclopropanecarboxamide,
N-[5-(3-Fluoropyridin-4-yl)-6-quinolin-3-ylpyrazin-2-yl]cyclopropanecarboxamide;
N-[5-(3-Fluoropyridin-4-yl)-6-(5-methoxypyridin-3-yl)pyrazin-2-yl]cyclopropanecarboxamide;
N-[5-(3-Fluoropyridin-4-yl)-6-(6-hydroxypyridin-3-yl)pyrazin-2-yl]cyclopropane carboxamide;
N-[5-(3-Fluoropyridin-4-yl)-6-(1-oxidopyridin-3-yl)pyrazin-2-yl]cyclopropane carboxamide;
N-[5-(3-fluoropyridin-4-yl)-6-pyrimidin-5-ylpyrazin-2-yl]cyclopropanecarboxamide;
N-[3-(3-fluoropyridin-4-yl)-2,2'-bipyrazin-6-yl]cyclopropanecarboxamide;
N-[5-(3-Fluoro-1-oxidopyridin-4-yl)-6-pyridin-3-ylpyrazin-2-yl]cyclopropanecarboxamide;
N-[5-(3-fluoropyridin-4-yl)-6-(5-fluoropyridin-2-yl)pyrazin-2-yl]cyclopropane-carboxamide;
N-[6-(2-Fluorophenyl)-5-(3-fluoropyridin-4-yl)pyrazin-2-yl]cyclopropane-carboxamide;
N-[6-(2,4-Difluorophenyl)-5-(3-fluoropyridin-4-yl)pyrazin-2-yl]cyclopropane-carboxamide;
N-[5-(3-Fluoropyridin-4-yl)-6-(1,3-oxazol-2-yl)pyrazin-2-yl]cyclopropane-carboxamide;
N-[5-(3-Fluoropyridin-4-yl)-6-pyridin-3-ylpyrazin-2-yl]propanamide;
2-Cyclopentyl-N-[5-(3-fluoropyridin-4-yl)-6-pyridin-3-ylpyrazin-2-yl]acetamide;
N-[5-(3-Fluoropyridin-4-yl)-6-pyridin-3-ylpyrazin-2-yl]cyclopentanecarboxamide;
3,3,3-Trifluoro-N-[5-(3-fluoropyridin-4-yl)-6-pyridin-3-ylpyrazin-2-yl]propanamide;
N-[5-(3-Fluoropyridin-4-yl)-6-pyridin-3-ylpyrazin-2-yl]cyclobutanecarboxamide;
N-[5-(3-Fluoropyridin-4-yl)-6-pyridin-3-ylpyrazin-2-yl]acetamide;
2-Cyclopropyl-N-[5-(3-fluoropyridin-4-yl)-6-pyridin-3-ylpyrazin-2-yl]acetamide;
N-[5-(3-Fluoropyridin-4-yl)-6-pyridin-3-ylpyrazin-2-yl]-2-morpholin-4-ylacetamide;
N-[5-(3-Fluoropyridin-4-yl)-6-pyridin-3-ylpyrazin-2-yl]-2-methylpropanamide;
N-[5-(3-Fluoropyridin-4-yl)-6-pyridin-3-ylpyrazin-2-yl]methanesulfonamide;
N-[5-(3,5-Difluoropyridin-4-yl)-6-pyridin-3-ylpyrazin-2-yl]cyclopropane carboxamide;
N-[5-(3,5-Difluoropyridin-4-yl)-6-pyridin-4-ylpyrazin-2-yl]cyclopropane carboxamide;

N-[5-(3,5-difluoropyridin-4-yl)-6-(1-oxidopyridin-3-yl)pyrazin-2-yl]cyclopropane-carboxamide;

N-[5-(3,5-difluoro-1-oxidopyridin-4-yl)-6-pyridin-3-ylpyrazin-2-yl]cyclopropane-carboxamide;

N-[6-(3,5-Difluoropyridin-2-yl)-5-(3-fluoropyridin-4-yl)pyrazin-2-yl]cyclopropanecarboxamide;

5-(3-Fluoropyridin-4-yl)-6-pyridin-3-ylpyrazine-2,3-diamine;

5-(3-Fluoropyridin-4-yl)-6-pyridin-3-yl-N-(2,2,2-trifluoro-1-methylethyl)pyrazin-2-amine; and 5-(3-Fluoropyridin-4-yl)-6-pyridin-3-yl-N-(2,2,2-trifluoroethyl)pyrazin-2-amine.

21. A pharmaceutical composition comprising a compound according to claim 1 and a pharmaceutically acceptable diluent or carrier.

\* \* \* \* \*

UNITED STATES PATENT AND TRADEMARK OFFICE
CERTIFICATE OF CORRECTION

PATENT NO. : 7,790,728 B2
APPLICATION NO. : 11/997048
DATED : September 7, 2010
INVENTOR(S) : Bernat Vidal Juan et al.

It is certified that error appears in the above-identified patent and that said Letters Patent is hereby corrected as shown below:

On the cover of the patent, the inventor's name, "Christina Esteve Trias," is misspelled and should read --Cristina Esteve Trias--.

In Claim 16, col. 167, line 64, "wherein L is –(O)–;" should read --wherein L is –(CO)–;--.

In Claim 20, col. 169, lines 11-12, "N-Cyclopentyl-N-[6-(2-furyl)-5-pyridin-4-ylpyrazin-2-yl]urea;" should read --N-Cyclopentyl-N'-[6-(2-furyl)-5-pyridin-4-ylpyrazin-2-yl]urea;--.

Signed and Sealed this
First Day of February, 2011

David J. Kappos
*Director of the United States Patent and Trademark Office*